US011207342B2

(12) United States Patent
Manoharan et al.

(10) Patent No.: US 11,207,342 B2
(45) Date of Patent: Dec. 28, 2021

(54) HIGH DENSITY LIPOPROTEIN BINDING PROTEIN (HDLBP/VIGILIN) IRNA COMPOSITIONS AND METHODS OF USE THEREOF

(71) Applicants: Alnylam Pharmaceuticals, Inc., Cambridge, MA (US); ETH Zurich, Zurich (CH)

(72) Inventors: Muthiah Manoharan, Weston, MA (US); Markus Stoffel, Herrliberg (CH); Mehrpouya Balaghy Mobin, Cologne (DE)

(73) Assignees: Alnylam Pharmaceuticals, Inc., Cambridge, MA (US); ETH Zurich, Zurich (CH)

( * ) Notice: Subject to any disclaimer, the term of this patent is extended or adjusted under 35 U.S.C. 154(b) by 108 days.

(21) Appl. No.: 16/162,705

(22) Filed: Oct. 17, 2018

(65) Prior Publication Data

US 2019/0038658 A1 Feb. 7, 2019

Related U.S. Application Data

(63) Continuation of application No. PCT/US2017/028291, filed on Apr. 19, 2017.

(60) Provisional application No. 62/324,480, filed on Apr. 19, 2016.

(51) Int. Cl.

| | |
|---|---|
| ***A61K 31/713*** | (2006.01) |
| ***C12N 15/113*** | (2010.01) |
| ***A61P 3/06*** | (2006.01) |

(52) U.S. Cl.

CPC .............. *A61K 31/713* (2013.01); *A61P 3/06* (2018.01); *C12N 15/113* (2013.01); *C12N 2310/14* (2013.01); *C12N 2310/315* (2013.01); *C12N 2310/3125* (2013.01); *C12N 2310/321* (2013.01); *C12N 2310/322* (2013.01); *C12N 2310/351* (2013.01); *C12N 2310/3521* (2013.01); *C12N 2310/3533* (2013.01)

(58) Field of Classification Search

None

See application file for complete search history.

(56) References Cited

U.S. PATENT DOCUMENTS

2012/0004160 A1 * 1/2012 Janssen .................. A61P 37/00 514/2.4

FOREIGN PATENT DOCUMENTS

| | | | |
|---|---|---|---|
| WO | WO-2009/073809 | A2 | 6/2009 |
| WO | WO-2010/148013 | A2 | 12/2010 |
| WO | WO-2012/028679 | A2 | 3/2012 |

OTHER PUBLICATIONS

Wei et al.: "Disruption of human vigilin impairs chromosome condensation and segregation", Cell Biology International, vol. 39, No. 11, Nov. 1, 2015, pp. 1234-1241.

Goolsby et al., "RNAi-mediated depletion of the 15 KH domain protein, vigilin, induces death of dividing and non-dividing human cells but does not initially inhibit protein synthesis", Nucleic Acids Research, vol. 31, No. 19, Oct. 1, 2003, pp. 5644-5653.

Schuh et al., "Protein Synthesis of Eucaryotic Cells Could Be Decreased by antisense-DNA of the Multi KH Domain Protein Vigilin", International Journal of Molecular Medicine, vol. 12, 2003, pp. 35-43.

Liu et al., "Vigilin interacts with CCCTC-binding factor (CTCF) and is involved in CTCF-dependent regulation of the imprinted genes Igf2 and H19", FEBS Journal, vol. 281, No. 12, 2014, pp. 2713-2725.

Yang et al.: "Vigilin is overexpressed in hepatocellular carcinoma and is required for HCC cell proliferation and tumor growth", Oncology Reports, 2014.

Woo et al., "Posttranscriptional suppression of proto-oncogene c-fms expression by Vigilin in breast cancer", Molecular and Cellular Biology, vol. 31, No. 1, 2011, pp. 215-225.

International Preliminary Report on Patentability from PCT/US2017/028291, dated Apr. 19, 2016.

* cited by examiner

*Primary Examiner* — Tracy Vivlemore

(74) *Attorney, Agent, or Firm* — McCarter & English, LLP; Maria Laccotripe Zacharakis; Deborah L. Nagle

(57) ABSTRACT

The invention relates to double stranded ribonucleic acid (dsRNA) agents and compositions targeting a High Density Lipoprotein Binding Protein (Hdlbp/Vigilin) gene, as well as methods of inhibiting expression of Hdlbp/Vigilin and methods of treating subjects having a disorder of lipid metabolism, such as mixed hyperlipidemia, hypertriglyceridemia or hypercholesterolemia, using such dsRNA agents and compositions.

25 Claims, 38 Drawing Sheets

Specification includes a Sequence Listing.

WT: GATTTAACTCCACCTACTTCCAGGGC
Mut: GATTTAAATCAACCTAATTACAGGGC
Scr: CCGGCAATCATGCCTTACGATTATCC

WT: CTACCTCAATAATCATCTTCTTCAGG
Mut: CTAACTAAATAATAATATTATTAAGG
Scr: CGCAACTTTTACATTCTATCATAGCC

SEQUENCE LISTING

<160> NUMBER OF SEQ ID NOS: 326

<210> SEQ ID NO 1
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1
gagaucaaca uugaccauaa a 21

<210> SEQ ID NO 2
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 2
uuuaugguca auguugaucu cua 23

<210> SEQ ID NO 3
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 3
aggaagaucg ggcuuuaagg a 21

<210> SEQ ID NO 4
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 4
uccuuaaagc ccgaucuucc ugc 23

<210> SEQ ID NO 5
<211> LENGTH: 6524
<212> TYPE: DNA
<213> ORGANISM: Homo sapiens

<400> SEQUENCE: 5
tttgccaact gcttcctggc tcagtgcgac ctggccttct tcccctcccc catgcggccg 60
gcttccgagt gcgcaagccc agagtcgtcc gcgttgtccg cctctgcgca agcgccgtgc 120
tcctcccacg gcagttggcc atatagaggc tgggggtggg gggggaggtc aagcgtagcc 180
tcttctcctt taccaagatg gcggcttgtc cctgtttcgc cacagttcct accttatgag 240
ctcggttttc ttatgcttat aagagtggaa cagcaaaagc tggcaggctg acagaggcgg 300
cctcaggacg gaccttctgg ctactgaccg ttttgctgtg gttttcccgg attgtgtgta 360
ggtgtgagat caaccatgag ttccgttgca gttttgaccc aagagagttt tgctgaacac 420
cgaagtgggc tggttccgca acaaatcaaa gttgccactc taaattcaga agaggagagc 480
gaccctccaa cctacaagga tgccttccct ccacttcctg agaaagctgc ttgcctggaa 540
agtgcccagg aacccgctgg agcctggggg aacaagatcc gacccatcaa ggcttctgtc 600
atcactcagg tgttccatgt accccctggag gagagaaaat acaaggatat gaaccagttt 660
ggagaaggtg aacaagcaaa aatctgcctt gagatcatgc agagaactgg tgctcacttg 720
gagctgtctt tggccaaaga ccaaggcctc tccatcatgg tgtcaggaaa gctggatgct 780
gtcatgaaag ctcggaagga cattgttgct agactgcaga ctcaggcctc agcaactgtt 840
gccattccca aagaacacca tcgctttgtt attggcaaaa atggagagaa actgcaagac 900
ttggagctaa aaactgcaac caaaatccag atcccacgcc cagatgaccc cagcaatcag 960
atcaagatca ctggcaccaa agagggcatc gagaaagctc gccatgaagt cttactcatc 1020
tctgccgagc aggacaaacg tgctgtggag aggctagaag tagaaaaggc attccacccc 1080
ttcatcgctg ggccgtataa tagactggtt ggcgagatca tgcaggagac aggcacgcgc 1140
atcaacatcc ccccacccag cgtgaaccgg acagagattg tcttcactgg agagaaggaa 1200
cagttggctc aggctgtggc tcgcatcaag aagatttatg aggagaagaa aaagaagact 1260
acaaccattg cagtggaagt gaagaaatcc caacacaagt atgtcattgg gcccaagggc 1320
aattcattgc aggagatcct tgagagaact ggagtttccg ttgagatccc accctcagac 1380
agcatctctg agactgtaat acttcgaggc gaacctgaaa agttaggtca ggcgttgact 1440
gaagtctatg ccaaggccaa tagcttcacc gtctcctctg tcgccgcccc ttcctggctt 1500
caccgtttca tcattggcaa gaaagggcag aacctggcca aaatcactca gcagatgcca 1560
aaggttcaca tcgagttcac agagggcgaa gacaagatca ccctggaggg ccctacagag 1620
gatgtcaatg tggcccagga acagatagaa ggcatggtca aagatttgat taaccggatg 1680
gactatgtgg agatcaacat cgaccacaag ttccacaggc acctcattgg gaagagcggt 1740
gccaacataa acagaatcaa agaccagtac aaggtgtccg tgcgcatccc tcctgacagt 1800
gagaagagca atttgatccg catcgagggg gacccacagg gcgtgcagca ggccaagcga 1860
gagctgctgg agcttgcatc tcgcatggaa aatgagcgta ccaaggatct aatcattgag 1920
caaagatttc atcgcacaat cattgggcag aagggtgaac ggatccgtga aattcgtgac 1980
aaattcccag aggtcatcat taactttcca gacccagcac aaaaaagtga cattgtccag 2040
ctcagaggac ctaagaatga ggtggaaaaa tgcacaaaat acatgcagaa gatggtggca 2100
gatctggtgg aaaatagcta ttcaatttct gttccgatct tcaaacagtt tcacaagaat 2160
atcattggga aaggaggcgc aaacattaaa aagattcgtg aagaaagcaa caccaaaatc 2220
gaccttccag cagagaatag caattcagag accattatca tcacaggcaa gcgagccaac 2280
tgcgaagctg cccggagcag gattctgtct attcagaaag acctggccaa catagccgag 2340
gtagaggtct ccatccctgc caagctgcac aactccctca ttggcaccaa gggccgtctg 2400
atccgctcca tcatggagga gtgcggcggg gtccacattc actttcccgt ggaaggttca 2460
ggaagcgaca ccgttgttat caggggccct tcctcggatg tggagaaggc caagaagcag 2520
ctcctgcatc tggcggagga gaagcaaacc aagagtttca ctgttgacat ccgcgccaag 2580
ccagaatacc acaaattcct catcggcaag gggggcggca aaattcgcaa ggtgcgcgac 2640
agcactggag cacgtgtcat cttccctgcg gctgaggaca aggaccagga cctgatcacc 2700
atcattggaa aggaggacgc cgtccgagag gcacagaagg agctggaggc cttgatccaa 2760

```
aacctggata atgtggtgga agactccatg ctggtggacc ccaagcacca ccgccacttc   2820
gtcatccgca gaggccaggt cttgcgggag attgctgaag agtatggcgg ggtgatggtc   2880
agcttcccac gctctggcac acagagcgac aaagtcaccc tcaagggcgc caaggactgt   2940
gtggaggcag ccaagaaacg cattcaggag atcattgagg acctggaagc tcaggtgaca   3000
ttagaatgtg ctataccccca gaaattccat cgatctgtca tgggccccaa aggttccaga   3060
atccagcaga ttactcggga tttcagtgtt caaattaaat tcccagacag agaggagaac   3120
gcagttcaca gtacagagcc agttgtccag gagaatgggg acgaagctgg ggaggggaga   3180
gaggctaaag attgtgaccc cggctctcca aggaggtgtg acatcatcat catctctggc   3240
cggaaagaaa agtgtgaggc tgccaaggaa gctctggagg cattggttcc tgtcaccatt   3300
gaagtagagg tgccctttga ccttcaccgt tacgttattg ggcagaaagg aagtgggatc   3360
cgcaagatga tggatgagtt tgaggtgaac atacatgtcc cggcacctga gctgcagtct   3420
gacatcatcg ccatcacggg cctcgctgca aatttggacc gggccaaggc tggactgctg   3480
gagcgtgtga aggagctaca ggccgagcag gaggaccggg ctttaaggag ttttaagctg   3540
agtgtcactg tagaccccaa ataccatccc aagattatcg ggagaaaggg ggcagtaatt   3600
acccaaatcc ggttggagca tgacgtgaac atccagtttc ctgataagga cgatgggaac   3660
cagccccagg accaaattac catcacaggg tacgaaaaga acacagaagc tgccagggat   3720
gctatactga gaattgtggg tgaacttgag cagatggttt ctgaggacgt cccgctggac   3780
caccgcgttc acgcccgcat cattggtgcc cgcggcaaag ccattcgcaa aatcatggac   3840
gaattcaagg tggacattcg cttcccacag agcggagccc cagaccccaa ctgcgtcact   3900
gtgacggggc tcccagagaa tgtggaggaa gccatcgacc acatcctcaa tctggaggag   3960
gaatacctag ctgacgtggt ggacagtgag gcgctgcagg tatacatgaa acccccagca   4020
cacgaagagg ccaaggcacc ttccagaggc tttgtggtgc gggacgcacc ctggaccgcc   4080
agcagcagtg agaaggctcc tgacatgagc agctctgagg aatttcccag ctttggggct   4140
caggtggctc ccaagaccct cccttggggc cccaaacgat aatgatcaaa aagaacagaa   4200
ccctctccag cctgctgacc caaacccaac cacacaatgg tttgtctcaa tctgacccag   4260
cggctggacc ctccgtaaat tgttgacgct cttcccccttt cccgaggtcc cgcagggagc   4320
ctagcgcctg gctgtgtgtg cggccgctcc tccaggcctg gccgtgcccg ctcaggacct   4380
gctccactgt ttaacactaa accaaggtca tgagcattcg tgctaagata acagactcca   4440
gctcctggtc cacccggcat gtcagtcagc actctggcct tcatcacgag agctccgcag   4500
ccgtggctag gattccactt cctgtgtcat gacctcagga aataaacgtc cttgacttta   4560
taaaagccaa acgtttgccc tcttcctttc ccacctccct cctgccagtt tcccttggtc   4620
cagacagtcc tgtttgtgga gtgcaatcag cctcctccag ctgccagagc gcctcagcac   4680
aggtgtcagg gtgcaaggaa gacctggcaa tggacagcag gaggcaggtt cctggagctg   4740
gggggtgacc tgagaggcag agggtgacgg gttctcaggc agtcctgatt ttacctgccg   4800
tggggtctga aagcaccaag ggtccctgcc cctacctcca ctgccagacc ctcagcctga   4860
ggtctggtga gtggagcctg gaggcaaggt ggtaggcacc atctgggtcc cctgtggccg   4920
tcacagtgtc tgctgtgatt gagatgcgca caggttgggg gaggtagggc cttacgcttg   4980
tcctcagtgg gggcagtttg ccttagatga cagctgggct cttcttcaca ccacctgcag   5040
cccctccctg cccctgccct agctgctgtg tgttcagttg ccttctttct acctcagccg   5100
gcgtggagtg gtctctgtgc agttagtgcc accccacaca cccgtctctt gattgagatg   5160
```

```
tttctggtgg ttatgggttt cccgtggagc tgggggtggg cgccgtgtac ctaagctgga   5220

ggctggcgct ctccctcagc acaggtgggt cagtggccag caggcccatc tggagtggga   5280

gtgggcactt ccaccccgcc cacaggccat ccggctgtgc aggccagccc ctaggagcag   5340

gtcccgggtg actggcagtt ttcacggtct agggccgaga cgatggcatg gggcctagag   5400

catgaggtag agcagaatgc agaccacgcc gctggatgcc gagagaccct gctctccgag   5460

ggaggcatct gtgtcatgct gtgagggctg aggacggggc cctagtctct ggttttctgg   5520

tcttaacatc cttatctgtg tccgccacgg aggtgactga gctgctagcg agttgtcctg   5580

tcccaggtac ttgagttttg gaaaagctga ctcacgccca tccatctcac agcccttccc   5640

tggggacagt cgcttccgcc ttgacacctc actctcagtt gaataactca agcttggtca   5700

tcttcagact cgaattcttg agtagaccca gacggcttag cccaagtcta gttgcagctg   5760

cctcggcaag tccccatttg ctcaggcagc cctgaatggg cctgtttaca ggaatggtaa   5820

attgggattg gaaggaatat agcttccagc ttcataggct agggtgacca cggcttagga   5880

aacagggaaa gaaagcaagg cccttttcct gcctttcccg ggatctgtct actccacctc   5940

cacgggggag gccagtgggg aagggctgtc acctcttccc catctgcatg agttctggaa   6000

ctctgtcctg ttggctgctt gcttccagct ccccccaatc tccatcgcag cgggttcctc   6060

ctgtcttttc tacagtgtca taaaacatcc tgcccctacc ctctcccaaa ggtcaatttt   6120

aattctcacc aagttttgca catctctgta tgtcgcttga tgtcttagac gcgagccctt   6180

tcctaaactg ttcagcgctc tcttttcctt tgggtggttg ttgcaagggt gatgacatga   6240

ctgtccccag gcctgtctcc ctgaagcgtc tgtgctgtca ggacagccct gggcagagat   6300

gaggcagggg tgaggcgtgc gtgtgctttt cctccttgtt ggatgtcttc catatcatct   6360

gtttccatag ctacaatcca tcccttggcc ttaactttgg aatttggaga ttatatgcaa   6420

acatgtgtaa aggctcatga atatggatga cactggaatt ttataaattc taaaataaaa   6480

cccgaaacca gatgtagcat gctgggactc attttgtcaa aaaa                    6524
```

```
<210> SEQ ID NO 6
<211> LENGTH: 6377
<212> TYPE: DNA
<213> ORGANISM: Homo sapiens

<400> SEQUENCE: 6

aggcgggatt gggccgccgc cctatatagc agccggggcc cgggcgccgc gcctcggagc     60

gtcccggctt ctcccgcgcg gggggcgagt aagccagcgg caggaccagc gggcgggggc    120

ccacgacaaa agctggcagg ctgacagagg cggcctcagg acggaccttc tggctactga    180

ccgttttgct gtggttttcc cggattgtgt gtaggtgtga gatcaaccat gagttccgtt    240

gcagttttga cccaagagag ttttgctgaa caccgaagtg ggctggttcc gcaacaaatc    300

aaagttgcca ctctaaattc agaagaggag agcgaccctc caacctacaa ggatgccttc    360

cctccacttc ctgagaaagc tgcttgcctg gaaagtgccc aggaacccgc tggagcctgg    420

gggaacaaga tccgacccat caaggcttct gtcatcactc aggtgttcca tgtacccctg    480

gaggagagaa aatacaagga tatgaaccag tttggagaag gtgaacaagc aaaaatctgc    540

cttgagatca tgcagagaac tggtgctcac ttggagctgt ctttggccaa agaccaaggc    600

ctctccatca tggtgtcagg aaagctggat gctgtcatga aagctcggaa ggacattgtt    660

gctagactgc agactcaggc ctcagcaact gttgccattc ccaaagaaca ccatcgcttt    720
```

-continued

```
gttattggca aaaatggaga gaaactgcaa gacttggagc taaaaactgc aaccaaaatc    780
cagatcccac gcccagatga ccccagcaat cagatcaaga tcactggcac caaagagggc    840
atcgagaaag ctcgccatga agtcttactc atctctgccg agcaggacaa acgtgctgtg    900
gagaggctag aagtagaaaa ggcattccac cccttcatcg ctgggccgta taatagactg    960
gttggcgaga tcatgcagga gacaggcacg cgcatcaaca tcccccccacc cagcgtgaac   1020
cggacagaga ttgtcttcac tggagagaag gaacagttgg ctcaggctgt ggctcgcatc   1080
aagaagattt atgaggagaa gaaaaagaag actacaacca ttgcagtgga agtgaagaaa   1140
tcccaacaca agtatgtcat tgggcccaag ggcaattcat tgcaggagat ccttgagaga   1200
actggagttt ccgttgagat cccaccctca gacagcatct ctgagactgt aatacttcga   1260
ggcgaacctg aaaagttagg tcaggcgttg actgaagtct atgccaaggc caatagcttc   1320
accgtctcct ctgtcgccgc cccttcctgg cttcaccgtt tcatcattgg caagaaaggg   1380
cagaacctgg ccaaaatcac tcagcagatg ccaaaggttc acatcgagtt cacagagggc   1440
gaagacaaga tcaccctgga gggccctaca gaggatgtca atgtggccca ggaacagata   1500
gaaggcatgg tcaaagattt gattaaccgg atggactatg tggagatcaa catcgaccac   1560
aagttccaca ggcacctcat tgggaagagc ggtgccaaca taaacagaat caaagaccag   1620
tacaaggtgt ccgtgcgcat ccctcctgac agtgagaaga gcaatttgat ccgcatcgag   1680
ggggacccac agggcgtgca gcaggccaag cgagagctgc tggagcttgc atctcgcatg   1740
gaaaatgagc gtaccaagga tctaatcatt gagcaaagat ttcatcgcac aatcattggg   1800
cagaagggtg aacggatccg tgaaattcgt gacaaattcc cagaggtcat cattaacttt   1860
ccagacccag cacaaaaaag tgacattgtc cagctcagag gacctaagaa tgaggtggaa   1920
aaatgcacaa aatacatgca gaagatggtg gcagatctgg tggaaaatag ctattcaatt   1980
tctgttccga tcttcaaaca gtttcacaag aatatcattg ggaaaggagg cgcaaacatt   2040
aaaaagattc gtgaagaaag caacaccaaa atcgaccttc cagcagagaa tagcaattca   2100
gagaccatta tcatcacagg caagcgagcc aactgcgaag ctgcccggag caggattctg   2160
tctattcaga aagacctggc caacatagcc gaggtagagg tctccatccc tgccaagctg   2220
cacaactccc tcattggcac caagggccgt ctgatccgct ccatcatgga ggagtgcggc   2280
ggggtccaca ttcactttcc cgtggaaggt tcaggaagcg acaccgttgt tatcaggggc   2340
ccttcctcgg atgtggagaa ggccaagaag cagctcctgc atctggcgga ggagaagcaa   2400
accaagagtt tcactgttga catccgcgcc aagccagaat accacaaatt cctcatcggc   2460
aagggggggcg gcaaaattcg caaggtgcgc gacagcactg gagcacgtgt catcttccct   2520
gcggctgagg acaaggacca ggacctgatc accatcattg gaaaggagga cgccgtccga   2580
gaggcacaga aggagctgga ggccttgatc caaaacctgg ataatgtggt ggaagactcc   2640
atgctggtgg accccaagca ccaccgccac ttcgtcatcc gcagaggcca ggtcttgcgg   2700
gagattgctg aagagtatgg cggggtgatg gtcagcttcc cacgctctgg cacacagagc   2760
gacaaagtca ccctcaaggg cgccaaggac tgtgtggagg cagccaagaa acgcattcag   2820
gagatcattg aggacctgga agctcaggtg acattagaat gtgctatacc ccagaaattc   2880
catcgatctg tcatgggccc caaaggttcc agaatccagc agattactcg ggatttcagt   2940
gttcaaatta aattcccaga cagagaggag aacgcagttc acagtacaga gccagttgtc   3000
caggagaatg gggacgaagc tggggagggg agagaggcta aagattgtga ccccggctct   3060
ccaaggaggt gtgacatcat catcatctct ggccggaaag aaaagtgtga ggctgccaag   3120
```

gaagctctgg aggcattggt tcctgtcacc attgaagtag aggtgccctt tgaccttcac 3180
cgttacgtta ttgggcagaa aggaagtggg atccgcaaga tgatggatga gtttgaggtg 3240
aacatacatg tcccggcacc tgagctgcag tctgacatca tcgccatcac gggcctcgct 3300
gcaaatttgg accgggccaa ggctggactg ctggagcgtg tgaaggagct acaggccgag 3360
caggaggacc gggctttaag gagttttaag ctgagtgtca ctgtagaccc caaataccat 3420
cccaagatta tcgggagaaa gggggcagta attacccaaa tccggttgga gcatgacgtg 3480
aacatccagt ttcctgataa ggacgatggg aaccagcccc aggaccaaat taccatcaca 3540
gggtacgaaa agaacacaga agctgccagg gatgctatac tgagaattgt gggtgaactt 3600
gagcagatgg tttctgagga cgtcccgctg gaccaccgcg ttcacgcccg catcattggt 3660
gcccgcggca aagccattcg caaaatcatg gacgaattca aggtggacat tcgcttccca 3720
cagagcggag ccccagaccc caactgcgtc actgtgacgg ggctcccaga gaatgtggag 3780
gaagccatcg accacatcct caatctggag gaggaatacc tagctgacgt ggtggacagt 3840
gaggcgctgc aggtatacat gaaaccccca gcacacgaag aggccaaggc accttccaga 3900
ggctttgtgg tgcgggacgc accctggacc gccagcagca gtgagaaggc tcctgacatg 3960
agcagctctg aggaatttcc cagctttggg gctcaggtgg ctcccaagac cctcccttgg 4020
ggccccaaac gataatgatc aaaaagaaca gaaccctctc cagcctgctg acccaaaccc 4080
aaccacacaa tggtttgtct caatctgacc cagcggctgg accctccgta aattgttgac 4140
gctcttcccc cttcccgagg tcccgcaggg agcctagcgc ctggctgtgt gtgcggccgc 4200
tcctccaggc ctggccgtgc ccgctcagga cctgctccac tgtttaacac taaaccaagg 4260
tcatgagcat tcgtgctaag ataacagact ccagctcctg gtccacccgg catgtcagtc 4320
agcactctgg ccttcatcac gagagctccg cagccgtggc taggattcca cttcctgtgt 4380
catgacctca ggaaataaac gtccttgact ttataaaagc caaacgtttg ccctcttcct 4440
ttcccacctc cctcctgcca gtttcccttg gtccagacag tcctgtttgt ggagtgcaat 4500
cagcctcctc cagctgccag agcgcctcag cacaggtgtc agggtgcaag gaagacctgg 4560
caatggacag caggaggcag gttcctggag ctggggggtg acctgagagg cagagggtga 4620
cgggttctca ggcagtcctg attttacctg ccgtggggtc tgaaagcacc aagggtccct 4680
gcccctacct ccactgccag accctcagcc tgaggtctgg tgagtggagc ctggaggcaa 4740
ggtggtaggc accatctggg tcccctgtgg ccgtcacagt gtctgctgtg attgagatgc 4800
gcacaggttg ggggaggtag ggccttacgc ttgtcctcag tgggggcagt ttgccttaga 4860
tgacagctgg gctcttcttc acaccacctg cagcccctcc ctgcccctgc cctagctgct 4920
gtgtgttcag ttgccttctt tctacctcag ccggcgtgga gtggtctctg tgcagttagt 4980
gccaccccac acacccgtct cttgattgag atgtttctgg tggttatggg tttcccgtgg 5040 agctggggggt gggcgccgtg tacctaagct ggaggctggc gctctccctc agcacaggtg 5100
ggtcagtggc cagcaggccc atctggagtg ggagtgggca cttccacccc gcccacaggc 5160
catccggctg tgcaggccag cccctaggag caggtcccgg gtgactggca gttttcacgg 5220
tctagggccg agacgatggc atggggccta gagcatgagg tagagcagaa tgcagaccac 5280
gccgctggat gccgagagac cctgctctcc gagggaggca tctgtgtcat gctgtgaggg 5340
ctgaggacgg ggccctagtc tctggttttc tggtcttaac atccttatct gtgtccgcca 5400
cggaggtgac tgagctgcta gcgagttgtc ctgtcccagg tacttgagtt ttggaaaagc 5460

-continued

```
tgactcacgc ccatccatct cacagccctt ccctggggac agtcgcttcc gccttgacac   5520
ctcactctca gttgaataac tcaagcttgg tcatcttcag actcgaattc ttgagtagac   5580
ccagacggct tagcccaagt ctagttgcag ctgcctcggc aagtccccat ttgctcaggc   5640
agccctgaat gggcctgttt acaggaatgg taaattggga ttggaaggaa tatagcttcc   5700
agcttcatag gctagggtga ccacggctta ggaaacaggg aaagaaagca aggccctttt   5760
cctgcctttc ccgggatctg tctactccac ctccacgggg gaggccagtg ggaagggct    5820
gtcacctctt ccccatctgc atgagttctg gaactctgtc ctgttggctg cttgcttcca   5880
gctcccccca atctccatcg cagcgggttc ctcctgtctt ttctacagtg tcataaaaca   5940
tcctgcccct accctctccc aaaggtcaat tttaattctc accaagtttt gcacatctct   6000
gtatgtcgct tgatgtctta gacgcgagcc ctttcctaaa ctgttcagcg ctctcttttc   6060
ctttgggtgg ttgttgcaag ggtgatgaca tgactgtccc caggcctgtc tccctgaagc   6120
gtctgtgctg tcaggacagc cctgggcaga gatgaggcag gggtgaggcg tgcgtgtgct   6180
tttcctcctt gttggatgtc ttccatatca tctgtttcca tagctacaat ccatcccttg   6240
gccttaactt tggaatttgg agattatatg caaacatgtg taaaggctca tgaatatgga   6300
tgacactgga attttataaa ttctaaaata aaacccgaaa ccagatgtag catgctggga   6360
ctcattttgt caaaaaa                                                  6377
```

<210> SEQ ID NO 7
<211> LENGTH: 6301
<212> TYPE: DNA
<213> ORGANISM: Homo sapiens

<400> SEQUENCE: 7

```
aggcgggatt gggccgccgc cctatatagc agccggggcc cgggcgccgc gcctcggagc     60
gtcccggctt ctcccgcgcg gggggcgagt aagccagcgg caggaccagc gggcgggggc    120
ccacgacaaa agctggcagg ctgacagagg cggcctcagg acggaccttc tggctactga    180
ccgttttgct gctaccactt ataaccacct ggttaagtcg agatttggag gtggtttagt    240
ttggggcctg gatgcacctt gcagagagag accgctggct ttttgtagca actgtcatga    300
tgcattttgt aagcattaag agtggttttc ccggattgtg tgtaggtgtg agatcaacca    360
tgagttccgt tgcagttttg acccaagaga gttttgctga acaccgaagt gggctggttc    420
cgcaacaaat caaagttgcc actctaaatt cagaagagga gagcgaccct ccaacctaca    480
aggatgcctt ccctccactt cctgagaaag ctgcttgcct ggaaagtgcc caggaacccg    540
ctggagcctg gggaacaag  atccgaccca tcaaggcttc tgtcatcact caggtgttcc    600
atgtacccct ggaggagaga aaatacaagg atatgaacca gtttggagaa ggtgaacaag    660
caaaaatctg ccttgagatc atgcagagaa ctggtgctca cttggagctg tctttggcca    720
aagaccaagg cctctccatc atggtgtcag gaaagctgga tgctgtcatg aaagctcgga    780
aggacattgt tgctagactg cagactcagg cctcagcaac tgttgccatt cccaaagaac    840
accatcgctt tgttattggc aaaaatggag agaaactgca agacttggag ctaaaaactg    900
caaccaaaat ccagatccca cgcccagatg accccagcaa tcagatcaag atcactggca    960
ccaaagaggg catcgagaaa gctcgccatg aagtcttact catctctgcc gagcaggaca   1020
aacgtgctgt ggagaggcta gaagtagaaa aggcattcca ccccttcatc gctgggccgt   1080
ataatagact ggttggcgag atcatgcagg agacaggcac gcgcatcaac atccccccac   1140
ccagcgtgaa ccggacagag attgtcttca ctggagagaa ggaacagttg gctcaggctg   1200
```

-continued

```
tggctcgcat caagaagatt tatgaggaga aggccaatag cttcaccgtc tcctctgtcg   1260
ccgccccttc ctggcttcac cgtttcatca ttggcaagaa agggcagaac ctggccaaaa   1320
tcactcagca gatgccaaag gttcacatcg agttcacaga gggcgaagac aagatcaccc   1380
tggagggccc tacagaggat gtcaatgtgg cccaggaaca gatagaaggc atggtcaaag   1440
atttgattaa ccggatggac tatgtggaga tcaacatcga ccacaagttc cacaggcacc   1500
tcattgggaa gagcggtgcc aacataaaca gaatcaaaga ccagtacaag gtgtccgtgc   1560
gcatccctcc tgacagtgag aagagcaatt tgatccgcat cgagggggac ccacagggcg   1620
tgcagcaggc caagcgagag ctgctggagc ttgcatctcg catggaaaat gagcgtacca   1680
aggatctaat cattgagcaa agatttcatc gcacaatcat tgggcagaag ggtgaacgga   1740
tccgtgaaat tcgtgacaaa ttcccagagg tcatcattaa ctttccagac ccagcacaaa   1800
aaagtgacat tgtccagctc agaggaccta agaatgaggt ggaaaaatgc acaaaataca   1860
tgcagaagat ggtggcagat ctggtggaaa atagctattc aatttctgtt ccgatcttca   1920
aacagtttca caagaatatc attgggaaag gaggcgcaaa cattaaaaag attcgtgaag   1980
aaagcaacac caaaatcgac cttccagcag agaatagcaa ttcagagacc attatcatca   2040
caggcaagcg agccaactgc gaagctgccc ggagcaggat tctgtctatt cagaaagacc   2100
tggccaacat agccgaggta gaggtctcca tccctgccaa gctgcacaac tccctcattg   2160
gcaccaaggg ccgtctgatc cgctccatca tggaggagtg cggcggggtc cacattcact   2220
ttcccgtgga aggttcagga agcgacaccg ttgttatcag ggcccttcc tcggatgtgg   2280
agaaggccaa gaagcagctc ctgcatctgg cggaggagaa gcaaaccaag agtttcactg   2340
ttgacatccg cgccaagcca gaataccaca aattcctcat cggcaagggg ggcggcaaaa   2400
ttcgcaaggt gcgcgacagc actggagcac gtgtcatctt ccctgcggct gaggacaagg   2460
accaggacct gatcaccatc attggaaagg aggacgccgt ccgagaggca cagaaggagc   2520
tggaggcctt gatccaaaac ctggataatg tggtggaaga ctccatgctg gtggacccca   2580
agcaccaccg ccacttcgtc atccgcagag gccaggtctt gcgggagatt gctgaagagt   2640
atggcggggt gatggtcagc ttcccacgct ctggcacaca gagcgacaaa gtcaccctca   2700
agggcgccaa ggactgtgtg gaggcagcca agaaacgcat tcaggagatc attgaggacc   2760
tggaagctca ggtgacatta gaatgtgcta taccccagaa attccatcga tctgtcatgg   2820
gccccaaagg ttccagaatc cagcagatta ctcgggattt cagtgttcaa attaaattcc   2880
cagacagaga ggagaacgca gttcacagta cagagccagt tgtccaggag aatggggacg   2940
aagctgggga ggggagagag gctaaagatt gtgaccccgg ctctccaagg aggtgtgaca   3000
tcatcatcat ctctggccgg aaagaaaagt gtgaggctgc caaggaagct ctggaggcat   3060
tggttcctgt caccattgaa gtagaggtgc cctttgacct tcaccgttac gttattgggc   3120
agaaaggaag tgggatccgc aagatgatgg atgagtttga ggtgaacata catgtcccgg   3180
cacctgagct gcagtctgac atcatcgcca tcacgggcct cgctgcaaat ttggaccggg   3240
ccaaggctgg actgctggag cgtgtgaagg agctacaggc cgagcaggag gaccgggctt   3300
taaggagttt taagctgagt gtcactgtag accccaaata ccatcccaag attatcggga   3360
gaaagggggc agtaattacc caaatccggt tggagcatga cgtgaacatc cagtttcctg   3420
ataaggacga tgggaaccag ccccaggacc aaattaccat cacagggtac gaaaagaaca   3480
cagaagctgc cagggatgct atactgagaa ttgtgggtga acttgagcag atggtttctg   3540
```

-continued

```
aggacgtccc gctggaccac cgcgttcacg cccgcatcat tggtgcccgc ggcaaagcca   3600
ttcgcaaaat catggacgaa ttcaaggtgg acattcgctt cccacagagc ggagccccag   3660
accccaactg cgtcactgtg acggggctcc cagagaatgt ggaggaagcc atcgaccaca   3720
tcctcaatct ggaggaggaa tacctagctg acgtggtgga cagtgaggcg ctgcaggtat   3780
acatgaaacc cccagcacac gaagaggcca aggcaccttc cagaggcttt gtggtgcggg   3840
acgcaccctg gaccgccagc agcagtgaga aggctcctga catgagcagc tctgaggaat   3900
ttcccagctt tggggctcag gtggctccca agaccctccc ttggggcccc aaacgataat   3960
gatcaaaaag aacagaaccc tctccagcct gctgacccaa acccaaccac acaatggttt   4020
gtctcaatct gacccagcgg ctggaccctc cgtaaattgt tgacgctctt ccccccttccc  4080
gaggtcccgc agggagccta gcgcctggct gtgtgtgcgg ccgctcctcc aggcctggcc   4140
gtgcccgctc aggacctgct ccactgttta acactaaacc aaggtcatga gcattcgtgc   4200
taagataaca gactccagct cctggtccac ccggcatgtc agtcagcact ctggccttca   4260
tcacgagagc tccgcagccg tggctaggat tccacttcct gtgtcatgac ctcaggaaat   4320
aaacgtcctt gactttataa aagccaaacg tttgccctct tcctttccca cctccctcct   4380
gccagtttcc cttggtccag acagtcctgt ttgtggagtg caatcagcct cctccagctg   4440
ccagagcgcc tcagcacagg tgtcagggtg caaggaagac ctggcaatgg acagcaggag   4500
gcaggttcct ggagctgggg ggtgacctga gaggcagagg gtgacgggtt ctcaggcagt   4560
cctgatttta cctgccgtgg ggtctgaaag caccaagggt ccctgcccct acctccactg   4620
ccagaccctc agcctgaggt ctggtgagtg gagcctggag gcaaggtggt aggcaccatc   4680
tgggtcccct gtggccgtca cagtgtctgc tgtgattgag atgcgcacag gttgggggag   4740
gtagggcctt acgcttgtcc tcagtggggg cagtttgcct tagatgacag ctgggctctt   4800
cttcacacca cctgcagccc ctccctgccc ctgccctagc tgctgtgtgt tcagttgcct   4860
tctttctacc tcagccggcg tggagtggtc tctgtgcagt tagtgccacc ccacacaccc   4920
gtctcttgat tgagatgttt ctggtggtta tgggtttccc gtggagctgg gggtgggcgc   4980
cgtgtaccta agctggaggc tggcgctctc cctcagcaca ggtgggtcag tggccagcag   5040
gcccatctgg agtgggagtg ggcacttcca ccccgcccac aggccatccg gctgtgcagg   5100
ccagccccta ggagcaggtc ccgggtgact ggcagttttc acggtctagg gccgagacga   5160
tggcatgggg cctagagcat gaggtagagc agaatgcaga ccacgccgct ggatgccgag   5220
agaccctgct ctccgaggga ggcatctgtg tcatgctgtg agggctgagg acggggccct   5280
agtctctggt tttctggtct taacatcctt atctgtgtcc gccacggagg tgactgagct   5340
gctagcgagt tgtcctgtcc caggtacttg agttttggaa aagctgactc acgcccatcc   5400
atctcacagc ccttccctgg ggacagtcgc ttccgccttg acacctcact ctcagttgaa   5460
taactcaagc ttggtcatct tcagactcga attcttgagt agacccagac ggcttagccc   5520
aagtctagtt gcagctgcct cggcaagtcc ccatttgctc aggcagccct gaatggccct   5580
gtttacagga atggtaaatt gggattggaa ggaatatagc ttccagcttc ataggctagg   5640
gtgaccacgg cttaggaaac agggaaagaa agcaaggccc ttttcctgcc tttcccggga   5700
tctgtctact ccacctccac gggggaggcc agtggggaag ggctgtcacc tcttccccat   5760
ctgcatgagt tctggaactc tgtcctgttg gctgcttgct tccagctccc cccaatctcc   5820
atcgcagcgg gttcctcctg tcttttctac agtgtcataa aacatcctgc ccctaccctc   5880
tcccaaaggt caattttaat tctcaccaag ttttgcacat ctctgtatgt cgcttgatgt   5940
```

cttagacgcg agccctttcc taaactgttc agcgctctct tttcctttgg gtggttgttg 6000
caagggtgat gacatgactg tccccaggcc tgtctccctg aagcgtctgt gctgtcagga 6060
cagccctggg cagagatgag gcaggggtga ggcgtgcgtg tgcttttcct ccttgttgga 6120
tgtcttccat atcatctgtt tccatagcta caatccatcc cttggcctta actttggaat 6180
ttggagatta tatgcaaaca tgtgtaaagg ctcatgaata tggatgacac tggaatttta 6240
taaattctaa aataaaaccc gaaaccagat gtagcatgct gggactcatt ttgtcaaaaa 6300
a 6301

<210> SEQ ID NO 8

<400> SEQUENCE: 8

000

<210> SEQ ID NO 9
<211> LENGTH: 16
<212> TYPE: PRT
<213> ORGANISM: Unknown
<220> FEATURE:
<221> NAME/KEY: source
<223> OTHER INFORMATION: /note="Description of Unknown: RFGF peptide"

<400> SEQUENCE: 9

Ala Ala Val Ala Leu Leu Pro Ala Val Leu Leu Ala Leu Leu Ala Pro
1 5 10 15

<210> SEQ ID NO 10
<211> LENGTH: 11
<212> TYPE: PRT
<213> ORGANISM: Unknown
<220> FEATURE:
<221> NAME/KEY: source
<223> OTHER INFORMATION: /note="Description of Unknown: RFGF analogue peptide"

<400> SEQUENCE: 10

Ala Ala Leu Leu Pro Val Leu Leu Ala Ala Pro
1 5 10

<210> SEQ ID NO 11
<211> LENGTH: 6524
<212> TYPE: DNA
<213> ORGANISM: Homo sapiens

<400> SEQUENCE: 11 tttttgaca aaatgagtcc cagcatgcta catctggttt cgggttttat tttagaattt 60
ataaaattcc agtgtcatcc atattcatga gcctttacac atgtttgcat ataatctcca 120
aattccaaag ttaaggccaa gggatggatt gtagctatgg aaacagatga tatggaagac 180
atccaacaag gaggaaaagc acacgcacgc ctcacccctg cctcatctct gcccagggct 240
gtcctgacag cacagacgct tcagggagac aggcctgggg acagtcatgt catcaccctt 300
gcaacaacca cccaaaggaa aagagagcgc tgaacagttt aggaaagggc tcgcgtctaa 360
gacatcaagc gacatacaga gatgtgcaaa acttggtgag aattaaaatt gacctttggg 420
agagggtagg ggcaggatgt tttatgacac tgtagaaaag acaggaggaa cccgctgcga 480
tggagattgg ggggagctgg aagcaagcag ccaacaggac agagttccag aactcatgca 540
gatggggaag aggtgacagc ccttccccac tggcctcccc cgtggaggtg gagtagacag 600

```
atcccgggaa aggcaggaaa agggccttgc tttctttccc tgtttcctaa gccgtggtca    660
ccctagccta tgaagctgga agctatattc cttccaatcc caatttacca ttcctgtaaa    720
caggcccatt cagggctgcc tgagcaaatg ggacttgcc gaggcagctg caactagact    780
tgggctaagc cgtctgggtc tactcaagaa ttcgagtctg aagatgacca agcttgagtt    840
attcaactga gagtgaggtg tcaaggcgga agcgactgtc cccagggaag ggctgtgaga    900
tggatgggcg tgagtcagct tttccaaaac tcaagtacct gggacaggac aactcgctag    960
cagctcagtc acctccgtgg cggacacaga taaggatgtt aagaccagaa aaccagagac   1020
tagggccccg tcctcagccc tcacagcatg acacagatgc ctccctcgga gagcagggtc   1080
tctcggcatc cagcggcgtg gtctgcattc tgctctacct catgctctag gccccatgcc   1140
atcgtctcgg ccctagaccg tgaaaactgc cagtcacccg ggacctgctc ctaggggctg   1200
gcctgcacag ccggatggcc tgtgggcggg gtggaagtgc ccactcccac tccagatggg   1260
cctgctggcc actgacccac ctgtgctgag ggagagcgcc agcctccagc ttaggtacac   1320
ggcgcccacc cccagctcca cgggaaaccc ataaccacca gaaacatctc aatcaagaga   1380
cgggtgtgtg gggtggcact aactgcacag agaccactcc acgccggctg aggtagaaag   1440
aaggcaactg aacacacagc agctagggca ggggcaggga ggggctgcag gtggtgtgaa   1500
gaagagccca gctgtcatct aaggcaaact gcccccactg aggacaagcg taaggcccta   1560
cctcccccaa cctgtgcgca tctcaatcac agcagacact gtgacggcca caggggaccc   1620
agatggtgcc taccaccttg cctccaggct ccactcacca gacctcaggc tgagggtctg   1680
gcagtggagg taggggcagg gacccttggt gctttcagac cccacggcag gtaaaatcag   1740
gactgcctga gaacccgtca ccctctgcct ctcaggtcac cccccagctc caggaacctg   1800
cctcctgctg tccattgcca ggtcttcctt gcaccctgac acctgtgctg aggcgctctg   1860
gcagctggag gaggctgatt gcactccaca aacaggactg tctggaccaa gggaaactgg   1920
caggagggag gtgggaaagg aagagggcaa acgtttggct tttataaagt caaggacgtt   1980
tatttcctga ggtcatgaca caggaagtgg aatcctagcc acggctgcgg agctctcgtg   2040
atgaaggcca gagtgctgac tgacatgccg ggtggaccag gagctggagt ctgttatctt   2100
agcacgaatg ctcatgacct tggtttagtg ttaaacagtg gagcaggtcc tgagcgggca   2160
cggccaggcc tggaggagcg gccgcacaca cagccaggcg ctaggctccc tgcgggacct   2220
cgggaagggg gaagagcgtc aacaatttac ggagggtcca gccgctgggt cagattgaga   2280
caaaccattg tgtggttggg tttgggtcag caggctggag agggttctgt tctttttgat   2340
cattatcgtt tggggcccca agggagggtc ttgggagcca cctgagcccc aaagctggga   2400
aattcctcag agctgctcat gtcaggagcc ttctcactgc tgctggcggt ccagggtgcg   2460
tcccgcacca caaagcctct ggaaggtgcc ttggcctctt cgtgtgctgg gggtttcatg   2520
tatacctgca gcgcctcact gtccaccacg tcagctaggt attcctcctc cagattgagg   2580
atgtggtcga tggcttcctc cacattctct gggagccccg tcacagtgac gcagttgggg   2640
tctggggctc cgctctgtgg gaagcgaatg tccaccttga attcgtccat gattttgcga   2700
atggctttgc cgcgggcacc aatgatgcgg gcgtgaacgc ggtggtccag cgggacgtcc   2760
tcagaaacca tctgctcaag ttcacccaca attctcagta tagcatccct ggcagcttct   2820
gtgttctttt cgtaccctgt gatggtaatt tggtcctggg gctggttccc atcgtcctta   2880
tcaggaaact ggatgttcac gtcatgctcc aaccggattt gggtaattac tgccccctttt   2940
```

-continued

```
ctcccgataa tcttgggatg gtatttgggg tctacagtga cactcagctt aaaactcctt   3000
aaagcccggt cctcctgctc ggcctgtagc tccttcacac gctccagcag tccagccttg   3060
gcccggtcca aatttgcagc gaggcccgtg atggcgatga tgtcagactg cagctcaggt   3120
gccgggacat gtatgttcac ctcaaactca tccatcatct tgcggatccc acttcctttc   3180
tgcccaataa cgtaacggtg aaggtcaaag ggcacctcta cttcaatggt gacaggaacc   3240
aatgcctcca gagcttcctt ggcagcctca cacttttctt tccggccaga gatgatgatg   3300
atgtcacacc tccttggaga gccggggtca caatctttag cctctctccc ctccccagct   3360
tcgtccccat tctcctggac aactggctct gtactgtgaa ctgcgttctc ctctctgtct   3420
gggaatttaa tttgaacact gaaatcccga gtaatctgct ggattctgga acctttgggg   3480
cccatgacag atcgatggaa tttctggggt atagcacatt ctaatgtcac ctgagcttcc   3540
aggtcctcaa tgatctcctg aatgcgtttc ttggctgcct ccacacagtc cttggcgccc   3600
ttgagggtga ctttgtcgct ctgtgtgcca gagcgtggga agctgaccat caccccgcca   3660
tactcttcag caatctcccg caagacctgg cctctgcgga tgacgaagtg gcggtggtgc   3720
ttggggtcca ccagcatgga gtcttccacc acattatcca ggttttggat caaggcctcc   3780
agctccttct gtgcctctcg gacggcgtcc tcctttccaa tgatggtgat caggtcctgg   3840
tccttgtcct cagccgcagg gaagatgaca cgtgctccag tgctgtcgcg caccttgcga   3900
attttgccgc ccccccttgcc gatgaggaat ttgtggtatt ctggcttggc gcggatgtca   3960
acagtgaaac tcttggtttg cttctcctcc gccagatgca ggagctgctt cttggccttc   4020
tccacatccg aggaagggcc cctgataaca acggtgtcgc ttcctgaacc ttccacggga   4080
aagtgaatgt ggaccccgcc gcactcctcc atgatggagc ggatcagacg gcccttggtg   4140
ccaatgaggg agttgtgcag cttggcaggg atggagacct ctacctcggc tatgttggcc   4200
aggtctttct gaatagacag aatcctgctc cgggcagctt cgcagttggc tcgcttgcct   4260
gtgatgataa tggtctctga attgctattc tctgctggaa ggtcgatttt ggtgttgctt   4320
tcttcacgaa tctttttaat gtttgcgcct cctttcccaa tgatattctt gtgaaactgt   4380
ttgaagatcg gaacagaaat tgaatagcta ttttccacca gatctgccac catcttctgc   4440
atgtattttg tgcatttttc cacctcattc ttaggtcctc tgagctggac aatgtcactt   4500
ttttgtgctg ggtctggaaa gttaatgatg acctctggga atttgtcacg aatttcacgg   4560
atccgttcac ccttctgccc aatgattgtg cgatgaaatc tttgctcaat gattagatcc   4620
ttggtacgct cattttccat gcgagatgca agctccagca gctctcgctt ggcctgctgc   4680
acgccctgtg ggtcccccctc gatgcggatc aaattgctct tctcactgtc aggagggatg   4740
cgcacggaca ccttgtactg gtctttgatt ctgtttatgt tggcaccgct cttcccaatg   4800
aggtgcctgt ggaacttgtg gtcgatgttg atctccacat agtccatccg gttaatcaaa   4860
tctttgacca tgccttctat ctgttcctgg gccacattga catcctctgt agggccctcc   4920
agggtgatct tgtcttcgcc ctctgtgaac tcgatgtgaa cctttggcat ctgctgagtg   4980
attttggcca ggttctgccc tttcttgcca atgatgaaac ggtgaagcca ggaaggggcg   5040
gcgacagagg agacggtgaa gctattggcc ttggcataga cttcagtcaa cgcctgacct   5100
aacttttcag gttcgcctcg aagtattaca gtctcagaga tgctgtctga gggtgggatc   5160
tcaacggaaa ctccagttct ctcaaggatc tcctgcaatg aattgccctt gggcccaatg   5220
acatacttgt gttgggattt cttcacttcc actgcaatgg ttgtagtctt ctttttcttc   5280
tcctcataaa tcttcttgat gcgagccaca gcctgagcca actgttcctt ctctccagtg   5340
```

-continued

```
aagacaatct ctgtccggtt cacgctgggt ggggggatgt tgatgcgcgt gcctgtctcc   5400

tgcatgatct cgccaaccag tctattatac ggcccagcga tgaaggggtg gaatgccttt   5460

tctacttcta gcctctccac agcacgtttg tcctgctcgg cagagatgag taagacttca   5520

tggcgagctt tctcgatgcc ctctttggtg ccagtgatct tgatctgatt gctggggtca   5580

tctgggcgtg ggatctggat tttggttgca gtttttagct ccaagtcttg cagtttctct   5640

ccatttttgc caataacaaa gcgatggtgt tctttgggaa tggcaacagt tgctgaggcc   5700

tgagtctgca gtctagcaac aatgtccttc cgagctttca tgacagcatc cagctttcct   5760

gacaccatga tggagaggcc ttggtctttg gccaaagaca gctccaagtg agcaccagtt   5820

ctctgcatga tctcaaggca gatttttgct tgttcacctt ctccaaactg gttcatatcc   5880

ttgtattttc tctcctccag gggtacatgg aacacctgag tgatgacaga agccttgatg   5940

ggtcggatct tgttccccca ggctccagcg ggttcctggg cactttccag gcaagcagct   6000

ttctcaggaa gtggagggaa ggcatccttg taggttggag ggtcgctctc ctcttctgaa   6060

tttagagtgg caactttgat ttgttgcgga accagcccac ttcggtgttc agcaaaactc   6120

tcttgggtca aaactgcaac ggaactcatg gttgatctca cacctacaca caatccggga   6180

aaaccacagc aaaacggtca gtagccagaa ggtccgtcct gaggccgcct ctgtcagcct   6240

gccagctttt gctgttccac tcttataagc ataagaaaac cgagctcata aggtaggaac   6300

tgtggcgaaa cagggacaag ccgccatctt ggtaaaggag aagaggctac gcttgacctc   6360

cccccccacc cccagcctct atatggccaa ctgccgtggg aggagcacgg cgcttgcgca   6420

gaggcggaca acgcggacga ctctgggctt gcgcactcgg aagccggccg catgggggag   6480

gggaagaagg ccaggtcgca ctgagccagg aagcagttgg caaa                    6524
```

<210> SEQ ID NO 12
<211> LENGTH: 6377
<212> TYPE: DNA
<213> ORGANISM: Homo sapiens

<400> SEQUENCE: 12

```
tttttgaca aaatgagtcc cagcatgcta catctggttt cgggttttat tttagaattt     60

ataaaattcc agtgtcatcc atattcatga gcctttacac atgtttgcat ataatctcca    120

aattccaaag ttaaggccaa gggatggatt gtagctatgg aaacagatga tatggaagac    180

atccaacaag gaggaaaagc acacgcacgc ctcacccctg cctcatctct gcccagggct    240

gtcctgacag cacagacgct tcagggagac aggcctgggg acagtcatgt catcaccctt    300

gcaacaacca cccaaaggaa aagagagcgc tgaacagttt aggaaagggc tcgcgtctaa    360

gacatcaagc gacatacaga gatgtgcaaa acttggtgag aattaaaatt gacctttggg    420

agagggtagg ggcaggatgt tttatgacac tgtagaaaag acaggaggaa cccgctgcga    480

tggagattgg ggggagctgg aagcaagcag ccaacaggac agagttccag aactcatgca    540

gatggggaag aggtgacagc ccttccccac tggcctcccc cgtggaggtg gagtagacag    600

atcccgggaa aggcaggaaa agggccttgc tttctttccc tgtttcctaa gccgtggtca    660

ccctagccta tgaagctgga agctatattc cttccaatcc caatttacca ttcctgtaaa    720

caggcccatt cagggctgcc tgagcaaatg gggacttgcc gaggcagctg caactagact    780

tgggctaagc cgtctgggtc tactcaagaa ttcgagtctg aagatgacca agcttgagtt    840

attcaactga gagtgaggtg tcaaggcgga agcgactgtc cccagggaag ggctgtgaga    900
```

-continued

```
tggatgggcg tgagtcagct tttccaaaac tcaagtacct gggacaggac aactcgctag    960
cagctcagtc acctccgtgg cggacacaga taaggatgtt aagaccagaa aaccagagac   1020
tagggccccg tcctcagccc tcacagcatg acacagatgc ctccctcgga gagcagggtc   1080
tctcggcatc cagcggcgtg gtctgcattc tgctctacct catgctctag gccccatgcc   1140
atcgtctcgg ccctagaccg tgaaaactgc cagtcacccg ggacctgctc ctaggggctg   1200
gcctgcacag ccggatggcc tgtgggcggg gtggaagtgc ccactcccac tccagatggg   1260
cctgctggcc actgacccac ctgtgctgag ggagagcgcc agcctccagc ttaggtacac   1320
ggcgcccacc cccagctcca cgggaaaccc ataaccacca gaaacatctc aatcaagaga   1380
cgggtgtgtg gggtggcact aactgcacag agaccactcc acgccggctg aggtagaaag   1440
aaggcaactg aacacacagc agctagggca ggggcaggga ggggctgcag gtggtgtgaa   1500
gaagagccca gctgtcatct aaggcaaact gcccccactg aggacaagcg taaggcccta   1560
cctcccccaa cctgtgcgca tctcaatcac agcagacact gtgacggcca caggggaccc   1620
agatggtgcc taccaccttg cctccaggct ccactcacca gacctcaggc tgagggtctg   1680
gcagtggagg taggggcagg gacccttggt gctttcagac cccacggcag gtaaaatcag   1740
gactgcctga gaacccgtca ccctctgcct ctcaggtcac cccccagctc caggaacctg   1800
cctcctgctg tccattgcca ggtcttcctt gcaccctgac acctgtgctg aggcgctctg   1860
gcagctggag gaggctgatt gcactccaca aacaggactg tctggaccaa gggaaactgg   1920
caggagggag gtgggaaagg aagagggcaa acgtttggct tttataaagt caaggacgtt   1980
tatttcctga ggtcatgaca caggaagtgg aatcctagcc acggctgcgg agctctcgtg   2040
atgaaggcca gagtgctgac tgacatgccg ggtggaccag gagctggagt ctgttatctt   2100
agcacgaatg ctcatgacct tggtttagtg ttaaacagtg gagcaggtcc tgagcgggca   2160
cggccaggcc tggaggagcg gccgcacaca cagccaggcg ctaggctccc tgcgggacct   2220
cgggaagggg gaagagcgtc aacaatttac ggagggtcca gccgctgggt cagattgaga   2280
caaaccattg tgtggttggg tttgggtcag caggctggag agggttctgt tctttttgat   2340
cattatcgtt tggggcccca agggagggtc ttgggagcca cctgagcccc aaagctggga   2400
aattcctcag agctgctcat gtcaggagcc ttctcactgc tgctggcggt ccagggtgcg   2460
tcccgcacca caaagcctct ggaaggtgcc ttggcctctt cgtgtgctgg gggtttcatg   2520
tatacctgca gcgcctcact gtccaccacg tcagctaggt attcctcctc cagattgagg   2580
atgtggtcga tggcttcctc cacattctct gggagccccg tcacagtgac gcagttgggg   2640
tctggggctc cgctctgtgg gaagcgaatg tccaccttga attcgtccat gattttgcga   2700
atggctttgc cgcgggcacc aatgatgcgg gcgtgaacgc ggtggtccag cgggacgtcc   2760
tcagaaacca tctgctcaag ttcacccaca attctcagta tagcatccct ggcagcttct   2820
gtgttctttt cgtaccctgt gatggtaatt tggtcctggg gctggttccc atcgtcctta   2880
tcaggaaact ggatgttcac gtcatgctcc aaccggattt gggtaattac tgcccccttt   2940
ctcccgataa tcttgggatg gtatttgggg tctacagtga cactcagctt aaaactcctt   3000
aaagcccggt cctcctgctc ggcctgtagc tccttcacac gctccagcag tccagccttg   3060
gcccggtcca aatttgcagc gaggcccgtg atggcgatga tgtcagactg cagctcaggt   3120
gccgggacat gtatgttcac ctcaaactca tccatcatct tgcggatccc acttcctttc   3180
tgcccaataa cgtaacggtg aaggtcaaag ggcacctcta cttcaatggt gacaggaacc   3240
aatgcctcca gagcttcctt ggcagcctca cacttttctt tccggccaga gatgatgatg   3300
```

atgtcacacc tccttggaga gccggggtca caatctttag cctctctccc ctccccagct 3360
tcgtccccat tctcctggac aactggctct gtactgtgaa ctgcgttctc ctctctgtct 3420
gggaatttaa tttgaacact gaaatcccga gtaatctgct ggattctgga acctttgggg 3480
cccatgacag atcgatggaa tttctggggt atagcacatt ctaatgtcac ctgagcttcc 3540
aggtcctcaa tgatctcctg aatgcgtttc ttggctgcct ccacacagtc cttggcgccc 3600
ttgagggtga ctttgtcgct ctgtgtgcca gagcgtggga agctgaccat caccccgcca 3660
tactcttcag caatctcccg caagacctgg cctctgcgga tgacgaagtg gcggtggtgc 3720
ttggggtcca ccagcatgga gtcttccacc acattatcca ggttttggat caaggcctcc 3780
agctccttct gtgcctctcg gacggcgtcc tcctttccaa tgatggtgat caggtcctgg 3840
tccttgtcct cagccgcagg gaagatgaca cgtgctccag tgctgtcgcg caccttgcga 3900
attttgccgc ccccctttgcc gatgaggaat ttgtggtatt ctggcttggc gcggatgtca 3960
acagtgaaac tcttggtttg cttctcctcc gccagatgca ggagctgctt cttggccttc 4020
tccacatccg aggaagggcc cctgataaca acggtgtcgc ttcctgaacc ttccacggga 4080
aagtgaatgt ggaccccgcc gcactcctcc atgatggagc ggatcagacg gcccttggtg 4140
ccaatgaggg agttgtgcag cttggcaggg atggagacct ctacctcggc tatgttggcc 4200
aggtctttct gaatagacag aatcctgctc cgggcagctt cgcagttggc tcgcttgcct 4260
gtgatgataa tggtctctga attgctattc tctgctggaa ggtcgatttt ggtgttgctt 4320
tcttcacgaa tctttttaat gtttgcgcct cctttcccaa tgatattctt gtgaaactgt 4380
ttgaagatcg gaacagaaat tgaatagcta ttttccacca gatctgccac catcttctgc 4440
atgtattttg tgcatttttc cacctcattc ttaggtcctc tgagctggac aatgtcactt 4500
ttttgtgctg ggtctggaaa gttaatgatg acctctggga atttgtcacg aatttcacgg 4560
atccgttcac ccttctgccc aatgattgtg cgatgaaatc tttgctcaat gattagatcc 4620
ttggtacgct cattttccat gcgagatgca agctccagca gctctcgctt ggcctgctgc 4680
acgccctgtg ggtccccctc gatgcggatc aaattgctct tctcactgtc aggagggatg 4740
cgcacggaca ccttgtactg gtctttgatt ctgtttatgt tggcaccgct cttcccaatg 4800
aggtgcctgt ggaacttgtg gtcgatgttg atctccacat agtccatccg gttaatcaaa 4860
tctttgacca tgccttctat ctgttcctgg gccacattga catcctctgt agggccctcc 4920
agggtgatct tgtcttcgcc ctctgtgaac tcgatgtgaa cctttggcat ctgctgagtg 4980
attttggcca ggttctgccc tttcttgcca atgatgaaac ggtgaagcca ggaaggggcg 5040
gcgacagagg agacggtgaa gctattggcc ttggcataga cttcagtcaa cgcctgacct 5100
aacttttcag gttcgcctcg aagtattaca gtctcagaga tgctgtctga gggtgggatc 5160
tcaacggaaa ctccagttct ctcaaggatc tcctgcaatg aattgccctt gggcccaatg 5220
acatacttgt gttgggattt cttcacttcc actgcaatgg ttgtagtctt ctttttcttc 5280
tcctcataaa tcttcttgat gcgagccaca gcctgagcca actgttcctt ctctccagtg 5340
aagacaatct ctgtccggtt cacgctgggt ggggggatgt tgatgcgcgt gcctgtctcc 5400
tgcatgatct cgccaaccag tctattatac ggcccagcga tgaaggggtg gaatgccttt 5460
tctacttcta gcctctccac agcacgtttg tcctgctcgg cagagatgag taagacttca 5520
tggcgagctt tctcgatgcc ctctttggtg ccagtgatct tgatctgatt gctggggtca 5580
tctgggcgtg ggatctggat tttggttgca gtttttagct ccaagtcttg cagtttctct 5640
ccatttttgc caataacaaa gcgatggtgt tctttgggaa tggcaacagt tgctgaggcc 5700
tgagtctgca gtctagcaac aatgtccttc cgagctttca tgacagcatc cagctttcct 5760
gacaccatga tggagaggcc ttggtctttg gccaaagaca gctccaagtg agcaccagtt 5820
ctctgcatga tctcaaggca gatttttgct tgttcacctt ctccaaactg gttcatatcc 5880
ttgtattttc tctcctccag gggtacatgg aacacctgag tgatgacaga agccttgatg 5940
ggtcggatct tgttcccccca ggctccagcg ggttcctggg cactttccag gcaagcagct 6000
ttctcaggaa gtggagggaa ggcatccttg taggttggag ggtcgctctc ctcttctgaa 6060
tttagagtgg caactttgat ttgttgcgga accagcccac ttcggtgttc agcaaaactc 6120
tcttgggtca aaactgcaac ggaactcatg gttgatctca cacctacaca caatccggga 6180
aaaccacagc aaaacggtca gtagccagaa ggtccgtcct gaggccgcct ctgtcagcct 6240
gccagctttt gtcgtgggcc cccgcccgct ggtcctgccg ctggcttact cgcccccccgc 6300 gcgggagaag ccgggacgct ccgaggcgcg gcgcccgggc cccggctgct atatagggcg 6360
gcggcccaat cccgcct 6377

<210> SEQ ID NO 13
<211> LENGTH: 6301
<212> TYPE: DNA
<213> ORGANISM: Homo sapiens

<400> SEQUENCE: 13 tttttgaca aaatgagtcc cagcatgcta catctggttt cgggttttat tttagaattt 60
ataaaattcc agtgtcatcc atattcatga gcctttacac atgtttgcat ataatctcca 120
aattccaaag ttaaggccaa gggatggatt gtagctatgg aaacagatga tatggaagac 180
atccaacaag gaggaaaagc acacgcacgc ctcacccctg cctcatctct gcccagggct 240
gtcctgacag cacagacgct tcagggagac aggcctgggg acagtcatgt catcaccctt 300
gcaacaacca cccaaaggaa aagagagcgc tgaacagttt aggaaagggc tcgcgtctaa 360
gacatcaagc gacatacaga gatgtgcaaa acttggtgag aattaaaatt gacctttggg 420
agagggtagg ggcaggatgt tttatgacac tgtagaaaag acaggaggaa cccgctgcga 480
tggagattgg ggggagctgg aagcaagcag ccaacaggac agagttccag aactcatgca 540
gatggggaag aggtgacagc ccttccccac tggcctcccc cgtggaggtg gagtagacag 600
atcccgggaa aggcaggaaa agggccttgc tttctttccc tgtttcctaa gccgtggtca 660
ccctagccta tgaagctgga agctatattc cttccaatcc caatttacca ttcctgtaaa 720
caggcccatt cagggctgcc tgagcaaatg gggacttgcc gaggcagctg caactagact 780
tgggctaagc cgtctgggtc tactcaagaa ttcgagtctg aagatgacca agcttgagtt 840
attcaactga gagtgaggtg tcaaggcgga agcgactgtc cccagggaag ggctgtgaga 900
tggatgggcg tgagtcagct tttccaaaac tcaagtacct gggacaggac aactcgctag 960
cagctcagtc acctccgtgg cggacacaga taaggatgtt aagaccagaa aaccagagac 1020
tagggccccg tcctcagccc tcacagcatg acacagatgc ctccctcgga gagcagggtc 1080
tctcggcatc cagcggcgtg gtctgcattc tgctctacct catgctctag gccccatgcc 1140
atcgtctcgg ccctagaccg tgaaaactgc cagtcacccg ggacctgctc ctaggggctg 1200
gcctgcacag ccggatggcc tgtgggcggg gtggaagtgc ccactcccac tccagatggg 1260
cctgctggcc actgacccac ctgtgctgag ggagagcgcc agcctccagc ttaggtacac 1320
ggcgcccacc cccagctcca cgggaaaccc ataaccacca gaaacatctc aatcaagaga 1380

-continued

```
cgggtgtgtg gggtggcact aactgcacag agaccactcc acgccggctg aggtagaaag   1440
aaggcaactg aacacacagc agctagggca ggggcaggga ggggctgcag gtggtgtgaa   1500
gaagagccca gctgtcatct aaggcaaact gcccccactg aggacaagcg taaggcccta   1560
cctcccccaa cctgtgcgca tctcaatcac agcagacact gtgacggcca caggggaccc   1620
agatggtgcc taccaccttg cctccaggct ccactcacca gacctcaggc tgagggtctg   1680
gcagtggagg taggggcagg gacccttggt gctttcagac cccacggcag gtaaaatcag   1740
gactgcctga gaacccgtca ccctctgcct ctcaggtcac cccccagctc caggaacctg   1800
cctcctgctg tccattgcca ggtcttcctt gcaccctgac acctgtgctg aggcgctctg   1860
gcagctggag gaggctgatt gcactccaca aacaggactg tctggaccaa gggaaactgg   1920
caggagggag gtgggaaagg aagagggcaa acgtttggct tttataaagt caaggacgtt   1980
tatttcctga ggtcatgaca caggaagtgg aatcctagcc acggctgcgg agctctcgtg   2040
atgaaggcca gagtgctgac tgacatgccg ggtggaccag gagctggagt ctgttatctt   2100
agcacgaatg ctcatgacct tggtttagtg ttaaacagtg gagcaggtcc tgagcgggca   2160
cggccaggcc tggaggagcg gccgcacaca cagccaggcg ctaggctccc tgcgggacct   2220
cgggaagggg gaagagcgtc aacaatttac ggagggtcca gccgctgggt cagattgaga   2280
caaaccattg tgtggttggg tttgggtcag caggctggag agggttctgt tctttttgat   2340
cattatcgtt tggggcccca agggagggtc ttgggagcca cctgagcccc aaagctggga   2400
aattcctcag agctgctcat gtcaggagcc ttctcactgc tgctggcggt ccagggtgcg   2460
tcccgcacca caaagcctct ggaaggtgcc ttggcctctt cgtgtgctgg gggtttcatg   2520
tatacctgca gcgcctcact gtccaccacg tcagctaggt attcctcctc cagattgagg   2580
atgtggtcga tggcttcctc cacattctct gggagccccg tcacagtgac gcagttgggg   2640
tctggggctc cgctctgtgg gaagcgaatg tccaccttga attcgtccat gattttgcga   2700
atggctttgc cgcgggcacc aatgatgcgg gcgtgaacgc ggtggtccag cgggacgtcc   2760
tcagaaacca tctgctcaag ttcacccaca attctcagta tagcatccct ggcagcttct   2820
gtgttctttt cgtaccctgt gatggtaatt tggtcctggg gctggttccc atcgtcctta   2880
tcaggaaact ggatgttcac gtcatgctcc aaccggattt gggtaattac tgccccccttt  2940
ctcccgataa tcttgggatg gtatttgggg tctacagtga cactcagctt aaaactcctt   3000
aaagcccggt cctcctgctc ggcctgtagc tccttcacac gctccagcag tccagccttg   3060
gcccggtcca aatttgcagc gaggcccgtg atggcgatga tgtcagactg cagctcaggt   3120
gccgggacat gtatgttcac ctcaaactca tccatcatct tgcggatccc acttcctttc   3180
tgcccaataa cgtaacggtg aaggtcaaag ggcacctcta cttcaatggt gacaggaacc   3240
aatgcctcca gagcttcctt ggcagcctca cacttttctt tccggccaga gatgatgatg   3300
atgtcacacc tccttggaga gccggggtca caatctttag cctctctccc ctccccagct   3360
tcgtccccat tctcctggac aactggctct gtactgtgaa ctgcgttctc ctctctgtct   3420
gggaatttaa tttgaacact gaaatcccga gtaatctgct ggattctgga acctttgggg   3480
cccatgacag atcgatggaa tttctggggt atagcacatt ctaatgtcac ctgagcttcc   3540
aggtcctcaa tgatctcctg aatgcgtttc ttggctgcct ccacacagtc cttggcgccc   3600
ttgagggtga ctttgtcgct ctgtgtgcca gagcgtggga agctgaccat caccccgcca   3660
tactcttcag caatctcccg caagacctgg cctctgcgga tgacgaagtg gcggtggtgc   3720
```

-continued

```
ttggggtcca ccagcatgga gtcttccacc acattatcca ggttttggat caaggcctcc   3780
agctccttct gtgcctctcg gacggcgtcc tcctttccaa tgatggtgat caggtcctgg   3840
tccttgtcct cagccgcagg gaagatgaca cgtgctccag tgctgtcgcg caccttgcga   3900
attttgccgc ccccttgcc gatgaggaat ttgtggtatt ctggcttggc gcggatgtca   3960
acagtgaaac tcttggtttg cttctcctcc gccagatgca ggagctgctt cttggccttc   4020
tccacatccg aggaagggcc cctgataaca acggtgtcgc ttcctgaacc ttccacggga   4080
aagtgaatgt ggaccccgcc gcactcctcc atgatggagc ggatcagacg gcccttggtg   4140
ccaatgaggg agttgtgcag cttggcaggg atggagacct ctacctcggc tatgttggcc   4200
aggtctttct gaatagacag aatcctgctc cgggcagctt cgcagttggc tcgcttgcct   4260
gtgatgataa tggtctctga attgctattc tctgctggaa ggtcgatttt ggtgttgctt   4320
tcttcacgaa tctttttaat gtttgcgcct cctttcccaa tgatattctt gtgaaactgt   4380
ttgaagatcg gaacagaaat tgaatagcta ttttccacca gatctgccac catcttctgc   4440
atgtattttg tgcatttttc cacctcattc ttaggtcctc tgagctggac aatgtcactt   4500
ttttgtgctg ggtctggaaa gttaatgatg acctctggga atttgtcacg aatttcacgg   4560
atccgttcac ccttctgccc aatgattgtg cgatgaaatc tttgctcaat gattagatcc   4620
ttggtacgct cattttccat gcgagatgca agctccagca gctctcgctt ggcctgctgc   4680
acgccctgtg ggtcccccctc gatgcggatc aaattgctct tctcactgtc aggagggatg   4740
cgcacggaca ccttgtactg gtctttgatt ctgtttatgt tggcaccgct cttcccaatg   4800
aggtgcctgt ggaacttgtg gtcgatgttg atctccacat agtccatccg gttaatcaaa   4860
tctttgacca tgccttctat ctgttcctgg gccacattga catcctctgt agggccctcc   4920
agggtgatct tgtcttcgcc ctctgtgaac tcgatgtgaa cctttggcat ctgctgagtg   4980
attttggcca ggttctgccc tttcttgcca atgatgaaac ggtgaagcca ggaaggggcg   5040
gcgacagagg agacggtgaa gctattggcc ttctcctcat aaatcttctt gatgcgagcc   5100
acagcctgag ccaactgttc cttctctcca gtgaagacaa tctctgtccg gttcacgctg   5160
ggtgggggga tgttgatgcg cgtgcctgtc tcctgcatga tctcgccaac cagtctatta   5220
tacggcccag cgatgaaggg gtggaatgcc ttttctactt ctagcctctc cacagcacgt   5280
ttgtcctgct cggcagagat gagtaagact tcatggcgag ctttctcgat gccctctttg   5340
gtgccagtga tcttgatctg attgctgggg tcatctgggc gtgggatctg gattttggtt   5400
gcagttttta gctccaagtc ttgcagtttc tctccatttt tgccaataac aaagcgatgg   5460
tgttctttgg gaatggcaac agttgctgag gcctgagtct gcagtctagc aacaatgtcc   5520
ttccgagctt tcatgacagc atccagcttt cctgacacca tgatggagag gccttggtct   5580
ttggccaaag acagctccaa gtgagcacca gttctctgca tgatctcaag gcagattttt   5640
gcttgttcac cttctccaaa ctggttcata tccttgtatt ttctctcctc caggggtaca   5700
tggaacacct gagtgatgac agaagccttg atgggtcgga tcttgttccc ccaggctcca   5760
gcgggttcct gggcactttc caggcaagca gctttctcag gaagtggagg gaaggcatcc   5820
ttgtaggttg gagggtcgct ctcctcttct gaatttagag tggcaacttt gatttgttgc   5880
ggaaccagcc cacttcggtg ttcagcaaaa ctctcttggg tcaaaactgc aacggaactc   5940
atggttgatc tcacacctac acacaatccg ggaaaaccac tcttaatgct tacaaaatgc   6000
atcatgacag ttgctacaaa aagccagcgg tctctctctg caaggtgcat ccaggcccca   6060
aactaaacca cctccaaatc tcgacttaac caggtggtta taagtggtag cagcaaaacg   6120
```

gtcagtagcc agaaggtccg tcctgaggcc gcctctgtca gcctgccagc ttttgtcgtg 6180
ggcccccgcc cgctggtcct gccgctggct tactcgcccc ccgcgcggga gaagccggga 6240
cgctccgagg cgcggcgccc gggccccggc tgctatatag ggcggcggcc caatcccgcc 6300
t 6301

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19
<211> LENGTH: 13
<212> TYPE: PRT
<213> ORGANISM: Human immunodeficiency virus

<400> SEQUENCE: 19

Gly Arg Lys Lys Arg Arg Gln Arg Arg Arg Pro Pro Gln
1 5 10

<210> SEQ ID NO 20
<211> LENGTH: 16
<212> TYPE: PRT
<213> ORGANISM: Drosophila sp.

<400> SEQUENCE: 20

Arg Gln Ile Lys Ile Trp Phe Gln Asn Arg Arg Met Lys Trp Lys Lys
1 5 10 15

<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6xHis tag"

<400> SEQUENCE: 21

His His His His His His 1 5

<210> SEQ ID NO 22
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 22
gagaucaaca uugaccauaa a 21

<210> SEQ ID NO 23
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23
aggaagaucg ggcuuuaagg a 21

<210> SEQ ID NO 24
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
uuuaugguca auguugaucu cua 23

<210> SEQ ID NO 25
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
uccuuaaagc ccgaucuucc ugc 23

<210> SEQ ID NO 26
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 26
tttttttttt tttttttttt ttttt 25

<210> SEQ ID NO 27
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 27

caugaguucc guugcaguuu u                                               21


<210> SEQ ID NO 28
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28

augaguuccg uugcaguuuu a                                               21


<210> SEQ ID NO 29
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29

ccguugcagu uuugacccaa a                                               21


<210> SEQ ID NO 30
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30

acccaagaga guuuugcuga a                                               21


<210> SEQ ID NO 31
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31

caaaucaaag uugccacucu a                                               21


<210> SEQ ID NO 32
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32

acaagcaaaa aucugccuug a                                               21


<210> SEQ ID NO 33
```

-continued

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 33
aacaccaucg cuuuguuauu a 21

<210> SEQ ID NO 34
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 34
aacugcaaga cuuggagcua a 21

<210> SEQ ID NO 35
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 35
cuaaaaacug caaccaaaau a 21

<210> SEQ ID NO 36
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 36
ugcaaccaaa auccagaucc a 21

<210> SEQ ID NO 37
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 37
aucaagaaga uuuaugagga a 21

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 38
gaaaaagaag acuacaacca u 21

<210> SEQ ID NO 39
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 39
aaaaagaaga cuacaaccau u 21

<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 40
aaaagaagac uacaaccauu a 21

<210> SEQ ID NO 41
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 41
acuacaacca uugcagugga a 21

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 42
ugcaguggaa gugaagaaau a 21

<210> SEQ ID NO 43
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 43
gaagagcaau uugauccgca u 21

<210> SEQ ID NO 44
<211> LENGTH: 21
<212> TYPE: RNA
<213> ORGANISM: Artificial Sequence
<220> FEATURE:

-continued

<221> NAME/KEY: source
<223> OTHER INFORMATION: /note="Description of Artificial Sequence:
Synthetic oligonucleotide"

<400> SEQUENCE: 44
ggaucuaauc auugagcaaa g 21

<210> SEQ ID NO 45
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 45
uaaucauuga gcaaagauuu a 21

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 46
gagcaaagau uucaucgcac a 21

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 47
caaagauuuc aucgcacaau a 21

<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 48
aagugacauu guccagcuca a 21

<210> SEQ ID NO 49
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 49
cacaaaauac augcagaaga u 21

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
cuguuccgau cuucaaacag u 21

<210> SEQ ID NO 51
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 51
uguuccgauc uucaaacagu u 21

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 52
ucuucaaaca guuucacaag a 21

<210> SEQ ID NO 53
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 53
cuucaaacag uuucacaaga a 21

<210> SEQ ID NO 54
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 54
uucaaacagu uucacaagaa u 21

<210> SEQ ID NO 55
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 55
ccagcagaga auagcaauuc a 21

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 56
gagaauagca auucagagac a 21

<210> SEQ ID NO 57
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 57
agaauagcaa uucagagacc a 21

<210> SEQ ID NO 58
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 58
aauucagaga ccauuaucau a 21

<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 59
uucagagacc auuaucauca a 21

<210> SEQ ID NO 60
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 60
ucagagacca uuaucaucac a 21

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 61
agagaccauu aucaucacag a 21

<210> SEQ ID NO 62
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 62
caaaccaaga guuucacugu u 21

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 63
aaaccaagag uuucacuguu a 21

<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 64
aagaguuuca cuguugacau a 21

<210> SEQ ID NO 65
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 65
cagaaauucc aucgaucugu a 21

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 66
ucaaauuaaa uucccagaca a 21

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 67
ccguaaauug uugacgcucu u 21

<210> SEQ ID NO 68
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 68
ggucaugagc auucgugcua a 21

<210> SEQ ID NO 69
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 69
gucaugagca uucgugcuaa a 21

<210> SEQ ID NO 70
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 70
augagcauuc gugcuaagau a 21

<210> SEQ ID NO 71
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 71
agcauucgug cuaagauaac a 21

<210> SEQ ID NO 72
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 72
ucgugcuaag auaacagacu a 21

<210> SEQ ID NO 73
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 73
aaaacugcaa cggaacucau ggu 23

<210> SEQ ID NO 74
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 74
uaaaacugca acggaacuca ugg 23

<210> SEQ ID NO 75
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 75
uuugggucaa aacugcaacg gaa 23

<210> SEQ ID NO 76
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 76
uucagcaaaa cucucuuggg uca 23

<210> SEQ ID NO 77
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 77
uagaguggca acuuugauuu guu 23

<210> SEQ ID NO 78
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 78
ucaaggcaga uuuuugcuug uuc 23

<210> SEQ ID NO 79
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 79
uaauaacaaa gcgauggugu ucu 23

<210> SEQ ID NO 80
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 80
uuagcuccaa gucuugcagu uuc 23

<210> SEQ ID NO 81
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 81
uauuuugguu gcaguuuuua gcu 23

<210> SEQ ID NO 82
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 82
uggaucugga uuuugguugc agu 23

<210> SEQ ID NO 83
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 83
uuccucauaa aucuucuuga ugc 23

<210> SEQ ID NO 84
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 84
augguuguag ucuucuuuuu cuu 23

<210> SEQ ID NO 85
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 85
aaugguugua gucuucuuuu ucu 23

<210> SEQ ID NO 86
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 86
uaaugguugu agucuucuuu uuc 23

<210> SEQ ID NO 87
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 87
uuccacugca augguuguag ucu 23

<210> SEQ ID NO 88
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 88
uauuucuuca cuuccacugc aau 23

<210> SEQ ID NO 89
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide”

<400> SEQUENCE: 89
augcggauca aauugcucuu cuc 23

<210> SEQ ID NO 90
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide”

<400> SEQUENCE: 90
cuuugcucaa ugauuagauc cuu 23

<210> SEQ ID NO 91
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide”

<400> SEQUENCE: 91
uaaaucuuug cucaaugauu aga 23

<210> SEQ ID NO 92
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide”

<400> SEQUENCE: 92
ugugcgauga aaucuuugcu caa 23

<210> SEQ ID NO 93
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide”

<400> SEQUENCE: 93
uauugugcga ugaaaucuuu gcu 23

<210> SEQ ID NO 94
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide”

<400> SEQUENCE: 94
uugagcugga caaugucacu uuu 23

<210> SEQ ID NO 95
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 95
aucuucugca uguauuuugu gca 23

<210> SEQ ID NO 96
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 96
acuguuugaa gaucggaaca gaa 23

<210> SEQ ID NO 97
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 97
aacuguuuga agaucggaac aga 23

<210> SEQ ID NO 98
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 98
ucuugugaaa cuguuugaag auc 23

<210> SEQ ID NO 99
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 99
uucuugugaa acuguuugaa gau 23

<210> SEQ ID NO 100
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 100
auucuuguga aacuguuuga aga 23

<210> SEQ ID NO 101
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101
ugaauugcua uucucugcug gaa 23

<210> SEQ ID NO 102
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
ugucucugaa uugcuauucu cug 23

<210> SEQ ID NO 103
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
uggucucuga auugcuauuc ucu 23

<210> SEQ ID NO 104
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
uaugauaaug gucucugaau ugc 23

<210> SEQ ID NO 105
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
uugaugauaa uggucucuga auu 23

<210> SEQ ID NO 106
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 106
ugugaugaua auggucucug aau 23

<210> SEQ ID NO 107
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 107
ucugugauga uaauggucuc uga 23

<210> SEQ ID NO 108
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 108
aacagugaaa cucuugguuu gcu 23

<210> SEQ ID NO 109
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 109
uaacagugaa acucuugguu ugc 23

<210> SEQ ID NO 110
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 110
uaugucaaca gugaaacucu ugg 23

<210> SEQ ID NO 111
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 111
uacagaucga uggaauuucu ggg 23

<210> SEQ ID NO 112

-continued

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 112
uugucuggga auuuaauuug aac 23

<210> SEQ ID NO 113
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 113
aagagcguca acaauuuacg gag 23

<210> SEQ ID NO 114
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 114
uuagcacgaa ugcucaugac cuu 23

<210> SEQ ID NO 115
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 115
uuuagcacga augcucauga ccu 23

<210> SEQ ID NO 116
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 116
uaucuuagca cgaaugcuca uga 23

<210> SEQ ID NO 117
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 117
uguuaucuua gcacgaaugc uca 23

<210> SEQ ID NO 118
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 118
uagucuguua ucuuagcacg aau 23

<210> SEQ ID NO 119
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 119
caugaguucc guugcaguuu u 21

<210> SEQ ID NO 120
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 120
augaguuccg uugcaguuuu a 21

<210> SEQ ID NO 121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 121
ccguugcagu uuugacccaa a 21

<210> SEQ ID NO 122
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 122
acccaagaga guuuugcuga a 21

<210> SEQ ID NO 123
<211> LENGTH: 21
<212> TYPE: RNA
<213> ORGANISM: Artificial Sequence
<220> FEATURE:

-continued

<221> NAME/KEY: source
<223> OTHER INFORMATION: /note="Description of Artificial Sequence:
      Synthetic oligonucleotide"

<400> SEQUENCE: 123
caaaucaaag uugccacucu a 21

<210> SEQ ID NO 124
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
acaagcaaaa aucugccuug a 21

<210> SEQ ID NO 125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
aacaccaucg cuuuguuauu a 21

<210> SEQ ID NO 126
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
aacugcaaga cuuggagcua a 21

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
cuaaaaacug caaccaaaau a 21

<210> SEQ ID NO 128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
ugcaaccaaa auccagaucc a 21

```
<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129

aucaagaaga uuuaugagga a                                              21


<210> SEQ ID NO 130
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130

gaaaaagaag acuacaacca u                                              21


<210> SEQ ID NO 131
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131

aaaaagaaga cuacaaccau u                                              21


<210> SEQ ID NO 132
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132

aaaagaagac uacaaccauu a                                              21


<210> SEQ ID NO 133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133

acuacaacca uugcagugga a                                              21


<210> SEQ ID NO 134
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 134
ugcaguggaa gugaagaaau a 21

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 135
gaagagcaau uugauccgca u 21

<210> SEQ ID NO 136
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 136
ggaucuaauc auugagcaaa g 21

<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 137
uaaucauuga gcaaagauuu a 21

<210> SEQ ID NO 138
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 138
gagcaaagau uucaucgcac a 21

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 139
caaagauuuc aucgcacaau a 21

<210> SEQ ID NO 140
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 140
aagugacauu guccagcuca a 21

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 141
cacaaaauac augcagaaga u 21

<210> SEQ ID NO 142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 142
cuguuccgau cuucaaacag u 21

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 143
uguuccgauc uucaaacagu u 21

<210> SEQ ID NO 144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 144
ucuucaaaca guuucacaag a 21

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 145
cuucaaacag uuucacaaga a 21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 146
uucaaacagu uucacaagaa u 21

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 147
ccagcagaga auagcaauuc a 21

<210> SEQ ID NO 148
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 148
gagaauagca auucagagac a 21

<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 149
agaauagcaa uucagagacc a 21

<210> SEQ ID NO 150
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 150
aauucagaga ccauuaucau a 21

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 151
uucagagacc auuaucauca a 21

<210> SEQ ID NO 152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 152
ucagagacca uuaucaucac a 21

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 153
agagaccauu aucaucacag a 21

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
caaaccaaga guuucacugu u 21

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
aaaccaagag uuucacuguu a 21

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
aagaguuuca cuguugacau a 21

<210> SEQ ID NO 157
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 157
cagaaauucc aucgaucugu a 21

<210> SEQ ID NO 158
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 158
ucaaauuaaa uucccagaca a 21

<210> SEQ ID NO 159
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 159
ccguaaauug uugacgcucu u 21

<210> SEQ ID NO 160
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 160
ggucaugagc auucgugcua a 21

<210> SEQ ID NO 161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 161
gucaugagca uucgugcuaa a 21

<210> SEQ ID NO 162
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 162
augagcauuc gugcuaagau a 21

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 163
agcauucgug cuaagauaac a 21

<210> SEQ ID NO 164
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
ucgugcuaag auaacagacu a 21

<210> SEQ ID NO 165
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 165
aaaacugcaa cggaacucau ggu 23

<210> SEQ ID NO 166
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 166
uaaaacugca acggaacuca ugg 23

<210> SEQ ID NO 167
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 167
uuugggucaa aacugcaacg gaa 23

<210> SEQ ID NO 168
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 168
uucagcaaaa cucucuuggg uca 23

<210> SEQ ID NO 169
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 169
uagaguggca acuuugauuu guu 23

<210> SEQ ID NO 170
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 170
ucaaggcaga uuuuugcuug uuc 23

<210> SEQ ID NO 171
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 171
uaauaacaaa gcgauggugu ucu 23

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 172
uuagcuccaa gucuugcagu uuc 23

<210> SEQ ID NO 173
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 173
uauuuugguu gcaguuuuua gcu 23

<210> SEQ ID NO 174
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 174
uggaucugga uuuugguugc agu 23

<210> SEQ ID NO 175
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 175
uuccucauaa aucuucuuga ugc 23

<210> SEQ ID NO 176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176
augguuguag ucuucuuuuu cuu 23

<210> SEQ ID NO 177
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 177
aaugguugua gucuucuuuu ucu 23

<210> SEQ ID NO 178
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178
uaaugguugu agucuucuuu uuc 23

<210> SEQ ID NO 179
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
uuccacugca augguuguag ucu 23

<210> SEQ ID NO 180
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
uauuucuuca cuuccacugc aau 23

<210> SEQ ID NO 181
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
augcggauca aauugcucuu cuc 23

<210> SEQ ID NO 182
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
cuuugcucaa ugauuagauc cuu 23

<210> SEQ ID NO 183
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
uaaaucuuug cucaaugauu aga 23

<210> SEQ ID NO 184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 184
ugugcgauga aaucuuugcu caa 23

<210> SEQ ID NO 185
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 185
uauugugcga ugaaaucuuu gcu 23

<210> SEQ ID NO 186
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 186
uugagcugga caaugucacu uuu 23

<210> SEQ ID NO 187
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 187
aucuucugca uguauuuugu gca 23

<210> SEQ ID NO 188
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 188
acuguuugaa gaucggaaca gaa 23

<210> SEQ ID NO 189
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 189
aacuguuuga agaucggaac aga 23

<210> SEQ ID NO 190
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 190
ucuugugaaa cuguuugaag auc 23

<210> SEQ ID NO 191

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 191
uucuugugaa acuguuugaa gau 23

<210> SEQ ID NO 192
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 192
auucuuguga aacuguuuga aga 23

<210> SEQ ID NO 193
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 193
ugaauugcua uucucugcug gaa 23

<210> SEQ ID NO 194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 194
ugucucugaa uugcuauucu cug 23

<210> SEQ ID NO 195
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 195
uggucucuga auugcuauuc ucu 23

<210> SEQ ID NO 196
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 196
uaugauaaug gucucugaau ugc 23

<210> SEQ ID NO 197
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197
uugaugauaa uggucucuga auu 23

<210> SEQ ID NO 198
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198
ugugaugaua auggucucug aau 23

<210> SEQ ID NO 199
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 199
ucugugauga uaauggucuc uga 23

<210> SEQ ID NO 200
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 200
aacagugaaa cucuugguuu gcu 23

<210> SEQ ID NO 201
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 201
uaacagugaa acucuugguu ugc 23

<210> SEQ ID NO 202
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 202
uaugucaaca gugaaacucu ugg 23

<210> SEQ ID NO 203
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 203
uacagaucga uggaauuucu ggg 23

<210> SEQ ID NO 204
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 204
uugucuggga auuuaauuug aac 23

<210> SEQ ID NO 205
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 205
aagagcguca acaauuuacg gag 23

<210> SEQ ID NO 206
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 206
uuagcacgaa ugcucaugac cuu 23

<210> SEQ ID NO 207
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 207
uuuagcacga augcucauga ccu 23

<210> SEQ ID NO 208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 208
uaucuuagca cgaaugcuca uga 23

<210> SEQ ID NO 209
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 209
uguuaucuua gcacgaaugc uca 23

<210> SEQ ID NO 210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 210
uagucuguua ucuuagcacg aau 23

<210> SEQ ID NO 211
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 211
accaugaguu ccguugcagu uuu 23

<210> SEQ ID NO 212
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 212
ccaugaguuc cguugcaguu uug 23

<210> SEQ ID NO 213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 213
uuccguugca guuuugaccc aag 23

<210> SEQ ID NO 214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 214
ugacccaaga gaguuuugcu gaa 23

<210> SEQ ID NO 215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 215
aacaaaucaa aguugccacu cua 23

<210> SEQ ID NO 216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 216
gaacaagcaa aaaucugccu uga 23

<210> SEQ ID NO 217
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 217
agaacaccau cgcuuuguua uug 23

<210> SEQ ID NO 218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 218
gaaacugcaa gacuuggagc uaa 23

<210> SEQ ID NO 219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 219
agcuaaaaac ugcaaccaaa auc 23

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 220
acugcaacca aaauccagau ccc 23

<210> SEQ ID NO 221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 221
gcaucaagaa gauuuaugag gag 23

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
aagaaaaaga agacuacaac cau 23

<210> SEQ ID NO 223
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 223
agaaaaagaa gacuacaacc auu 23

<210> SEQ ID NO 224
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 224
gaaaaagaag acuacaacca uug 23

<210> SEQ ID NO 225
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225
agacuacaac cauugcagug gaa 23

<210> SEQ ID NO 226
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 226
auugcagugg aagugaagaa auc 23

<210> SEQ ID NO 227
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 227
gagaagagca auuugauccg cau 23

<210> SEQ ID NO 228
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 228
aaggaucuaa ucauugagca aag 23

<210> SEQ ID NO 229
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 229
ucuaaucauu gagcaaagau uuc 23

<210> SEQ ID NO 230
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 230
uugagcaaag auuucaucgc aca 23

<210> SEQ ID NO 231
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 231
agcaaagauu ucaucgcaca auc 23

<210> SEQ ID NO 232
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 232
aaaagugaca uuguccagcu cag 23

<210> SEQ ID NO 233
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 233
ugcacaaaau acaugcagaa gau 23

<210> SEQ ID NO 234
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 234
uucuguuccg aucuucaaac agu 23

<210> SEQ ID NO 235
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 235
ucuguuccga ucuucaaaca guu 23

<210> SEQ ID NO 236
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 236
gaucuucaaa caguuucaca aga 23

<210> SEQ ID NO 237
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 237
aucuucaaac aguuucacaa gaa 23

<210> SEQ ID NO 238
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 238
ucuucaaaca guuucacaag aau 23

<210> SEQ ID NO 239
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 239
uuccagcaga gaauagcaau uca 23

<210> SEQ ID NO 240
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 240
cagagaauag caauucagag acc 23

<210> SEQ ID NO 241
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 241
agagaauagc aauucagaga cca 23

<210> SEQ ID NO 242
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 242
gcaauucaga gaccauuauc auc 23

<210> SEQ ID NO 243
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 243
aauucagaga ccauuaucau cac 23

<210> SEQ ID NO 244
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 244
auucagagac cauuaucauc aca 23

<210> SEQ ID NO 245
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 245
ucagagacca uuaucaucac agg 23

<210> SEQ ID NO 246
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 246
agcaaaccaa gaguuucacu guu 23

<210> SEQ ID NO 247
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 247
gcaaaccaag aguuucacug uug 23

<210> SEQ ID NO 248
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 248
ccaagaguuu cacuguugac auc 23

<210> SEQ ID NO 249
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 249
cccagaaauu ccaucgaucu guc 23

<210> SEQ ID NO 250
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 250
guucaaauua aauucccaga cag 23

<210> SEQ ID NO 251
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 251
cuccguaaau uguugacgcu cuu 23

<210> SEQ ID NO 252
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 252
aaggucauga gcauucgugc uaa 23

<210> SEQ ID NO 253
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
aggucaugag cauucgugcu aag 23

<210> SEQ ID NO 254
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 254
ucaugagcau ucgugcuaag aua 23

<210> SEQ ID NO 255
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 255
ugagcauucg ugcuaagaua aca 23

<210> SEQ ID NO 256
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 256
auucgugcua agauaacaga cuc 23

<210> SEQ ID NO 257
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 257
aaaaaaaaaa aaaaaaaa 18

<210> SEQ ID NO 258
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 258
uuuuuuuuuu uuuuuuuu 18

<210> SEQ ID NO 259
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
cccccccccc cccccccc 18

<210> SEQ ID NO 260
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 260
cucucucucu cucucucu 18

<210> SEQ ID NO 261
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 261
ccuccuccuc cuccuccu 18

<210> SEQ ID NO 262
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 262
cuucuucuuc uucuucuu 18

<210> SEQ ID NO 263
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 263
acuacuacua cuacuacu 18

<210> SEQ ID NO 264
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 264
uuccucuucu uccucuuc 18

<210> SEQ ID NO 265
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 265
uuacuuuaau uacuuuaa 18

<210> SEQ ID NO 266
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 266
caacaacaac aacaacaa 18

<210> SEQ ID NO 267
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 267
ggugguggug gugguggu 18

<210> SEQ ID NO 268
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 268
guuguuguug uuguuguu 18

<210> SEQ ID NO 269
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 269
caucaucauc aucaucau 18

<210> SEQ ID NO 270

```
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270

gaugaugaug augaugau                                                18


<210> SEQ ID NO 271
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271

caccaccacc accaccac                                                18


<210> SEQ ID NO 272
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272

guaguaguag uaguagua                                                18


<210> SEQ ID NO 273
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273

gccgccgccg ccgccgcc                                                18


<210> SEQ ID NO 274
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274

auuauuauua uuauuauu                                                18


<210> SEQ ID NO 275
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
```

aacaaccucc uccuccua 18

<210> SEQ ID NO 276
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 276
aaccaacucc uccuccua 18

<210> SEQ ID NO 277
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 277
aaccuaaucc uccuccua 18

<210> SEQ ID NO 278
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 278
aaccucaacc uccuccua 18

<210> SEQ ID NO 279
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 279
aaccuccaac uccuccua 18

<210> SEQ ID NO 280
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 280
aaccuccuaa uccuccua 18

<210> SEQ ID NO 281
<211> LENGTH: 18
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 281
aaccuccuca accuccua 18

<210> SEQ ID NO 282
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 282
aaccuccucc aacuccua 18

<210> SEQ ID NO 283
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 283
aaccuccucc uaauccua 18

<210> SEQ ID NO 284
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 284
aaccuccucc ucaaccua 18

<210> SEQ ID NO 285
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 285
aaccuccucc uccaacua 18

<210> SEQ ID NO 286
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 286
aaccuccucc uccuaaua 18

<210> SEQ ID NO 287
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
ccuccuccuc cuccu 15

<210> SEQ ID NO 288
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
ccuccuccuc cu 12

<210> SEQ ID NO 289
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
ccuccuccuc cuccuccucc uccu 24

<210> SEQ ID NO 290
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
ccuccuccuc cuccuccucc uccuccuccu 30

<210> SEQ ID NO 291
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
gagatttaac tccacctact tccagggcac caaccag 37

<210> SEQ ID NO 292
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 292
atttaactcc acctactccc ag 22

<210> SEQ ID NO 293
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 293
atttaactcc acctacctcc ag 22

<210> SEQ ID NO 294
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 294
atttaactcc acccacttcc ag 22

<210> SEQ ID NO 295
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 295
atttaactcc acctacctcc a 21

<210> SEQ ID NO 296
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 296
atttaacccc acctacttcc ag 22

<210> SEQ ID NO 297
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 297
atctaactcc acctacttcc ag 22

<210> SEQ ID NO 298
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 298
atctaactcc acctacttcc 20

<210> SEQ ID NO 299
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 299
atttaactcc acctactccc a 21

<210> SEQ ID NO 300
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 300
attcaactcc acctacttcc ag 22

<210> SEQ ID NO 301
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 301
attcaactcc acctacttcc 20

<210> SEQ ID NO 302
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 302
atttaactcc acctacctcc 20

<210> SEQ ID NO 303
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 303
atttaacccc acctacttcc 20

<210> SEQ ID NO 304
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 304
atttaactcc acccacttcc a 21

<210> SEQ ID NO 305
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 305
atctaactcc acctacttcc a 21

<210> SEQ ID NO 306
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 306
gatttaactc cacctacttc cagggc 26

<210> SEQ ID NO 307
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 307
gatttaaatc aacctaatta cagggc 26

<210> SEQ ID NO 308
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 308
ccggcaatca tgccttacga ttatcc 26

<210> SEQ ID NO 309
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 309
gtggactacc tcaataatca tcttcttcag ggattca 37

<210> SEQ ID NO 310
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 310
actacctcaa taaccatctt cttcag 26

<210> SEQ ID NO 311
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 311
actacctcaa taatcacctt cttcag 26

<210> SEQ ID NO 312
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 312
actacctcaa caatcatctt cttcag 26

<210> SEQ ID NO 313
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 313
actacctcaa taatcatcct cttcag 26

<210> SEQ ID NO 314
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 314
actacctcaa taatcatctt cctcag 26

<210> SEQ ID NO 315
<211> LENGTH: 26
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 315
actacctcaa taatcatctt ctccag 26

<210> SEQ ID NO 316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 316
actacctcaa taaccatctt 20

<210> SEQ ID NO 317
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 317
actaccccaa taatcatctt cttcag 26

<210> SEQ ID NO 318
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 318
actacctcaa taatcacctt 20

<210> SEQ ID NO 319
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 319
accacctcaa taatcatctt cttcag 26

<210> SEQ ID NO 320
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 320
ctcaataacc atcttcttca g 21

<210> SEQ ID NO 321
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 321
actacctcaa taatcacctt c 21

<210> SEQ ID NO 322
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 322
actacctcaa taaccatctt cttca 25

<210> SEQ ID NO 323
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 323
actacctcaa taatcatctc cttcag 26

<210> SEQ ID NO 324
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 324
ctacctcaat aatcatcttc ttcagg 26

<210> SEQ ID NO 325
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

-continued

<400> SEQUENCE: 325
ctaactaaat aataatatta ttaagg 26

<210> SEQ ID NO 326
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 326
cgcaactttt acattctatc atagcc 26

HIGH DENSITY LIPOPROTEIN BINDING PROTEIN (HDLBP/VIGILIN) IRNA COMPOSITIONS AND METHODS OF USE THEREOF

RELATED APPLICATIONS

This application is a 35 § U.S.C. 111(a) continuation application which claims the benefit of priority to PCT/US2017/028291, filed on Apr. 19, 2017, which claims priority to U.S. Provisional Application No. 62/324,480, filed on Apr. 19, 2016. The entire contents of each of the foregoing applications are hereby incorporated herein by reference.

SEQUENCE LISTING

The instant application contains a Sequence Listing which has been submitted electronically in ASCII format and is hereby incorporated by reference in its entirety. The ASCII copy, created on Oct. 12, 2018, is named 121301-06102_SL.txt and is 132,229 bytes in size.

BACKGROUND OF THE INVENTION

High density lipoprotein binding protein (Hdlbp/Vigilin) is the largest RNA-binding protein of the KH domain family with a unique structure of 14 consecutively arranged RNA binding KH domains that are conserved from human to yeast (Dodson & Shapiro 1997; Weber et al., 1997; Cortes et al., 1999; Chen et al., 2003; Brykailo et al., 2007). Vigilin is ubiquitously expressed with the highest levels of expression in organs with preferential epithelial cell origin, including the liver (FIG. 1A). Vigilin has been implicated in diverse biological processes such as sterol metabolism (Dodson & Shapiro, 1997), carcinogenesis (Molyneux et al., 2013; Yang et al., 2014), control of translation (Hirschmann et al., 2014), formation of heterochromatin (Wang et al., 2005), nuclear export of tRNA (Kruse et al., 2000), cytoplasmic transport of RNA (Gelin-Licht et al., 2012), and metabolism of specific mRNAs (Weber et al., 1997; Baum et al., 2004; Frey et al., 2001; Lang & Fridovich-Keil, 2000; Mendelsohn et al., 2003).

Although the exact function of vigilin has not been addressed in a systematical and unbiased manner, Viligin has been implicated to function in the removal of excess cellular cholesterol, and its expression in plaque macrophages suggests a role for this molecule in atherogenesis (Chui et al., 1997, *Arterioscler Thromb Vasc Biol.* 17(11):2350-8). As described in the appended example below, it has been discovered that vigilin is upregulated in the livers of insulin resistant obese mice. Gain and loss of function studies revealed that Vigilin regulates VLDL secretion through the modulation of ApoB mRNA translation. Photoactivatable ribonucleoside-enhanced crosslinking and immunoprecipitation (PAR-CLIP) analysis in primary hepatocytes demonstrated that Vigilin predominantly binds to CU-rich regions in coding sequences of transcripts of further metabolically relevant secretory proteins such as Ahsg/Fetuin-A, ApoC3, Fn1/Fibronectin, Orm1/Orosomucoid and Serpina1/Alpha-1-Antitrypsin. While mRNA levels of these targets did not change, protein levels were substantially decreased upon knockdown of Vigilin. Hepatic long-term knockdown via GalNAc-conjugated siRNAs ameliorated elevated VLDL/LDL levels and the formation of atherosclerotic plaques in Ldlr−/− mice. These studies uncover a role for Vigilin as a key regulator of hepatic ApoB translation and secretion through binding to its mRNA and demonstrate the therapeutic potential of inhibiting Vigilin for disorders of lipid metabolism.

For example, disorders of lipid metabolism can lead to elevated levels of serum lipids, such as triglycerides and/or cholesterol. High cholesterol levels have been associated with an increased risk of atherosclerosis and cardiovascular disease (Lewington S, et al. (2007), *Lancet* 370 (9602): 1829-39). Elevated cholesterol levels contribute to formation of atherosclerotic plaque in the arteries which may lead to progressive narrowing or blockage of the involved arteries. Occlusion of a coronary artery can result in myocardial infarction or heart attack, while occlusion of an artery supplying the brain may lead to stroke.

Statins are a widely known drug class of cholesterol lowering drugs. Although statins have been found to reduce cardiovascular disease and mortality in those who are at high risk, some patients experience side effects of statins including muscle pain, increased risk of diabetes mellitus, and abnormalities in liver enzyme tests (Naci H, et al. (2013). *Circ Cardiovasc Qual Outcomes* 6 (4): 390-9). Additionally, patients may experience rare but severe adverse effects, particularly statin-induced myopathy (Abd T T, et al. (2011) *Expert opinion on drug safety* 10 (3): 373-87). Accordingly, there is a need in the art for alternative treatments for subjects having disorders of lipid metabolism.

SUMMARY OF THE INVENTION

The present invention provides iRNA compositions which effect the RNA-induced silencing complex (RISC)-mediated cleavage of RNA transcripts of a High Density Lipoprotein Binding Protein (Hdlbp/Vigilin) gene. The Hdlbp/Vigilin gene may be within a cell, e.g., a cell within a subject, such as a human. The present invention also provides methods of using the iRNA compositions of the invention for inhibiting the expression of an Hdlbp/Vigilin gene and/or for treating a subject who would benefit from inhibiting or reducing the expression of an Hdlbp/Vigilin gene, e.g., a subject suffering or prone to suffering from a disorder of lipid metabolism, such as a subject suffering or prone to suffering from mixed hyperlipidemia, hypertriglyceridemia or hypercholesterolemia.

Accordingly, in one aspect, the present invention provides double stranded ribonucleic acid (RNAi) agents for inhibiting expression of a High Density Lipoprotein Binding Protein (Hdlbp/Vigilin) gene, wherein the dsRNA agents comprise a sense strand and an antisense strand, wherein the sense strand comprises at least 15 contiguous nucleotides differing by no more than 3 nucleotides from the nucleotide sequence of SEQ ID NO:5 and the antisense strand comprises at least 15 contiguous nucleotides differing by no more than 3 nucleotides from the nucleotide sequence of SEQ ID NO:11.

In another aspect, the present invention provides double stranded ribonucleic acid (dsRNA) agents for inhibiting expression of a High Density Lipoprotein Binding Protein (Hdlbp/Vigilin) gene, wherein the dsRNA agents comprise a sense strand and an antisense strand, the antisense strand comprising a region of complementarity which comprises at least 15 contiguous nucleotides differing by no more than 3 nucleotides from the nucleotide sequence of SEQ ID NO:11.

In one embodiment, the antisense strand comprises at least 15 contiguous nucleotides differing by no more than 3 nucleotides from the complement of the nucleotide sequence of any one of nucleotides 373-395; 374-396; 381-403; 395-417; 440-462; 670-692; 852-874; 888-910; 905-927; 913-935; 1223-1245; 1246-1268; 1247-1269; 1248-1270; 1256-1278; 1267-1289; 1801-1823; 1903-1925; 1908-1930; 1916-1938; 1919-1941; 2023-2045; 2071-2093; 2127-2149; 2128-2150; 2136-2158; 2137-2159; 2138-2160; 2225-2247; 2231-2253; 2232-2254; 2240-2262; 2242-2264; 2243-2265; 2245-2267; 2543-2565; 2544-2566; 2549-2571; 3017-3039; 3088-3110; 4271-4293; 4404-4426; 4405-4427; 4408-4430; 4411-4433; or 4416-4438 of the nucleotide sequence of SEQ ID NO:5.

In another embodiment, the antisense strand comprises any one of the antisense nucleotide sequences in any one of Tables 2-4.

In one embodiment, the sense and antisense strands comprise nucleotide sequences selected from the group consisting one of any of the sense and antisense nucleotide sequences listed in any one of Tables 2-4.

In one embodiment, the dsRNA agent comprises at least one nucleotide comprising a nucleotide modification.

In one embodiment, substantially all of the nucleotides of said sense strand and substantially all of the nucleotides of said antisense strand comprise a nucleotide modification.

In another embodiment, all of the nucleotides of said sense strand and all of the nucleotides of said antisense strand comprise a nucleotide modification.

In one embodiment, the modified nucleotides are independently selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In one aspect, the present invention provides double stranded ribonucleic acid (dsRNA) agents for inhibiting expression of a High Density Lipoprotein Binding Protein (Hdlbp/Vigilin) gene, wherein the dsRNA agents comprise a sense strand and an antisense strand forming a double stranded region, the antisense strand comprising a region of complementarity which comprises at least 15 contiguous nucleotides differing by no more than 3 nucleotides from the nucleotide sequence of SEQ ID NO:11, wherein substantially all of the nucleotides of the sense strand and substantially all of the nucleotides of said antisense strand comprise a nucleotide modification, and wherein the sense strand is conjugated to a ligand attached at the 3'-terminus.

In one embodiment, the antisense strand comprises at least 15 contiguous nucleotides differing by no more than 3 nucleotides from the complement of the nucleotide sequence of any one of nucleotides 373-395; 374-396; 381-403; 395-417; 440-462; 670-692; 852-874; 888-910; 905-927; 913-935; 1223-1245; 1246-1268; 1247-1269; 1248-1270; 1256-1278; 1267-1289; 1801-1823; 1903-1925; 1908-1930; 1916-1938; 1919-1941; 2023-2045; 2071-2093; 2127-2149; 2128-2150; 2136-2158; 2137-2159; 2138-2160; 2225-2247; 2231-2253; 2232-2254; 2240-2262; 2242-2264; 2243-2265; 2245-2267; 2543-2565; 2544-2566; 2549-2571; 3017-3039; 3088-3110; 4271-4293; 4404-4426; 4405-4427; 4408-4430; 4411-4433; or 4416-4438 of the nucleotide sequence of SEQ ID NO:5.

In one embodiment, all of the nucleotides of the sense strand and all of the nucleotides of the antisense strand comprise a nucleotide modification.

In one embodiment, the modified nucleotides are independently selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

The region of complementarity may be at least 17 nucleotides in length; 19 to 21 nucleotides in length; or 19 nucleotides in length.

In one embodiment, each strand is no more than 30 nucleotides in length.

In one embodiment, at least one strand comprises a 3' overhang of at least 1 nucleotide.

In another embodiment, at least one strand comprises a 3' overhang of at least 2 nucleotides.

In one embodiment, the dsRNA agent further comprises a ligand.

In one embodiment, the ligand is conjugated to the 3' end of the sense strand of the dsRNA agent.

In one embodiment, the ligand is an N-acetylgalactosamine (GalNAc) derivative.

In one embodiment, the ligand is one or more GalNAc derivatives attached through a bivalent or trivalent branched linker.

In one embodiment, the ligand is

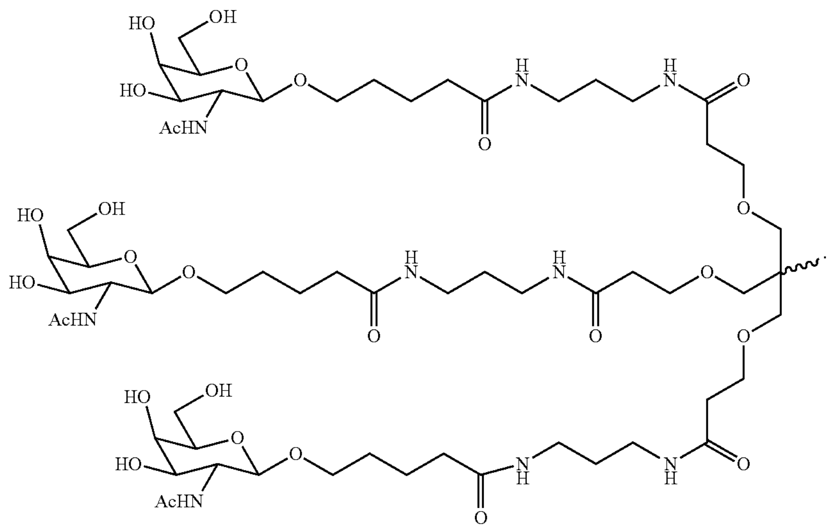 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the dsRNA agent is conjugated to the ligand as shown in the following schematic

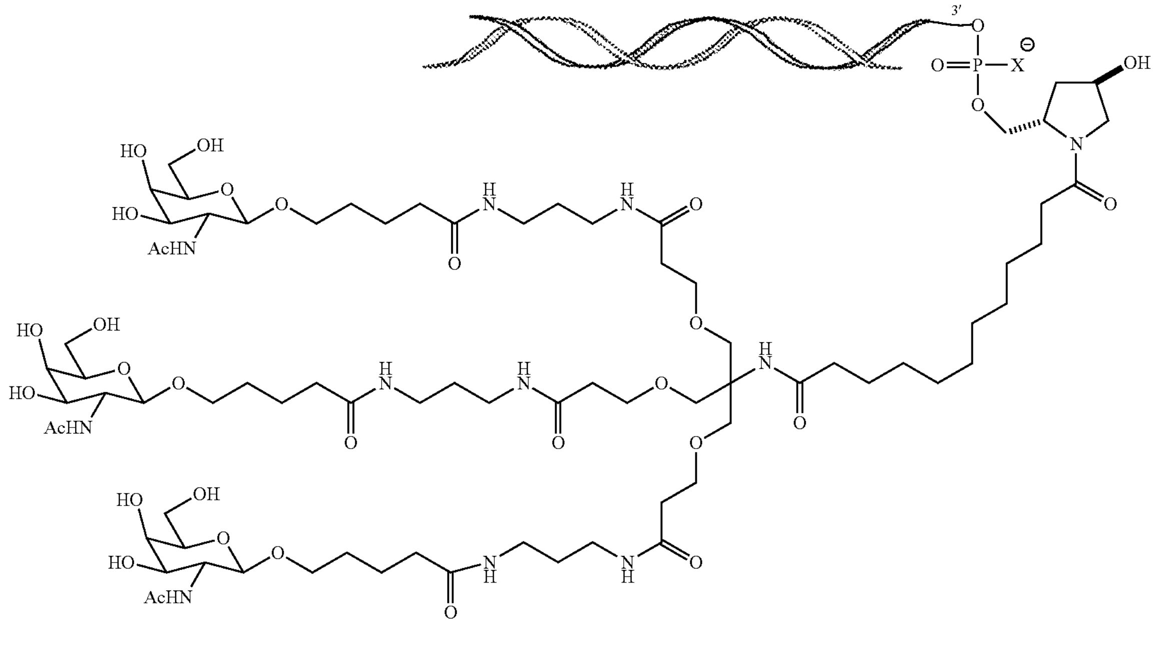

and, wherein X is O or S.

In one embodiment, the X is O.

In one embodiment, the region of complementarity comprises any one of the antisense nucleotide sequences of any one of Tables 2-4.

In another embodiment, the region of complementarity consists of any one of the antisense nucleotide sequences of any one of Tables 2-4.

In one embodiment, the modifications on the nucleotides are 2'-O-methyl or 2'-fluoro modifications.

In one embodiment, the agent further comprises at least one phosphorothioate or methylphosphonate internucleotide linkage.

In one embodiment, the phosphorothioate or methylphosphonate internucleotide linkage is at the 3'-terminus of one strand. In one embodiment, the strand is the antisense strand. In another embodiment, thestrand is the sense strand.

In one embodiment, the phosphorothioate or methylphosphonate internucleotide linkage is at the 5'-terminus of one strand. In one embodiment, the strand is the antisense strand. In another embodiment, the strand is the sense strand.

In one embodiment, the phosphorothioate or methylphosphonate internucleotide linkage is at the both the 5'- and 3'-terminus of one strand. In one embodiment, the strand is the antisense strand.

In one embodiment, thedsRNA agent is selected from the group of dsRNA agents listed in any one of Tables 2-4.

In one aspect, the present invention provides double stranded ribonucleic acid (dsRNA) agents for inhibiting expression of a High Density Lipoprotein Binding Protein (Hdlbp/Vigilin) gene in a cell, wherein the dsRNA agent comprises a sense strand and an antisense strand forming a double stranded region, the antisense strand comprising a region of complementarity which comprises at least 15 contiguous nucleotides differing by no more than 3 nucleotides from the nucleotide sequence of SEQ ID NO:11, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus, wherein substantially all of the nucleotides of the antisense strand comprise a nucleotide modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, and wherein the sense strand is conjugated to one or more GalNAc derivatives attached through a branched bivalent or trivalent linker at the 3'-terminus.

In one aspect, the present invention provides double stranded ribonucleic acid (RNAi) agents for inhibiting expression of a High Density Lipoprotein Binding Protein (Hdlbp/Vigilin) gene. The double stranded RNAi agents include a sense strand and an antisense strand, wherein the sense strand comprising the nucleotide sequence of 5'-GfsasGfaUfcAfaCfAfUfuGfaCfcAfuAfaAf-3' (SEQ ID NO: 1) and the antisense strand comprising the nucleotide sequence of 5'-usUfsuAfuGfgUfcAfaugUfuGfaUfcUfcsusa-3' (SEQ ID NO: 2), wherein A, C, G, and U are ribose A, C, G, or U; a, c, g, and u are 2'-O-methyl (2'-OMe) A, C, G, or U; Af, Cf, Gf, and Uf are 2'-fluoro A, C, G, or U; and s is a phosphorothioate linkage.

In another aspect, the present invention provides double stranded ribonucleic acid (RNAi) agents for inhibiting expression of a High Density Lipoprotein Binding Protein (Hdlbp/Vigilin) gene. The double stranded RNAi agents include a sense strand and an antisense strand, wherein the sense strand comprising the nucleotide sequence of 5'-AfsgsGfaAfgAfuCfGfGfgCfuUfuAfaGfgAf-3' (SEQ ID NO: 3) and the antisense strand comprising the nucleotide sequence of 5'-usCfscUfuAfaAfgCfccgAfuCfuUfcCfusgsc-3' (SEQ ID NO: 4), wherein A, C, G, and U are ribose A, C, G, or U; a, c, g, and u are 2'-O-methyl (2'-OMe) A, C, G, or U; Af, Cf, Gf, and Uf are 2'-fluoro A, C, G, or U; and s is a phosphorothioate linkage.

In certain embodiments, the double stranded RNAi agent further comprises a ligand. In certain embodiments, the ligand is conjugated to the 3' end of the sense strand of the double stranded RNAi agent. In certain embodiments, the ligand is an N-acetylgalactosamine (GalNAc) derivative. In certain embodiments, the ligand is

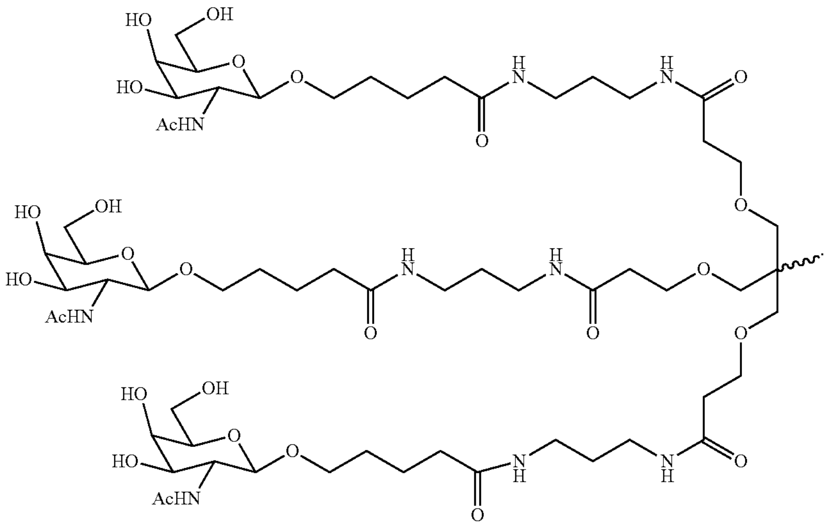 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In certain embodiments, the double stranded RNAi agent is conjugated to the ligand as shown in the following schematic

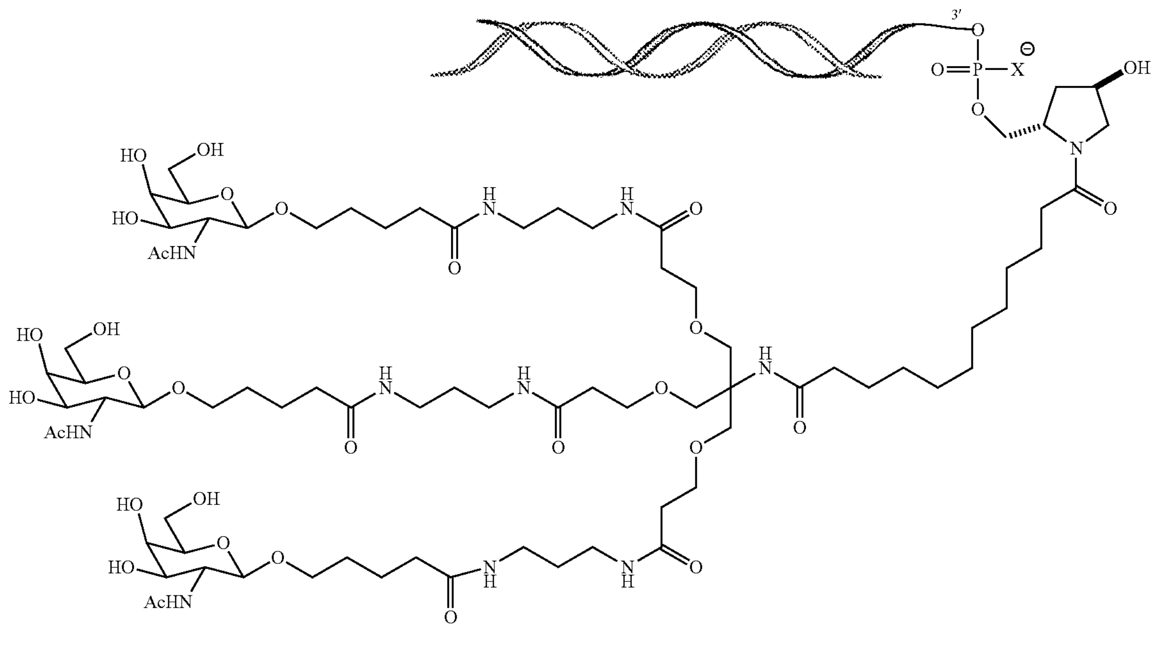

and, wherein X is O or S.

In some embodiments, the X is O.

In another aspect, the present invention provides a cell containing the double stranded RNAi agent as described herein.

In yet another aspect, the present invention provides a pharmaceutical composition for inhibiting expression of an Hdlbp/Vigilin gene comprising the double stranded RNAi agent as described herein.

In some embodiments, the double stranded RNAi agent is administered in an unbuffered solution. In other embodiments, the unbuffered solution is saline or water.

In some embodiments, the double stranded RNAi agent is administered with a buffer solution. In other embodiments, the buffer solution comprises acetate, citrate, prolamine, carbonate, or phosphate or any combination thereof. In certain embodiments, the buffer solution is phosphate buffered saline (PBS).

In one aspect, the present invention provides a pharmaceutical composition comprising the double stranded RNAi agent as described herein and a lipid formulation. In some embodiments, the lipid formulation comprises a LNP. In other embodiments, the lipid formulation comprises a MC3.

The invention also provides methods of inhibiting Hdlbp/Vigilin expression in a cell. The methods include contacting the cell with the double stranded RNAi agent or the pharmaceutical composition as described herein; and maintaining the cell for a time sufficient to obtain degradation of the mRNA transcript of an Hdlbp/Vigilin gene, thereby inhibiting expression of the Hdlbp/Vigilin gene in the cell.

In certin embodiments, the cell is within a subject. In certain embodiments, the subject is a human. In certain embodiments, the human subject suffers from a disorder of lipid metabolism. In certain embodiments, the disorder of lipid metabolism is hyperlipidemia, such as hypercholesterolemia, hypertriglyceridemia, and mixed hyperlipidemia.

In another aspect, the invention provides methods of treating a subject having a disorder that would benefit from reduction in expression of a High Density Lipoprotein Binding Protein (Hdlbp/Vigilin) gene. The methods include administering to the subject a therapeutically effective amount of any of the double stranded RNAi agents or the pharmaceutical composition provided herein, thereby treating the subject.

In certain embodiments, the subject is a human.

In certain embodiments, the disorder is a disorder of lipid metabolism. In certain embodiments, the disorder of lipid metabolism is a hyperlipidemia. In certain embodiments, the disorder of lipid metabolism is hypercholesterolemia. In certain embodiments, the disorder of lipid metabolism is hypertriglyceridemia. In certain embodiments, the disorder of lipid metabolism is mixed hyperlipidemia.

In certain embodiments, the methods of the present invention further comprise administering an additional therapeutic agent.

In some embodiments, the double stranded RNAi agent is administered at a dose of about 0.01 mg/kg to about 50 mg/kg. In other embodiments, the dsRNA agent is administered to the subject subcutaneously.

In certain embodiments, the methods of the present invention further comprise measuring serum lipid levels, plasma glucose levels, fasting blood glucose levels, plasma insulin levels, plasma triglyceride levels, and/or plasma cholesterol levels in the subject.

In some embodiments, following administration of the double stranded RNAi agent to the subject Hdlbp/Vigilin protein accumulation is decreased; the plasma cholesterol level in the subject is decreased; the plasma triglyceride level in the subject is decreased; the serum VLDL level in the subject is decreased; the serum LDL level in the subject is decreased; the plasma insulin level in the subject is decreased; insulin sensitivity in the subject is increased; glucose tolerance in the subject is increased; and/or atherosclerotic plaque formation in the subject is decreased.

In a further aspect, the present invention also provides methods of inhibiting the expression of Hdlbp/Vigilin in a subject. The methods include administering to the subject a therapeutically effective amount of any of the double stranded RNAi agents or the pharmaceutical compositions provided herein, thereby inhibiting the expression of Hdlbp/Vigilin in the subject.

BRIEF DESCRIPTION OF THE DRAWINGS

(FIG. 3A) Autoradiograph of crosslinked, $^{32}$P-labelled, hVigilin-RNA immunoprecipitate separated by SDS-polyacrylamide gel electrophoresis after PAR-CLIP and overlap of binding sites for the two biological replicates. Distribution of PAR-CLIP binding sites (overlap of replicates) identified by PARalyzer in various RNA-species; (FIG. 3B) distribution of T-C reads along ORFs and 3'UTRs of mRNA targets (FIG. 3C). (FIG. 3D) kmer-plot and sequence logo representation of the Vigilin RRE derived from PAR-CLIP binding sites: CxxC and CxyC (x=A/C/U; y=C/U). (FIG. 3E) Electrophoretic Mobility Shift Assays (EMSAs) validated affinity of Vigilin to CU-rich sequences: synthetic RNAs representing 18-nt di- or trinucleotide repeats were radiolabeled (10 nM), incubated with 2 μM $His_6$-tagged (SEQ ID NO: 21) recombinant human Vigilin and separated on 1% agarose gel. (FIG. 3F) Enrichment analysis of cluster fractions from PAR-CLIP containing tandem RREs from FIG. 3D separated by 0-8 nt spacers compared to mouse ORF sequences (background). Steady state mRNA expression changes in gain (FIG. 3G) and loss of function (FIG. 3H) of Vigilin were determined by RNA-seq. The empirical cumulative distribution function (CDF) of Vigilin PAR-CLIP targets (colored lines) was plotted and compared to expressed non-targets (FPKM≥1, black and grey lines). (FIG. 3I) CDF of ribosome association changes of the top 100 PAR-CLIP-targets (based on cumulative T-to-C counts, red line) compared to poor targets (remaining targets, blue line) and non-targets (grey line) upon knockdown of Vigilin. The median transcript abundance change is indicated by a dot on the x-axis. ***P≤0.001. Significance and p-values were determined by the Kolmogorov-Smirnov-test. FIG. 3F discloses SEQ ID NOS: 257-265, 261, and 266-274, respectively, in order of appearance.

FIG. 4B). CyyC-2 nt-CyyC RRE is indicated in bold letters. FIG. 4A discloses SEQ ID NOS 275-286, respectively, in order of appearance. FIG. 4B discloses SEQ ID NOS 261, 261, 287, 288, 263, 261, 289, 290, 263, 261, 287, and 288, respectively, in order of appearance.

(FIG. 5A) CDF plot displaying fold changes in secretion upon knockdown of Vigilin in primary hepatocytes of Top100 PAR-CLIP targets (based on T-to-C counts, red line), poor targets (remaining targets, blue line) and non-targets (grey line). (FIG. 5B) Volcano plot of differentially secreted proteins upon Vigilin knockdown in primary hepatocytes. x-axis: Log2 fold change of intensities, y-axis: $-Log_{10}$ p-values. Significant hits among secreted Top100 PAR-CLIP targets (based on T-to-C counts) are indicated in red dots, other significant targets in blue, non-targets and non-significant hits in grey. Significance was determined via false discovery rate (FDR)-corrected, permutation-based multiple t-tests (250×) and curve bend s0. (FIG. 5C) Plot of differentially secreted PAR-CLIP targets (x-axis) against T-to-C counts (y-axis) indicates downregulation of more frequently bound targets. (FIG. 5D) Validation of MS-LFQ data using western blotting of 5 targets from medium of primary hepatocytes and in vivo from blood plasma of DIO mice injected with Ad-shCTRL or Ad-shVIG. (FIG. 5E) Vigilin EMSAs representing binding sites on ApoB and Fetuin-A mRNAs identified by PAR-CLIP. Upper panel: alignment of Vigilin PAR-CLIP sequence reads to gene loci of ApoB and Fetuin-A mRNA ORFs. RREs are highlighted in yellow. Lower panel: autoradiograph of EMSAs performed using binding site sequences identified by PAR-CLIP, mutated RREs (indicated in red) and scrambled sequences of these sites. RNA sequences indicated below. (FIG. 5F) $^{14}C$ counts of radiolabeled palmitic acid incorporated into triglycerides and secreted into the medium by primary hepatocytes upon knockdown of Vigilin. Primary hepatocytes were isolated from C57Bl6 mice injected with either Ad-GFP versus Ad-hVigilin (for gain of function) or Ad-shCTRL versus Ad-shVIG (for loss of function) and pulse chased with $^{14}C$-labeled palmitic acid for incorporation into triglycerides. Lipids from the medium were extracted and quantified using $^{14}C$ scintillation counting. (FIG. 5G) Autoradiograph of in vitro translation assays using fresh liver extracts from Ad-shCTRL or Ad-shVIG injected mice. Synthetic mRNAs (scheme indicated in lower panel) of Fetuin-A and ApoM (as control for non-target) were translated into V5-tagged and $^{35}S$-Met radiolabelled protein, immunoprecipitated and separated by SDS-polyacrylamide gel electrophoresis. Fetuin-A mRNA with premature stop-codon before C-terminal V5-tag (#3) was used as a negative control for immunoprecipitation. FIG. 5E discloses SEQ ID NOS 291-326, respectively, in order of appearance.

(FIG. 6A) 82 of the top 100 Vigilin targets identified by PAR-CLIP are secretory pathway proteins either containing a signal peptide (SignalP; 34), ≥1 transmembrane domains (32) or both (16). qPCR analysis of secreted mRNA targets among top 100 with highest downregulation of protein levels upon knockdown of Vigilin in primary hepatocytes (FIG. 6B). Immunoblot analysis of targets from FIG. 6B in blood plasma of chow fed wildtype (Chow), diet-induced obese (DIO) and ob/ob mice (FIG. 6C) and their correlation with hepatic Vigilin expression (FIG. 6D). Primary hepatocytes were treated with cycloheximide for translational stop and harvested at indicated time points for half-life assessment of ApoB (FIG. 6E) and FetuinA (FIG. 6F). *P≤0.05, **P≤0.01; p-values and $R^2$ were determined by two-tailed Pearson's correlation test (FIG. 6D).

(FIG. 7A) Quantification of hepatic Vigilin knockdown in male $Ldlr^{-/-}$ mice with weekly injections of two different GalNAc-conjugated siRNAs targeting Vigilin (siVIG-GalNAc#1: n=10, siVIG-GalNAc#2: n=10) or PBS (n=9) for 18 weeks starting at 4 weeks of age. Values are shown relative to PBS injected mice controls. (FIG. 7M Western blot analysis of Vigilin targets from blood plasma. Non-target ApoM and unregulated target ApoA-I were used as controls for protein synthesis and secretion. Time course of plasma cholesterol (FIG. 7C) and triglyceride (FIG. 7D) levels throughout treatment period. Fractionated blood plasma from treated mice indicating VLDL, LDL and HDL particles that were quantified through cholesterol (FIG. 7E) and triglyceride (FIG. 7F) levels in each fraction. Quantification of hepatic cholesterol (FIG. 7G) and triglyceride (FIG. 7H) levels. Quantification of plasma bile acid (FIG. 7I), insulin (FIG. 7J) and NEFA levels (FIG. 7K). (FIGS. 7L and 7M) Characterization of atherosclerosis in mice from FIG. 1A. H&E- and Oil-Red O stained aortic root sections (FIG. 7L) and quantification of the lesion areas (FIG. 7M). *P<0.05, **P<0.01 and $^{\#}$ P<0.05, $^{\#\#}$ P<0.01, $^{\#\#\#}$ P<0.001 determined by ANOVA with Tukey's (FIGS. 7C and 7D) or Holm-Sidak (FIGS. 7A, G-K and M) post hoc analysis. Ail data are shown as the mean±s.d.

FIG. 8C) and intraperitoneal insulin tolerance test (ITT, FIG. 8D) were performed after 17 weeks of treatment (n=8 per group). *P<0.05, **P<0.01 determined by ANOVA with Tukey's post hoc analysis. All data are shown as the mean±s.d.

DETAILED DESCRIPTION OF THE INVENTION

Figure 1B:
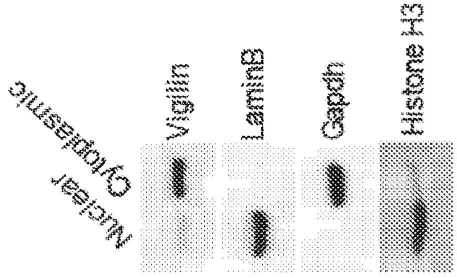
FIGS. 1A-R depict that hepatic modulation of Vigilin regulates lipid metabolism. Western blot analysis of Vigilin in mouse tissues (FIG. 1A) as well as nuclear and cytoplasmic fractions from primary hepatocytes (FIG. 1B) Immunoblot analysis of hepatic Vigilin levels in chow fed wildtype (Chow), diet-induced obese (DIO) and ob/ob mice (FIG. 1C). Correlation between hepatic Vigilin expression quantified by densitometry from C (n=6 per group) and plasma triglyceride, non-esterified fatty acid (NEFA) and cholesterol levels (FIG. 1D) as well as HOMA IR (FIG. 1E). Correlation between steatosis BMI, HOMA IR and hepatic Vigilin expression quantified by immunoblotting and densitometry from human liver biopsies including 5 healthy, 10 non-alcoholic fatty liver disease (NAFLD) and 10 non-alcoholic steatohepatitis (NASH) patients (FIGS. 1F-H). Relative expression of human Vigilin (hVigilin) in livers of 10-week-old C57BL/6 mice injected with Ad-GFP or Ad-hVigilin for gain of function (i; n=5 per group). Values are densitometric readouts normalized to tubulin. Plasma triglyceride (FIG. 1J), NEFA (FIG. 1K) and cholesterol (FIG. 1L) levels of mice from i. Fractionated blood plasma from mice injected with Ad-GFP or Ad-hVigilin into Very Low Density Lipoprotein (VLDL), Low Density Lipoprotein (LDL) and High Density Lipoprotein (HDL) particles that were quantified through measurements of triglyceride and cholesterol levels in each fraction and used for western blot analysis of VLDL/LDL (ApoB48/100) as well as HDL (ApoA-I) markers (FIG. 1M). Relative expression of Vigilin in livers of 10-week-old wildtype (WT) and DIO C57Bl/6 mice injected with Ad-shCTRL (n=6 for WT, n=8 for DIO), Ad-shVIG (n=6 for WT, n=8 for DIO) or PBS (n=3 for WT, n=5 for DIO) for loss of function (FIG. 1N). Values are densitometric readouts normalized to tubulin. Plasma triglyceride (FIG. 1O), NEFA (FIG. 1P) and cholesterol (FIG. 1Q) levels of DIO mice treated as in FIG. 1N. Fractionated plasma from DIO mice injected with Ad-shCTRL or Ad-shVIG into VLDL/LDL/HDL particles that were quantified as in FIG. 1M (FIG. 1R). All values are expressed as mean±s.d. *P≤0.05, P≤0.01, *P≤0.001; p-values and $R^2$ were determined by two-tailed Pearson's correlation test (FIGS. 1G and 1H), student's t-test (FIGS. 1I-L) or ANOVA with Holm-Sidak post hoc analysis (FIGS. 1N-Q).
Figure 1A:
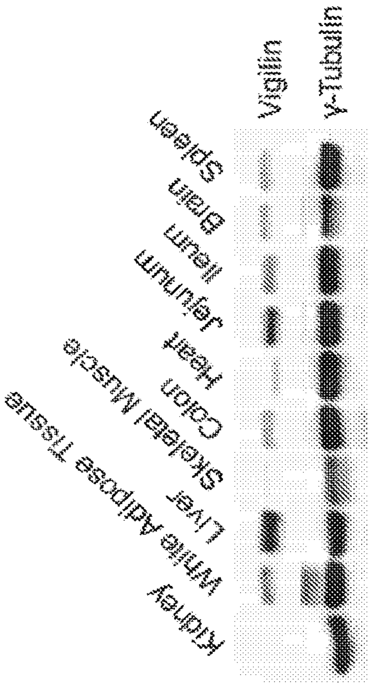

The present invention provides iRNA compositions, which effect the RNA-induced silencing complex (RISC)-mediated cleavage of RNA transcripts of a High Density Lipoprotein Binding Protein (Hdlbp/Vigilin) gene. The iRNA agents of the invention have been designed to target an Hdlbp/Vigilin gene, including portions of the gene that are conserved in the Hdlbp/Vigilin othologs of other mammalian species. The Hdlbp/Vigilin gene may be within a cell, e.g., a cell within a subject, such as a human. The use of these iRNAs agents enable the targeted degradation of mRNAs of the corresponding gene (Hdlbp/Vigilin) in mammals. Accordingly, the present invention also provides methods of using the iRNA compositions of the invention for inhibiting the expression of an Hdlbp/Vigilin gene and/or for treating a subject having a disorder that would benefit from inhibiting or reducing the expression of an Hdlbp/Vigilin gene, e.g., a disorder of lipid metabolism, such as a hyperlipidemia, e.g, mixed hyperlipidemia, hypertriglyceridemia and hypercholesterolemia.

The iRNA agents of the invention may include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an Hdlbp/Vigilin gene.

In certain embodiments, the iRNAs of the invention include an RNA strand (the antisense strand) which can include longer lengths, for example up to 66 nucleotides, e.g., 36-66, 26-36, 25-36, 31-60, 22-43, 27-53 nucleotides in length with a region of at least 19 contiguous nucleotides that is substantially complementary to at least a part of an mRNA transcript of a Hdlbp/Vigilin gene. These iRNAs with the longer length antisense strands preferably include a second RNA strand (the sense strand) of 20-60 nucleotides in length wherein the sense and antisense strands form a duplex of 18-30 contiguous nucleotides.

The use of these iRNAs enables the targeted degradation of mRNAs of an Hdlbp/Vigilin gene in mammals. Very low dosages of Hdlbp/Vigilin iRNAs, in particular, can specifically and efficiently mediate RNA interference (RNAi), resulting in significant inhibition of expression of an Hdlbp/Vigilin gene. Using cell-based assays, the present inventors have demonstrated that iRNAs targeting Hdlbp/Vigilin can mediate RNAi, resulting in significant inhibition of expression of an Hdlbp/Vigilin gene. Thus, methods and compositions including these iRNAs are useful for treating a subject who would benefit by a reduction in the levels and/or activity of an Hdlbp/Vigilin protein, such as a subject having a disorder of lipid metabolism, such as mixed hyperlipidemia, hypertriglyceridemia or hypercholesterolemia.

The following detailed description discloses how to make and use compositions containing iRNAs to inhibit the expression of an Hdlbp/Vigilin gene, as well as compositions and methods for treating subjects having diseases and disorders that would benefit from inhibition and/or reduction of the expression of this gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to". The term "or" is used herein to mean, and is used interchangeably with, the term "and/or," unless context clearly indicates otherwise.

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

The term "Hdlbp/Vigilin" refers to High Density Lipoprotein Binding Protein having an amino acid sequence from any vertebrate or mammalian source, including, but not limited to, human, bovine, chicken, rodent, mouse, rat, porcine, ovine, primate, monkey, and guinea pig, unless specified otherwise. The term also refers to fragments and variants of native Hdlbp/Vigilin that maintain at least one in vivo or in vitro activity of a native Hdlbp/Vigilin. The term encompasses full-length unprocessed precursor forms of Hdlbp/Vigilin as well as mature forms resulting from post-translational cleavage of the signal peptide. The nucleotide and amino acid sequence of a human Hdlbp/Vigilin can be found at, for example, GenBank Accession No. GI: 1004170703 (NM_005336.5; SEQ ID NO:5), GenBank Accession No. GI: 1004170704 (NM_203346.4; SEQ ID NO:6), and GenBank Accession No. GI: 1004170705 (NM_001243900.2; SEQ ID NO:7). Additional examples of Hdlbp/Vigilin sequences are readily available using publicly available databases, e.g., GenBank, UniProt, and OMIM.

The term"Hdlbp/Vigilin" as used herein also refers to a particular polypeptide expressed in a cell by naturally occurring DNA sequence variations of the Hdlbp/Vigilin gene, such as a single nucleotide polymorphism in the Hdlbp/Vigilin gene. Numerous SNPs within the Hdlbp/Vigilin gene have been identified and may be found at, for example, NCBI dbSNP (see, e.g., www.ncbi.nlm nih.gov/snp).

As used herein, "target sequence" refers to a contiguous portion of the nucleotide sequence of an mRNA molecule formed during the transcription of an Hdlbp/Vigilin gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of an Hdlbp/Vigilin gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent," "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of Hdlbp/Vigilin in a cell, e.g., a cell within a subject, such as a mammalian subject.

In one embodiment, an RNAi agent of the invention includes a single stranded RNAi that interacts with a target RNA sequence, e.g., an Hdlbp/Vigilin target mRNA sequence, to direct the cleavage of the target RNA. Without wishing to be bound by theory it is believed that long double stranded RNA introduced into cells is broken down into double stranded short interfering RNAs (siRNAs) comprising a sense strand and an antisense strand by a Type III endonuclease known as Dicer (Sharp et al. (2001) *Genes Dev.* 15:485). Dicer, a ribonuclease-III-like enzyme, processes these dsRNA into 19-23 base pair short interfering RNAs with characteristic two base 3' overhangs (Bernstein, et al., (2001) *Nature* 409:363). These siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (ssRNA) (the antisense strand of an siRNA duplex) generated within a cell and which promotes the formation of a RISC complex to effect silencing of the target gene, i.e., an Hdlbp/Vigilin gene. Accordingly, the term "siRNA" is also used herein to refer to an RNAi as described above.

In another embodiment, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In another embodiment, an "iRNA" for use in the compositions and methods of the invention is a double stranded RNA and is referred to herein as a "double stranded RNAi agent," "double stranded RNA (dsRNA) molecule," "dsRNA agent" or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., an Hdlbp/Vigilin gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified internucleotide linkage, and/or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

In some embodiments, a dsRNA agent of the invention comprises a tetraloop. As used herein, "tetraloop" in the context of a dsRNA refers to a loop (a single stranded region) consisting of four nucleotides that forms a stable secondary structure that contributes to the stability of adjacent Watson-Crick hybridized nucleotides. Without being limited to theory, a tetraloop may stabilize an adjacent Watson-Crick base pair by stacking interactions. In addition, interactions among the four nucleotides in a tetraloop include but are not limited to non-Watson-Crick base pairing, stacking interactions, hydrogen bonding, and contact interactions (Cheong et al., Nature 1990 Aug. 16; 346 (6285):680-2; Heus and Pardi, Science 1991 Jul. 12; 253 (5016): 191-4). A tetraloop confers an increase in the melting temperature (Tm) of an adjacent duplex that is higher than expected from a simple model loop sequence consisting of four random bases. For example, a tetraloop can confer a melting temperature of at least 55° C. in 10 mM NaHPO4 to a hairpin comprising a duplex of at least 2 base pairs in length. A tetraloop may contain ribonucleotides, deoxyribonucleotides, modified nucleotides, and combinations thereof. Examples of RNA tetraloops include the UNCG family of tetraloops (e.g., UUCG), the GNRA family of tetraloops (e.g., GAAA), and the CUUG tetraloop. (Woese et al., Proc Natl Acad Sci USA. 1990 November; 87(21): 8467-71; Antao et al., Nucleic Acids Res. 1991 Nov. 11; 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, the d(TNCG) family of tetraloops (e.g., d(TTCG)). (Nakano et al. Biochemistry, 41 (48), 14281-14292, 2002; SHINJI et al. Nippon Kagakkai Koen Yokoshu VOL. 78th; NO. 2; PAGE. 731 (2000).)

In certain embodiments of the invention, tetraloop- and modified nucleotide-containing dsNAs are contemplated as described, e.g., in US 2011/0288147, the entire contents of which are incorporated by reference herein. In certain such embodiments, a dsNA of the invention possesses a first strand and a second strand, where the first strand and the second strand form a duplex region of 19-25 nucleotides in length, wherein the first strand comprises a 3' region that extends beyond the first strand-second strand duplex region and comprises a tetraloop, and the dsNA comprises a discontinuity between the 3' terminus of the first strand and the 5' terminus of the second strand.

Optionally, the discontinuity is positioned at a projected dicer cleavage site of the tetraloop-containing dsNA. It is contemplated that, as for any of the other dupexed oligonucleotides of the invention, tetraloop-containing duplexes of the invention can possess any range of modifications disclosed herein or otherwise known in the art, including, e.g., 2'-O-methyl, 2'-fluoro, inverted base, GalNAc moieties, etc. Typically, every nucleotide on both strands of the tetraloop-containing dsNA is chemically modified if the tetraloop-containing dsNA is going to be delivered without using lipid nanoparticles or some other delivery method that protects the dsNA from degradation during the delivery process. However, in certain embodiments, one or more nucleotides are not modified.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one embodiment, an RNAi agent of the invention is a dsRNA, interacts with a target RNA sequence, e.g., an Hdlbp/Vigilin target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt.

Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double stranded over its entire length.

The term "antisense strand" or "guide strand" refers to the strand of an iRNA, e.g., a dsRNA, which includes a region that is substantially complementary to a target sequence, e.g., an Hdlbp/Vigilin mRNA.

As used herein, the term "region of complementarity" refers to the region on the antisense strand that is substantially complementary to a sequence, for example a target sequence, e.g., an Hdlbp/Vigilin nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand" or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding Hdlbp/Vigilin). For example, a polynucleotide is complementary to at least a part of an Hdlbp/Vigilin mRNA if the sequence is substantially complementary to a non-interrupted portion of an mRNA encoding Hdlbp/Vigilin.

Accordingly, in some embodiments, the antisense polynucleotides disclosed herein are fully complementary to the target Hdlbp/Vigilin sequence. In some embodiments, the sense polynucleotides disclosed herein are fully complementary to the antisense sequence of a target Hdlbp/Vigilin sequence.

In other embodiments, the antisense polynucleotides disclosed herein are substantially complementary to the target Hdlbp/Vigilin sequence and comprise a contiguous nucleotide sequence which is at least about 80% complementary over its entire length to the equivalent region of the nucleotide sequence of SEQ ID NO:5, or a fragment of SEQ ID NO:5, such as about 85%, about 86%, about 87%, about 88%, about 89%, about 90%, about % 91%, about 92%, about 93%, about 94%, about 95%, about 96%, about 97%, about 98%, or about 99% complementary.

In other embodiments, the sense polynucleotides disclosed herein are substantially complementary to the antisense sequence of a target Hdlbp/Vigilin sequence and comprise a contiguous nucleotide sequence which is at least about 80% complementary over its entire length to the equivalent region of the nucleotide sequence of SEQ ID NO:11, or a fragment of SEQ ID NO:11, such as about 85%, about 86%, about 87%, about 88%, about 89%, about 90%, about % 91%, about 92%, about 93%, about 94%, about 95%, about 96%, about 97%, about 98%, or about 99% complementary.

In one embodiment, an RNAi agent of the invention includes a sense strand that is substantially complementary to an antisense polynucleotide which, in turn, is complementary to a target Hdlbp/Vigilin sequence and comprises a contiguous nucleotide sequence which is at least about 80% complementary over its entire length to any one of the sense strand nucleotide sequences in any one of Tables 2-4, or a fragment of any one of the sense strand nucleotide sequences in any one of Tables 2-4, such as about 85%, about 86%, about 87%, about 88%, about 89%, about 90%, about % 91%, about 92%, about 93%, about 94%, about 95%, about 96%, about 97%, about 98%, or about 99% complementary.

In some embodiments, an iRNA of the invention includes an antisense strand that is substantially complementary to the target Hdlbp/Vigilin sequence and comprises a contiguous nucleotide sequence which is at least about 80% complementary over its entire length to the equivalent region of the nucleotide sequence of any one of the antisense strand nucleotide sequences in any one of Tables 2-4, or a fragment of any one of the antisense strand nucleotide sequences in any one of Tables 2-4, such as at least 85%, 90%, 95% complementary, or 100% complementary.

In other embodiments, the antisense strand polynucleotides disclosed herein are substantially complementary to the target Hdlbp/Vigilin sequence and comprise the nucleotide sequence of 5'-usUfsuAfuGfgUfcAfaugUfuGfaUfcUfcsusa-3' (SEQ ID NO: 2). In certain embodiments, the antisense strand polynucleotides disclosed herein are substantially complementary to the target Hdlbp/Vigilin sequence and comprise the nucleotide sequence of 5'-usCfscUfuAfaAfgCfccgAfuCfuUfcCfusgsc-3' (SEQ ID NO: 4).

In one embodiment, an RNAi agent of the invention includes a sense strand that is substantially complementary to an antisense polynucleotide which, in turn, is the same as a target Hdlbp/Vigilin sequence. In some embodiments, and wherein the sense strand polynucleotide comprises the nucleotide sequence of 5'-GfsasGfaUfcAfaCfAfUfuGfaCfcAfuAfaAf-3' (SEQ ID NO: 1). In certain embodiments, the sense strand polynucleotides disclosed herein comprise the nucleotide sequence of 5'-AfsgsGfaAfgAfuCfGfGfgCfuUfuAfaGfgAf-3' (SEQ ID NO: 3).

In one embodiment, at least partial suppression of the expression of an Hdlbp/Vigilin gene, is assessed by a reduction of the amount of Hdlbp/Vigilin mRNA which can be isolated from or detected in a first cell or group of cells in which an Hdlbp/Vigilin gene is transcribed and which has or have been treated such that the expression of an Hdlbp/Vigilin gene is inhibited, as compared to a second cell or group of cells substantially identical to the first cell or group of cells but which has or have not been so treated (control cells). The degree of inhibition may be expressed in terms of:

$$\frac{(mRNA \text{ in control cells}) - (mRNA \text{ in treated cells})}{(mRNA \text{ in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one embodiment, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vitro introduction into a cell includes methods known in the art such as electroporation and lipofection. Further approaches are described herein below and/or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in Hdlbp/Vigilin expression; a human at risk for a disease, disorder or condition that would benefit from reduction in Hdlbp/Vigilin expression; a human having a disease, disorder or condition that would benefit from reduction in Hdlbp/Vigilin expression; and/or human being treated for a disease, disorder or condition that would benefit from reduction in Hdlbp/Vigilin expression as described herein.

As used herein, the terms "treating" or "treatment" refer to a beneficial or desired result including, such as lowering levels of triglycerides in a subject. The terms "treating" or "treatment" also include, but are not limited to, alleviation or amelioration of one or more symptoms of a disorder of lipid metabolism, such as, e.g., a decrease in the size of atherosclerotic plaque. "Treatment" can also mean prolonging survival as compared to expected survival in the absence of treatment.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, "prevention" or "preventing," when used in reference to a disease, disorder or condition thereof, that would benefit from a reduction in expression of an Hdlbp/Vigilin gene, such as a hyperlipidemia, refers to a reduction in the likelihood that a subject will develop a symptom associated with such disease, disorder, or condition, e.g., high triglyceride levels or large atherosclerotic plaques. The likelihood of developing a high tryglyceride level or large atherosclerotic plaque is reduced, for example, when an individual having one or more risk factors for a high tryglyceride level or a large atherosclerotic plaque either fails to develop high tryglyceride levels or atherosclerotic plaques or develops high tryglyceride levels or atherosclerotic plaques with less severity relative to a population having the same risk factors and not receiving treatment as described herein. The failure to develop a disease, disorder or condition, or the reduction in the development of a symptom associated with such a disease, disorder or condition i (e.g., by at least about 10% on a clinically accepted scale for that disease or disorder), or the exhibition of delayed symptoms delayed (e.g., by days, weeks, months or years) is considered effective prevention.

The interchangeably used terms "Hdlbp/Vigilin-associated disease" and "disorder that would benefit from a reduction in Hdlbp/Vigilin expression," as used herein, are intended to include any disease, disorder, or condition associated with the Hdlbp/Vigilin gene or protein. Exemplary Hdlbp/Vigilin-associated diseases include acquired or inherited "disorders of lipid metabolism" which include any disorder associated with or caused by a disturbance in lipid metabolism. For example, this term includes any disorder, disease or condition characterized by abnormal elevation of levels of any or all lipids and/or lipoproteins in the blood or a condition that can lead to abnormal elevation of levels of any or all lipids and/or lipoproteins in the blood, such as a hyperlipidemia, and other forms of lipid imbalance such as hypercholesterolemia, hypertriglyceridemia, mixed hyperlipidemia, as well as the pathological conditions associated with these disorders, e.g., congestive heart disease (CHD) and atherosclerosis.

Exemplary disorders of lipid metabolism include, but are not limited to, atherosclerosis, dyslipidemia, hypertriglyceridemia (including drug-induced hypertriglyceridemia, diuretic-induced hypertriglyceridemia, alcohol-induced hypertriglyceridemia, β-adrenergic blocking agent-induced hypertriglyceridemia, estrogen-induced hypertriglyceridemia, glucocorticoid-induced hypertriglyceridemia, retinoid-induced hypertriglyceridemia, and cimetidine-induced hypertriglyceridemia, and familial hypertriglyceridemia), acute pancreatitis associated with hypertriglyceridemia, chylomicron syndrom, familial chylomicronemia, Apo-E deficiency or resistance, LPL deficiency or hypoactivity, hyperlipidemia (including familial combined hyperlipidemia), familial partial lipodystrophy type 1 (FPLD1), hypercholesterolemia, mixed hyperlipidemia (or mixed hyperlipoproteinemia familial, gout associated with hypercholesterolemia, xanthomatosis (subcutaneous cholesterol deposits), hyperlipidemia with heterogeneous LPL deficiency, and hyperlipidemia with high LDL, heterogeneous LPL deficiency, and an induced or acquired disorder, such as a disorder induced or acquired as a result of a disease.

As used herein, the term "serum lipid" refers to any major lipid present in the blood. Serum lipids may be present in the blood either in free form or as a part of a protein complex, e.g., a lipoprotein complex. Non-limiting examples of serum lipids include triglycerides, cholesterol, such as total cholesterol, low density lipoprotein cholesterol (LDL-C), high-density lipoprotein cholesterol (HDL-C), very low density lipoprotein cholesterol (VLDL-C) and intermediate-density lipoprotein cholesterol (IDL-C).

In some embodiments, the disorder of lipid metabolism is a hyperlipidemia. As used herein, the term "hyperlipidemia" refers to any any disorder, disease or condition characterized by abnormal elevation of levels of any or all lipids, such as cholesterol and triglycerides, and/or lipoproteins in the blood or a condition that can lead to abnormal elevation of levels of any or all lipids and/or lipoproteins in the blood.

In one embodiment, the hyperlipidemia is hypertriglyceridemia.

As used herein, the term "hypertriglyceridemia" refers to a condition in which triglyceride levels are elevated, often caused or exacerbated by uncontrolled diabetes mellitus, obesity, and sedentary habits. This condition is a risk factor for coronary artery disease. Hypertriglyceridemia is usually asymptomatic until triglycerides are greater than 1000-2000 mg/dL. Signs and symptoms may include the following: pain in the mid-epigastric, chest, or back regions; nausea, vomiting, dyspnea, xanthomas, corneal arcus, and/or xanthelasmas In some embodiments, the hyperlipidemia is hypercholesterolemia.

As used herein the term "hypercholesterolemia" refers to a form of hyperlipidemia (elevated levels of lipids in the blood) in which there are high levels of cholesterol in the serum of a subject, e.g., at least about 240 mg/dL of total cholesterol.

In other embodiments, the hyperlipidemia is mixed hyperlipidemia.

As used herein the term "mixed hyperlipidemia" also referred to as type 5 hyperlipidemia refers to a form of hyperlipidemia in which there are elevated levels of VLDL and chylomicrons found in plasma in the serum of a subject, e.g., at least about 240 mg/dL of total cholesterol.

Cardiovascular diseases associated with disorders of lipid metabolism are also considered "disorders of lipid metabolism", as defined herein. These diseases may include coronary artery disease (also called ischemic heart disease), atherosclerosis, inflammation associated with coronary artery disease, restenosis, peripheral vascular diseases, and stroke.

Disorders related to body weight are also considered "disorders of lipid metabolism", as defined herein. Such disorders may include obesity, metabolic syndrome including independent components of metabolic syndrome (e.g., central obesity, FBG/pre-diabetes/diabetes, hypercholesterolemia, hypertriglyceridemia, and hypertension), hypothyroidism, uremia, and other conditions associated with weight gain (including rapid weight gain), weight loss, maintenance of weight loss, or risk of weight regain following weight loss.

Blood sugar disorders are further considered "disorders of lipid metabolism", as defined herein. Such disorders may include diabetes, hypertension, and polycystic ovarian syndrome related to insulin resistance. Other exemplary disorders of lipid metabolism may also include renal transplantation, nephrotic syndrome, Cushing's syndrome, acromegaly, systemic lupus erythematosus, dysglobulinemia, lipodystrophy, glycogenosis type I, and Addison's disease.

"Therapeutically effective amount," as used herein, is intended to include the amount of an RNAi agent that, when administered to a subject having a disorder of lipid metabolism, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an iRNA that, when administered to a subject having a disorder of lipid metabolism, is sufficient to prevent or ameliorate the disease or one or more symptoms of the disease. Ameliorating the disease includes slowing the course of the disease or reducing the severity of later-developing disease. The "prophylactically effective amount" may vary depending on the iRNA, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of an RNAi agent that produces some desired local or systemic effect at a reasonable benefit/risk ratio applicable to any treatment. iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to blood or plasma drawn from the subject.

II. iRNAs of the Invention

Described herein are iRNA agents which inhibit the expression of an Hdlbp/Vigilin gene. In one embodiment, the iRNA agent includes double stranded ribonucleic acid (dsRNA) molecules for inhibiting the expression of an Hdlbp/Vigilin gene in a cell, such as a cell within a subject, e.g., a mammal, such as a human having a disorder of lipid metabolism, e.g., mixed hyperlipidemia, hypertriglyceridemia or hypercholesterolemia. The dsRNA includes an antisense strand having a region of complementarity which is complementary to at least a part of an mRNA formed in the expression of an Hdlbp/Vigilin gene. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the Hdlbp/Vigilin gene, the iRNA inhibits the expression of the Hdlbp/Vigilin gene (e.g., a human Hdlbp/Vigilin gene) by at least about 10% as assayed by, for example, a PCR or branched DNA (bDNA)-based method, or by a protein-based method, such as by immunofluorescence analysis, using, for example, Western Blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an Hdlbp/Vigilin gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is between about 15 and about 23 nucleotides in length, or between about 25 and about 30 nucleotides in length. In general, the dsRNA is long enough to serve as a substrate for the Dicer enzyme. For example, it is well known in the art that dsRNAs longer than about 21-23 nucleotides can serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target Hdlbp/Vigilin expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an antisense sequence. The sense strand sequence may be selected from the group of sequences provided in any one of Tables 2-4, and the corresponding nucleotide sequence of the antisense strand of the sense strand may be selected from the group of sequences in any one of Tables 2-4. In this aspect, one of the two sequences is complementary to the other of the two sequences, with one of the sequences being substantially complementary to a sequence of an mRNA generated in the expression of an Hdlbp/Vigilin gene. As such, in this aspect, a dsRNA will include two oligonucleotides, where one oligonucleotide is described as the sense strand (passenger strand) in any one of Tables 2-4, and the second oligonucleotide is described as the corresponding antisense strand (guide strand) of the sense strand in any one of Tables 2-4. In one embodiment, the substantially complementary sequences of the dsRNA are contained on separate oligonucleotides. In another embodiment, the substantially complementary sequences of the dsRNA are contained on a single oligonucleotide.

It will be understood that, although the sequences in Tables 2 and 4 are described as modified and/or conjugated sequences, the RNA of the iRNA of the invention e.g., a dsRNA of the invention, may comprise any one of the sequences set forth in any one of Tables 2-4 that is unmodified, un-conjugated, and/or modified and/or conjugated differently than described therein.

The skilled person is well aware that dsRNAs having a duplex structure of between about 20 and 23 base pairs, e.g., 21, base pairs have been hailed as particularly effective in inducing RNA interference (Elbashir et al., (2001) *EMBO J.*, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided herein, dsRNAs described herein can include at least one strand of a length of minimally 21 nucleotides. It can be reasonably expected that shorter duplexes minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences provided herein, and differing in their ability to inhibit the expression of an Hdlbp/Vigilin gene by not more than about 5, 10, 15, 20, 25, or 30% inhibition from a dsRNA comprising the full sequence, are contemplated to be within the scope of the present invention.

In addition, the RNAs described herein identify a site(s) in an Hdlbp/Vigilin transcript that is susceptible to RISC-mediated cleavage. As such, the present invention further features iRNAs that target within this site(s). As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided herein coupled to additional nucleotide sequences taken from the region contiguous to the selected sequence in an Hdlbp/Vigilin gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified herein represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified herein, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA agent as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. The methods described herein or methods known in the art can be used to determine whether an iRNA containing a mismatch to a target sequence is effective in inhibiting the expression of an Hdlbp/Vigilin gene. Consideration of the efficacy of iRNAs with mismatches in inhibiting expression of an Hdlbp/Vigilin gene is important, especially if the particular region of complementarity in an Hdlbp/Vigilin gene is known to have polymorphic sequence variation within the population.

III. Modified iRNAs of the Invention

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA of the invention are modified. iRNAs of the invention in which "substantially all of the nucleotides are modified" are largely but not wholly modified and can include not more than 5, 4, 3, 2, or 1 unmodified nucleotides.

The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)._nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$) and 2'-fluoro (2'-F) Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA of the invention can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) *Angewandte Chemie, International Edition,* 30:613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

An iRNA of the invention can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research*

33(1):439-447; Mook, O R. et al., (2007) *Mol Canc Ther* 6(3):833-843; Grunweller, A. et al., (2003) *Nucleic Acids Research* 31(12):3185-3193).

In some embodiments, the iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series,* 52, 133-134 (2008) and Fluiter et al., *Mol. Biosyst.,* 2009, 10, 1039 hereby incorporated by reference).

Representative US publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

An iRNA of the invention can also be modified to include one or more bicyclic sugar moities. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.,* 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

An iRNA of the invention can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and -C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US Patent Publication No. 2012/0157511, the entire contents of which are incorporated herein by reference.

In certain specific embodiments, the RNAi agent for use in the methods of the invention is an agent selected from the group of agents listed in Table2. These agents may further comprise a ligand.

IV. iRNAs Conjugated to Ligands

In one embodiment, the iRNA of the invention involves chemically linking to one or more ligands, moieties or conjugates that enhance the activity, cellular distribution or cellular uptake of the iRNA. Such moieties include but are not limited to lipid moieties such as a cholesterol moiety (Letsinger et al., (1989) *Proc. Natl. Acid. Sci. USA,* 86: 6553-6556), cholic acid (Manoharan et al., (1994) *Biorg. Med. Chem. Let.,* 4:1053-1060), a thioether, e.g., beryl-S-tritylthiol (Manoharan et al., (1992) *Ann. N.Y. Acad. Sci.,* 660:306-309; Manoharan et al., (1993) *Biorg. Med. Chem. Let.,* 3:2765-2770), a thiocholesterol (Oberhauser et al., (1992) *Nucl. Acids Res.,* 20:533-538), an aliphatic chain, e.g., dodecandiol or undecyl residues (Saison-Behmoaras et al., (1991) *EMBO J*, 10:1111-1118; Kabanov et al., (1990) *FEBS Lett.*, 259:327-330; Svinarchuk et al., (1993) *Biochimie*, 75:49-54), a phospholipid, e.g., di-hexadecyl-rac-glycerol or triethyl-ammonium 1,2-di-O-hexadecyl-rac-glycero-3-phosphonate (Manoharan et al., (1995) *Tetrahedron Lett.*, 36:3651-3654; Shea et al., (1990) *NucL Acids Res.*, 18:3777-3783), a polyamine or a polyethylene glycol chain (Manoharan et al., (1995) *Nucleosides & Nucleotides*, 14:969-973), or adamantane acetic acid (Manoharan et al., (1995) *Tetrahedron Lett.*, 36:3651-3654), a palmityl moiety (Mishra et al., (1995) *Biochim. Biophys. Acta*, 1264:229-237), or an octadecylamine or hexylamino-carbonyloxycholesterol moiety (Crooke et al., (1996) *J. Pharmacol. Exp. Ther.*, 277:923-937).

In one embodiment, a ligand alters the distribution, targeting or lifetime of an iRNA agent into which it is incorporated. In some embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conujugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 9). An RFGF analogue (e g, amino acid sequence AALLPVLLAAP (SEQ ID NO: 10) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 19) and the *Drosophila* Antennapedia protein (RQIKIWFQNRRMKWKK (SEQ ID NO: 20) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glyciosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, a α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In one embodiment, the monosaccharide is an N-acetylgalactosamine, such as Formula II

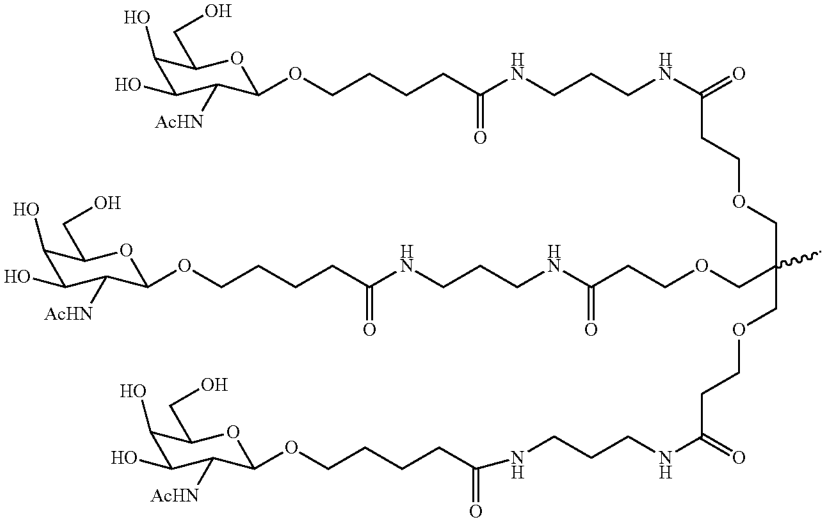

In another embodiment, a carbohydrate conjugate for use in the compositions and methods of the invention is selected from the group consisting of:

Formula II

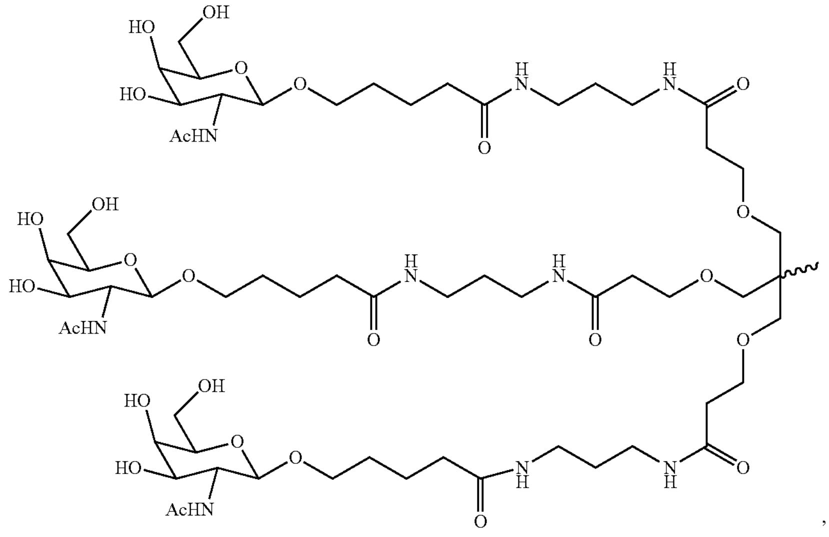

,

-continued
Formula III
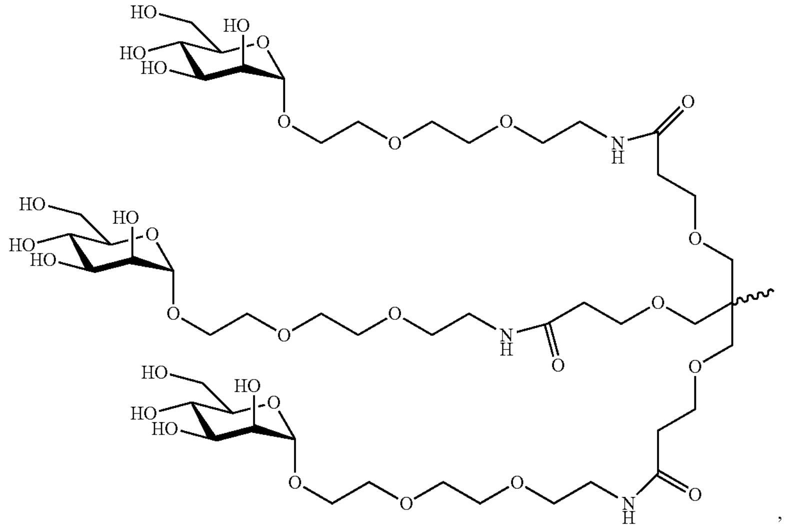
,
Formula IV
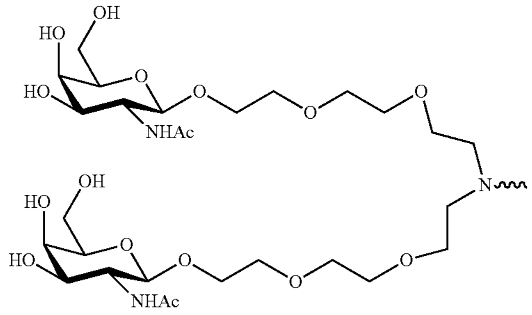
,
Formula V
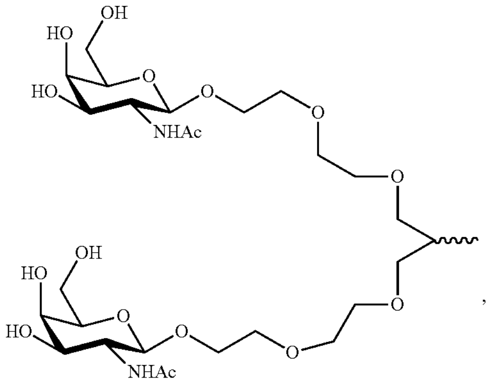
,
Formula VI
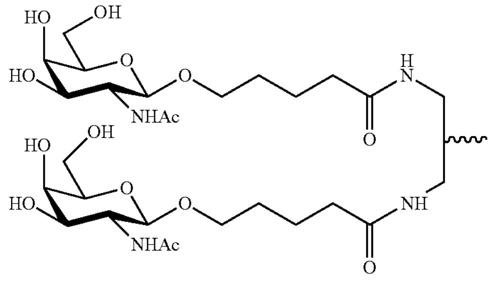
,
Formula VII
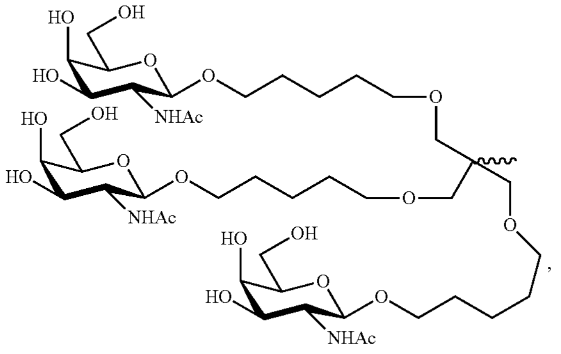
,
Formula VIII
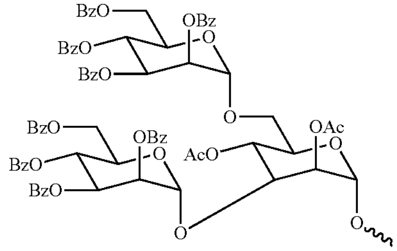
, -continued
Formula IX
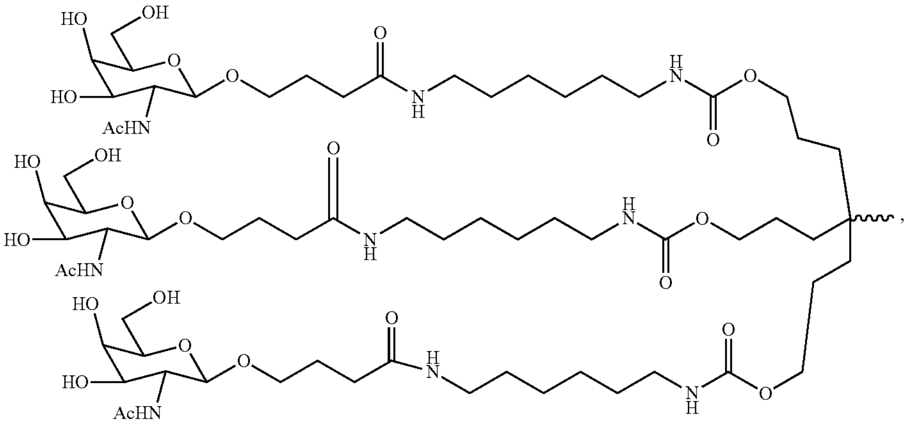
Formula X
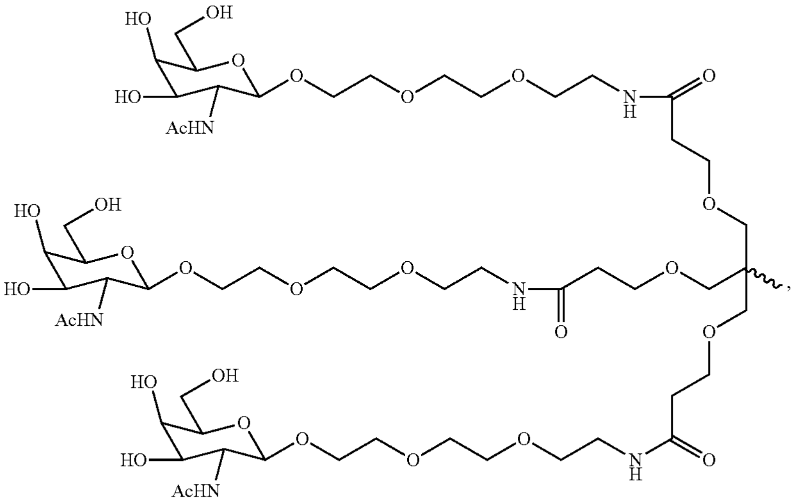
Formula XI
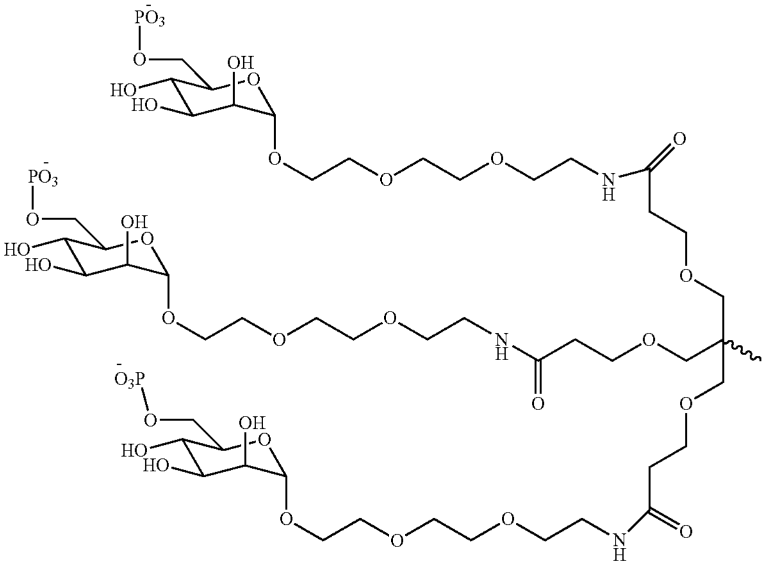
, -continued
Formula XII
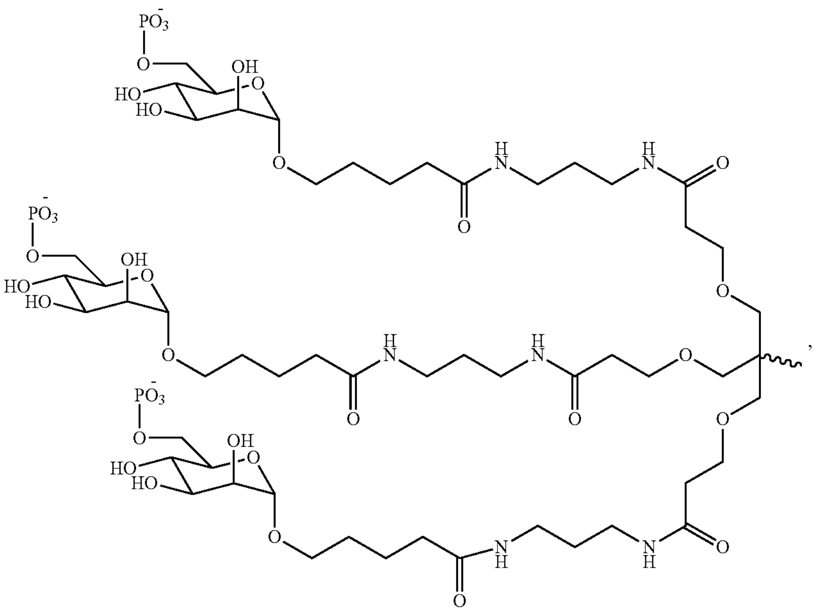
Formula XIII
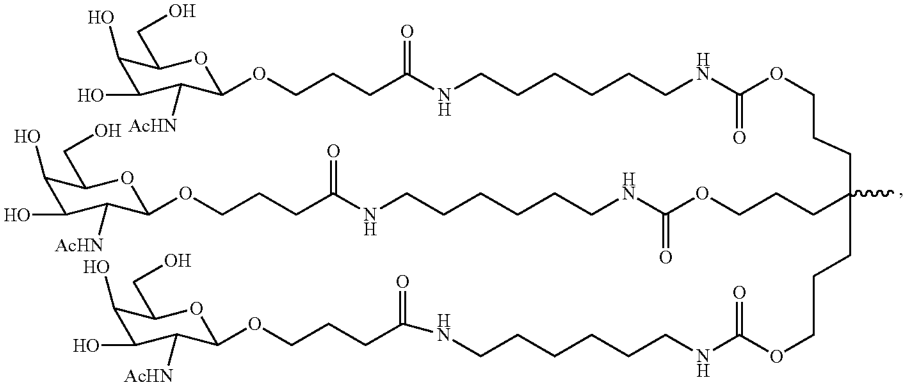
Formula XIV
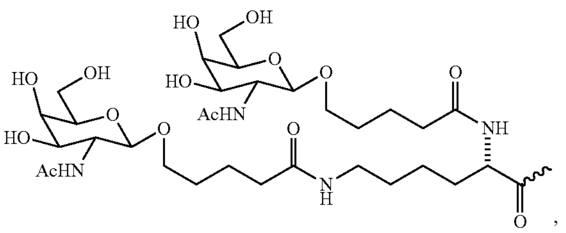
Formula XV
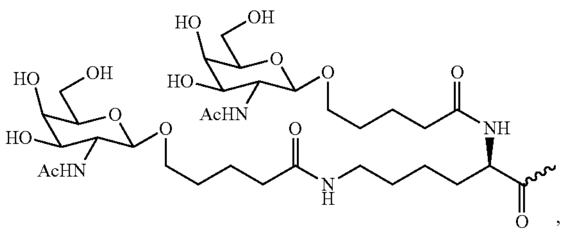
Formula XVI
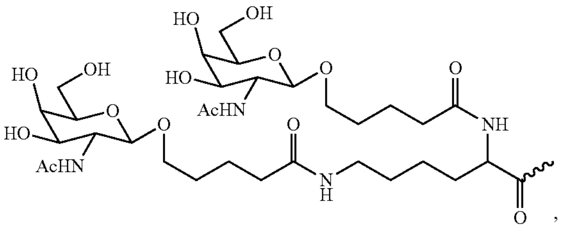
Formula XVII
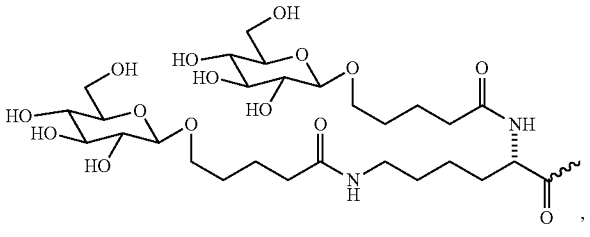

-continued
Formula XVIII
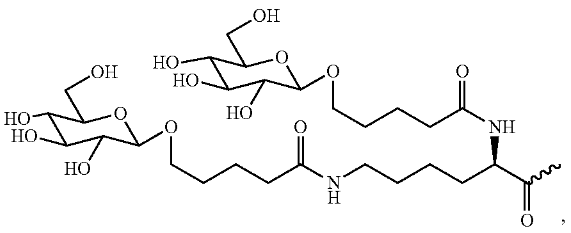
Formula XIX
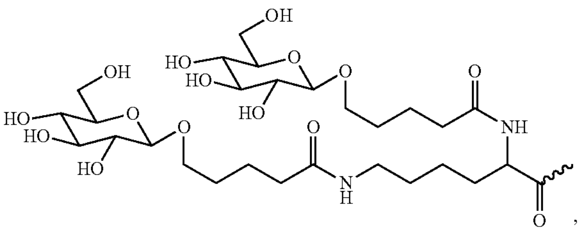
Formula XX
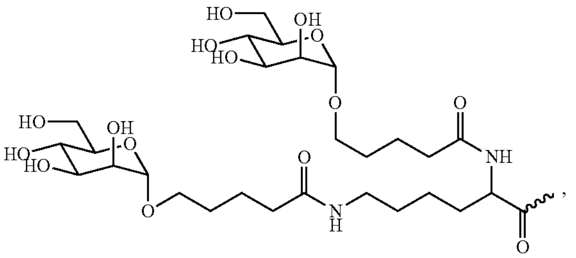
Formula XXI
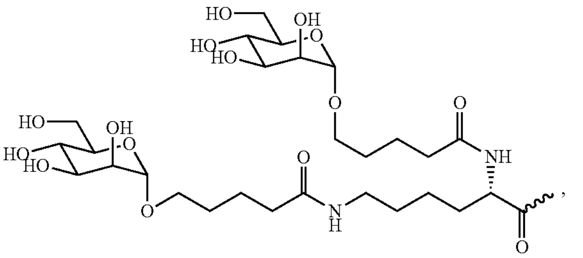
Formula XXII
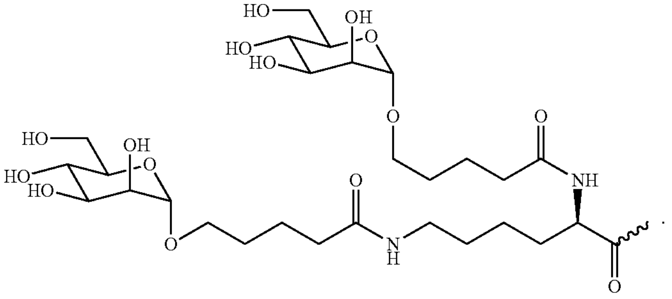
Another representative carbohydrate conjugate for use in the embodiments described herein includes, but is not limited to,
(Formula XXIII)
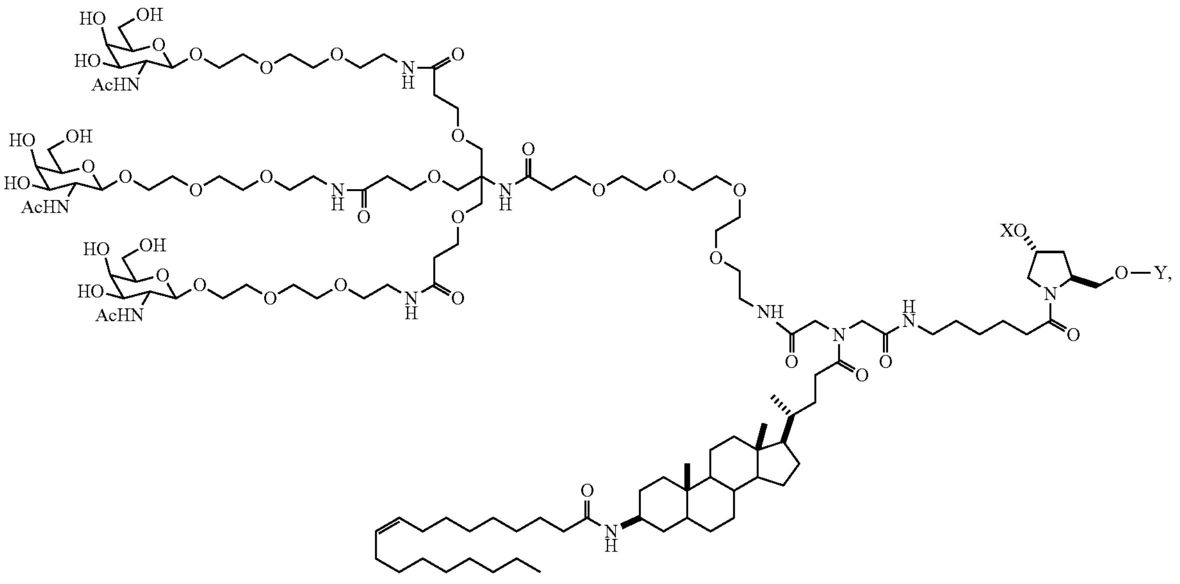

when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GalNAc or GalNAc derivative attached to the iRNA agent. In another embodiment, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator and/or a cell permeation peptide.

Additional carbohydrate conjugates (and linkers) suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-17, or 8-16 atoms.

A cleavable linking group is one which is sufficiently stable outside the cell, but which upon entry into a target cell is cleaved to release the two parts the linker is holding together. In some embodiments, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In certain embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

IV. Delivery of an iRNA of the Invention

The delivery of an iRNA of the invention to a cell e.g., a cell within a subject, such as a human subject (e.g., a subject in need thereof, such as a subject having a disorder of lipid metabolism) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian RL., (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J. et al., (2004) *Retina* 24:132-138) and subretinal injections in mice (Reich, S J. et al. (2003) *Mol. Vis.* 9:210-216) were both shown to prevent neovascularization in an experimental model of age-related macular degeneration. In addition, direct intratumoral injection of a dsRNA in mice reduces tumor volume (Pille, J. et al. (2005) *Mol. Ther.* 11:267-274) and can prolong survival of tumor-bearing mice (Kim, W J. et al., (2006) *Mol. Ther.* 14:343-350; Li, S. et al., (2007) *Mol. Ther.* 15:515-523). RNA interference has also shown success with local delivery to the CNS by direct injection (Dorn, G. et al., (2004) *Nucleic Acids* 32:e49; Tan, P H. et al. (2005) *Gene Ther.* 12:59-66; Makimura, H. et a.l (2002) *BMC Neurosci.* 3:18; Shishkina, G T., et al. (2004) *Neuroscience* 129:521-528; Thakker, E R., et al. (2004) *Proc. Natl. Acad. Sci. U.S.A.* 101:17270-17275; Akaneya,Y., et al. (2005) *J. Neurophysiol.* 93:594-602) and to the lungs by intranasal administration (Howard, K A. et al., (2006) *Mol. Ther.* 14:476-484; Zhang, X. et al., (2004) *J. Biol. Chem.* 279:10677-10684; Bitko, V. et al., (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J. et al., (2004) *Nature* 432:173-178). Conjugation of an iRNA to an aptamer has been shown to inhibit tumor growth and mediate tumor regression in a mouse model of prostate cancer (McNamara, J O. et al., (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim SH. et al., (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al. (2003) *J. Mol. Biol* 327:761-766; Verma, U N. et al., (2003) *Clin. Cancer Res.* 9:1291-1300; Arnold, A S et al., (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N. et al., (2003), supra), Oligofectamine, "solid nucleic acid lipid particles" (Zimmermann, T S. et al., (2006) *Nature* 441:111-114), cardiolipin (Chien, P Y. et al., (2005) *Cancer Gene Ther.* 12:321-328; Pal, A. et al., (2005) *Intl. Oncol.* 26:1087-1091), polyethyleneimine (Bonnet M E. et al., (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A. et al., (2007) *Biochem. Soc. Trans.* 35:61-67; Yoo, H. et al., (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Patent No. 7, 427, 605, which is herein incorporated by reference in its entirety.

A. Vector Encoded iRNAs of the Invention iRNA targeting the Hdlbp/Vigilin gene can be expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., (1995) *Proc. Natl. Acad. Sci. USA* 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are known in the art.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of an Hdlbp/Vigilin gene, e.g., a disorder of lipid metabolism, e.g., mixed hyperlipidemia, hypertriglyceridemia or hypercholesterolemia.

Such pharmaceutical compositions are formulated based on the mode of delivery. One example is compositions that are formulated for systemic administration via parenteral delivery, e.g., by intravenous (IV), intramuscular (IM), or for subcutaneous (subQ) delivery. Another example is compositions that are formulated for direct delivery into the liver, e.g., by infusion into the liver, such as by continuous pump infusion.

The pharmaceutical compositions of the invention may be administered in dosages sufficient to inhibit expression of an Hdlbp/Vigilin gene. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, preferably about 0.3 mg/kg and about 3.0 mg/kg.

A repeat-dose regimine may include administration of a therapeutic amount of iRNA on a regular basis, such as every other day to once a year. In certain embodiments, the iRNA is administered about once per month to about once per quarter (i.e., about once every three months).

After an initial treatment regimen, the treatments can be administered on a less frequent basis.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as disorders of lipid metabolism that would benefit from reduction in the expression of Hdlbp/Vigilin. Such models can be used for in vivo testing of iRNA, as well as for determining a therapeutically effective dose. Suitable mouse models are known in the art and include, for example, an obese (ob/ob) mouse containing a mutation in the obese (ob) gene (Wiegman et al., (2003) *Diabetes,* 52:1081-1089); a mouse containing homozygous knock-out of an LDL receptor (LDLR−/− mouse; Ishibashi et al., (1993) *J Clin Invest* 92(2):883-893); diet-induced artherosclerosis mouse model (Ishida et al., (1991) *J. Lipid. Res.,* 32:559-568); and heterozygous lipoprotein lipase knockout mouse model (Weistock et al., (1995) *J. Clin. Invest.* 96(6):2555-2568).

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

A. Lipid Particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

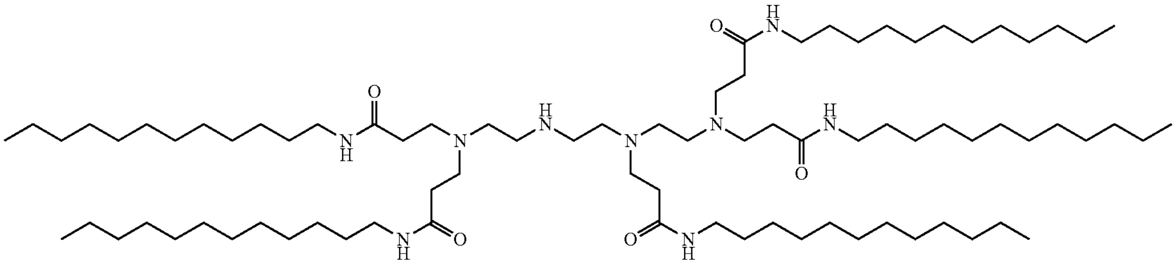

ND98 Isomer I

LNP01 formulations are described, e.g., in International Application Publication No. WO 2008/042973, which is hereby incorporated by reference.

Additional exemplary lipid-dsRNA formulations are described in the table below.

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |

-continued

| | Ionizable/Cationic Lipid | cationic lipid/non-cationic lipid/cholesterol/PEG-lipid conjugate Lipid:siRNA ratio |
|---|---|---|
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Serial No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include polyamino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The iRNAs of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich NG., and Ansel HC., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution either in the aqueous phase, oily phase or itself as a separate phase. Pharmaceutical excipients such as emulsifiers, stabilizers, dyes, and antioxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich NG., and Ansel HC., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich NG., and Ansel HC., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic, and amphoteric (see e.g., Ansel's Pharmaceutical Dosage Forms and Drug Delivery Systems, Allen, L V., Popovich NG., and Ansel HC., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate, and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives, and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral, and parenteral routes, and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich NG., and Ansel HC., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins, and high fat nutritive preparations are among the materials that have commonly been administered orally as o/w emulsions.

ii. Microemulsions

In one embodiment of the present invention, the iRNAs are formulated as microemulsions. A microemulsion can be defined as a system of water, oil, and amphiphile which is a single optically isotropic and thermodynamically stable liquid solution (see e.g., Ansel's Pharmaceutical Dosage Forms and Drug Delivery Systems, Allen, L V., Popovich NG., and Ansel HC., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich NG., and Ansel HC., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij® 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex® 300, Captex® 355, Capmul® MCM, fatty acid esters, medium chain (C8-C12) mono, di, and triglycerides, polyoxyethylated glyceryl fatty acid esters, fatty alcohols, polyglycolized glycerides, saturated polyglycolized C8-C10 glycerides, vegetable oils, and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill® 3), Labrasol®, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles

An iRNA of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Such compounds are well known in the art.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent, or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone, and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone, and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings or aromatic substances and the like which do not deleteriously interact with the nucleic acid(s) of the formulation.

Aqueous suspensions can contain substances which increase the viscosity of the suspension including, for example, sodium carboxymethylcellulose, sorbitol, or dextran. The suspension can also contain stabilizers.

In some embodiments, pharmaceutical compositions featured in the invention include (a) one or more iRNA and (b) one or more agents which function by a non-iRNA mechanism and which are useful in treating a KHK-associated disorder.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans Levels in plasma can be measured, for example, by high performance liquid chromatography.

In addition to their administration, as discussed above, the iRNAs featured in the invention can be administered in combination with other known agents effective in treatment of pathological processes mediated by KHK expression. In any event, the administering physician can adjust the amount and timing of iRNA administration on the basis of results observed using standard measures of efficacy known in the art or described herein.

VI. Methods for Inhibiting Hdlbp/Vigilin Expression

The present invention also provides methods of inhibiting expression of a Hdlbp/Vigilin gene in a cell. The methods include contacting a cell with an RNAi agent, e.g., double stranded RNAi agent, in an amount effective to inhibit expression of Hdlbp/Vigilin in the cell, thereby inhibiting expression of Hdlbp/Vigilin in the cell. In certain embodiments of the invention, Hdlbp/Vigilin is inhibited preferentially in liver cells.

Contacting of a cell with an iRNA, e.g., a double stranded RNAi agent, may be done in vitro or in vivo. Contacting a cell in vivo with the iRNA includes contacting a cell or group of cells within a subject, e.g., a human subject, with the iRNA. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In some embodiments, the targeting ligand is a carbohydrate moiety, e.g., a $GalNAc_3$ ligand, or any other ligand that directs the RNAi agent to a site of interest.

The term "inhibiting," as used herein, is used interchangeably with "reducing," "silencing," "downregulating," "suppressing" and other similar terms, and includes any level of inhibition.

The phrase "inhibiting expression of an Hdlbp/Vigilin," as used herein, includes inhibition of expression of any Hdlbp/Vigilin gene (such as, e.g., a human Hdlbp/Vigilin gene) as well as variants or mutants of an Hdlbp/Vigilin gene that encode an Hdlbp/Vigilin protein. Thus, the Hdlbp/Vigilin gene may be a wild-type Hdlbp/Vigilin gene, a mutant Hdlbp/Vigilin gene, or a transgenic Hdlbp/Vigilin gene in the context of a genetically manipulated cell, group of cells, or organism.

"Inhibiting expression of a Hdlbp/Vigilin gene" includes any level of inhibition of a Hdlbp/Vigilin gene, e.g., at least partial suppression of the expression of a Hdlbp/Vigilin gene. The expression of the Hdlbp/Vigilin gene may be assessed based on the level, or the change in the level, of any variable associated with Hdlbp/Vigilin gene expression, e.g., Hdlbp/Vigilin mRNA level or Hdlbp/Vigilin protein level. This level may be assessed in an individual cell or in a group of cells, including, for example, a sample derived from a subject. It is understood that expression of Hdlbp/Vigilin may be near or below the level of detection in a normal subject in many cell types and body fluids. The expression of an Hdlbp/Vigilin may also be assessed indirectly based on the levels of a serum lipid, a triglyceride, cholesterol (including LDL-C, HDL-C, VLDL-C, IDL-C and total cholesterol), or free fatty acids. The expression of an Hdlbp/Vigilin may also be assessed indirectly based on the levels of plasma glucose, fasting blood glucose, plasma insulin, aor the size of atherosclerotic plaque.

Inhibition may be assessed by a decrease in an absolute or relative level of one or more variables that are associated with Hdlbp/Vigilin expression compared with a control level. The control level may be any type of control level that is utilized in the art, e.g., a pre-dose baseline level, or a level determined from a similar subject (e.g., historical control), cell, or sample that is untreated or treated with a control (such as, e.g., buffer only control or inactive agent control).

In certain embodiments, surrogate markers can be used to detect inhibition of Hdlbp/Vigilin. For example, effective treatment of a disorder of lipid metabolism as demonstrated by acceptable diagnostic and monitoring criteria with an agent to reduce Hdlbp/Vigilin expression can be understood to demonstrate a clinically relevant reduction in Hdlbp/Vigilin.

In some embodiments of the methods of the invention, expression of a Hdlbp/Vigilin gene is inhibited by at least 20%, a 25%, 30%, 35%, 40%, 45%, 50%, 55%, 60%, 65%, 70%, 75%, 80%, 85%, 90%, or 95%, or to below the level of detection of the assay. In certain embodiments, the methods include a clinically relevant inhibition of expression of Hdlbp/Vigilin, e.g. as demonstrated by a clinically relevant outcome after treatment of a subject with an agent to reduce the expression of Hdlbp/Vigilin.

Inhibition of the expression of a Hdlbp/Vigilin gene may be manifested by a reduction of the amount of mRNA expressed by a first cell or group of cells (such cells may be present, for example, in a sample derived from a subject) in which a Hdlbp/Vigilin gene is transcribed and which has or have been treated (e.g., by contacting the cell or cells with an iRNA of the invention, or by administering an iRNA of the invention to a subject in which the cells are or were present) such that the expression of a Hdlbp/Vigilin gene is inhibited, as compared to a second cell or group of cells substantially identical to the first cell or group of cells but which has not or have not been so treated (control cell(s) not treated with an iRNA or not treated with an iRNA targeted to the gene of interest). The degree of inhibition may be expressed in terms of:

$$\frac{(mRNA \text{ in control cells}) - (mRNA \text{ in treated cells})}{(mRNA \text{ in control cells})} \cdot 100\%$$

In other embodiments, inhibition of the expression of a Hdlbp/Vigilin gene may be assessed in terms of a reduction of a parameter that is functionally linked to Hdlbp/Vigilin gene expression, e.g., Hdlbp/Vigilin protein expression or Hdlbp/Vigilin signaling pathways. Hdlbp/Vigilin gene silencing may be determined in any cell expressing Hdlbp/Vigilin, either endogenous or heterologous from an expression construct, and by any assay known in the art.

Inhibition of the expression of a Hdlbp/Vigilin protein may be manifested by a reduction in the level of the Hdlbp/Vigilin protein that is expressed by a cell or group of cells (e.g., the level of protein expressed in a sample derived from a subject). As explained above, for the assessment of mRNA suppression, the inhibiton of protein expression levels in a treated cell or group of cells may similarly be expressed as a percentage of the level of protein in a control cell or group of cells.

A control cell or group of cells that may be used to assess the inhibition of the expression of a Hdlbp/Vigilin gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of Hdlbp/Vigilin mRNA that is expressed by a cell or group of cells may be determined using any method known in the art for assessing mRNA expression. In one embodiment, the level of expression of Hdlbp/Vigilin in a sample is determined by detecting a transcribed polynucleotide, or portion thereof, e.g., mRNA of the Hdlbp/Vigilin gene. RNA may be extracted from cells using RNA extraction techniques including, for example, using acid phenol/guanidine isothiocyanate extraction (RNAzol B; Biogenesis), RNeasy™ RNA preparation kits (Qiagen®) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Circulating Hdlbp/Vigilin mRNA may be detected using methods the described in PCT Publication WO2012/177906, the entire contents of which are hereby incorporated herein by reference.

In some embodiments, the level of expression of Hdlbp/Vigilin is determined using a nucleic acid probe. The term "probe", as used herein, refers to any molecule that is capable of selectively binding to a specific Hdlbp/Vigilin. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to Hdlbp/Vigilin mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of Hdlbp/Vigilin mRNA.

An alternative method for determining the level of expression of Hdlbp/Vigilin in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of Hdlbp/Vigilin is determined by quantitative fluorogenic RT-PCR (i.e., the TaqMan™ System) or the Dual-Glo® Luciferase assay.

The expression levels of Hdlbp/Vigilin mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of Hdlbp/Vigilin expression level may also comprise using nucleic acid probes in solution.

In some embodiments, the level of mRNA expression is assessed using branched DNA (bDNA) assays or real time PCR (qPCR). The use of this PCR method is described and exemplified in the Examples presented herein. Such methods can also be used for the detection of Hdlbp/Vigilin nucleic acids.

The level of Hdlbp/Vigilin protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like. Such assays can also be used for the detection of proteins indicative of the presence or replication of Hdlbp/Vigilin proteins.

In some embodiments, the efficacy of the methods of the invention in the treatment of a disease or disorder that would benefir from reduction in the expression of Hdlbp/Vigilin is assessed by a decrease in Hdlbp/Vigilin mRNA level (by liver biopsy).

In some embodiments of the methods of the invention, the iRNA is administered to a subject such that the iRNA is delivered to a specific site within the subject. The inhibition of expression of Hdlbp/Vigilin may be assessed using measurements of the level or change in the level of Hdlbp/Vigilin mRNA or Hdlbp/Vigilin protein in a sample derived from a specific site within the subject, e.g., the liver. In certain embodiments, the methods include a clinically relevant inhibition of expression of Hdlbp/Vigilin, e.g. as demonstrated by a clinically relevant outcome after treatment of a subject with an agent to reduce the expression of Hdlbp/Vigilin.

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

VII. Methods of Treating or Preventing Hdlbp/Vigilin-Associated Diseases

The present invention also provides methods of using an iRNA of the invention and/or a composition containing an iRNA of the invention to reduce and/or inhibit Hdlbp/Vigilin expression in a cell. The methods include contacting the cell with a dsRNA of the invention and maintaining the cell for a time sufficient to obtain degradation of the mRNA transcript of an Hdlbp/Vigilin gene, thereby inhibiting expression of the Hdlbp/Vigilin gene in the cell. Reduction in gene expression can be assessed by any methods known in the art. For example, a reduction in the expression of Hdlbp/Vigilin may be determined by determining the mRNA expression level of Hdlbp/Vigilin using methods routine to one of ordinary skill in the art, e.g., Northern blotting, qRT-PCR; by determining the protein level of Hdlbp/Vigilin using methods routine to one of ordinary skill in the art, such as Western blotting, immunological techniques. A reduction in the expression of Hdlbp/Vigilin may also be assessed indirectly by measuring a decrease in biological activity of Hdlbp/Vigilin, e.g., a decrease in the level of serum lipid, triglycerides, cholesterol, free fatty acids, plasma glucose, fasting blood glucose, plasma insulin and/or the size of atherosclerotic plaque.

The methods of the invention further comprise measuring serum lipid levels, plasma glucose levels, fasting blood glucose levels, plasma insulin levels, plasma triglyceride levels, and/or plasma cholesterol levels in the subject. In certain embodiments, following administration of the double stranded RNAi agent to the subject, the Hdlbp/Vigilin protein accumulation is decreased; the plasma cholesterol level in the subject is decreased; the plasma triglyceride level in the subject is decreased; the serum VLDL level in the subject is decreased; the serum LDL level in the subject is decreased; the plasma insulin level in the subject is decreased; insulin sensitivity in the subject is increased; glucose tolerance in the subject is increased; and/or atherosclerotic plaque formation in the subject is decreased.

In the methods of the invention the cell may be contacted in vitro or in vivo, i.e., the cell may be within a subject.

A cell suitable for treatment using the methods of the invention may be any cell that expresses an Hdlbp/Vigilin gene. A cell suitable for use in the methods of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

Hdlbp/Vigilin expression is inhibited in the cell by at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100%. In some embodiments, Hdlbp/Vigilin expression is inhibited by at least 20%.

The in vivo methods of the invention may include administering to a subject a composition containing an iRNA, where the iRNA includes a nucleotide sequence that is complementary to at least a part of an RNA transcript of the Hdlbp/Vigilin gene of the mammal to be treated. When the organism to be treated is a mammal such as a human, the composition can be administered by any means known in the art including, but not limited to, oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection.

In some embodiments, the administration is via a depot injection. A depot injection may release the iRNA in a consistent way over a prolonged time period. Thus, a depot injection may reduce the frequency of dosing needed to obtain a desired effect, e.g., a desired inhibition of Hdlbp/Vigilin, or a therapeutic or prophylactic effect. A depot injection may also provide more consistent serum concentrations. Depot injections may include subcutaneous injections or intramuscular injections. In some embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In some embodiments, the infusion pump is a subcutaneous infusion pump. In other embodiments, the pump is a surgically implanted pump that delivers the iRNA to the liver.

The mode of administration may be chosen based upon whether local or systemic treatment is desired and based upon the area to be treated. The route and site of administration may be chosen to enhance targeting.

In one aspect, the present invention also provides methods for inhibiting the expression of an Hdlbp/Vigilin gene in a mammal. The methods include administering to the mammal a composition comprising a dsRNA that targets an Hdlbp/Vigilin gene in a cell of the mammal and maintaining the mammal for a time sufficient to obtain degradation of the mRNA transcript of the Hdlbp/Vigilin gene, thereby inhibiting expression of the Hdlbp/Vigilin gene in the cell. Reduction in gene expression can be assessed by any methods known it the art and by methods, e.g. qRT-PCR, described herein. Reduction in protein production can be assessed by any methods known it the art and by methods, e.g. ELISA, described herein. In one embodiment, a puncture liver biopsy sample serves as the tissue material for monitoring the reduction in Hdlbp/Vigilin gene and/or protein expression.

The present invention further provides methods of treatment of a subject in need thereof. The treatment methods of the invention include administering an iRNA of the invention to a subject, e.g., a subject that would benefit from a reduction and/or inhibition of Hdlbp/Vigilin expression, in a therapeutically effective amount of an iRNA targeting an Hdlbp/Vigilin gene or a pharmaceutical composition comprising an iRNA targeting an Hdlbp/Vigilin gene.

An iRNA of the invention may be administered as a "free iRNA." A free iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of Hdlbp/Vigilin gene expression are those having a disorder of lipid metabolism. In one embodiment, a subject having disorder of lipid metabolism has a hyperlipidemia. In one embodiment, a subject having the hyperlipidemia has hypercholesterolemia. In certain embodiments, the hyperlipidemia is hypertriglyceridemia. In certain embodiments, the hyperlipidemia is mixed hyperlipidemia.

The invention further provides methods for the use of an iRNA or a pharmaceutical composition thereof, e.g., for treating a subject that would benefit from reduction and/or inhibition of Hdlbp/Vigilin expression, e.g., a subject having a disorder of lipid metabolism, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting Hdlbp/Vigilin is administered in combination with, e.g., an agent useful in treating a disorder of lipid metabolism as described elsewhere herein. For example, additional agents suitable for treating a subject that would benefit from reducton in Hdlbp/Vigilin expression, e.g., a subject having a disorder of lipid metabolism, may include agents that lower one or more serum lipids. Non-limiting examples of such agents may include cholesterol synthesis inhibitors, e.g., statins. Statins may include atorvastatin (Lipitor), fluvastatin (Lescol), lovastatin (Mevacor), lovastatin extended-release (Altoprev), pitavastatin (Livalo), pravastatin (Pravachol), rosuvastatin (Crestor), and simvastatin (Zocor). Other agents useful in treating a disorder of lipid metabolism may include bile sequestering agents, such as cholestyramine and other resins; VLDL secretion inhibitors, such as niacin; lipophilic antioxidants, such as Probucol; acyl-CoA cholesterol acyl transferase inhibitors; farnesoid X receptor antagonists; sterol regulatory binding protein cleavage activating protein (SCAP) activators; microsomal triglyceride transfer protein (MTP) inhibitors; ApoE-related peptide; and therapeutic antibodies against Hdlbp/Vigilin. The additional therapeutic agents may also include agents that raise high density lipoprotein (HDL), such as cholesteryl ester transfer protein (CETP) inhibitors. Furthermore, the additional therapeutic agents may also include dietary supplements, e.g., fish oil. The iRNA and additional therapeutic agents may be administered at the same time and/or in the same combination, e.g., parenterally, or the additional therapeutic agent can be administered as part of a separate composition or at separate times and/or by another method known in the art or described herein.

In one embodiment, the method includes administering a composition featured herein such that expression of the target Hdlbp/Vigilin gene is decreased, such as for about 1, 2, 3, 4, 5, 6, 7, 8, 12, 16, 18, 24 hours, 28, 32, or about 36 hours. In one embodiment, expression of the target Hdlbp/Vigilin gene is decreased for an extended duration, e.g., at least about two, three, four days or more, e.g., about one week, two weeks, three weeks, or four weeks or longer.

Preferably, the iRNAs useful for the methods and compositions featured herein specifically target RNAs (primary or processed) of the target Hdlbp/Vigilin gene. Compositions and methods for inhibiting the expression of these genes using iRNAs can be prepared and performed as described herein.

Administration of the dsRNA according to the methods of the invention may result in a reduction of the severity, signs, symptoms, and/or markers of such diseases or disorders in a patient with a disorder of lipid metabolism. By “reduction” in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a disorder of lipid metabolism may be assessed, for example, by periodic monitoring of one or more serum lipid levels. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting Hdlbp/Vigilin or pharmaceutical composition thereof, “effective against” a disorder of lipid metabolism indicates that administration in a clinically appropriate manner results in a beneficial effect for at least a statistically significant fraction of patients, such as a improvement of symptoms, a cure, a reduction in disease, extension of life, improvement in quality of life, or other effect generally recognized as positive by medical doctors familiar with treating disorder of lipid metabolisms and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale, as but one example the Child-Pugh score (sometimes the Child-Turcotte-Pugh score). Any positive change resulting in e.g., lessening of severity of disease measured using the appropriate scale, represents adequate treatment using an iRNA or iRNA formulation as described herein.

Subjects can be administered a therapeutic amount of dsRNA, such as about 0.01 mg/kg to about 200 mg/kg.

The iRNA can be administered by intravenous infusion over a period of time, on a regular basis. In certain embodiments, after an initial treatment regimen, the treatments can be administered on a less frequent basis. Administration of the iRNA can reduce Hdlbp/Vigilin levels, e.g., in a cell, tissue, blood, urine or other compartment of the patient by at least about 5%, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 39, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or at least about 99% or more. In some embodiments, administration of the iRNA can reduce Hdlbp/Vigilin levels, e.g., in a cell, tissue, blood, urine or other compartment of the patient by at least 20%.

Before administration of a full dose of the iRNA, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Alternatively, the iRNA can be administered subcutaneously, i.e., by subcutaneous injection. One or more injections may be used to deliver the desired daily dose of iRNA to a subject. The injections may be repeated over a period of time. The administration may be repeated on a regular basis. In certain embodiments, after an initial treatment regimen, the treatments can be administered on a less frequent basis. A repeat-dose regimine may include administration of a therapeutic amount of iRNA on a regular basis, such as every other day or to once a year. In certain embodiments, the iRNA is administered about once per month to about once per quarter (i.e., about once every three months).

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. iRNA Design, Synthesis, Selection, and In Vitro Evaluation

This Example describes methods for the design, synthesis, selection, and in vitro evaluation of Hdlbp/Vigilin iRNA agents.

Source of Reagents

Where the source of a reagent is not specifically given herein, such reagent can be obtained from any supplier of reagents for molecular biology at a quality/purity standard for application in molecular biology.

Bioinformatics

A set of siRNA agents targeting the human Hdlbp/Vigilin, "High Density Lipoprotein Binding Protein", (human: NCBI refseqID NM_005336.5; NCBI GeneID: 3069) is designed using custom R and Python scripts. The human NM_005336.5 REFSEQ mRNA, has a length of 6524 bases. The rationale and method for the set of siRNA designs is as follows: the predicted efficacy for every potential 19mer siRNA from position 10 through position 4620 is determined with a linear model derived the direct measure of mRNA knockdown from more than 20,000 distinct siRNA designs targeting a large number of vertebrate genes. For each strand of the siRNA, a custom Python script is used in a brute force search to measure the number and positions of mismatches between the siRNA and all potential alignments in the target species transcriptome. Extra weight is given to mismatches in the seed region, defined here as positions 2-9 of the antisense oligonucleotide, as well the cleavage site of the siRNA, defined here as positions 10-11 of the antisense oligonucleotide. The relative weight of the mismatches is 2.8; 1.2:1 for seed mismatches, cleavage site, and other positions up through antisense position 19. Mismatches in the first position are ignored. A specificity score is calculated for each strand by summing the value of each weighted mismatch. Preference is given to siRNAs whose antisense score in human is >=2.0 and predicted efficacy is >=50% knockdown of the Hdlbp/Vigilin transcript.

Synthesis of Hdlbp/Vigilin Single Strands and Duplexes

Hdlbp/Vigilin siRNA sequences are synthesized at 1 μmol scale on Mermade 192 synthesizer (BioAutomation) using the solid support mediated phosphoramidite chemistry. The solid support is controlled pore glass (500° A) loaded with custom GalNAc ligand or universal solid support (AM biochemical). Ancillary synthesis reagents, 2'-F and 2'-O-Methyl RNA and deoxy phosphoramidites are obtained from Thermo-Fisher (Milwaukee, Wis.) and Hongene (China). 2'F, 2'-O-Methyl, RNA, DNA and other modified nucleosides are introduced in the sequences using the corresponding phosphoramidites. Synthesis of 3' GalNAc conjugated single strands is performed on a GalNAc modified CPG support. Custom CPG universal solid support is used for the synthesis of antisense single strands. Coupling time for all phosphoramidites (100 mM in acetonitrile) is 5 min employing 5-Ethylthio-1H-tetrazole (ETT) as activator (0.6 M in acetonitrile). Phosphorothioate linkages are generated using a 50 mM solution of 3-((Dimethylamino-methylidene) amino)-3H-1, 2, 4-dithiazole-3-thione (DDTT, obtained from Chemgenes (Wilmington, Mass., USA) in anhydrous acetonitrile/pyridine (1:1 v/v). Oxidation time was 3 minutes. All sequences are synthesized with final removal of the DMT group ("DMT off").

Upon completion of the solid phase synthesis, single strands are cleaved from the solid support and deprotected in sealed 96 deep well plates using 200 μL Aqueous Methylamine reagent at 60° C. for 20 minutes. For sequences containing 2' ribo residues (2'-OH) that are protected with tert-butyl dimethyl silyl (TBDMS) group, a second step deprotection is performed using TEA.3HF (triethylamine trihydro fluoride) reagent. To the methylamine deprotection solution, 200 uL of dimethyl sulfoxide (DMSO) and 300 ul TEA.3HF reagent is added and the solution is incubated for additional 20 min at 60° C. At the end of cleavage and deprotection step, the synthesis plate is allowed to come to room temperature and is precipitated by addition of 1 mL of acetontile: ethanol mixture (9:1). The plates are cooled at −80° C. for 2 hrs and the supernatant decanted carefully with the aid of a multi-channel pipette. The oligonucleotide pellet is re-suspended in 20 mM NaOAc buffer and is desalted using a 5 mL HiTrap size exclusion column (GE Healthcare) on an AKTA Purifier System equipped with an A905 autosampler and a Frac 950 fraction collector. Desalted samples are collected in 96 well plates. Samples from each sequence are analyzed by LC-MS to confirm the identity, UV (260 nm) for quantification and a selected set of samples by IEX chromatography to determine purity.

Annealing of Hdlbp/Vigilin single strands is performed on a Tecan liquid handling robot. Equimolar mixture of sense and antisense single strands are combined and annealed in 96 well plates. After combining the complementary single strands, the 96 well plate is sealed tightly and heated in an oven at 100° C. for 10 minutes and allowed to come slowly to room temperature over a period 2-3 hours. The concentration of each duplex is normalized to 10 uM in 1×PBS and then submitted for in vitro screening assays.

In Vitro Screening:

Cell Culture and Transfections:

Hep3b cells (ATCC, Manassas, Va.) are grown to near confluence at 37° C. in an atmosphere of 5% $CO_2$ in Eagle's Minimum Essential Medium (Gibco) supplemented with 10% FBS (ATCC) before being released from the plate by trypsinization.

Primary mouse hepatocytes (PMH) are freshly isolated from a C57BL/6 female mouse (Charles River Labortories International, Inc. Willmington, Mass.) less than 1 hour prior to transfections and grown in primary hepatocyte media. Cells are resuspended at $0.11\times10^6$ cells/ml in InVitroGRO CP Rat (plating) medium (Celsis In Vitro Technologies, catalog number SO1494). During transfections, cells are plated onto a BD BioCoat 96 well collagen plate (BD, 356407) at 10,000 cells per well and incubated at 37° C. in an atmosphere of 5% $CO_2$.

Transfection is carried out by adding 4.9 μl of Opti-MEM plus 0.1 μl of Lipofectamine RNAiMax per well (Invitrogen, Carlsbad Calif. cat #13778-150) to 5 μl of each siRNA duplex to an individual well in a 384-well plate. The mixture is then incubated at room temperature for 15 minutes. Forty μl of William's E Medium (Life Tech) containing about 5,000 Hep3b cells are then added to the siRNA mixture. Cells are incubated for 24 hours prior to RNA purification.

Single dose experiments are performed at 10 nM and 0.1 nM final duplex concentration in Hep3b cells and single dose experiments are performed at 20 nM final duplex concentration in PMH.

Total RNA isolation using DYNABEADS mRNA Isolation Kit (Invitrogen, part #: 610-RNA is isolated using an automated protocol on a BioTek-EL406 platform using DYNABEADS (Invitrogen, cat #61012). Fifty μl of Lysis/Binding Buffer and 25 μl of Lysis Buffer containing 34 of magnetic beads are added to the plate with cells. Plates are incubated on an electromagnetic shaker for 10 minutes at room temperature and then magnetic beads are captured and the supernatant is removed. Bead-bound RNA is then washed 2 times with 150 μl Wash Buffer A and once with Wash Buffer B. Beads are then washed with 150 μl Elution Buffer, re-captured and supernatant is removed.

cDNA Synthesis Using ABI High Capacity cDNA Reverse Transcription Kit (Applied Biosystems, Foster City, Calif., Cat #4368813):

Ten μl of a master mix containing 1 μl 10× Buffer, 0.4 μl 25× dNTPs, Random primers, 0.5 μl Reverse Transcriptase, 0.5 μl RNase inhibitor and 6.6 μl of $H_2O$ per reaction are added to RNA isolated per well. Plates are sealed, mixed and incubated on an electromagnetic shaker for 10 minutes at room temperature, and then incubated at 37° C. for 2 hours. Plates are then incubated at 81° C. for 8 minutes.

Real Time PCR:

Two μl of cDNA are added to a master mix containing 0.5 μl of human GAPDH TaqMan Probe (4326317E), 0.5 μl human Hdlbp/Vigilin, and 5 μl Lightcycler 480 probe master mix (Roche Cat #04887301001) per well in a 384 well plates (Roche cat #04887301001). Real time PCR is done in a LightCycler480 Real Time PCR system (Roche) using the ΔΔCt(RQ) assay. Each duplex is tested in at least two times and data are normalized to cells transfected with a non-targeting control siRNA.

To calculate relative fold change, real time data is analyzed using the ΔΔCt method and normalized to assays performed with cells transfected with a non-targeting control siRNA.

TABLE 1

Abbreviations of nucleotide monomers used in nucleic acid sequence representation.
It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| dT | 2'-deoxythymidine-3'-phosphate |
| dC | 2'-deoxycytidine-3'-phosphate |
| P | Phosphate |
| VP | Vinyl-phosphate |

Example 2. Increased Expression of Hdlbp/Vigilin in Hepatic Steatosis and Regulation of VLDL Secretion Through Modulation of ApoB mRNA Translation by Hdlbp/Vigilin Methods and Materials

TABLE 2

Hdlbp/Vigilin Modified Sequences

| Duplex Name | Sense Sequence (5' to 3') | Antisense Sequence (5' to 3') |
|---|---|---|
| GalNAc#1 | GfsasGfaUfcAfaCfAfUfuGfaCfc AfuAfaAfL96 (SEQ ID NO: 22) | usUfsuAfuGfgUfcAfaugUfuGfaUfc Ufcsusa (SEQ ID NO: 24) |
| GalNAc#2 | AfsgsGfaAfgAfuCfGfGfgCfuUfu AfaGfgAfL96 (SEQ ID NO: 23) | usCfscUfuAfaAfgCfccgAfuCfuUfc Cfusgsc (SEQ ID NO: 25) |
| GalNAc#1 | GfsasGfaUfcAfaCfAfUfuGfaCfc AfuAfaAfL96 (SEQ ID NO: 22) | usUfsuAfuGfgUfcAfaugUfuGfaUfc Ufcsusa (SEQ ID NO: 24) |

TABLE 2-continued

| Hdlbp/Vigilin Modified Sequences | | |
|---|---|---|
| Duplex Name | Sense Sequence (5' to 3') | Antisense Sequence (5' to 3') |
| GalNAc#2 | AfsgsGfaAfgAfuCfGfGfgCfuUfu AfaGfgAfL96 (SEQ ID NO: 23) | usCfscUfuAfaAfgCfccgAfuCfuUfc Cfusgsc (SEQ ID NO: 25) |

Animal Experiments

All animal models shown were male and on a C57BL/6N background and purchased from Janvier or Charles River. Mice were housed in a pathogen-free animal facility at the Institute of Molecular Health Sciences at ETH Zurich. The animals were maintained in a temperature- and humidity controlled room on a 12 h light-dark cycle (lights on from 6 a.m. to 6 p.m.). Mice were either fed a standard laboratory chow, a high fat diet (for DIO mice; fat, carbohydrate, protein content was 45, 35 and 20 kcal %, respectively) (Research Diets, D12451) or chow diet AIN76 supplemented with 0.02% cholesterol (Teupser et al., 2003) (for $Ldlr^{-/-}$ mice; Ssniff). All animal experiments were approved by the Kantonale Veterinaramt Zurich.

Adenoviral Infections

The sequence of V5-tagged hVigilin was cloned into pVQAd CMV K-NpA (Viraquest) using the restriction sites BamHI and XhoI (NEB). Ad-CTRL was based on the same vector backbone (including GFP) but lacked the insert transgene. shRNAs targeting Vigilin were cloned under a U6 promoter into. All pVQAd plasmids constructs were sent for adenovirus production to Viraquest Inc., USA. All adenoviruses expressed GFP from an independent promoter. Mice were administered adenovirus through a single tail-vein injection of $3\times10^9$ plaque-forming units in a final volume of 0.2 ml diluted in PBS and sacrificed 7 (for gain of function experiments) or 10 days (for loss of function experiments) postinjection.

Primary Hepatocytes Isolation

Primary hepatocytes were isolated as described before (Zhang et al., 2012) with the following modifications and conditions. Mice were anesthetized by intraperitoneal injection of 150 μl pentobarbital (Esconarkon US vet) pre-diluted 1:5 in PBS. The liver was perfused by cannulation of the hepatic portal vein with the caudal vena cava as a drain. The liver was perfused with pre-warmed Hank's Balanced Salt Solution (Life Technologies) containing 0.5 mM EGTA followed by pre-warmed digestion medium [DMEM 1 g/l glucose (Life Technologies), 1% Penicillin-Streptomycin (Life Technologies), 15 mM HEPES (Life Technologies), 30 μg/ml Liberase™ Research Grade medium Thermolysin concentration (Roche)] each for four minutes with a flow rate of 3 ml $min^{-1}$. The liver was surgically removed, hepatocytes released into 10 ml digestion media by shaking and supplemented with 15 ml ice cold low glucose media [DMEM 1 g/l glucose (Life Technologies), 1% Penicillin-Streptomycin (Life Technologies), 10% heat-inactivated fetal bovine serum (Sigma), 1% GlutaMax (Life Technologies)] and filtered through a 100 μm Cell Strainer (BD). The suspension was then washed three times with 25 ml of ice-cold low glucose media at 50× g and 4° C. for 2 min. Hepatocytes were counted and plated at $4\times10^6$ cells surface-treated P10 plates (BD Primaria) in low glucose media. 3 hrs after plating, cells were washed once with PBS and medium was changed to Williams E medium (or methionine-free DMEM for cell extracts used for in vitro translation; Life Technologies) supplemented with 1% Penicillin-Streptomycin (Life Technologies), 1% GlutaMax (Life Technologies) and harvested 16 hrs (or 2 hrs for in vitro translation) after medium change. All cells were incubated at 37° C. in a humidified atmosphere containing 5% $CO_2$.

Blood Glucose Measurements

Blood glucose was measured using a Contour glucometer (Bayer). For intraperitoneal glucose tolerance tests, mice were fasted for 4 h and then injected with of 2 g/kg body weight D-glucose in PBS. For intraperitoneal insulin tolerance tests, animals were injected with 0.75 U/kg body weight of a $5\times10^{-2}$ U/ml insulin solution in PBS after a 3-h fasting period.

Blood Plasma Collection and Measurements

For measuring blood plasma insulin, ALT, triglyceride, cholesterol and NEFA levels, blood was collected from the submandibular vein in non-heparinized capillary tubes. EDTA was added to a final concentration of ~5 mM as an anti-coagulant. Plasma was then separated by centrifugation at 8,000×g for 4 min. Measurements were performed using commercial kits. Plasma insulin was measured with the Rat Insulin ELISA Kit (Crystalchem). Plasma cholesterol (Roche), triglycerides (Roche), NEFA (Wako) and bile acids (Crystalchem) were measured by colorimetric assays, according to the manufacturer's instructions.

Antibodies

The following antibodies were used in immunoblotting: rabbit anti-Hdlbp/Vigilin (Abcam, #ab109324), mouse anti-γ-Tubulin (Sigma, #T6557), rabbit anti-Lamin B (Cell Signaling, #9087S), rabbit anti-Gapdh (Santa Cruz, #2118S), rabbit anti-Rbm47 (abcam, #ab167164), rabbit anti-HuR (Santa Cruz, #sc-20694), rabbit anti-Histone H3 (Cell Signaling, #4499S), rabbit anti-ApoB (Meridian, #K23300R), rabbit anti-ApoA-I (Meridian, #K23500R), rabbit anti-Fibronectin (Abcam, #ab2413), goat anti-Fetuin-A (Santa Cruz, #sc-9668), rabbit anti-Alpha-1-Antitrypsin (Proteintech, #16382-1-AP), rabbit anti-Orosomucoid (Proteintech, #16439-1-AP), rabbit anti-ApoM (home-made, #aa140-159), goat anti-Albumin (Bethyl, #A90-134A).

PAR-CLIP in Primary Hepatocytes

For PAR-CLIP, primary hepatocytes from Ad-hVigilin injected mice (for overexpression of V5-tagged human Vigilin) were isolated and supplemented with 100 μM 4SU for 16 hrs prior to crosslinking. After decanting the growth medium, cells were irradiated uncovered with 0.15 $J/cm^2$ of 365 nm UV light. V5-tagged-hVigilin was immunoprecipitated with a V5 antibody conjugated to protein G Dynabeads (Life Technologies). The radiolabeled band corresponding to the 155 kDa hVigilin-RNA complex was excised and the associated RNA was isolated by phenol-chloroform extraction following proteinase K treatment, conversion to a cDNA library, and Illumina sequencing at the Rockefeller University Genomics Center as described before (Hafner, 2010). Reads were adapter extracted, clipped with length of at least 20 nts and mapped to the mm10 mouse genome with Bowtie 0.12.9 (Bowtie parameters "-v 1 -m 10 --all --best-strata"), allowing for one mismatch. Processing and annotation of clusters to the ENCODE GRCm38 genome annotation was performed using the PARalyzer software as described in Corcoran et al. (2011) (http://www.genome.duke.edu/labs/ohler/research/PARalyzer/).

Motif Analysis

Motif analysis was carried out calculating kmer enrichment of PAR-CLIP clusters in protein-coding regions over the shuffled (10,000 times) GRCm38 mouse protein-coding open reading frames. Shuffled sequences were generated with the HMMER-3.0 suite. The MEME suite, MEME (http://meme-suite.org/tools/meme) (DREME, 2011), was used to define the motif of the top 759 protein-coding clusters (5'UTR, CDS, 3'UTR) as defined by PARalyzer, which had at least 10 reads.

RNA Isolation and Quantification

RNA was extracted using Trizol (Life Technologies) according to the manufacturer's instructions, except for a 30 min isopropanol precipitation at −20° C. RNA integrity was analyzed on an Agilent 2100 Bioanalyzer for all samples that were sequenced. RNA was subjected to DNase I treatment with the DNA-free kit (Invitrogen), when necessary. RNA was reverse transcribed using the High Capacity cDNA Reverse Transcription Kit (Applied Biosystems). Quantitative PCR was performed in an LC480 II Lightcycler (Roche) and using gene specific primers and Sybr Fast 2× Universal Master mix (Kapa). Results were normalized to 36B4 or Actb mRNA levels.

Illumina RNA Sequencing

The quality of the isolated RNA was determined with a Qubit (1.0) Fluorometer (Life Technologies) and a Bioanalyzer 2100 (Agilent). Only those samples with a 260/280 nm ratio between 1.8 and 2.1 and a 28S/18S ratio within 1.5 and 2.0 were further processed. The TruSeq RNA Sample Prep Kit v2 (Illumina) was used for cDNA library preparation. Quality and quantity of the enriched libraries were validated using Qubit (1.0) Fluorometer and the Caliper GX LabChip GX (Caliper Life Sciences). Libraries were normalized to 10 nM and sequenced on the Illumina HiSeq 2000 at the Functional Genomics Center Zurich.

Data Analysis.

RNA-sequencing reads were quality checked with FASTQC, adapter extracted, clipped with minimum size of at least 20 bases length and aligned against the mouse mm10 genome using TopHat 2. TopHat 2 was run with default options. On the basis of these alignments, the distribution of the reads across genomic features as well as isoform expression was quantified using Cufflinks2 and with the GENCODE mm10 genome annotation. Ribosome profiling reads were quality checked with FASTQC and reads with at least 20 bases, a tail phred quality score greater than 15 and an overall average phred quality score greater than 20 were selected and aligned against the mouse mm10 genome with Bowtie2. Downstream analysis was performed in R.

Western Blot Analysis

Cells and tissues (using the Tissue Lyser II, Qiagen) were homogenized with 3 volumes of RIPA lysis buffer [50 mM Tris-HCl pH 8, 150 mM NaCl, 1% NP-40, 0.5% sodium deoxycholate, 0.1% SDS and 1 tablet cOmplete EDTA-free protease inhibitor cocktail (Roche) per 50 ml buffer], incubated for 10 min on ice and centrifuged for 10 min at 20,000×g and 4° C. Protein concentrations were determined using the Bicinchoninic Acid Assay (Sigma-Aldrich). Equal protein amounts were boiled in Laemmli buffer (1.7% SDS, 5% glycerol, 0.002% bromophenol blue, 60 mM Tris-HCl pH 6.8, 100 mM DTT) for 5 min at 95° C., separated by SDS-PAGE and transferred onto nitrocellulose membranes by electroblotting in a wet chamber (Bio-Rad). The membranes were blocked for one hour with 5% non-fat dry milk TBS-0.1% Tween (Sigma-Aldrich), incubated with the primary antibodies overnight at 4° C., followed by 3× washes in TBS-0.1% Tween and incubation with a horseradish peroxidase-conjugated secondary antibodies (Calbiochem) for 2-3 hrs. Blots were then developed by chemiluminescent detection with a Fujifilm analyzer (LAS-4000) and signals quantified using ImageJ.

Bacterial Recombinant Protein Expression and Purification

Three liter cultures of *E. coli* BL21 (DE3)pLysS competent cells transformed with the pETM30-Vigilin-$His_6$ ($His_6$ disclosed as SEQ ID NO: 21) construct were grown at 37° C. and 180 rpm in Terrific Broth medium containing 75 μg/ml Kanamycin until the OD600 reached 1.3. The culture was then incubated at 18° C. for 1 h and protein expression was induced with 0.2 mM isopropyl-D-thiogalactopyranoside (IPTG). Incubation was then continued at 18° C. for 12 hrs. Cells were harvested by centrifugation for 10 min at 6,000×g and 4° C. All subsequent procedures were performed at 4° C. Bacterial pellets were resuspended in chilled lysis buffer [50 mM Tris-HCl pH 7.5, 150 mM NaCl, 5 mM $MgCl_2$, 10% Glycerol, 1 mM beta-Mercaptoethanol, 1 mM PMSF, 1 tablet EDTA-free Protease Inhibitor Cocktail (Roche) per 50 ml, 1 mg/ml Lysozyme 0, 5 μg/ml DNase (Company)] in a ratio of 1 g cell-wet weight to 1 ml lysis buffer. The lysates were further sonicated in a pre-chilled 50 ml tube (Falcon) to reduce viscosity [5 sec on, 20 sec off, for 2 min, Amplitude: 28%], and insoluble material was removed by centrifugation for 30 min at 20,000×g. The resulting supernatant was filtered through 0.45 μm polyethersulfone filter membranes (Filtropur S 0.45, Sarstedt). The lysate was diluted in 50 ml HisTrap-Buffer [50 mM Tris-HCl pH 7.5, 1 M NaCl, 5 mM $MgCl_2$, 10% Glycerol, 30 mM Imidazole pH 8.5, adjust buffer pH to 7.6 with HCl conc.] prior to loading onto a 5 ml HisTrap™HP column (GE Healthcare Life Science) pre-equilibrated in HisTrap-Buffer and attached to an ÄKTA Explorer FPLC. Diluted lysate was passed through the column at 2 ml/min and then gradually eluted with increasing concentrations of HisTrap-Buffer containing 500 mM imidazole, collecting 1-ml-sized fractions. The peak of fractions containing Vigilin were determined by SDS-PAGE and Coomassie-staining of the gel (typically at 150-200 mM imidazole). Vigilin containing fractions were pooled, diluted in 50 ml Heparin-Buffer [50 mM Tris-HCl pH 7.6, 150 mM NaCl, 5 mM $MgCl_2$, 10% Glycerol, adjust buffer pH to 7.6] and loaded on a 5 ml HiTrap™ Heparin HP column (GE Healthcare Life Science). RNA-depleted Vigilin was eluted gradually using increasing concentrations of Heparin-Buffer containing 2 M NaCl and collected in 1 ml fractions. Eluate fractions were monitored by SDS-PAGE and Coomassie staining. Fractions containing Vigilin were pooled and dialyzed overnight using a 50 kDa MWCO Pur-A-Lyzer™ (Sigma-Aldrich) into storage buffer [20 mM Tris-HCl pH 7.6, 300 mM KCl, 5 mM $MgCl_2$, 50% glycerol, 1 mM DTT, 1 mM PMSF, 1 tablet EDTA-free Protease Inhibitor Cocktail (Roche) per 50 ml]. Aliquots of Vigilin were stored at −80° C. Protein concentrations were determined by Coomassie staining intensity in comparison to bovine serum albumin.

Electrophoretic Mobility Shift Assays

Oligoribonucleotides were labeled with [$\gamma$-$^{32}$P]ATP and T4 polynucleotide kinase using standard conditions. A total of 10 nM $^{32}$P-labeled RNA was incubated with 0-10 μM protein in 20-μL reactions containing 250 mM KCl, 5 mM $MgCl_2$, 25 mM Tris-HCl pH 7.5, 10% glycerol, 1 mg/mL acetylated BSA (Ambion), 1.5 μM of yeast tRNA (Invitrogen). Reactions were incubated at 25° C. for 5 min and separated on 1.2% agarose gel for 1 h at 130 V at room temperature using 1×TBE. Agarose gels were dried under vacuum gel dryers at 60° C. for 2-3 hrs, exposed to a phosphoimager screen.

Ribosome Profiling

Immediately before sample collection, primary hepatocytes were incubated with media containing 100 $\mu g \times ml^{-1}$ cycloheximide for 15 min at 37° C. to stop translation elongation. Cells were washed twice with ice-cold 9.5 mM PBS, pH 7.3, containing 100 $\mu g\ ml^{-1}$ cycloheximide, and lysed by adding lysis buffer (10 mM Tris-HCl, pH 7.4, 5 mM $MgCl_2$, 100 mM KCl, 2 mM dithiothreitol, 100 $\mu g\ ml^{-1}$ cycloheximide, 1% Triton X-100, 500 U $ml^{-1}$ RNasin Plus, and protease inhibitor (1× complete, EDTA-free, Roche)). Crude lysates were centrifuged at 1,300 g for 10 min at 4° C. and the supernatant was transferred to a fresh tube. Ribosome profiling and RNA-seq were performed on cleared lysates essentially as described (Guo et al., 2010), using rRNA depleted RNAs with a detailed protocol available at http://bartellab.wi.mit.edu/protocols.html. Libraries for Illumina sequencing were prepared using the NEBNext® Small RNA Library Prep Set according to the manufacturer's instructions.

Data Analysis

Reads were quality-checked with FastQC. Reads at least 20 bases long, with a tail phred quality score greater than 15 and an overall average phred quality score greater than 20 were aligned to the reference genome and transcriptome (FASTA and GTF files, respectively, downloaded from the UCSC, genome build mm10) with Bowtie2 (Langmead et al., 2012) with default settings for single end reads. Distribution of the reads across genomic isoform expression was quantified using the R package GenomicRanges (Lawrence et al., 2013) from Bioconductor Version 3.0. Differentially expressed genes were identified using the R package edgeR (Robinson et al., 2010) from Bioconductor Version 3.0.

Label Free Mass-Spectrometry

Medium from primary hepatocytes was collected 24 hrs after medium change and centrifuged at 14,000×g to pellet insoluble remnants. 60-80 μl supernatants were precipitated with 1 volume of 20% TCA precipitation and washed twice with cold acetone. Dry pellets were dissolved in 45 μl buffer (10 mM Tris, 2 mM $CaCl_2$, pH 8.2) and trypsinized with 5 μl of 100 ng/μl trypsin in 10 mM HCl for 30 min at 60° C. Samples were dried, dissolved in 20 μl 0.1% formic acid and transferred to an autosampler vial for LC/MS/MS. 2 μl were injected. Label-free quantification of MS-data was performed by matching raw data to the Mouse Swiss-Prot database using MaxQuant. Statistical analysis was then performed using Perseus.

Blood Plasma Fractionation

Lipoproteins from pooled plasma (200 μl total) were diluted in 1 mM EDTA-PBS and separated by FPLC using two Superose-6 FPLC columns in series (HR10/30) in 1 mM EDTA-PBS at 0.5 ml/min. Columns were calibrated using high and low molecular weight standards (GE Healthcare).

Liver Triglyceride and Cholesterol Content

Lipids from 50 mg liver were extracted with 1 ml hexane: isopropanol (3:2) by homogenizing tissues using the tissue lyzer. Lysates were centrifuged at 20,000×g for 3 min and the supernatant was transferred to a fresh tube. The pellet was re-extracted with 0.5 ml hexane:isopropanol, spun again and the supernatants were combined. 0.5 ml of 0.5 M $Na_2SO_4$ solution was added and the tubes mixed. The samples were centrifuged for 3 min at full speed and the upper organic phase was transferred to a fresh tube, avoiding contamination with the aqueous phase. The samples were spun again and the upper phase was transferred to a fresh tube and evaporated overnight under the fume hood. Lipids were dissolved in 1 ml of TritonX-100:methanol:butanol (1:1:3) mixture. 5 μl were used for lipid quantifications.

Oil Red O Stainings

Frozen OCT-embedded liver pieces were stained with Oil Red O as described before (Mehlem et al., 2013).

In Vitro Translation Assay

Full-length V5-tagged Fetuin-A and ApoM mRNAs were in vitro transcribed from pcDNA3.1 vectors using the mMESSAGE mMACHINE kit (Ambion). mRNAs were utilized for in vitro translation as described before (Rakotondrafara et al., 2011) in 100 μl reactions using methionine-free amino acid mix and nuclease treated extracts from primary hepatocytes isolated from mice injected with Ad-shCTRL or Ad-shVIG. Proteins were co-translationally radiolabeled by addition of 50 μCi [$^{35}$S]-methionine (PerkinElmer) to the reaction. V5-tagged protein products were immunoprecipitated with a V5-antibody conjugated to protein G Dynabeads (Life Technologies), washed 10× with IP wash buffer [50 mM HEPES-KOH pH 7.5, 500 mM KCl, 0.05% NP-40, 0.5 mM DTT, 1 tablet cOmplete EDTA-free protease inhibitor cocktail (Roche) per 50 ml] separated by SDS-PAGE and visualized by autoradiography using x-ray films (Fuji).

Preparation of Nuclear/Cytoplasmic Extracts

Primary hepatocytes were permeabilized on ice in hypotonic lysis buffer [10 mM HEPES-KOH, pH 7.5, 1.5 mM $MgCl_2$, 10 mM KCl, 0.5 mM EDTA, 0.1% NP-40, 1 mm DTT, 1 tablet cOmplete pProtease Inhibitor Cocktail] per 50 ml buffer (Roche)] for 30 sec, vortexed briefly and immediately centrifuged for 30 sec at 8,000×g and 4° C. After centrifugation, the supernatants (cytoplasmic extracts) were collected, and nuclear pellets were washed 8 times in nuclear wash buffer [50 mM HEPES-KOH pH 7.5, 150 mM KCl, 2 mM EDTA, 0.5% NP-40, 1 mm DTT, 1 tablet cOmplete pProtease Inhibitor Cocktail per 50 ml buffer (Roche)] by brief resuspension and centrifugation at 8,000×g for 30 sec. Nuclear pellets were resuspended in RIPA buffer [50 mM Tris-HCl pH 8, 150 mM NaCl, 1% NP-40, 0.5% sodium deoxycholate, 0.1% SDS and 1 tablet cOmplete EDTA-free protease inhibitor cocktail (Roche) per 50 ml buffer].

Triglyceride Secretion Assay

Seeded primary mouse hepatocytes extracted from mice injected with adenovirus were pulsed with 1 mM of pre-warmed albumin bound $^{14}$C-palmitic acid for 1 h and then washed 3× with PBS. Williams E medium (Life Technologies) supplemented with 1% Penicillin-Streptomycin (Life Technologies), 1% GlutaMax (Life Technologies) was re-added to the cells and harvested 4 hours after medium change. Incorporation of palmitic acid into triglycerides and subsequent secretion of radiolabeled triglycerides was quantified by extraction of the lipid fraction from the medium followed by liquid scintillation counting.

Quantification of Atherosclerotic Plaques

Atherosclerosis was quantified in aortic root cross-sections from fresh-frozen optimal cutting temperature medium (OCT)-embedded hearts. Serial 10 μm frozen sections of the aortic root were stained with Oil red O and H&E for visualization of atherosclerotic lesions. Lesion areas were quantified using XY software. Analysis of the aortic roots was performed blindly without knowledge of the treatments.

Statistical Analysis

Numerical values are reported as average±s.d. unless stated otherwise. No statistical method was used to predetermine sample size, but sample size was based on preliminary data and previous publications as well as observed effect sizes. Outliers that were two standard deviations outside of the mean were routinely excluded from all analyses. Animals were sex- and age-matched. Animal studies were performed without blinding of the investigator. The data was assessed for normal distribution and similar variance between groups using GraphPad Prism 6.0 if applicable. Some data sets had a statistical difference in the variation between groups. If not mentioned otherwise in the figure legend, statistical significance (*P≤0.05, P≤0.01, *P≤0.001) was determined by unpaired two-tailed t-test, one-way ANOVA (when comparing ≥3 groups) or two-way ANOVA (for repeated measurements and time courses) with relevant post hoc tests (Holm-Sidak for =3 groups and Tukey's for repeated time measurements and time courses). GraphPad Prism 6.0 software was used for statistical analysis of all data sets.

Results and Discussion

Figure 1C:
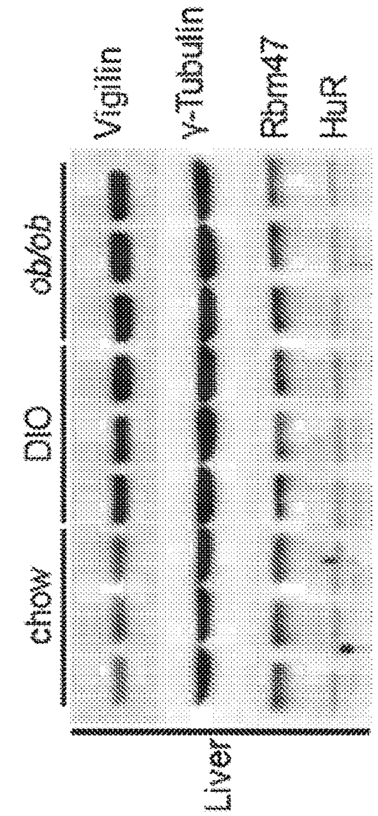
Figures 1D, 1E:
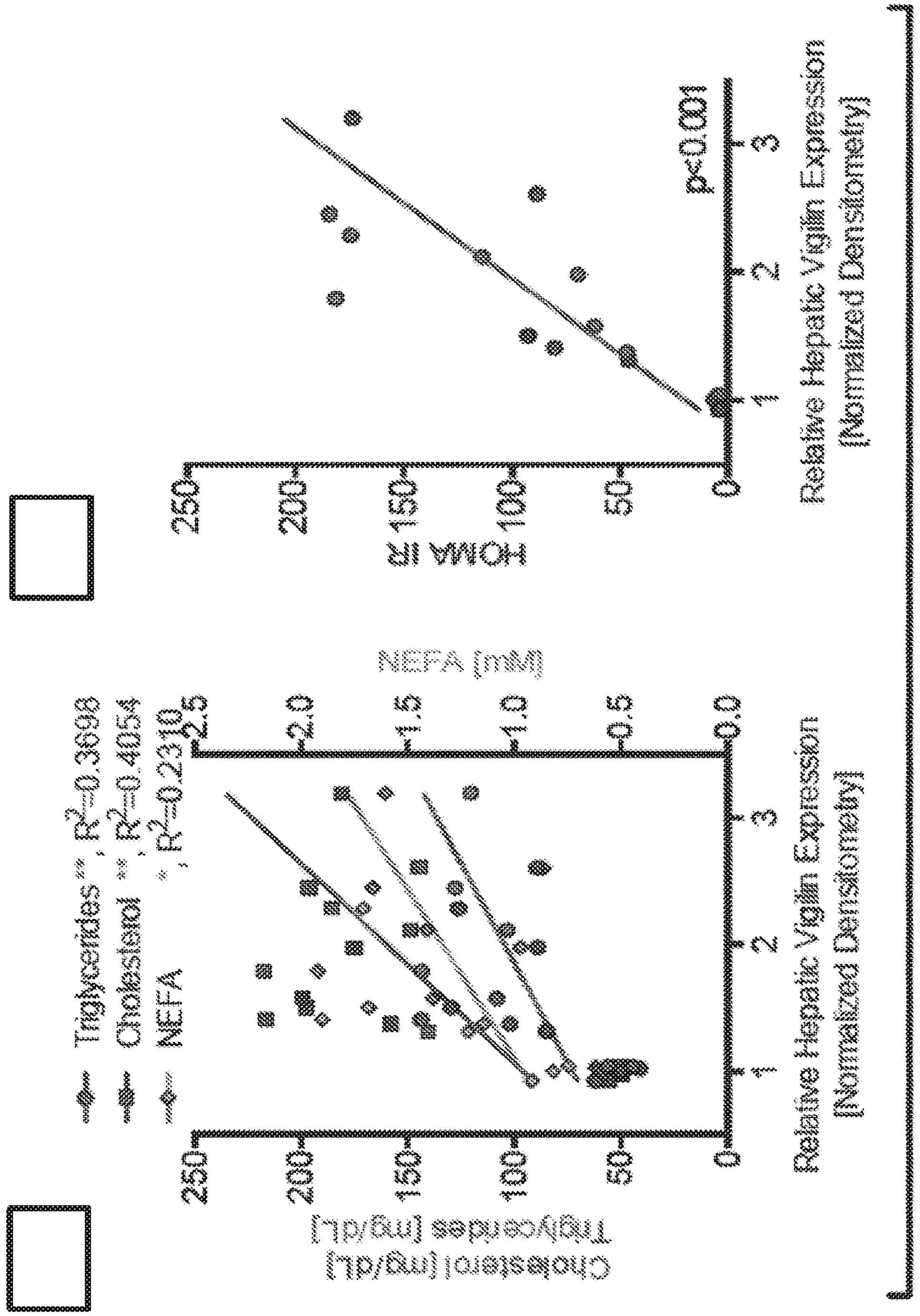
Figures 1F, 1G, 1H:
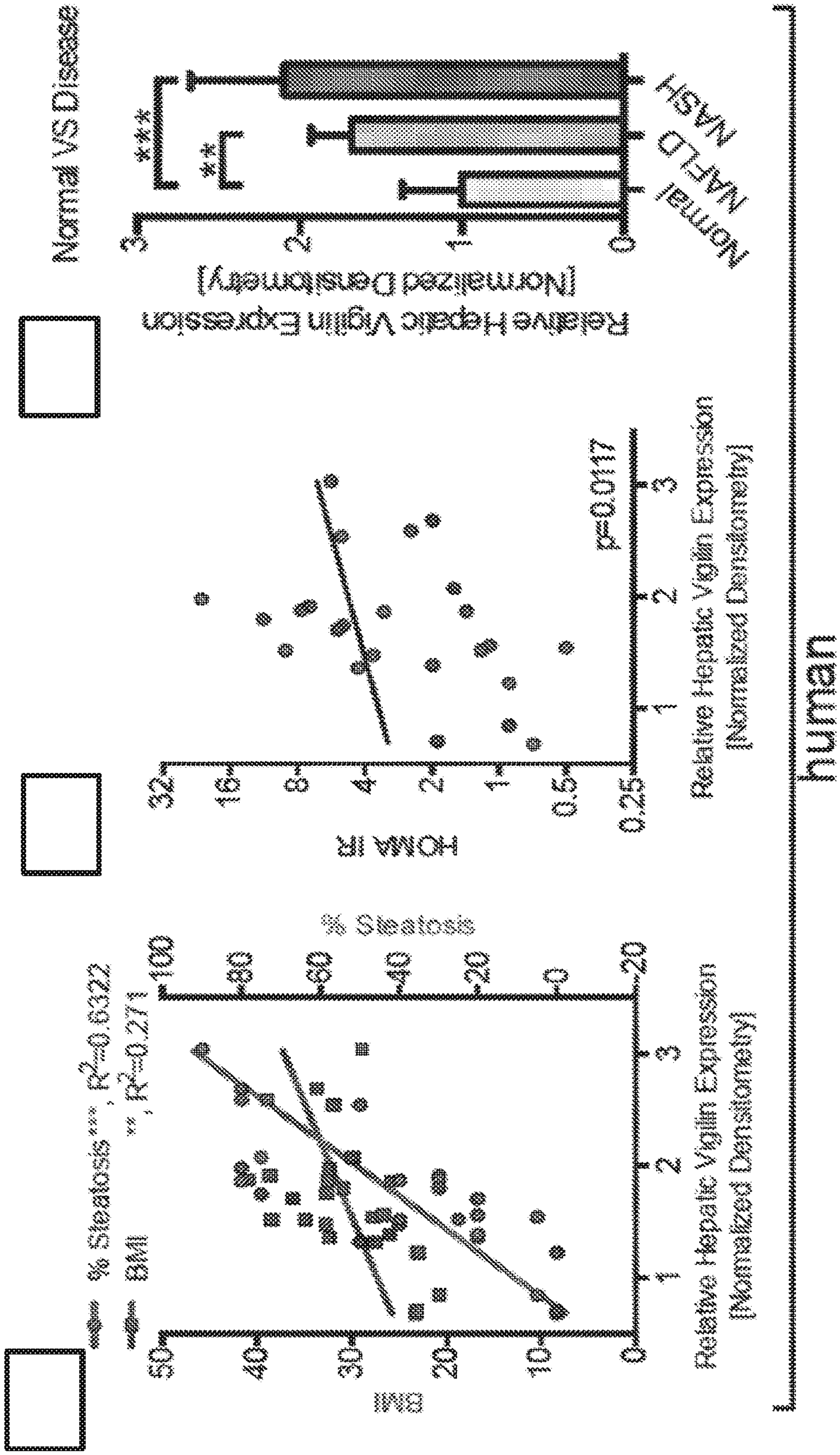
Figure 2A:
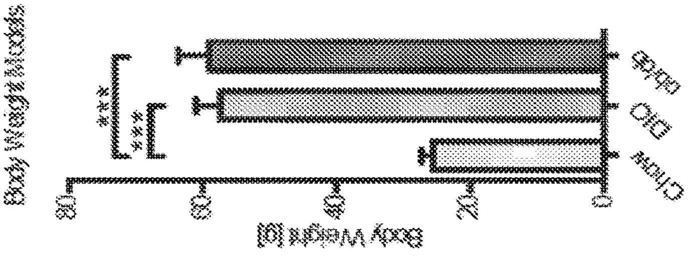
FIGS. 2A-V depict additional metabolic parameters from mouse models under study. Body weight, blood glucose and HOMA IR of chow fed wildtype (Chow), diet-induced obese (DIO) and ob/ob mice (FIGS. 2A-C) under study (n=6 per group) in immunoblot (main figure) and qPCR analysis (FIG. 2D) for hepatic Vigilin levels. Liver triglyceride content (FIG. 2E), liver Oil-Red O stainings (FIG. 2F), blood glucose (FIG. 2G), insulin (FIG. 2H) and alanine transaminase (ALT) levels (FIG. 2I) in gain of function (GOF) study of 8-week-old C57BL/6 mice injected with Ad-GFP or Ad-hVigilin (n=5 per group) for 7 days. 8-week-old wildtype (WT) or 20-week old DIO C57BL/6 mice were injected with either Ad-shCTRL (n=6 for WT, n=8 for DIO), Ad-shVIG (n=6 for WT, n=8 for DIO) or PBS (n=3 for WT, n=5 for DIO) for 10 days for loss of function (LOF). Tissue panel from LOF study indicating liver specific knockdown of Vigilin from mice treated with Ad-shVIG as opposed to Ad-shCTRL or PBS treated mice (FIG. 2J). Blood glucose, insulin and ALT levels in mice from LOF study in chow fed wildtype (WT) and diet-induced obese (DIO) mice (FIGS. 2K-P). qPCR analysis of inflammation markers from livers in LOF study (FIG. 2Q). Liver triglyceride content (FIG. 2R), liver Oil-Red O stainings (FIG. 2S), blood triglyceride (FIG. 2T), non-esterified fatty acid (NEFA.
Figure 2B:
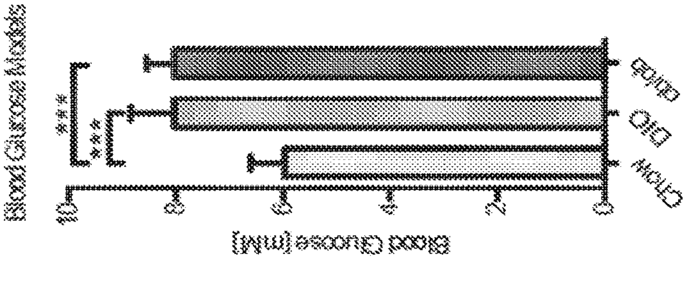
FIG. 2U) and cholesterol levels (FIG. 2V) in LOF study in wildtype mice. All values are expressed as mean±s.d. *P≤0.05, P≤0.01, *P≤0.001; Student's t-test (FIGS. 2E, G-I) or ANOVA with Holm-Sidak post hoc analysis (FIGS. 2A-D, K-R, T-V).
Figure 2C:
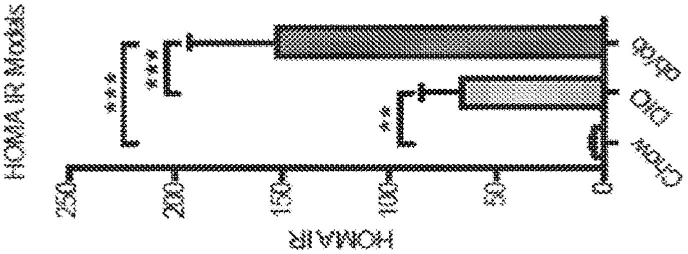
Figure 2D:
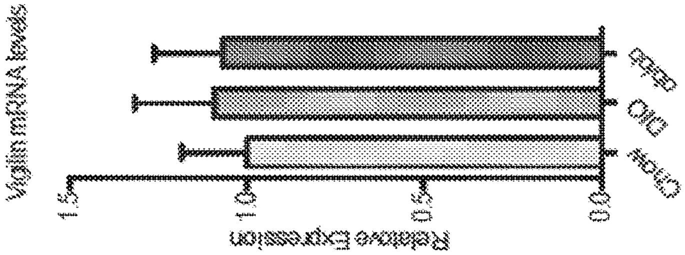
Figure 2E:
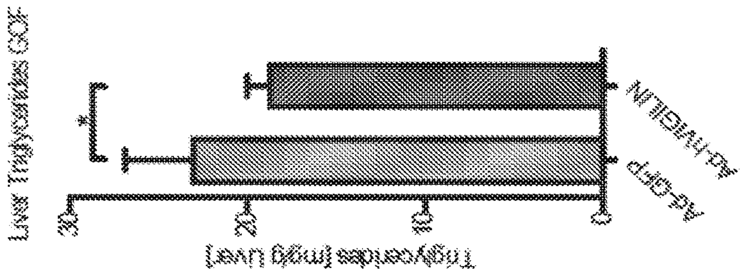
Figure 2F:
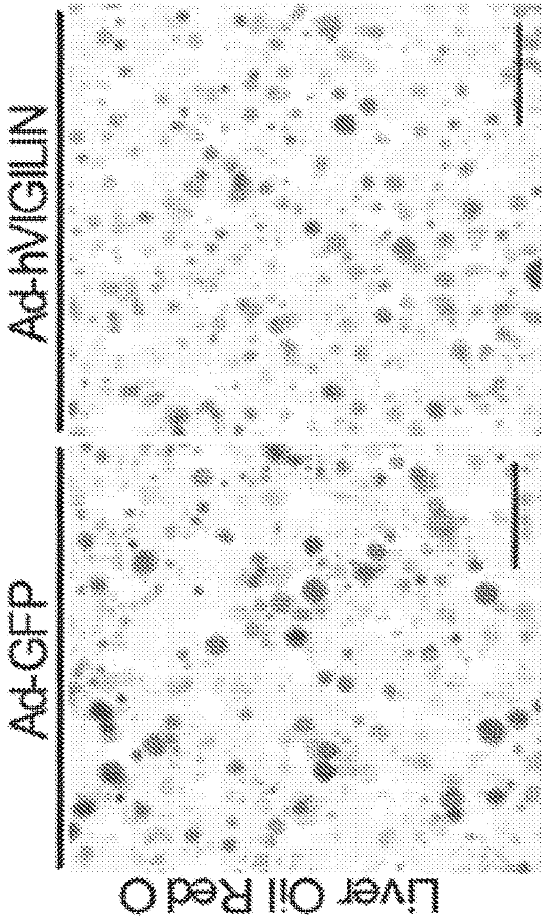

The cellular localization of Vigilin in primary hepatocytes was studied and it was found the predominant localization of Vigilin is the cytoplasmic fractions (FIG. 1*b*). To investigate if Vigilin is deregulated in obese, insulin resistant mice, its expression in livers of diet induced obese C57Bl/6J (DIO) and ob/ob mice was measured (FIGS. 2*a-c*). Hepatic protein levels of Vigilin, but not those of other RBPs with high expression levels such as Elavl1/HuR and Rbm47, were markedly increased in obese mice compared to chow fed control animals (FIG. 1*c*), while Vigilin mRNA levels were similar (FIGS. 2*d*). Furthermore, cholesterol, triglycerides, NEFA and HOMA IR all correlated significantly with hepatic Vigilin expression (FIGS. 1*d, e*). Vigilin protein levels were also measured in liver biopsies of a cohort of 5 healthy, 10 non-alcoholic fatty liver disease (NAFLD) and 10 non-alcoholic steatohepatitis (NASH) patients. A strong positive correlation was noted between the subjects' Vigilin expression levels and BMI as well as liver steatosis (FIG. 1*f*), concomitant with insulin resistance as measured by the HOMA IR index (FIG. 1*g*). Furthermore, Vigilin levels were highest in liver biopsies of subjects with NASH (FIG. 1*h*), indicating that Vigilin's expression may be regulated by inflammatory mediators.

Figures 1I, 1J, 1K, 1L:
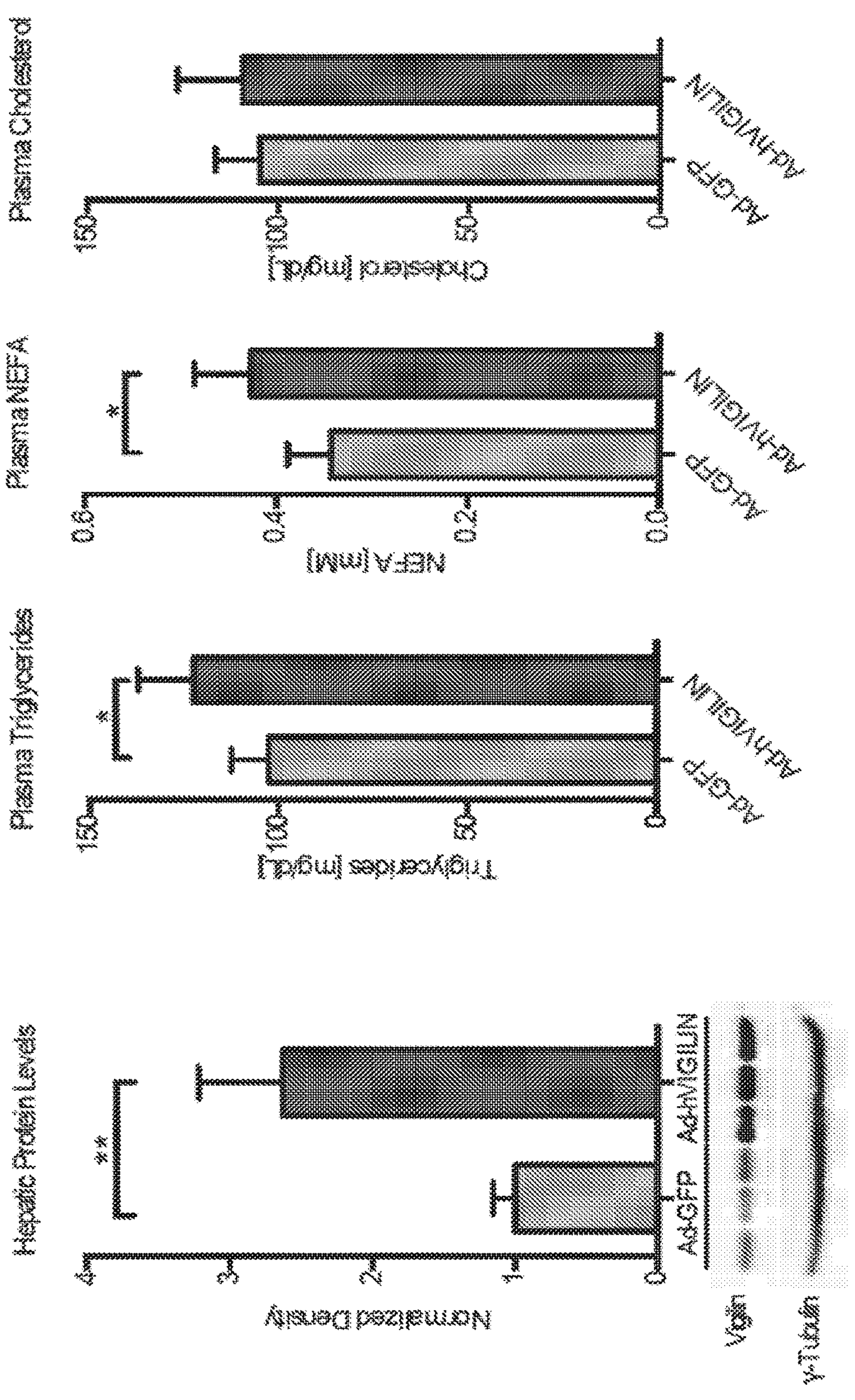
Figure 1M:
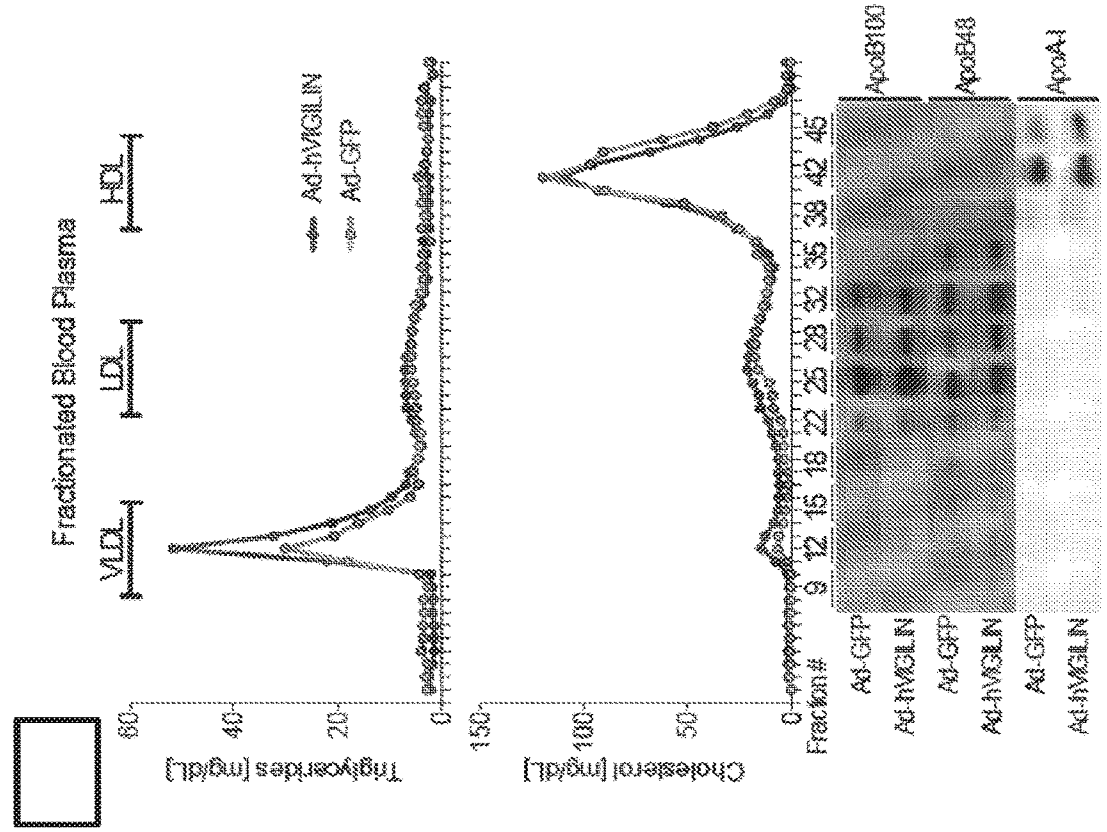
Figure 2I:
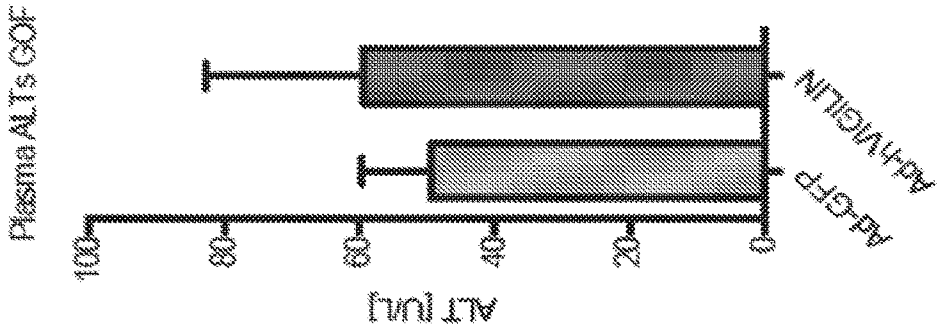
Figure 2H:
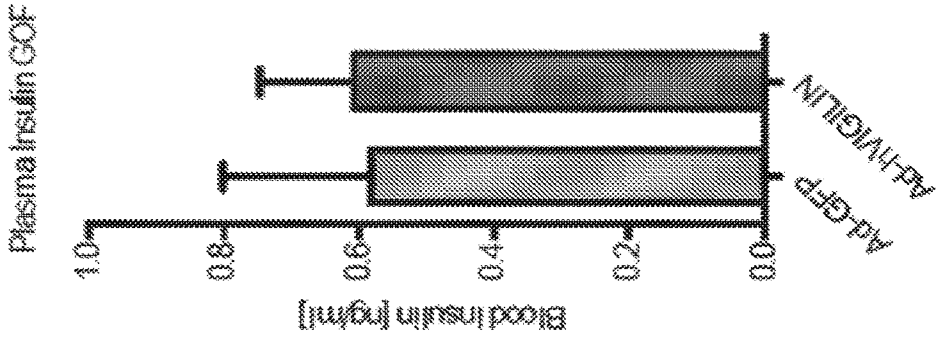
Figure 2G:
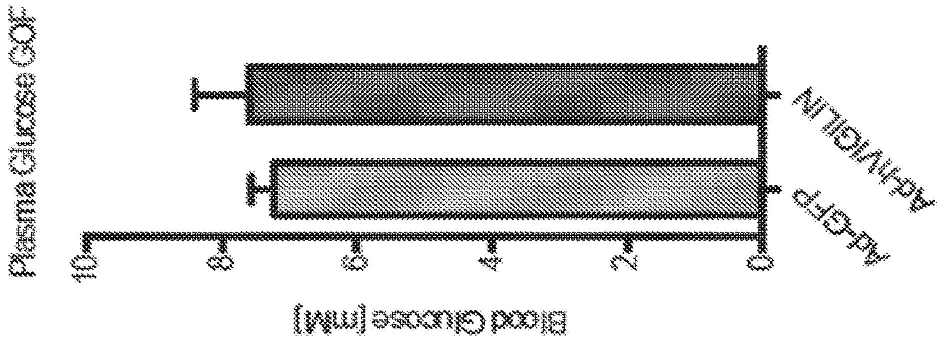
Figure 2L:
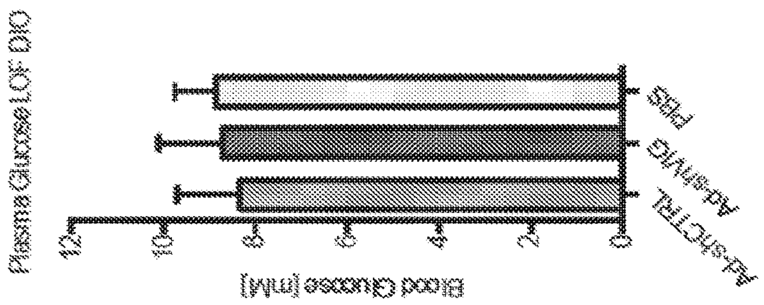
Figure 2K:
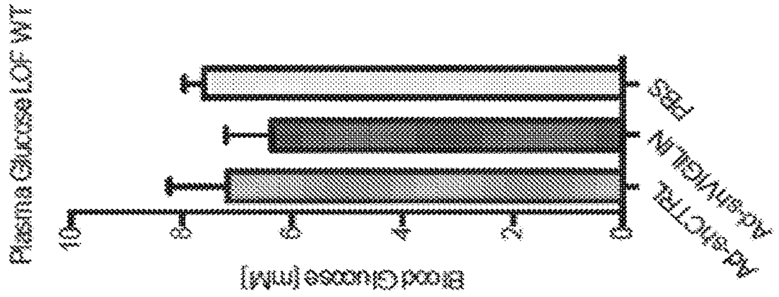
Figure 2J:
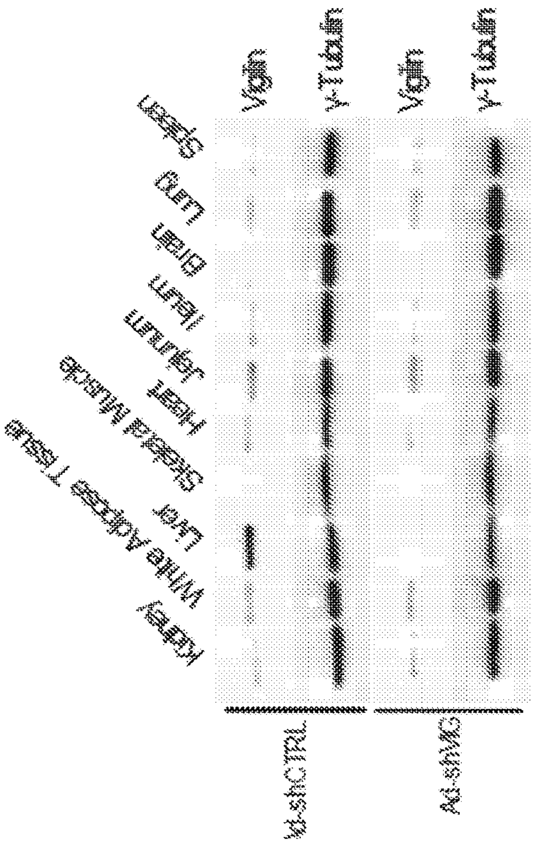
Figure 2M:
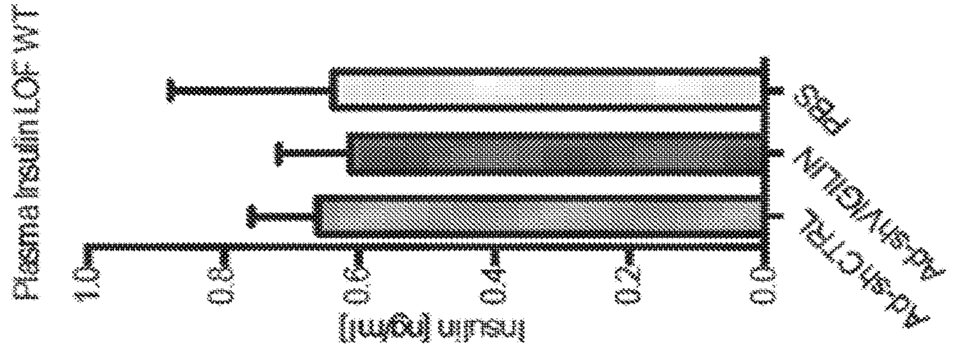
Figure 2N:
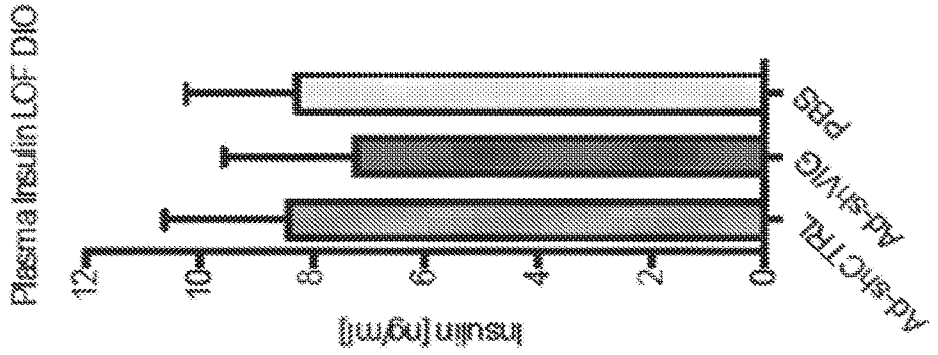

To investigate the functional consequence of elevated Vigilin levels in livers of insulin resistant obese mice, a recombinant adenovirus expressing human Vigilin (Ad-hVigilin) was generated. Injection of male C57Bl/6J mice with Ad-hVigilin resulted in a comparable overexpression as measured in ob/ob mice of ~3-fold (FIG. 1*i*). This gain of function was sufficient to elevate plasma triglyceride, NEFA, as well as very low density lipoprotein (VLDL) levels and lower triglyceride content in the liver, when compared to Ad-GFP infected, age- and weight-matched control mice (FIGS. 1*j-m*, FIGS. 2*e, f*). No changes in the levels of plasma glucose, insulin, cholesterol and the liver damage marker alanine transaminase (ALT) were observed (FIGS. 2*g-i*; FIG. 1*l*). These data demonstrate that Vigilin expression is increased in steatotic livers of insulin resistant subjects and that elevated hepatic Vigilin levels increase triacylglycerol metabolism/VLDL secretion from the liver.

Figures 1N, 1O, 1P, 1Q:
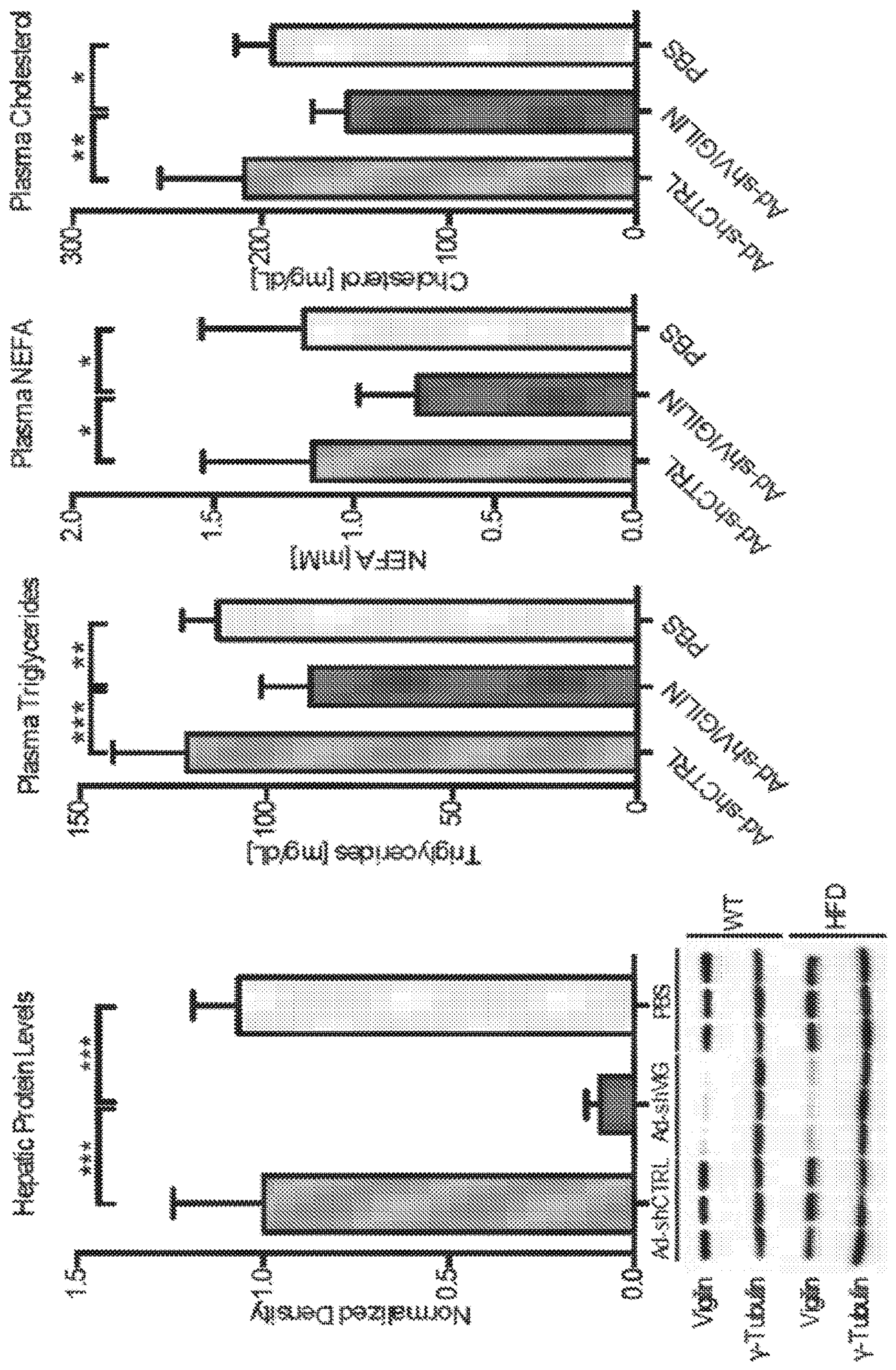
Figure 1R:
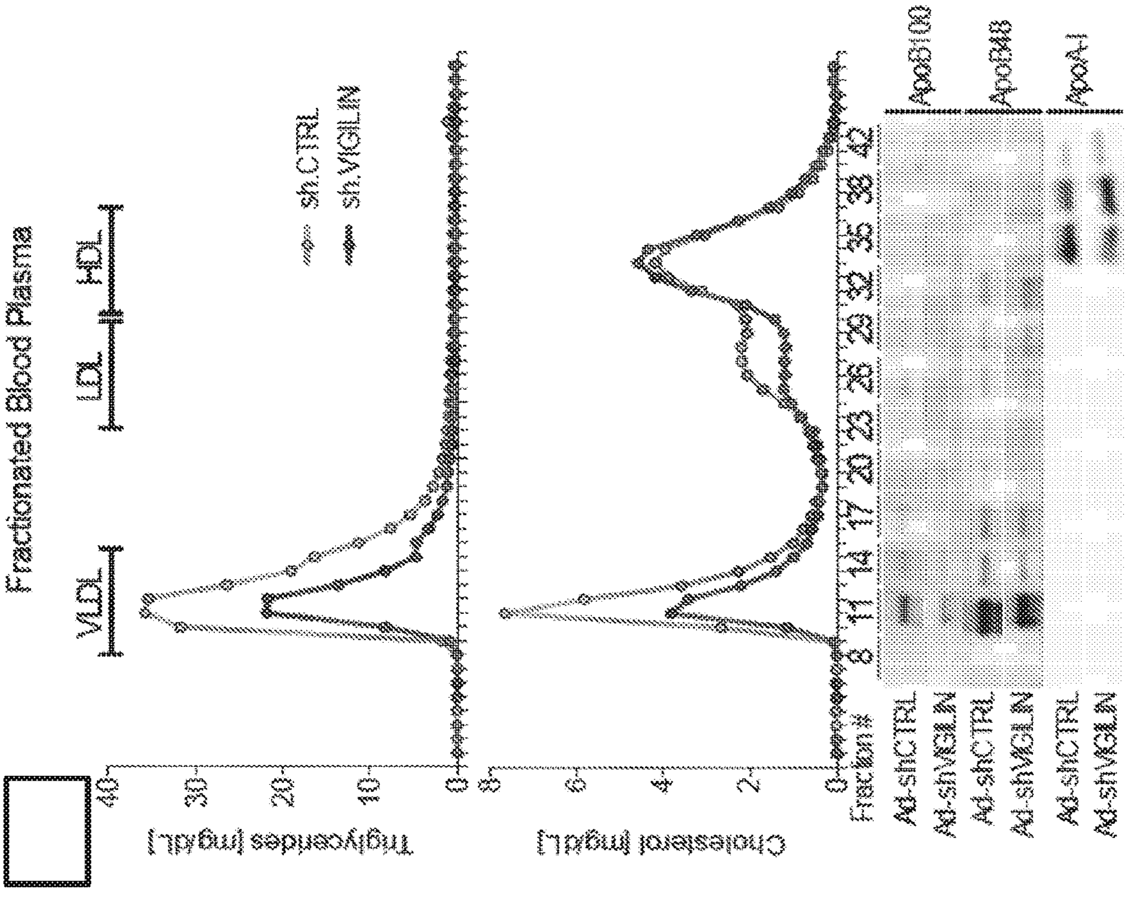
Figure 2O:
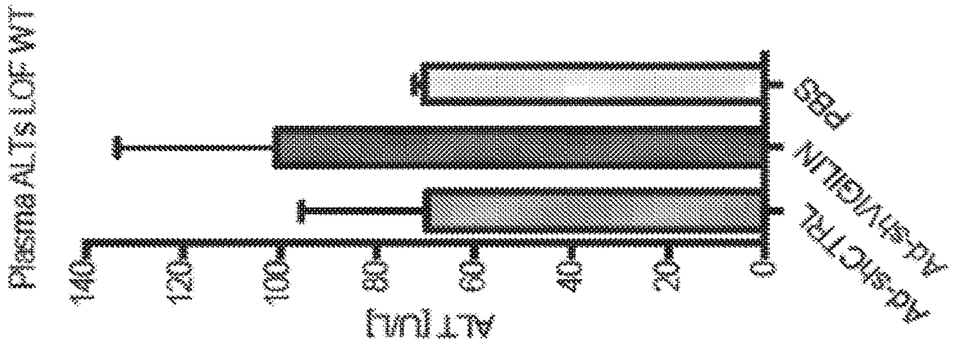
Figure 2P:
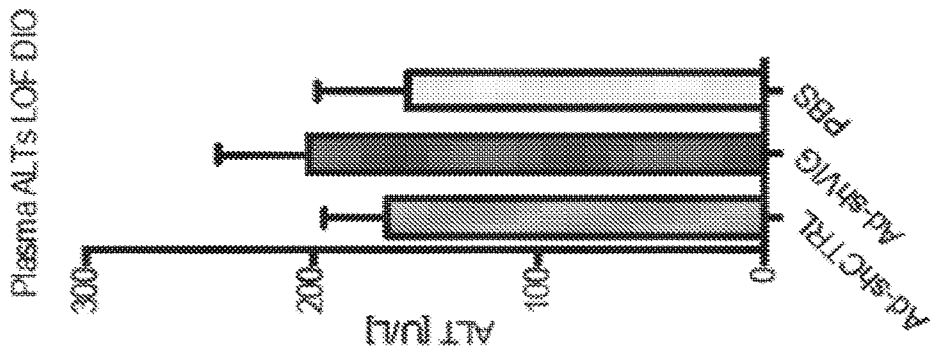
Figure 2R:
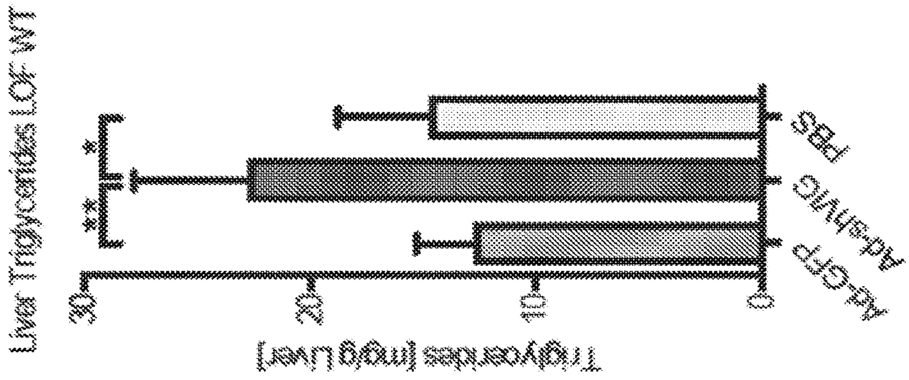
Figure 2Q:
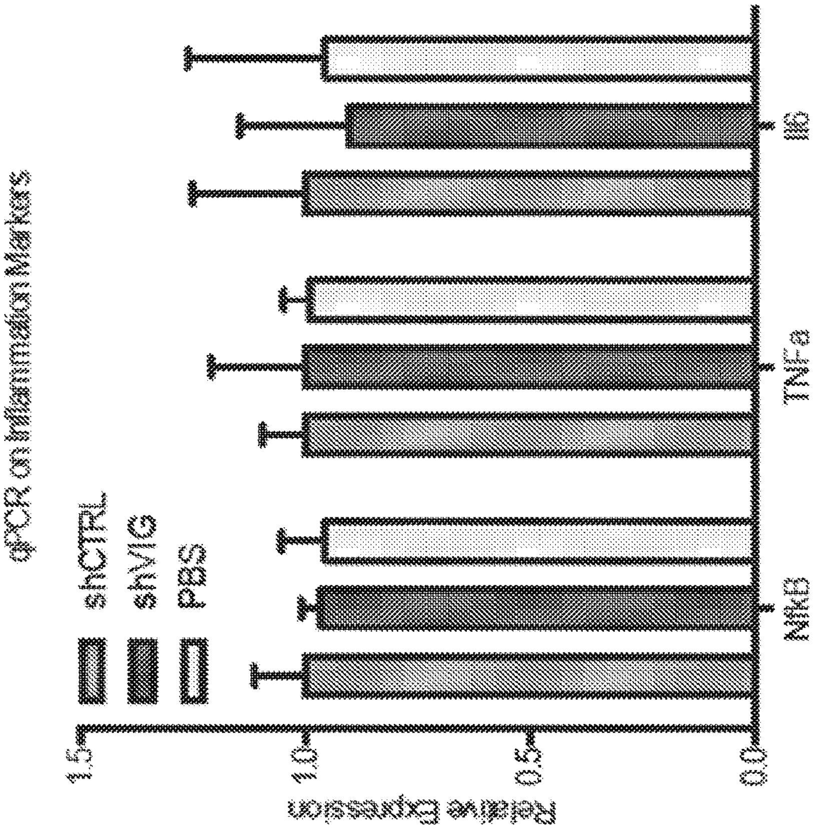
Figure 2S:
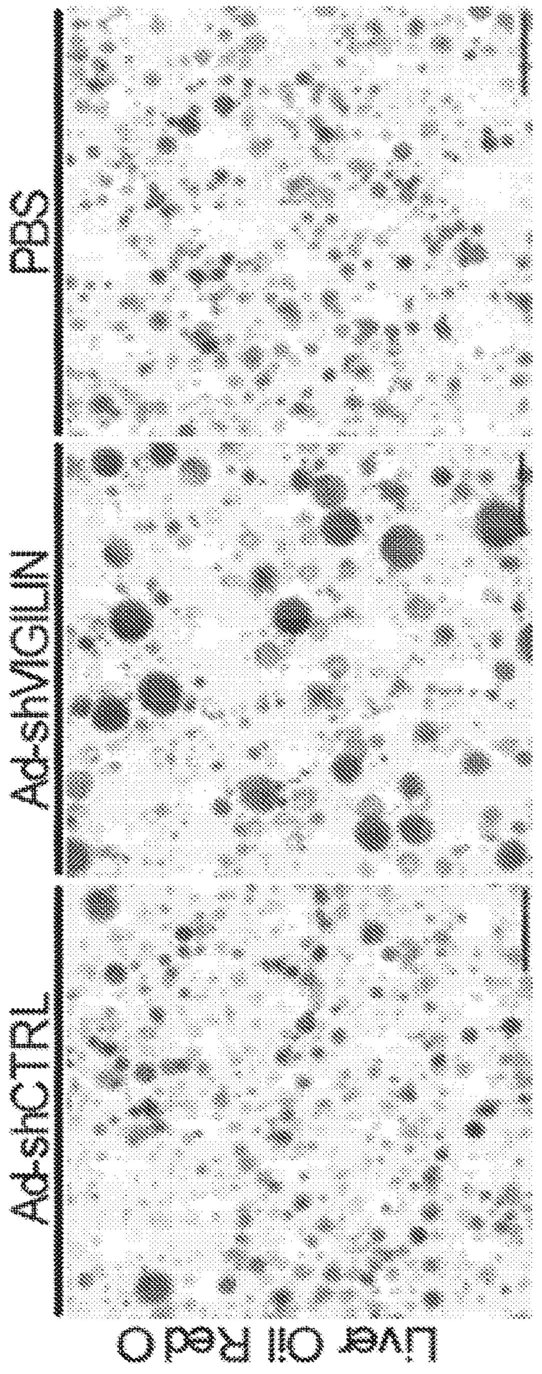
Figure 2T:
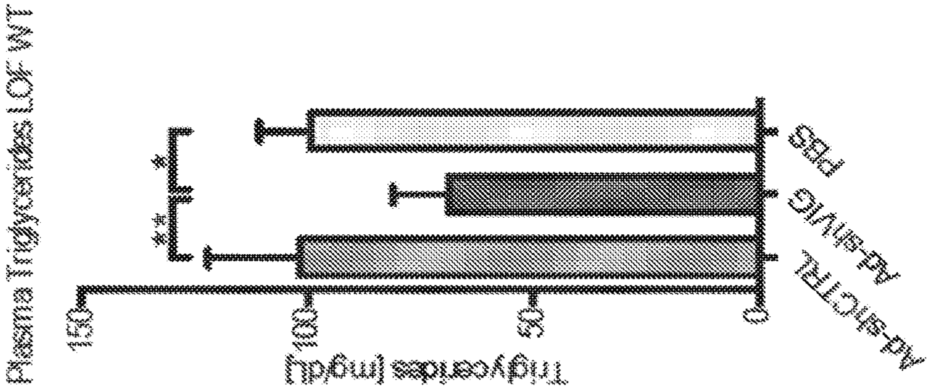
Figure 2U:
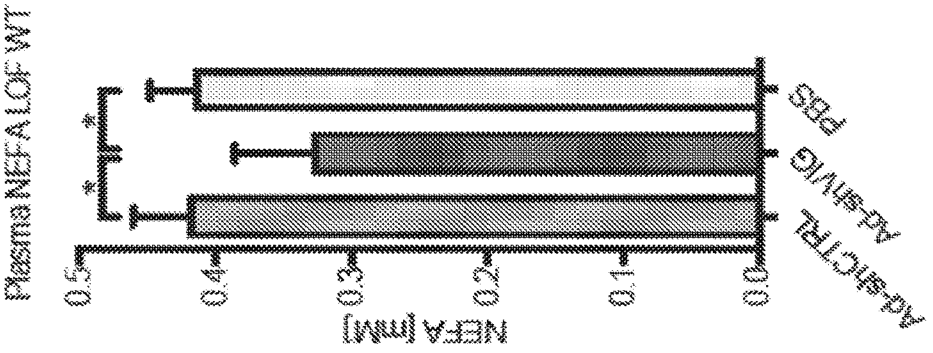
Figure 2V:
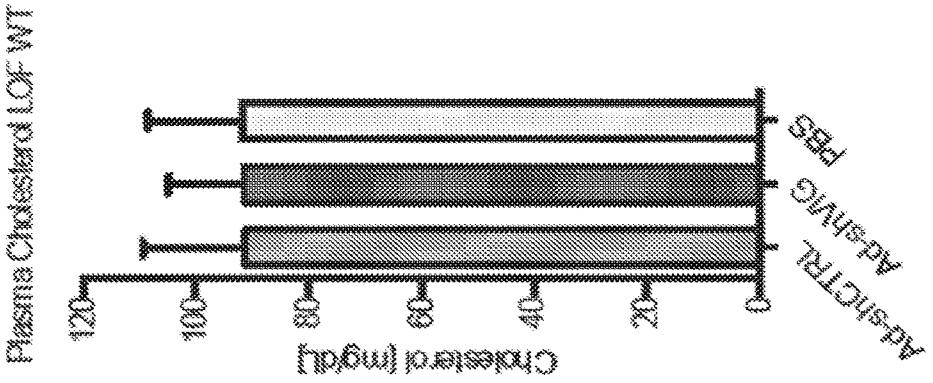

The effect of silencing Vigilin by employing a recombinant adenovirus expressing an shRNA (Ad-shVIG) targeting Vigilin mRNA was studied. Injection of Ad-shVIG resulted in a >90% reduction of Vigilin protein compared to injection of PBS or control adenovirus expressing a nonfunctional shRNA (Ad-shCTRL) in both wildtype and DIO mice (FIG. 1*n*). Knockdown of Vigilin was restricted to the liver and did not reveal any significant changes in blood glucose or insulin levels in chow and DIO mice under ad libitum fed conditions (FIGS. 2*j-n*). ALT levels as well as inflammation markers NFkB, IL-6 and TNFα remained in a normal range in adenovirus and PBS-injected mice (FIGS. 2*o-q*). Silencing of Vigilin in wildtype mice resulted in increased liver triglycerides and decreased plasma triglycerides and NEFA levels, whereas knockdown of Vigilin in DIO mice also lowered cholesterol levels through VLDL and LDLs when compared to Ad-shCTRL injected control mice (FIGS. 2*r-v*, FIGS. 1*o-r*).

Figure 3B:
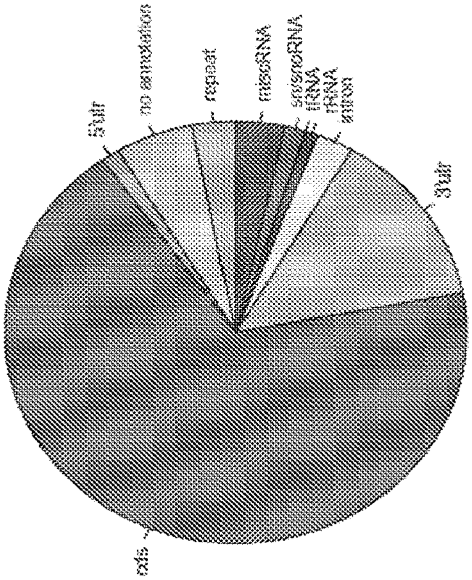
FIGS. 3A-I depict that Vigilin binds to CU-rich sequences in ORFs and promotes translation of its targets.
Figure 3A:
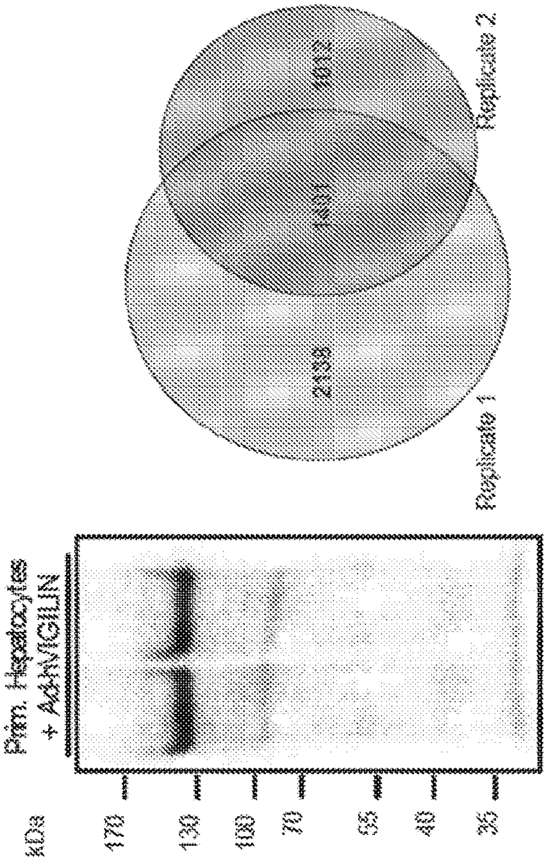
Figure 3C:
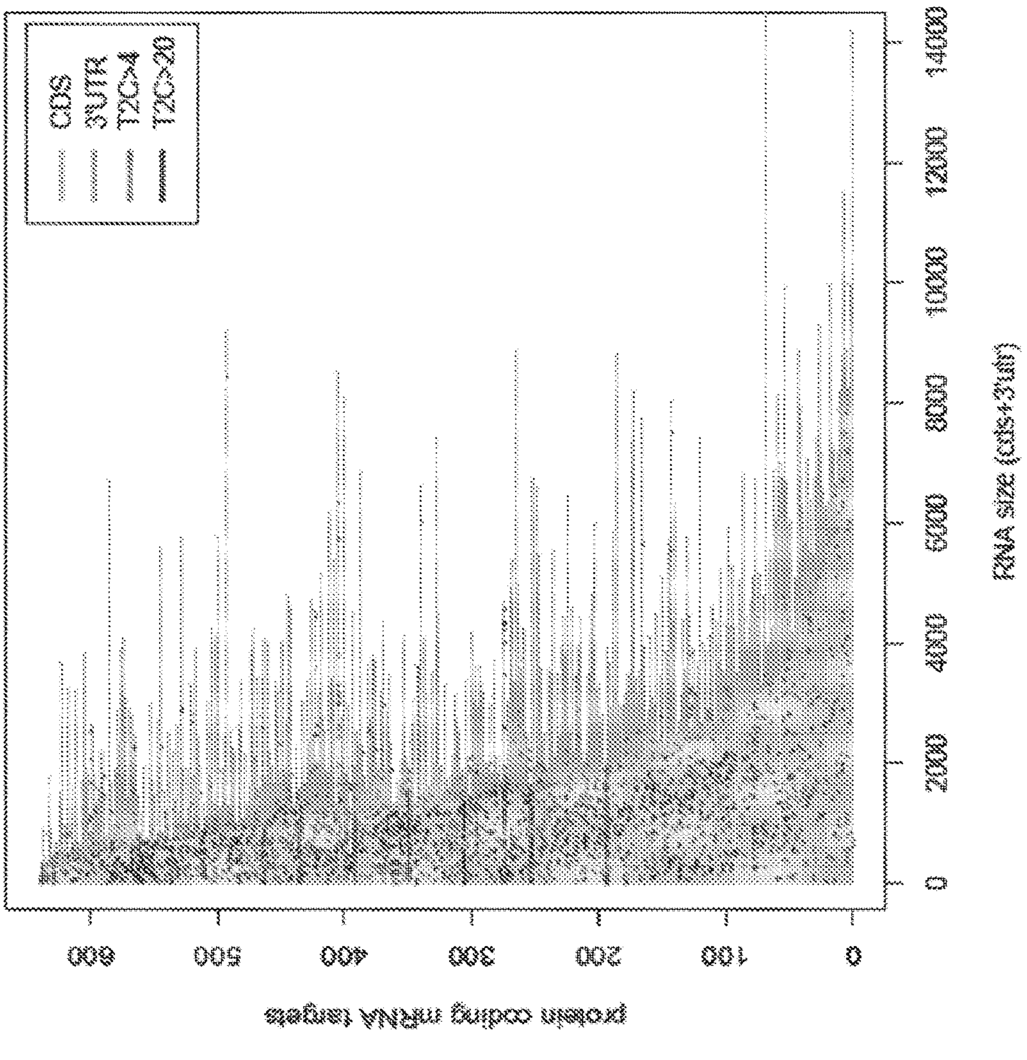
Figure 3D:
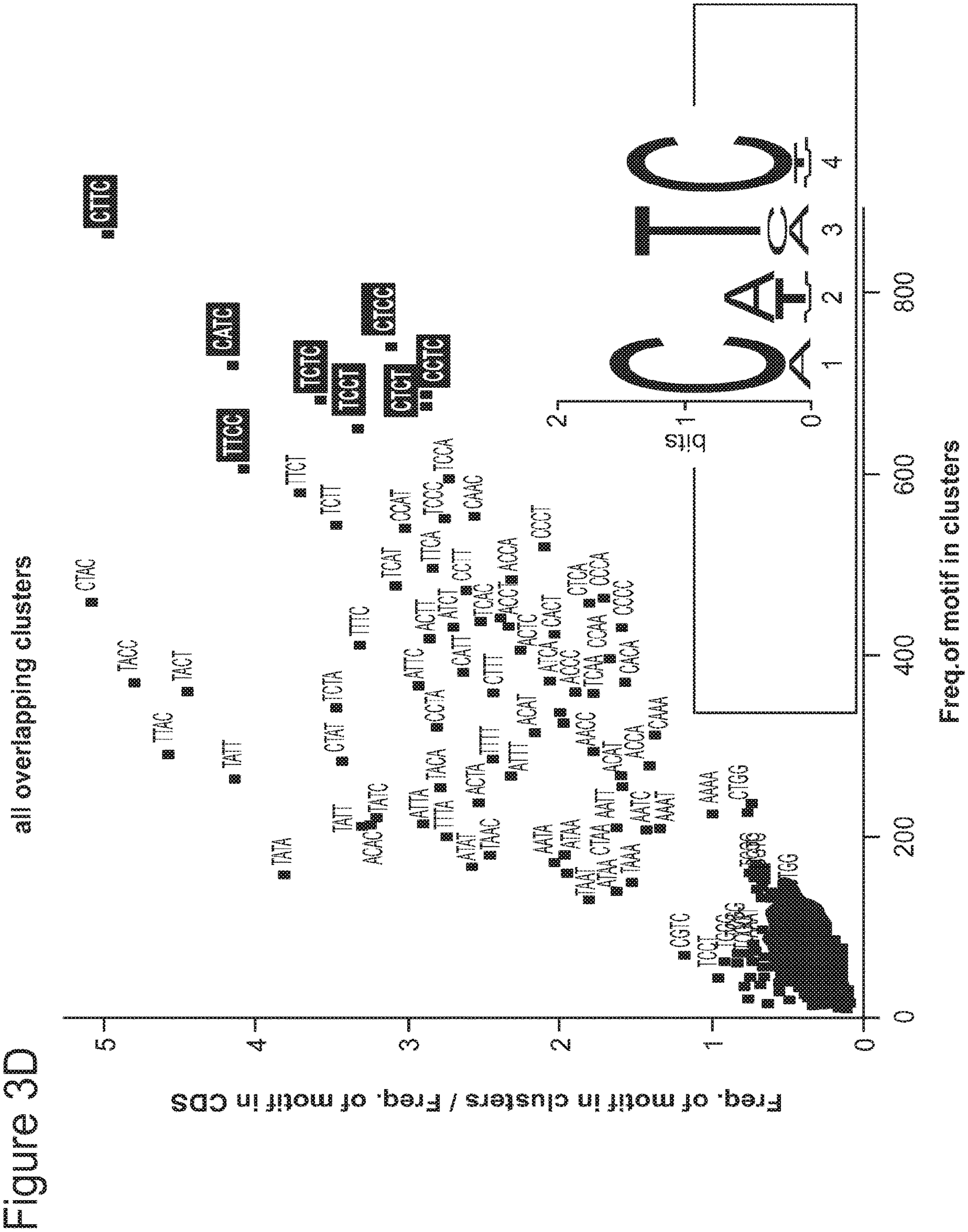
Figure 3E:
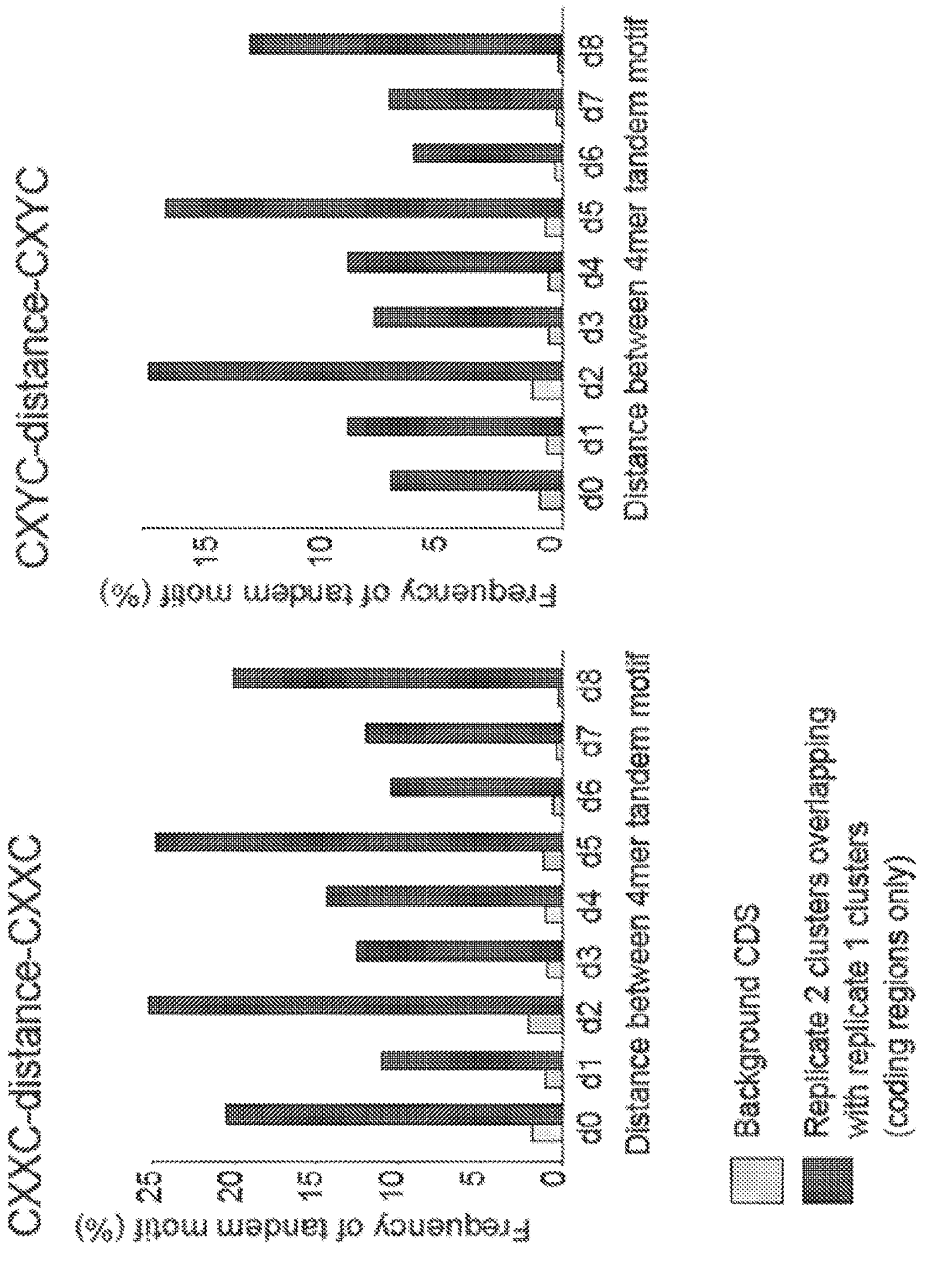
Figure 3F:
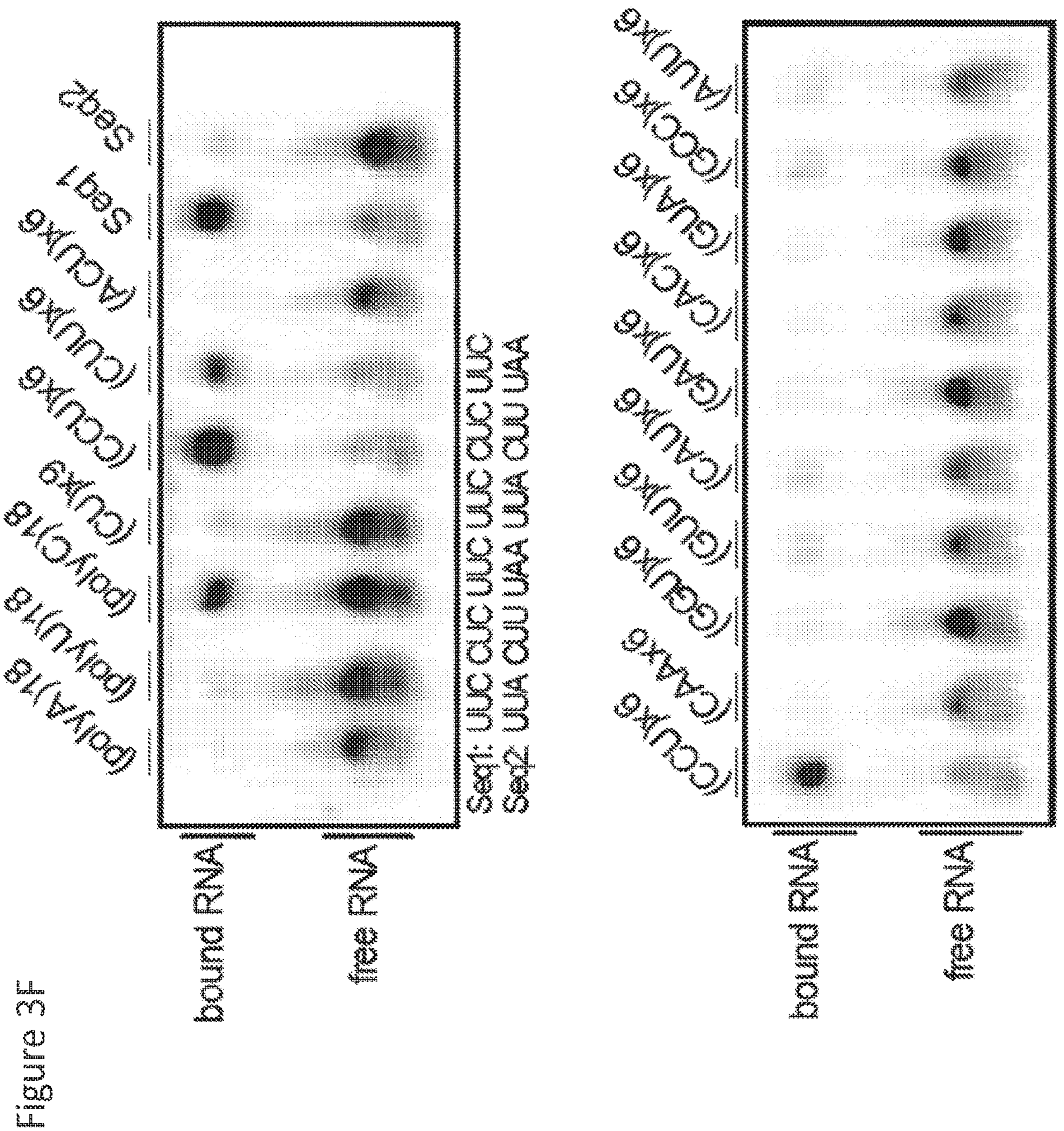
Figure 4A:
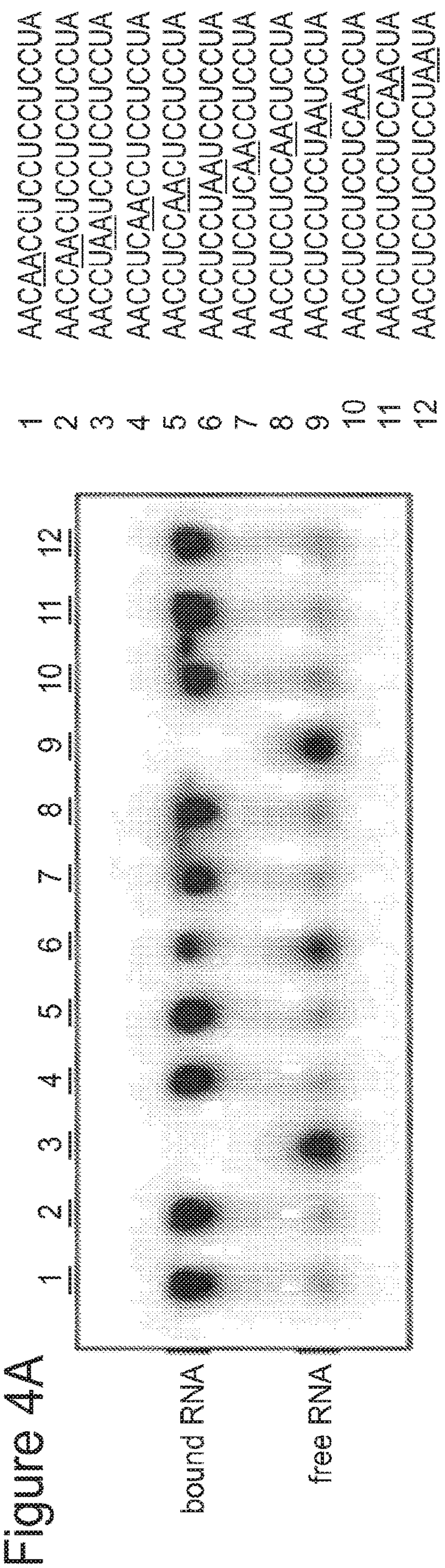
FIGS. 4A-B depict autoradiographs of Electrophoretic Mobility Shift Assays (EMSAs) using recombinant human Vigilin. Synthetic RNAs representing various CCU trinucleotide repeats were radiolabeled (10 nM), incubated with 2 μM $His_6$-tagged (SEQ ID NO: 21) hVigilin recombinant protein and separated on 1% agarose gel. Sequences of ≥18-nt containing ≥4 CCU were required for efficient RNA binding (FIG. 4A). An 18-nt long RNA sequence containing 5×CCU-repeats (SEQ ID NO: 287) was systematically mutated at two adjacent sites with As (underlined) and used for EMSAs. Shifts were only observed with sequences containing a CyyC-2 nt-CyyC RRE (in which y=C/U.
Figure 4B:
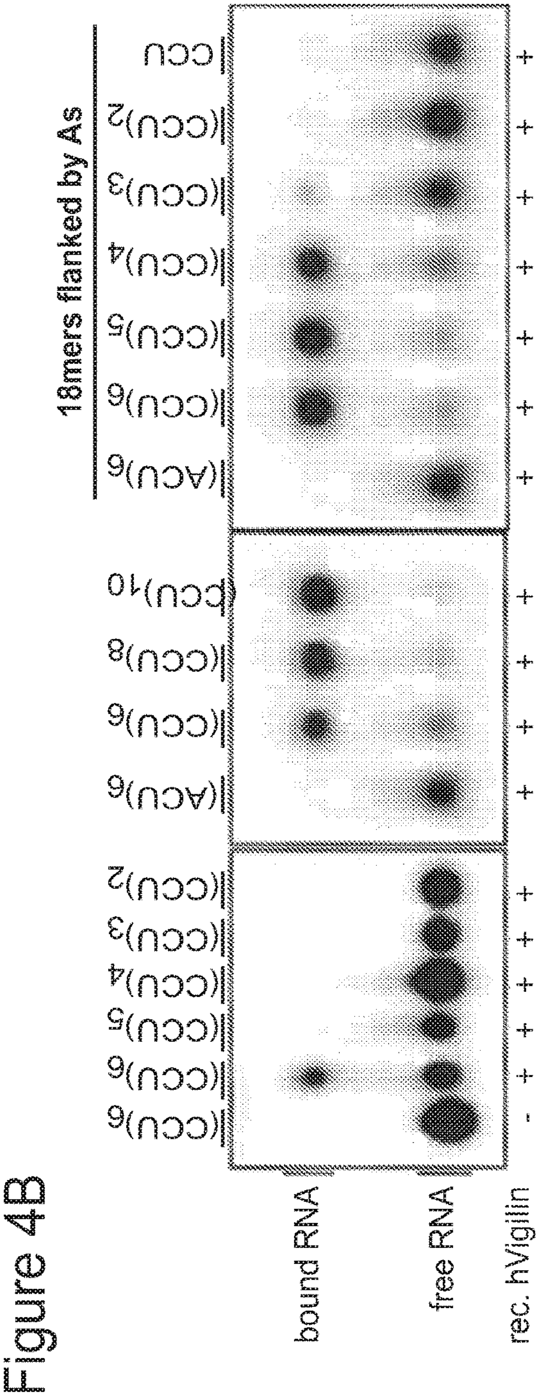

To identify RNA targets of Vigilin, PAR-CLIP in primary hepatocytes was performed. PAR-CLIP takes advantage of T-to-C conversions that are created during reverse transcription as a result of incorporated 4-thiouridine (4SU) being covalently UV-crosslinked to the RBP (Hafner et al., 2010). Hence, RNA sequences obtained from PAR-CLIP intrinsically contain the information of specific crosslinking events and distinguish true RNA-protein interactions from background RNA. PARalyzer, an algorithm that calculates the density of T-C conversions in PAR-CLIP reads, was used to detect binding sites in 2 biological replicates (Corcoran et al., 2011). Keeping only targets found in both replicates, Vigilin crosslinked to 867 gene transcripts of which 793 were mRNAs, corresponding to ~6% of the murine liver transcriptome. A total of 1401 binding sites were identified, 1165 of which were in mature mRNAs. Vigilin binding sites predominantly resided in the open reading frames (ORFs; 956) comprising RNA recognition elements of CHHC or CHYC sequence segments (H=A/C/U and Y=C/U; FIGS. 3*a-d*). Further in silico analysis of the motif revealed a preferred binding of Vigilin to a tandem of CHHC or CHYC 4mers spaced by 2, 5 or 8 nt (FIG. 3*e*). As the PAR-CLIP protocol involves cleavage of protein-bound RNA substrates with RNaseT1, an endoribonuclease that specifically cleaves 3' of G nucleotides, binding sites within G-rich sequence contexts may be underrepresented (Kishore et al., 2011). T The RNA recognition element (RRE) was validated by electrophoretic mobility shift assays (EMSAs) using recombinant full-length human Vigilin and synthetic single-stranded RNAs comprising a panel of 18-nt di- and trinucleotide repeats. Consistent with the PAR-CLIP derived RRE, RNA shifts were observed for CU-rich motifs, while insertions of A and G nucleotides resulted in decreased binding affinity (FIG. 3*f*; FIG. 4*a*). Furthermore, testing RNAs of different lengths, demonstrating that oligonucleotides of ≥18 nt were required to observe RNA-protein shifts, suggesting that, in addition to the RRE, RNA backbone contacts outside of the RRE were necessary for binding in vitro (FIG. 4*b*).

Figures 3G, 3H, 3I:
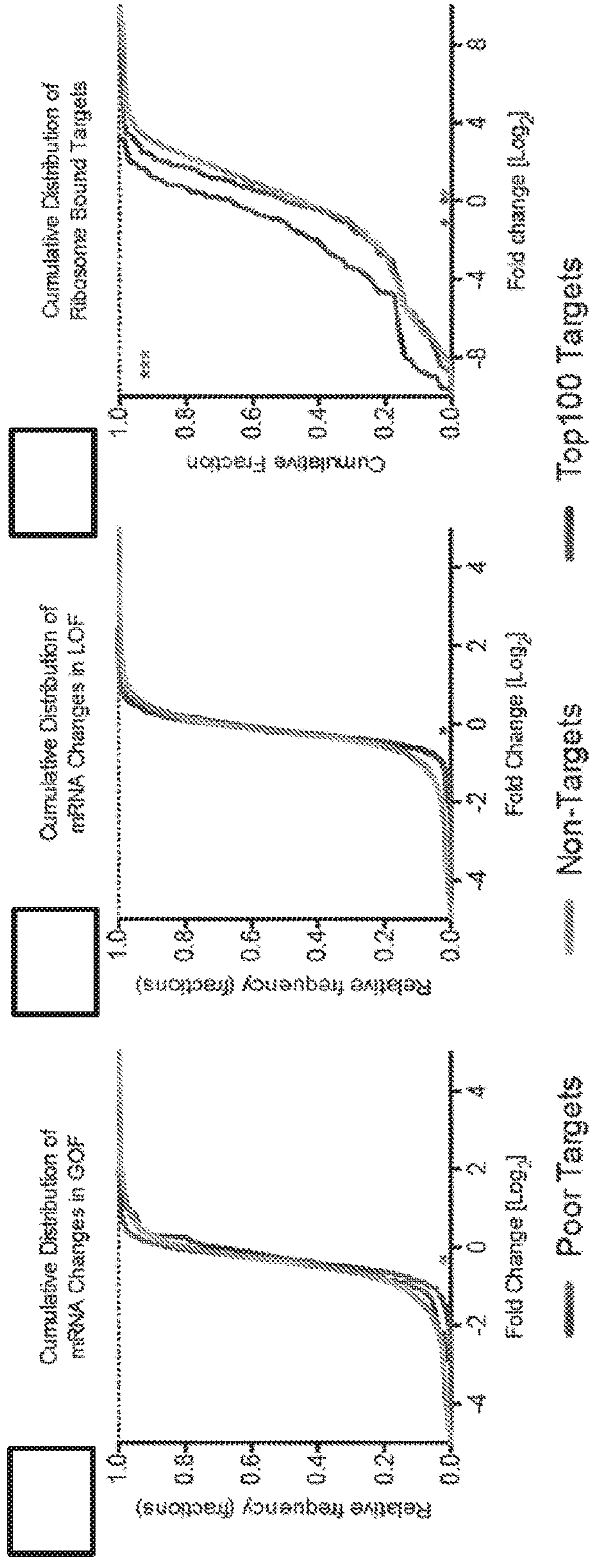

Notably, mRNA levels of the targets identified by PAR-CLIP showed no significant variation upon adenovirus-mediated overexpression or knockdown of Vigilin in the liver (FIGS. 3*g, h*). To assess a putative role of Vigilin in translation of its targets, ribosome profiling was carried out in primary hepatocytes depleted of Vigilin. Ribosome profiling captured 345 of the identified 793 mRNA targets and 270 non-target mRNAs. Comparison of target to non-target mRNA read counts revealed substantially reduced ribosome association upon Vigilin knockdown, substantiating the requirement of Vigilin for its targets to be efficiently translated (FIG. 3*i*).

Figure 5A:
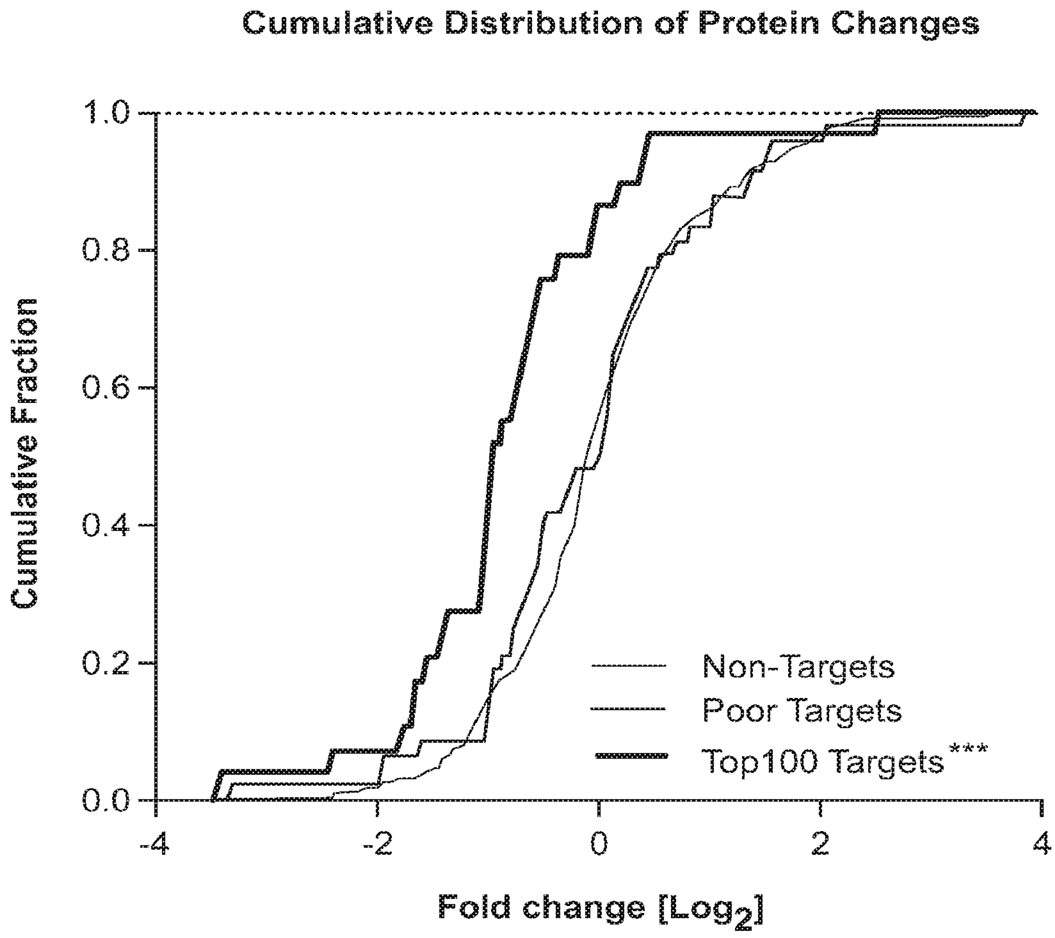
FIGS. 5A-G depict that Vigilin promotes translation of mRNAs coding for secretory proteins, including ApoB and Fetuin-A. Secretome of primary hepatocytes isolated from mice injected with either Ad-shCTRL or Ad-shVIG was collected from the medium and quantified using label-free mass-spectrometry (MS-LFQ).
Figure 5B:
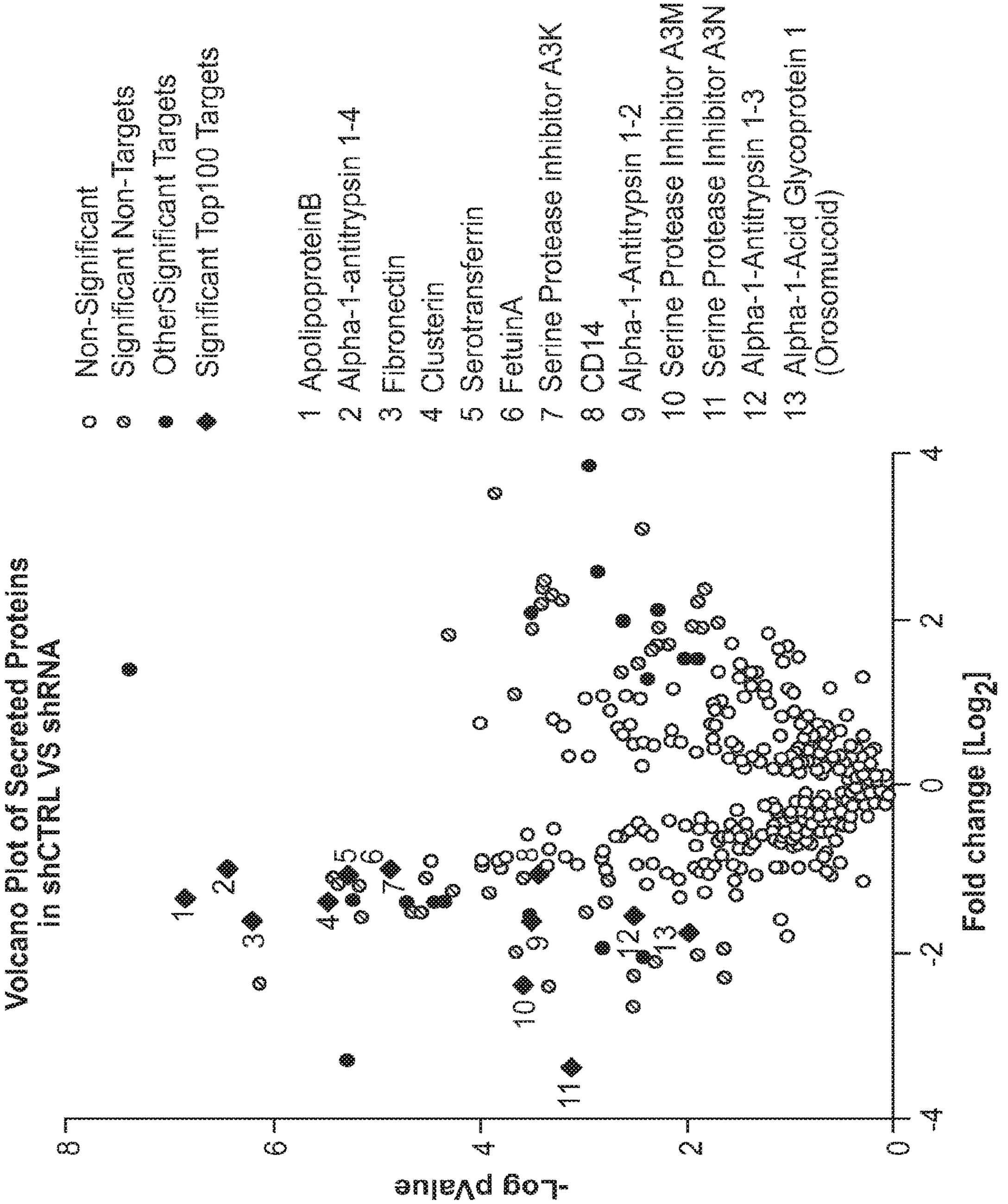
Figure 5C:
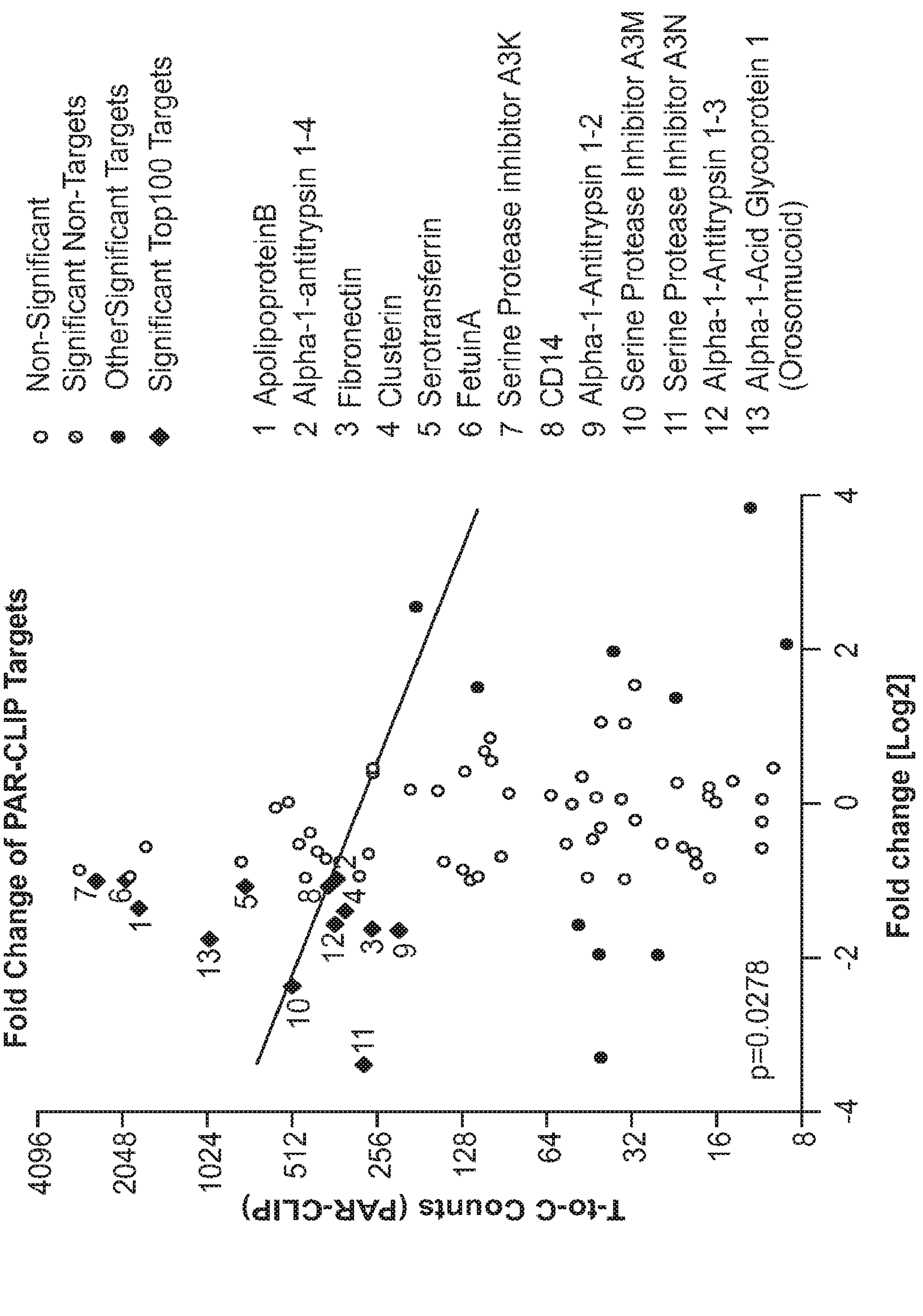
Figure 5D:
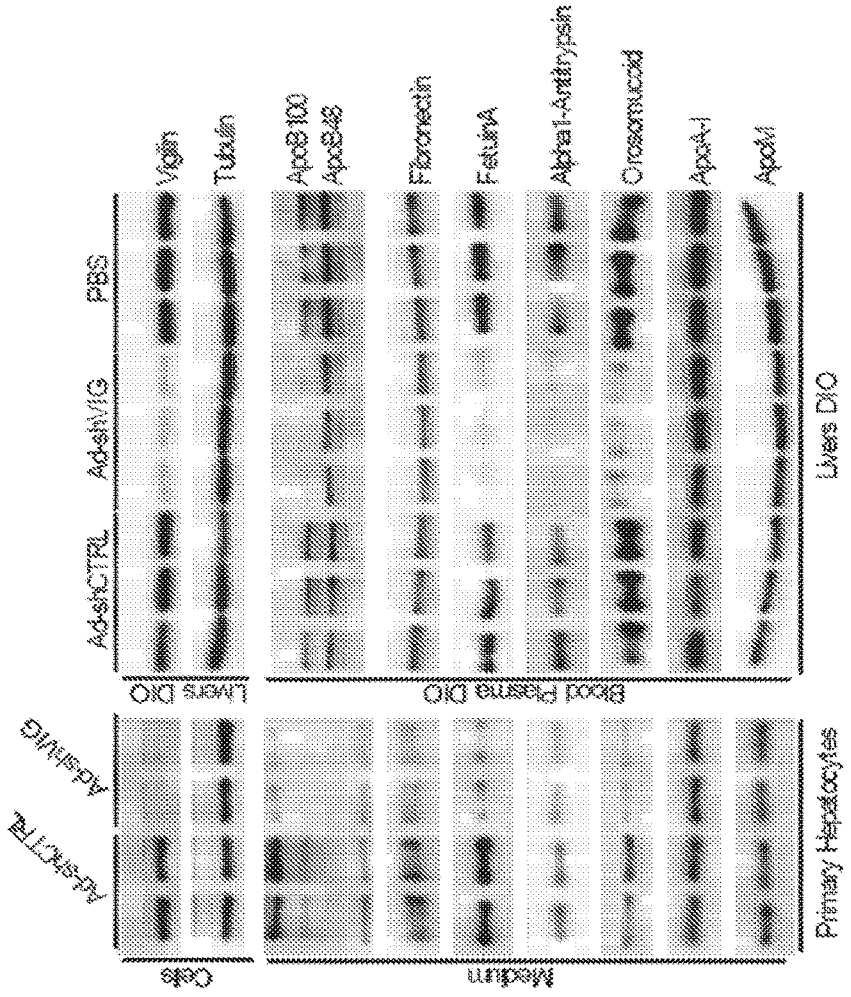
Figure 6A:
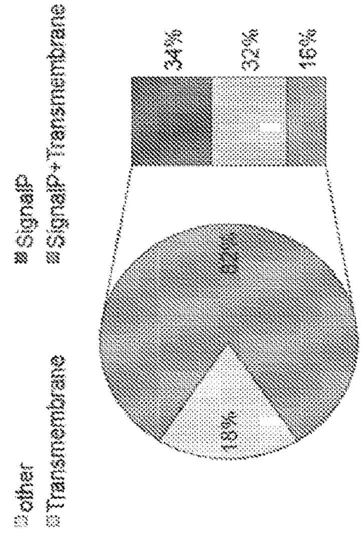
FIGS. 6A-F depict the characterization and regulation of strongest Vigilin targets.
Figure 6B:
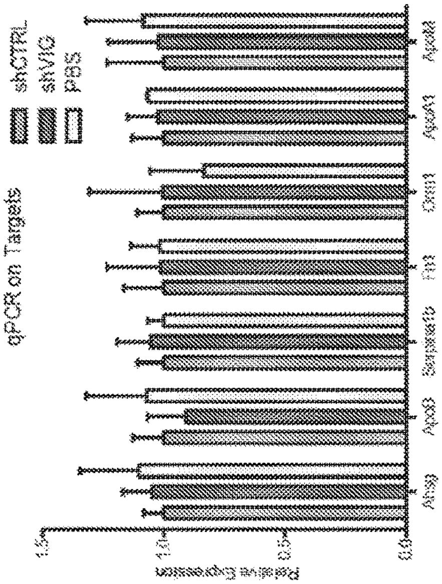

Strikingly, 82 of the top 100 targets harbored signal peptides, transmembrane domains or both, indicating a function in the secretory pathway (FIG. 6*a*). This function is consistent with the reported role of the yeast homologue SCP160 (Hirschmann et al., 2014) but distinct from that of other RBPs recently proposed to participate in translocation of alternative 3' UTRs to the cell surface (Berkovits & Mayr, 2015). Overall, 436 of the ~2400 liver-expressed secretory pathway proteins (~18%) were captured as targets with ≥1 T-to-C conversion in both PAR-CLIP replicates (or 786 as total sum of both replicates; ~33%), indicating that only a specific subset of this class of proteins was targeted by Vigilin. To assess Vigilin-dependent regulation of these hits on the protein level, the secretome from the medium of primary hepatocytes infected with Ad-shCTRL or Ad-shVIG was harvested and label-free quantification by mass-spectrometry was performed. Significant downregulation of Vigilin targets identified by PAR-CLIP and Ribosome Profiling in hepatocytes in which Vigilin was silenced was observed (FIGS. 5*a, b*). The strongest regulation of these proteins was found in PAR-CLIP targets with ≥250 T-to-C crosslinked reads (FIG. 5*c*). While reduced protein levels of 5 targets in the medium of Ad-shVIG treated primary hepatocytes by immunoblotting was validated, 4 of them were also significantly downregulated in blood plasma of mice infected with Ad-shVIG, including ApoB, Fetuin-A, Alpha-1-Antitrypsin and Orosomucoid without significant changes at the mRNA level (FIG. 5*d*; FIG. 6*b*). Since primary hepatocytes were used as an autonomous ex vivo system to study Vigilin in the liver, the unchanged blood plasma levels of Fibronectin in mice with reduced hepatic Vigilin expression is most likely due to extrahepatic compensation from the reticuloendothelial system. One target, ApoA1, was neither regulated in primary hepatocytes nor in vivo.

Figure 5E:
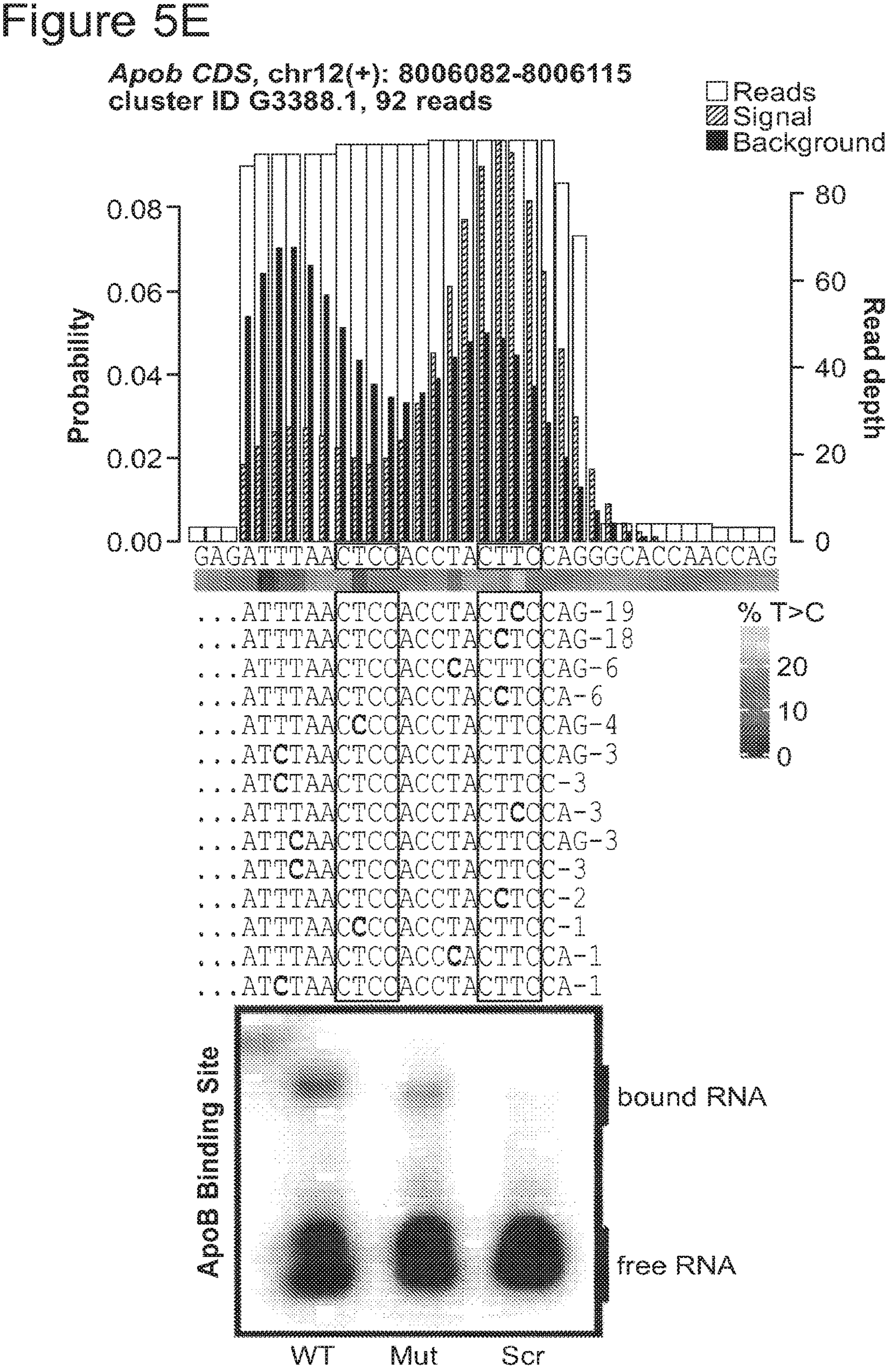
Figure 5E:
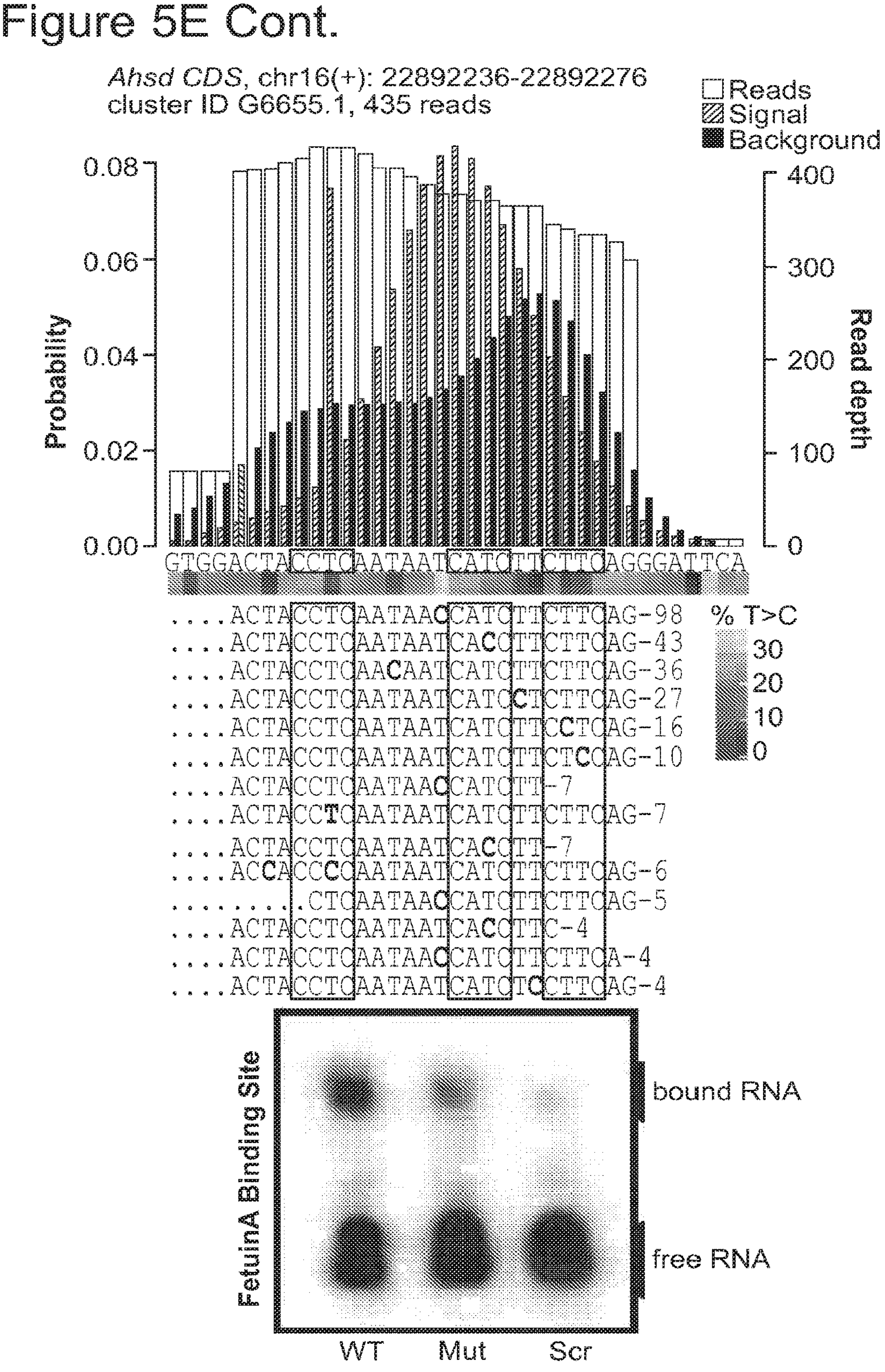
Figure 5F:
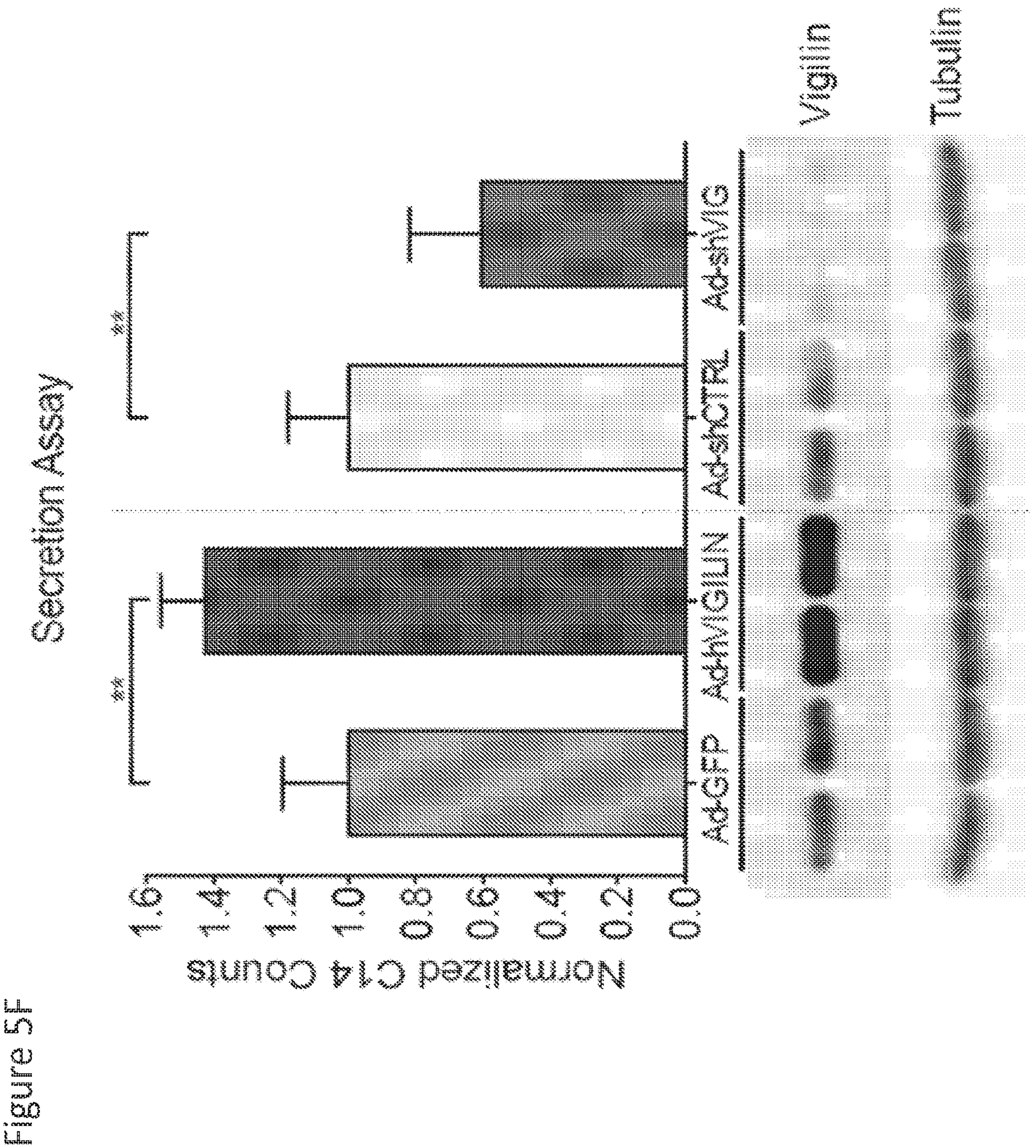
Figure 6C:
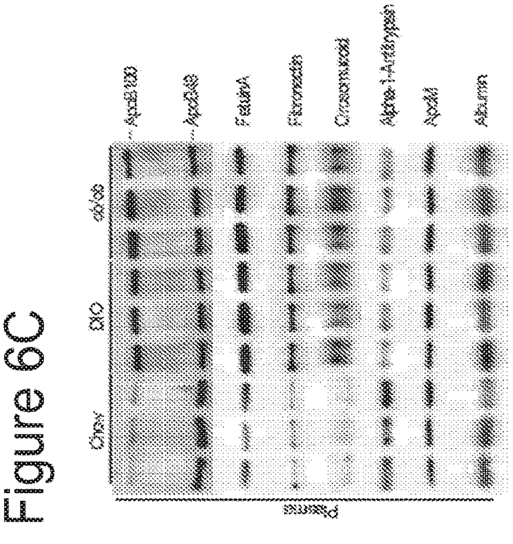
Figure 6D:
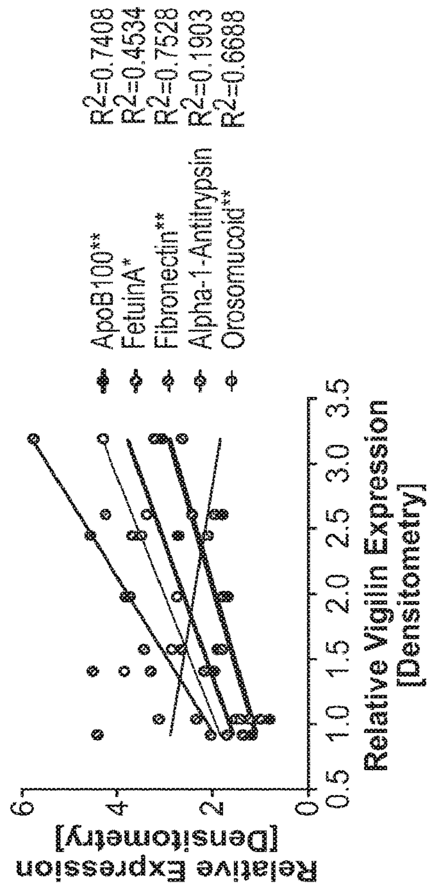
Figure 6F:
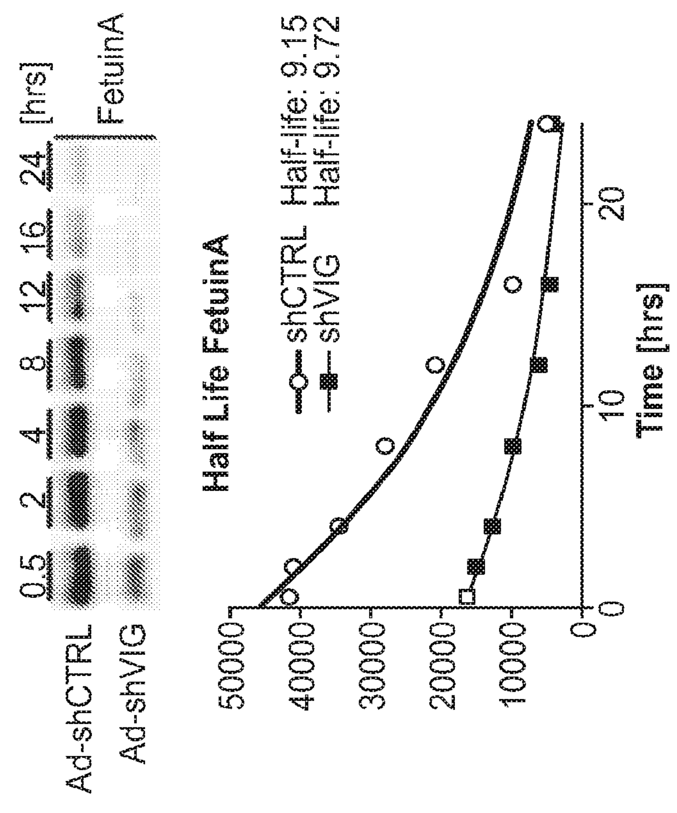
Figure 6E:
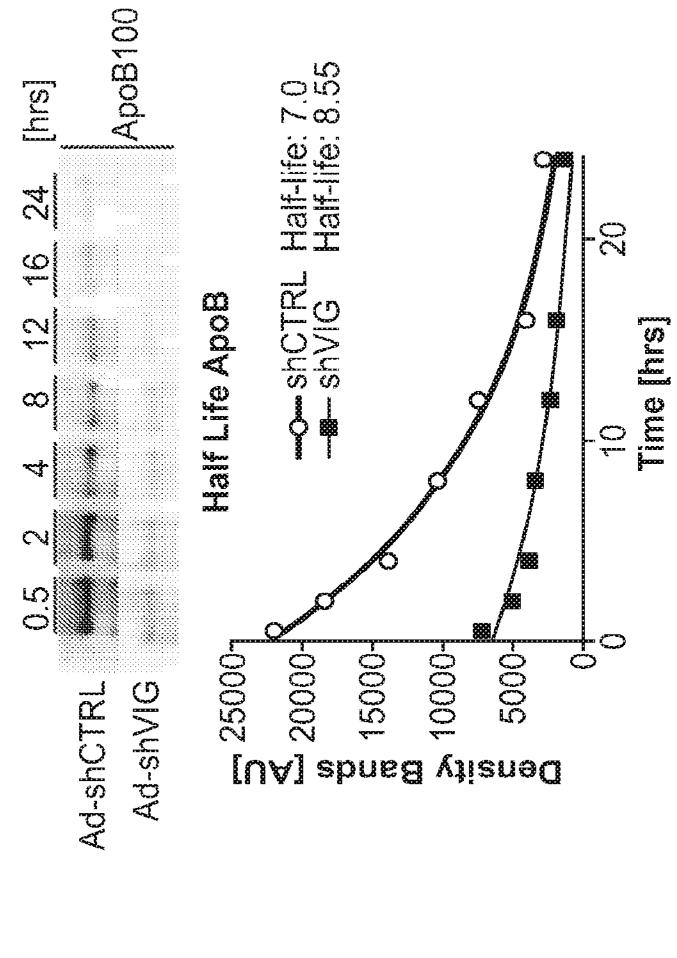

ApoB is the core protein of VLDL and LDLs that are produced and secreted from the liver and supply peripheral tissues with triglycerides and cholesterol. With one copy per particle, ApoB is an essential protein for the formation and secretion of VLDLs and LDLs. Increased plasma VLDL and LDL levels are independent risk factors for cardiovascular disease with further amplification when both VLDL and LDL cholesterol are elevated (Ren J et al., 2010). Fetuin-A is a hepatokine that is positively associated with diabetes risk in humans (Mori et al., 2006; Stefan et al., 2008) and inhibits insulin signaling by binding to the insulin receptors (Auberger et al., 1989; Rauth et al., 1992; Srinivas et al., 1993). Fetuin-A has also been reported to form a complex with free fatty acids and to induce inflammatory cytokines from adipose tissue through the TLR4 pathway (Pal et al., 2012). Increase of both ApoB and Fetuin-A protein levels were strongly correlated with elevated expression of Vigilin in DIO and ob/ob mice (FIGS. 6*c, d*). EMSAs validated the affinity of Vigilin to their RNA sites identified by PAR-CLIP, whereas mutation of the RRE and scrambled sequences of these sites showed decreased or no binding affinity (FIG. 5*e*). To rule out elevated ApoB and Fetuin-A degradation upon Vigilin knockdown, half-lives of these proteins in primary hepatocytes were monitored upon cycloheximide-mediated translational inhibition. Half-lives of neither ApoB nor Fetuin-A were changed significantly (FIGS. 6*e, f*). To confirm that Vigilin is a key regulator of lipid secretion in hepatocytes, primary hepatocytes were pulse chased with $^{14}C$-palmitate and secretion of thereby radiolabeled triglycerides into the medium was measured. While $^{14}C$ counts were significantly higher in the medium of primary hepatocytes upon overexpression, less $^{14}C$ was detected upon knockdown of Vigilin (FIG. 5*f*).

Figure 5G:
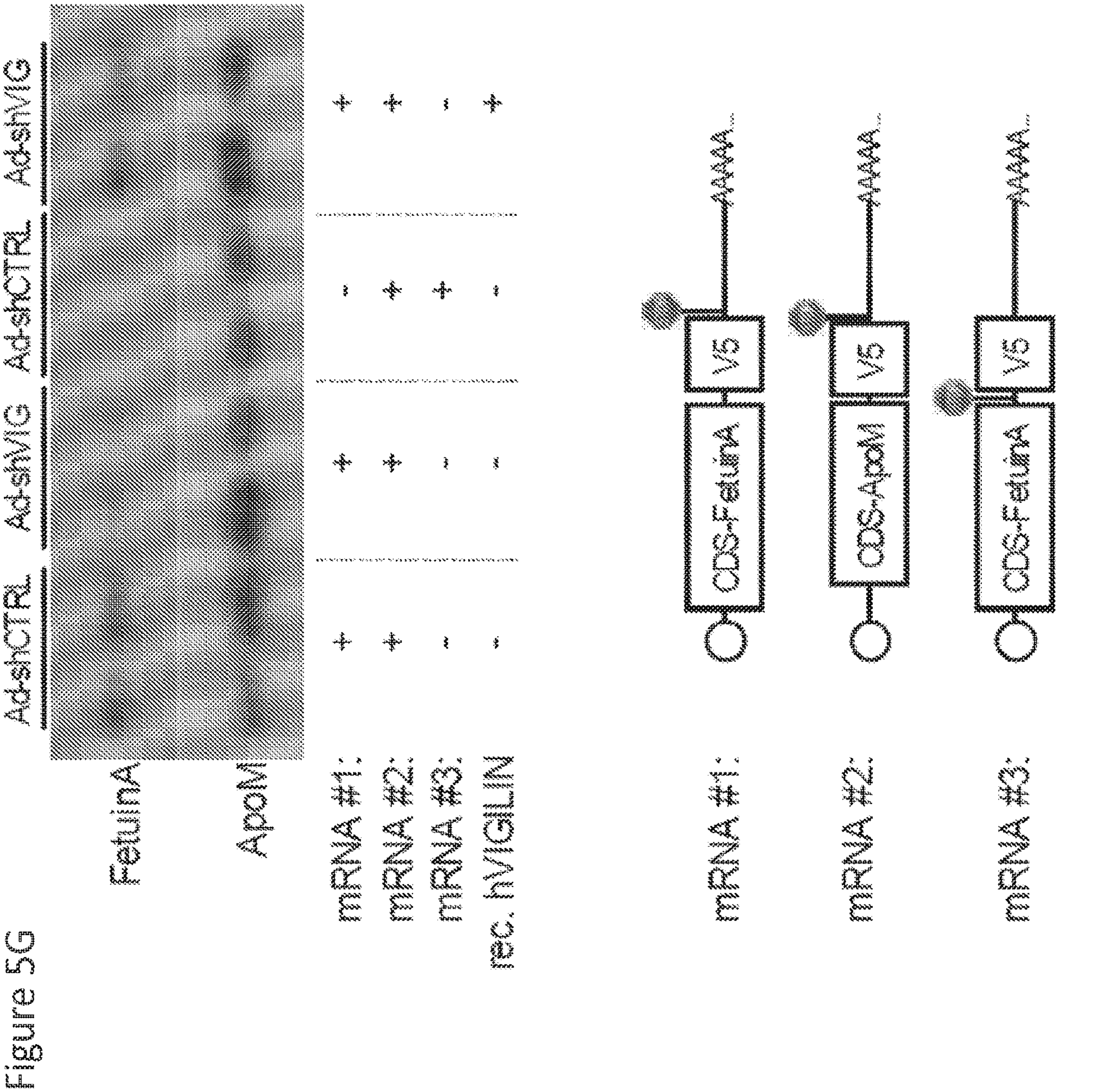

To test if Vigilin was required for efficient translation of its targets and reconstructed translation in vitro, using a cell-free system from liver extracts, using Fetuin-A mRNA as a model target followed by immunopurification of the translated protein, in vitro transcribed mRNAs of V5-tagged Fetuin-A and ApoM (as a non-Vigilin-target) were efficiently translated and purified under wildtype conditions. However, liver extracts with shRNA-mediated depletion of Vigilin showed decreased translation of Fetuin-A, but not ApoM (FIG. 5*g*). In these extracts, Fetuin-A production could be rescued by addition of recombinant human Vigilin. In vitro translation of ApoB was technically not feasible due to its ~14 kb long mRNA. These results confirmed that translation of Vigilin targets, including ApoB and Fetuin-A, was directly affected by the amount of Vigilin protein present during translation.

Figure 7B:
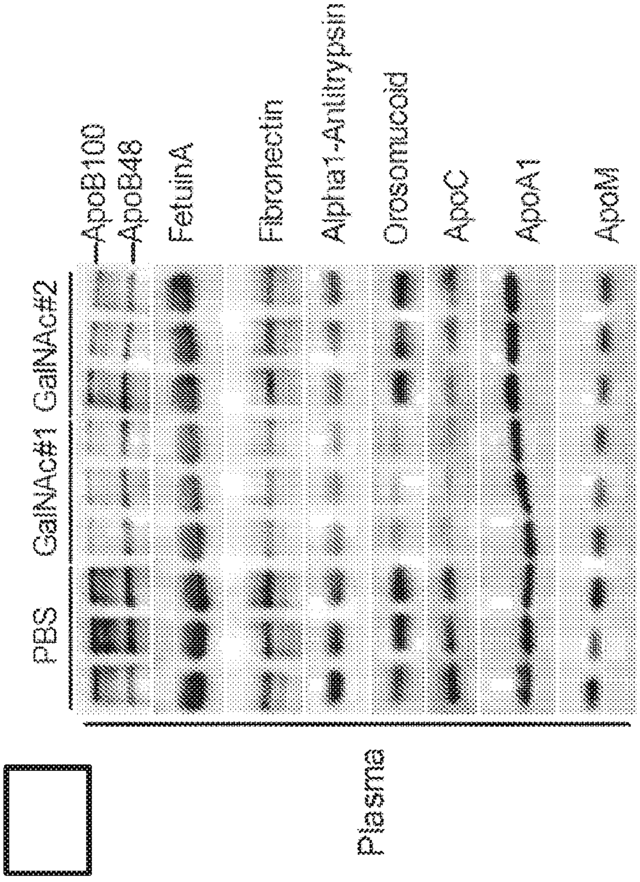
FIGS. 7A-M depict that long-term knockdown of hepatic Vigilin ameliorates elevated. VLDL/LDL levels and reduces atherosclerotic plaque size in aortic roots of $Ldlr^{-/-}$ mice.
Figure 7A:
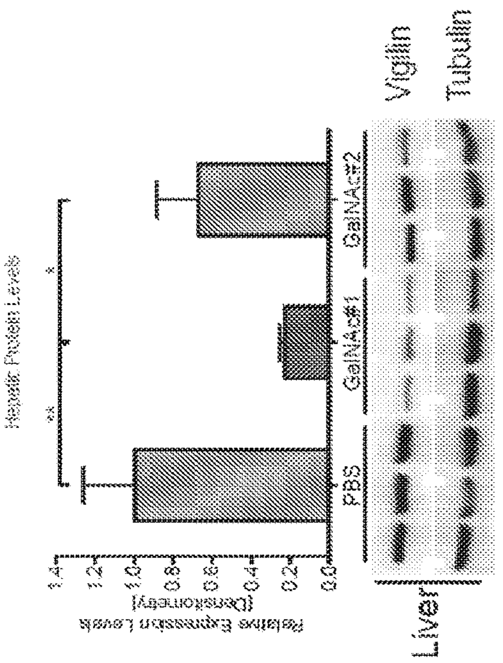
Figure 7C:
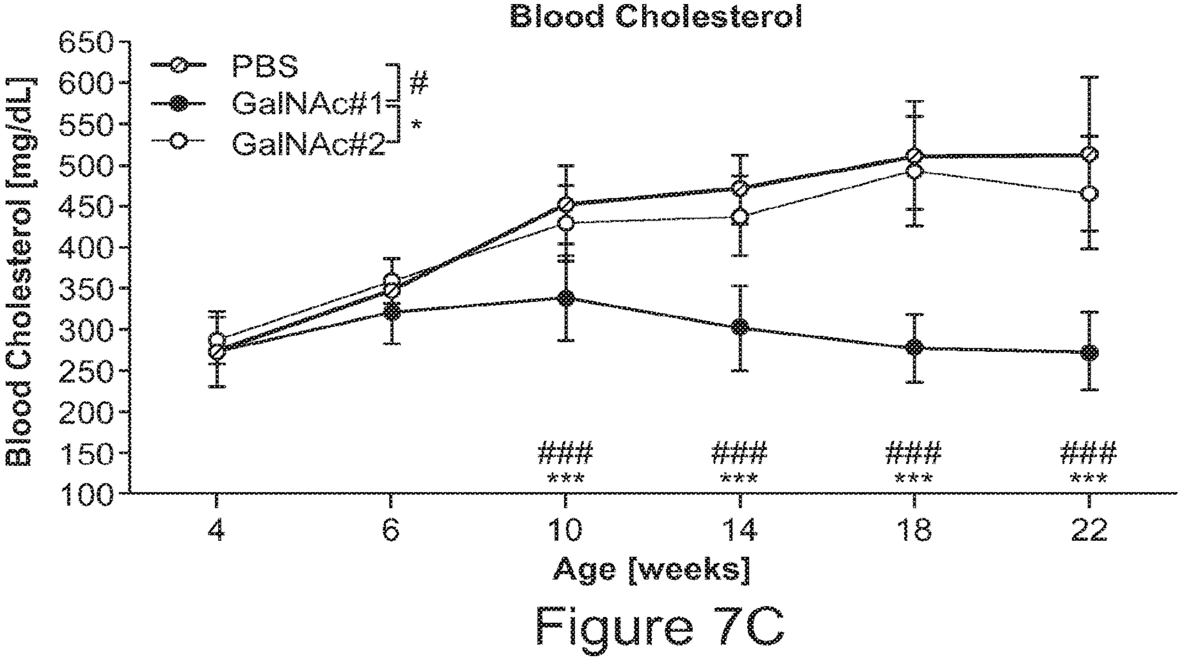
Figure 7D:
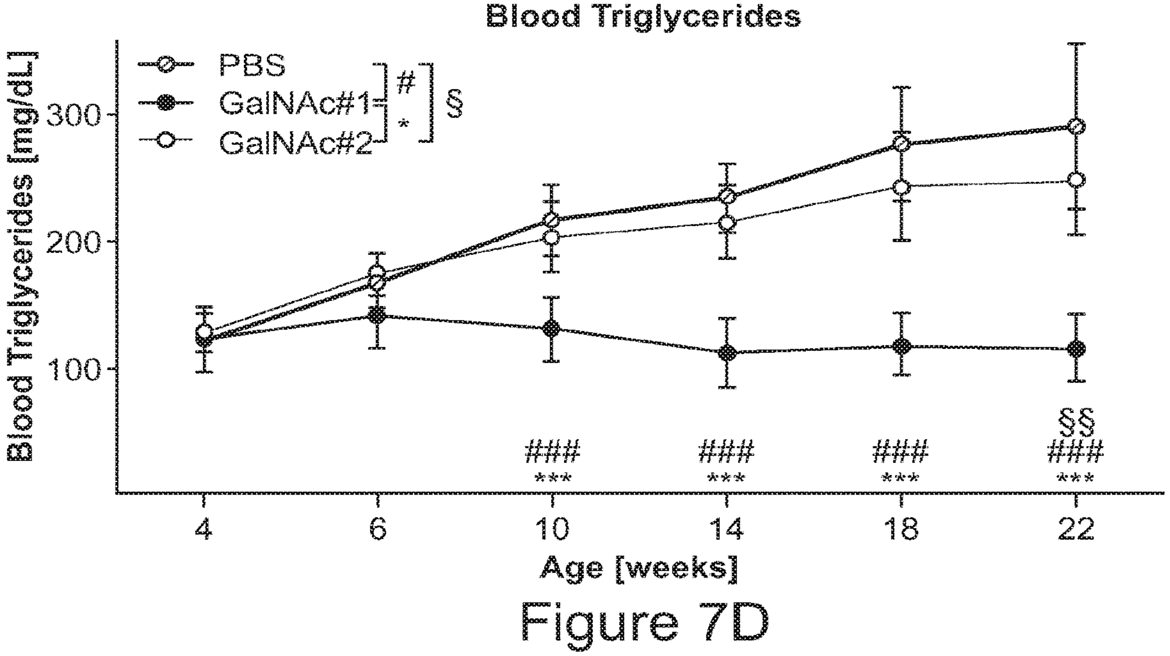
Figure 7E:
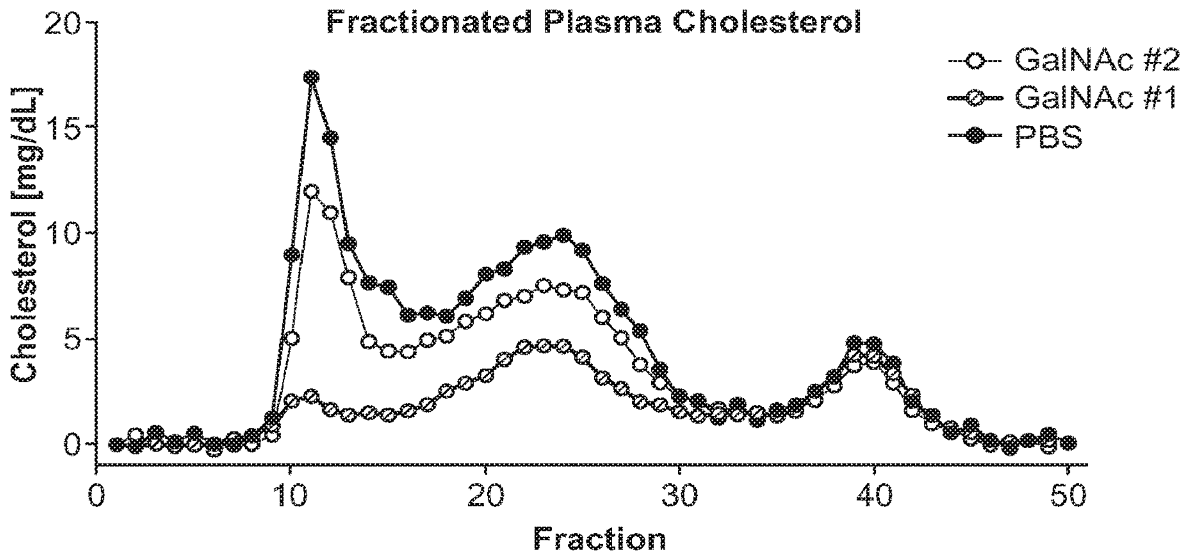
Figure 7F:
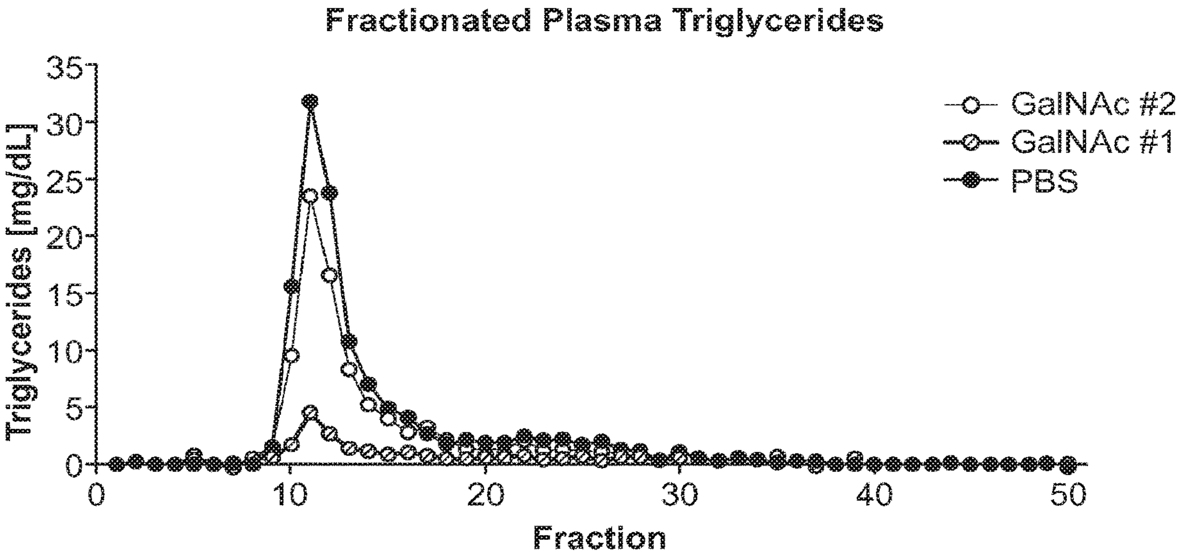
Figures 7G, 7H, 7I, 7J, 7K:
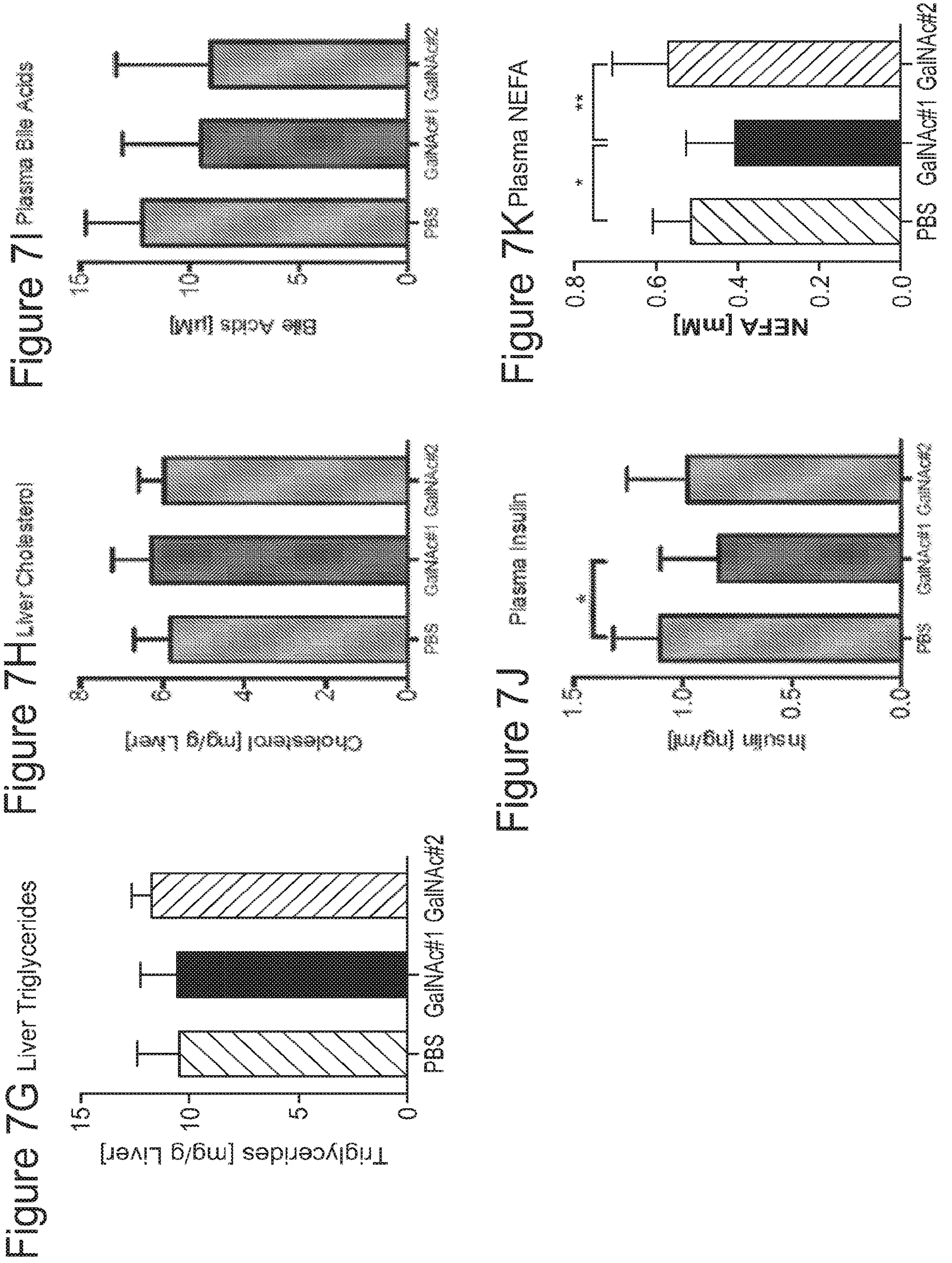
Figure 7L:
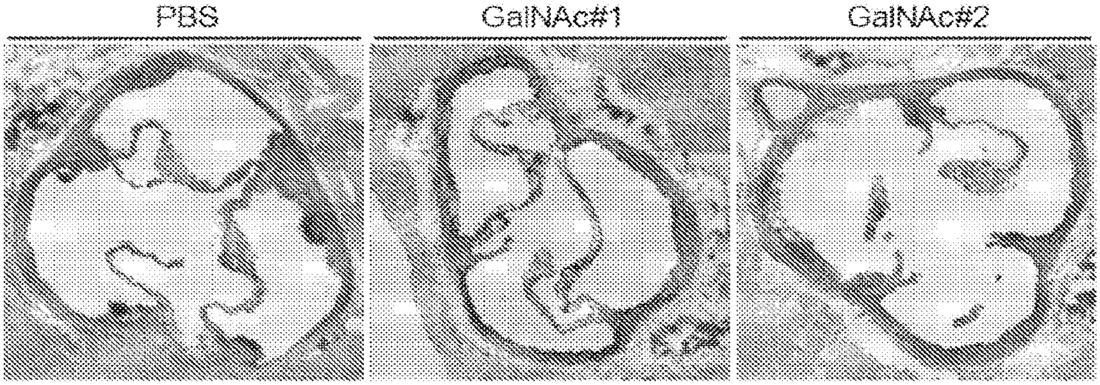
Figure 7M:
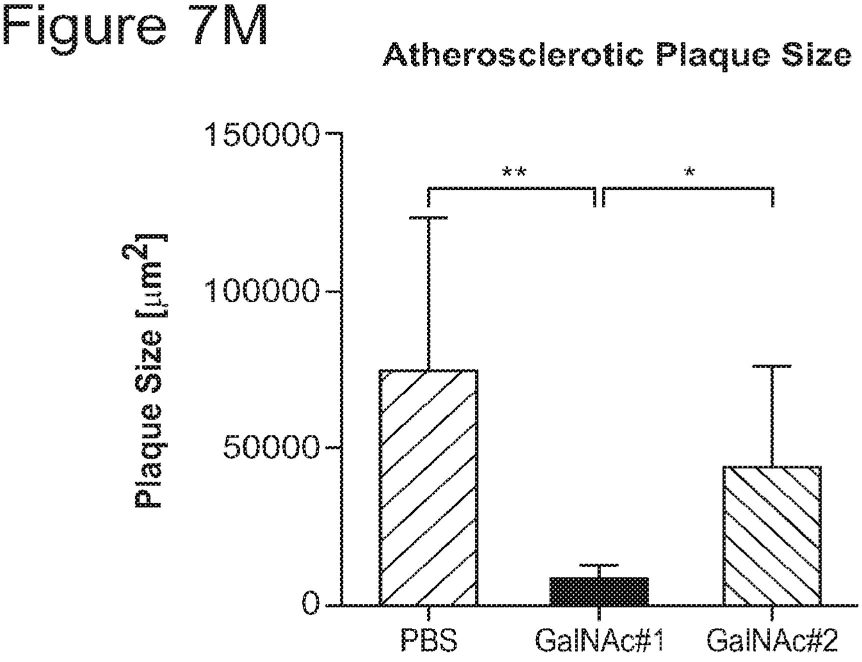
Figure 8A:
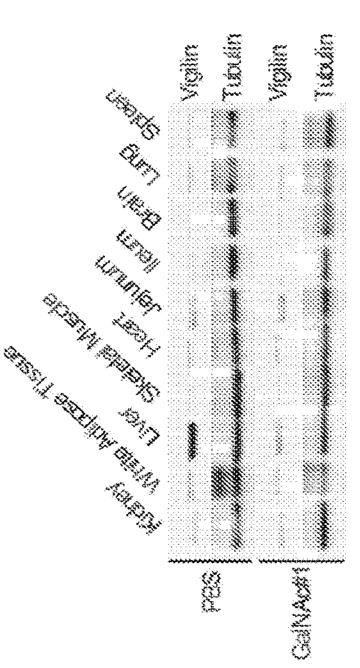
FIGS. 8A-D depict additional characterization of long-term knockdown of hepatic Vigilin in $Ldlr^{-/-}$ mice. Tissue panel indicating liver specific knockdown of Vigilin from mice treated with siVIG-GalNAc#1 as opposed to PBS treated mice (FIG. 8A). Blood alanine transaminase (ALT) levels after 18 weeks of treatment (FIG. 8B). Intraperitoneal glucose tolerance test (IPGTT.
Figure 8B:
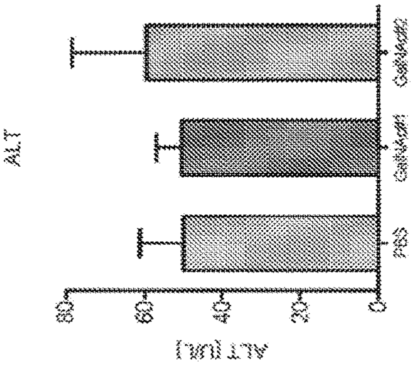
Figure 8C:
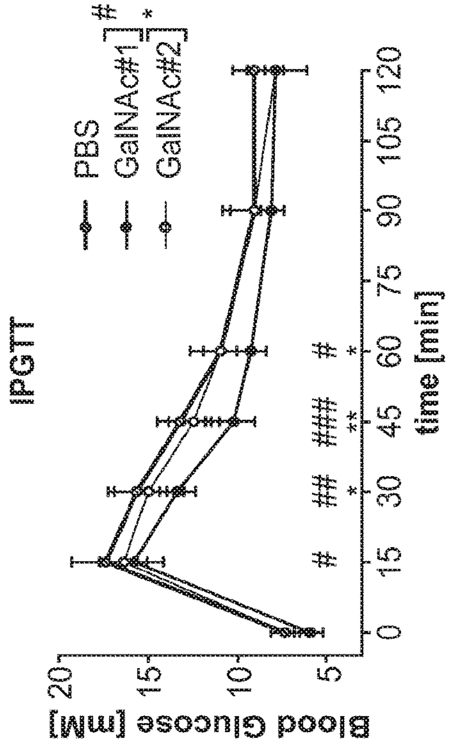
Figure 8D:
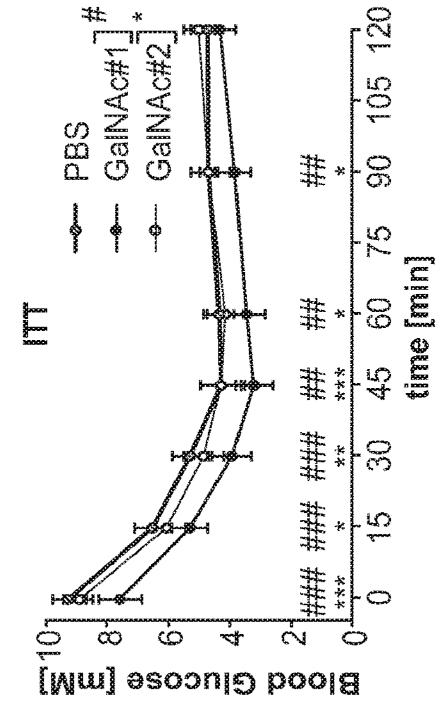

Since short term silencing of Vigilin revealed decreased de novo expression of atherogenic proteins (ApoB, Fibronectin), lowered VLDL, plasma triglyceride and NEFA levels, the long-term effect of hepatic Vigilin knockdown were evaluated in atherosclerosis prone $Ldlr^{-/-}$ mice that were fed a 0.02% cholesterol enriched diet. Vigilin was silenced in the liver by two different siRNAs that were chemically modified and covalently conjugated to multivalent N-acetylgalactosamine (GalNAc), a highly efficient ligand for clathrin-mediated endocytosis through the Asialoglycoprotein Receptor (ASGPR). siVIG-GalNAc conjugates (GalNAc#1 and GalNAc#2), weekly administered subcutaneously for 18 weeks, suppressed hepatic Vigilin by ~80 and ~30%, respectively (FIG. 7*a*). Knockdown of Vigilin was specific for the liver and was not observed in other tissues (FIG. 8*a*). No elevation of transaminases or other signs of liver toxicity were noted (FIG. 8*b*). The expression of Vigilin targets in the plasma of siVIG-GalNAc treated mice was measured by immunoblotting. The Vigilin targets ApoB, Fetuin-A, Fibronectin, Alpha1-Antitrypsin, Orosomucoid and the proatherogenic ApoC3 (which remained undetected in mass-spectrometry) were decreased in siVIG-GalNAc#1 treated mice compared to control animals with no changes in ApoA-I and ApoM (FIG. 7*b*). Plasma cholesterol and triglycerides were decreased in GalNAc#1 treated mice compared to PBS and GalNAc#2 injected control animals (FIGS. 7*c, d*). Furthermore, lipid profiling of FPLC-separated lipoprotein fractions in plasma of these mice revealed decreased VLDL and LDL levels (FIGS. 7*e, f*). Liver triglyceride and cholesterol content as well as plasma bile acids were similar in Vigilin knockdown and control mice (FIGS. 7*g-i*), Interestingly, plasma insulin levels were decreased in siVIG-GalNAc#1 treated mice compared to controls accompanied by lower NEFA levels (FIGS. 7*j, k*). Increased insulin sensitivity upon hepatic knockdown of Vigilin was also demonstrated by an augmented insulin tolerance test (ITT), while a glucose tolerance test (GTT) revealed improved glucose clearance following an intraperitoneal glucose injection (FIGS. 8*c, d*). Lastly, characterization of atherosclerosis in mice treated with siVIG-GalNAc#1 revealed smaller lesions in H&E- and Oil Red O-stained aortic root sections (FIGS. 7*l, m*). Together, these data demonstrate that long-term knockdown of Vigilin in the liver decreases VLDL and LDL levels, improves insulin sensitivity and reduces atherosclerotic plaque formation in mice.

Combining in vivo gain and loss of function studies with PAR-CLIP, ribosome profiling and label-free mass-spectrometry quantification, Vigilin was identified as a translational factor for mRNAs coding for a subset of proteins of the secretory pathway by binding to the CHHC motif. Given the potential bias of RNaseT1 recovered binding sites (Kishore et al., 2011), the motif was validated through EMSAs and it was found Vigilin preferentially binds to a tandem repeat of CHHC separated by 2-8 nt. These data revealed ApoB among the strongest targets of hepatic Vigilin. As the core protein of VLDL and LDL particles, ApoB is of paramount importance for maintaining triglyceride balance within the liver. Although regulation of apoB by post-translational degradation pathways within the ER, post-ER (Fisher et al., 2001), and by autophagy (Pan et al., 2008; Qiu et al., 2011) is well established, translational regulatory mechanisms that govern ApoB expression are poorly understood (Fisher et al., 2014). This study demonstrates that. Vigilin is a major determinant of ApoB translation and VLDL secretion by hepatocytes and therefore a regulator of net triglyceride production and secretion by the liver. The increased expression of Vigilin in subjects with liver steatosis may contribute to the overproduction and secretion of VLDL in obese, insulin resistant subjects (Adiels et al., 2006; Adiels et al., 2008). Short term and strong (≥90%) hepatic ApoB silencing (using Ad-shVIGILIN) in the liver was accompanied by mild steatosis, consistent with studies in which apoB was silenced using shRNAs (Maczuga et al., 2014), Long-term knockdown of Vigilin via GalNAc-conjugated siRNAs did not result in a steatotic liver. Protection against hepatic triglyceride accumulation is likely due to other Vigilin targets and associated mechanisms, such as the reduction of apoC3, which increases the catabolism of triglyceride rich particles and lowers plasma triglyceride levels in mice and humans (Maeda et al., 1994; Ginsberg et al., 1986; Pollin et al., 2008; The TG and HDL Working Group of the Exome Sequencing Project, 2014). Long term silencing of hepatic Vigilin in $Ldlr^{-/-}$ mice was also sufficient to lower VLDL and LDL levels, reduce atherosclerotic plaque formation and improve glucose tolerance as well as insulin sensitivity. Knockdown of Vigilin resulted in substantially decreased protein levels of its targets without affecting mRNA levels. In contrast, other highly expressed liver secreted proteins that were not identified as targets in both PAR-CLIP replicates such as Fetuin-B or the lipoprotein ApoE, showed no significant perturbation upon Vigilin knockdown, further substantiating Vigilin's specificity for a distinct subset of metabolic transcripts. Hence, these findings support the emerging view of RBPs organizing nascent RNA transcripts into functional groups that are coordinately regulated, especially at the level of mRNA stability and translation (Keene, 2007). Combinatorial binding of additional RBPs to these mRNAs and controlled proteosomal degradation provides a mechanism for multi-dimensional regulation of protein fates and explain the general poor correlation between the mRNA and protein pools in eukaryotic cells (De Sousa et al., 2009; Vogel et al., 2010; Moore et al., 2005) and the low susceptibility of some targets towards a Vigilin knockdown ex and in vivo as observed for ApoA1. Targets that remained unchanged upon Vigilin silencing is subject to further regulatory mechanisms controlling their protein levels or be due to secondary effects of the resulting phenotype. Taken together, this study provides the first evidence that the mammalian Vigilin is involved in translational regulation of mRNA targets encoding for proteins of the secretory pathway, including the atherogenic proteins ApoB, ApoC3 and Fibronectin as well as the insulin inhibitor Fetuin-A, and thereby serves as an important regulator of protein production and secretion from the liver.

Example 3. iRNA Design, Synthesis, Selection, and In Vitro Evaluation of Additional Agents Targeting Hdlbp/Vigilin This Example describes methods for the design, synthesis, selection, and in vitro evaluation of additional Hdlbp/Vigilin iRNA agents (see Tables 3 and 4).

Bioinformatics

A set of siRNAs targeting the human HDLBP, "high density lipoprotein binding protein" (human: NCBI refseqID NM_005336; NCBI GeneID: 3069; SEQ ID NO:5) were designed using custom R and Python scripts. The human NM_005336 REFSEQ mRNA, version 5, has a length of 6524 bases. The rationale and method for the set of siRNA designs is as follows: the predicted efficacy for every potential 23mer siRNA from position 10 through the end was determined with a random forest algorithm derived from the direct measure of mRNA knockdown from several thousand distinct siRNA designs targeting a variety of human genes. Subsets of the HDLBP siRNAs were designed with perfect or near-perfect matches to the human transcript. For each strand of the siRNA, a custom Python script was used in a brute force search to measure the number and positions of mismatches between the siRNA and all potential alignments in the human transcriptome. Extra weight was given to mismatches in the seed region, defined here as positions 2-9 of the antisense oligonucleotide, as well the cleavage site of the siRNA, defined here as positions 10-11 of the antisense oligonucleotide. The relative weight of the mismatches was 2.8; 1.2:1 for seed mismatches, cleavage site, and other positions up through antisense position 19. Mismatches in the first position were ignored. A specificity score was calculated for each strand by summing the value of each weighted mismatch. Preference was given to siRNAs whose antisense score in human was >=2.2 and predicted efficacy was >=50% knockdown of the transcript.

In Vitro Screening

Cell Culture and Transfections

Hep3B cells (ATCC, Manassas, Va.) were grown to near confluence at 37° C. in an atmosphere of 5% CO2 in EMEM (ATCC® 30-2003™) supplemented with 10% FBS, before being released from the T-75 flask by trypsinization. The siRNA's against the target HDLBP were diluted from the original deepwell (DW897 at 10 uM) in two different 96 well duplex plates at 100 nM and 1 nM stock concentrations using the Janus duplex dilution machine. The reverse transfection of the siRNA's was performed using Lipofectamine RNAiMax (Invitrogen, Carlsbad Calif. cat #13778-150). For each well of a 384 well plate, 5 μl of mixture containing Opti-MEM (Cat #31985-062) and RNAiMax was added to 5 μl of siRNA using the viaFlow 384 and allowed to complex at room temperature for 15 minutes. One duplex is added to 4 wells (A1 of 96 well plate goes to A1, A2, B1 and B2 of the 384 well plate). The Hep3B cells were counted on the Vi-cell counter and seeded at 5000 cells/well in a 384 well cell culture plate contaning the mixture to make the final volume of cell suspension to 504/well. Cells were incubated the 37° C. incubator with 5% CO2 for 24 hours before carrying out lysis of cells and isolating RNA. Screen was performed at 10 nM and 0.1 nM final duplex concentration.

RNA Isolation, cDNA Synthesis and qPCR

After the 24 hours, the supernatant was discarded by inverting the plate over the sink and gently tapping on a paper towel to dry the remaining of the media from the side of the wells. Briefly 50 μl of the lysis buffer was added to each well using viaflo384. The Dynabeads (Lifetech dynabeads oligodt25; Cat #10902D (SEQ ID NO: 26)) were prepared in the 50 ml falcon tube containing lysis buffer and 25 μl beads were added to each well using the viaflo384. The plates were kept on the vibratranslator for 10 mins and then stacked in the Biotek machine to run program current wash multiple V6c.LHC. cDNA synthesis was performed using the Applied biosystems high capacity cDNA reverse transcriptase kit (Cat #4368813). Briefly 12 µl of the cDNA synthesis mix was added to each well using an integra multichannel pipettor. The plates were sealed and spun briefly (5-10 secs) and incubated at 37 C for 2 hours. After the 2 hours incubation, the qPCR assay was ran to screen for expression of HDLBP gene. Briefly the qPCR master mix was prepared by adding the probe against HDLBP (Hs00245546_m1) and GAPDH control. Two 1 µl of the cDNA was added using Viaflo384 into the qPCR plates to which 8 µl of this mix was added using an integra multi-channel pipettor. The plates were sealed with the PCR film and ran on Roche Light Cycler.

Table 5 shows the results of a single dose screen in Hep3B cells transfected with the indicated iRNAs.

TABLE 3

Additional HDLBP unmodified sequences

| Duplex Name | Sense Sequence (5' to 3') | SEQ ID NO | Antisense Sequence (5' to 3') | SEQ ID NO | Range in SEQ ID NO: 5 |
|---|---|---|---|---|---|
| AD-93225 | CAUGAGUUCCGUUGCAGUUUU | 27 | AAAACUGCAACGGAACUCAUGGU | 73 | 373-395 |
| AD-93226 | AUGAGUUCCGUUGCAGUUUUA | 28 | UAAAACUGCAACGGAACUCAUGG | 74 | 374-396 |
| AD-93233 | CCGUUGCAGUUUUGACCCAAA | 29 | UUUGGGUCAAAACUGCAACGGAA | 75 | 381-403 |
| AD-93247 | ACCCAAGAGAGUUUUGCUGAA | 30 | UUCAGCAAAACUCUCUUGGGUCA | 76 | 395-417 |
| AD-93292 | CAAAUCAAAGUUGCCACUCUA | 31 | UAGAGUGGCAACUUUGAUUUGUU | 77 | 440-462 |
| AD-93483 | ACAAGCAAAAAUCUGCCUUGA | 32 | UCAAGGCAGAUUUUUGCUUGUUC | 78 | 670-692 |
| AD-93665 | AACACCAUCGCUUUGUUAUUA | 33 | UAAUAACAAAGCGAUGGUGUUCU | 79 | 852-874 |
| AD-93701 | AACUGCAAGACUUGGAGCUAA | 34 | UUAGCUCCAAGUCUUGCAGUUUC | 80 | 888-910 |
| AD-93718 | CUAAAAACUGCAACCAAAAUA | 35 | UAUUUUGGUUGCAGUUUUUAGCU | 81 | 905-927 |
| AD-93726 | UGCAACCAAAAUCCAGAUCCA | 36 | UGGAUCUGGAUUUUGGUUGCAGU | 82 | 913-935 |
| AD-93974 | AUCAAGAAGAUUUAUGAGGAA | 37 | UUCCUCAUAAAUCUUCUUGAUGC | 83 | 1223-1245 |
| AD-93991 | GAAAAAGAAGACUACAACCAU | 38 | AUGGUUGUAGUCUUCUUUUUCUU | 84 | 1246-1268 |
| AD-93992 | AAAAAGAAGACUACAACCAUU | 39 | AAUGGUUGUAGUCUUCUUUUUCU | 85 | 1247-1269 |
| AD-93993 | AAAAGAAGACUACAACCAUUA | 40 | UAAUGGUUGUAGUCUUCUUUUUC | 86 | 1248-1270 |
| AD-94001 | ACUACAACCAUUGCAGUGGAA | 41 | UUCCACUGCAAUGGUUGUAGUCU | 87 | 1256-1278 |
| AD-94012 | UGCAGUGGAAGUGAAGAAAUA | 42 | UAUUUCUUCACUUCCACUGCAAU | 88 | 1267-1289 |
| AD-94526 | GAAGAGCAAUUUGAUCCGCAU | 43 | AUGCGGAUCAAAUUGCUCUUCUC | 89 | 1801-1823 |
| AD-94608 | GGAUCUAAUCAUUGAGCAAAG | 44 | CUUUGCUCAAUGAUUAGAUCCUU | 90 | 1903-1925 |
| AD-94613 | UAAUCAUUGAGCAAAGAUUUA | 45 | UAAAUCUUUGCUCAAUGAUUAGA | 91 | 1908-1930 |
| AD-94621 | GAGCAAAGAUUUCAUCGCACA | 46 | UGUGCGAUGAAAUCUUUGCUCAA | 92 | 1916-1938 |
| AD-94624 | CAAAGAUUUCAUCGCACAAUA | 47 | UAUUGUGCGAUGAAAUCUUUGCU | 93 | 1919-1941 |
| AD-94710 | AAGUGACAUUGUCCAGCUCAA | 48 | UUGAGCUGGACAAUGUCACUUUU | 94 | 2023-2045 |
| AD-94758 | CACAAAAUACAUGCAGAAGAU | 49 | AUCUUCUGCAUGUAUUUUGUGCA | 95 | 2071-2093 |
| AD-94813 | CUGUUCCGAUCUUCAAACAGU | 50 | ACUGUUUGAAGAUCGGAACAGAA | 96 | 2127-2149 |
| AD-94814 | UGUUCCGAUCUUCAAACAGUU | 51 | AACUGUUUGAAGAUCGGAACAGA | 97 | 2128-2150 |
| AD-94822 | UCUUCAAACAGUUUCACAAGA | 52 | UCUUGUGAAACUGUUUGAAGAUC | 98 | 2136-2158 |
| AD-94823 | CUUCAAACAGUUUCACAAGAA | 53 | UUCUUGUGAAACUGUUUGAAGAU | 99 | 2137-2159 |
| AD-94824 | UUCAAACAGUUUCACAAGAAU | 54 | AUUCUUGUGAAACUGUUUGAAGA | 100 | 2138-2160 |
| AD-94909 | CCAGCAGAGAAUAGCAAUUCA | 55 | UGAAUUGCUAUUCUCUGCUGGAA | 101 | 2225-2247 |
| AD-94915 | GAGAAUAGCAAUUCAGAGACA | 56 | UGUCUCUGAAUUGCUAUUCUCUG | 102 | 2231-2253 |
| AD-94916 | AGAAUAGCAAUUCAGAGACCA | 57 | UGGUCUCUGAAUUGCUAUUCUCU | 103 | 2232-2254 |
| AD-94924 | AAUUCAGAGACCAUUAUCAUA | 58 | UAUGAUAAUGGUCUCUGAAUUGC | 104 | 2240-2262 |

TABLE 3-continued

Additional HDLBP unmodified sequences

| Duplex Name | Sense Sequence (5' to 3') | SEQ ID NO | Antisense Sequence (5' to 3') | SEQ ID NO | Range in SEQ ID NO: 5 |
|---|---|---|---|---|---|
| AD-94926 | UUCAGAGACCAUUAUCAUCAA | 59 | UUGAUGAUAAUGGUCUCUGAAUU | 105 | 2242-2264 |
| AD-94927 | UCAGAGACCAUUAUCAUCACA | 60 | UGUGAUGAUAAUGGUCUCUGAAU | 106 | 2243-2265 |
| AD-94929 | AGAGACCAUUAUCAUCACAGA | 61 | UCUGUGAUGAUAAUGGUCUCUGA | 107 | 2245-2267 |
| AD-95191 | CAAACCAAGAGUUUCACUGUU | 62 | AACAGUGAAACUCUUGGUUUGCU | 108 | 2543-2565 |
| AD-95192 | AAACCAAGAGUUUCACUGUUA | 63 | UAACAGUGAAACUCUUGGUUUGC | 109 | 2544-2566 |
| AD-95197 | AAGAGUUUCACUGUUGACAUA | 64 | UAUGUCAACAGUGAAACUCUUGG | 110 | 2549-2571 |
| AD-95586 | CAGAAAUUCCAUCGAUCUGUA | 65 | UACAGAUCGAUGGAAUUUCUGGG | 111 | 3017-3039 |
| AD-95637 | UCAAAUUAAAUUCCCAGACAA | 66 | UUGUCUGGGAAUUUAAUUUGAAC | 112 | 3088-3110 |
| AD-96564 | CCGUAAAUUGUUGACGCUCUU | 67 | AAGAGCGUCAACAAUUUACGGAG | 113 | 4271-4293 |
| AD-96641 | GGUCAUGAGCAUUCGUGCUAA | 68 | UUAGCACGAAUGCUCAUGACCUU | 114 | 4404-4426 |
| AD-96642 | GUCAUGAGCAUUCGUGCUAAA | 69 | UUUAGCACGAAUGCUCAUGACCU | 115 | 4405-4427 |
| AD-96645 | AUGAGCAUUCGUGCUAAGAUA | 70 | UAUCUUAGCACGAAUGCUCAUGA | 116 | 4408-4430 |
| AD-96648 | AGCAUUCGUGCUAAGAUAACA | 71 | UGUUAUCUUAGCACGAAUGCUCA | 117 | 4411-4433 |
| AD-96653 | UCGUGCUAAGAUAACAGACUA | 72 | UAGUCUGUUAUCUUAGCACGAAU | 118 | 4416-4438 |

TABLE 4

Additional HDLBP modified sequences

| Duplex Name | Sense Sequence (5' to 3') | SEQ ID NO | Antisense Sequence (5' to 3') | SEQ ID NO | mRNA Target Sequence | SEQ ID NO |
|---|---|---|---|---|---|---|
| AD-93225 | csasugagUfuCfCfGfuugcaguuuuL96 | 119 | asAfsaacUfgCfAfacggAfaCfucau gsgsu | 165 | ACCAUGAGUUCCGUUGCAGUUUU | 211 |
| AD-93226 | asusgaguUfcCfGfUfugcaguuuuaL96 | 120 | usAfsaaaCfuGfCfaacgGfaAfcuca usgsg | 166 | CCAUGAGUUCCGUUGCAGUUUUG | 212 |
| AD-93233 | cscsguugCfaGfUfUfuugacccaaaL96 | 121 | usUfsuggGfuCfAfaaacUfgCfaacg gsasa | 167 | UUCCGUUGCAGUUUUGACCCAAG | 213 |
| AD-93247 | ascsccaaGfaGfAfGfuuuugcugaaL96 | 122 | usUfscagCfaAfAfacucUfcUfuggg uscsa | 168 | UGACCCAAGAGAGUUUUGCUGAA | 214 |
| AD-93292 | csasaaucAfaAfGfUfugccacucuaL96 | 123 | usAfsgagUfgGfCfaacuUfuGfauuu gsusu | 169 | AACAAAUCAAAGUUGCCACUCUA | 215 |
| AD-93483 | ascsaagcAfaAfAfAfucugccuugaL96 | 124 | usCfsaagGfcAfGfauuuUfuGfcuug ususc | 170 | GAACAAGCAAAAAUCUGCCUUGA | 216 |
| AD-93665 | asascaccAfuCfGfCfuuuguuauuaL96 | 125 | usAfsauaAfcAfAfagcgAfuGfgugu uscsu | 171 | AGAACACCAUCGCUUUGUUAUUG | 217 |
| AD-93701 | asascugcAfaGfAfCfuuggagcuaaL96 | 126 | usUfsagcUfcCfAfagucUfuGfcagu ususc | 172 | GAAACUGCAAGACUUGGAGCUAA | 218 |
| AD-93718 | csusaaaaAfcUfGfCfaaccaaaauaL96 | 127 | usAfsuuuUfgGfUfugcaGfuUfuuua gscsu | 173 | AGCUAAAAACUGCAACCAAAAUC | 219 |
| AD-93726 | usgscaacCfaAfAfAfuccagauccaL96 | 128 | usGfsgauCfuGfGfauuuUfgGfuugc asgsu | 174 | ACUGCAACCAAAAUCCAGAUCCC | 220 |
| AD-93974 | asuscaagAfaGfAfUfuuaugaggaaL96 | 129 | usUfsccuCfaUfAfaaucUfuCfuug ausgsc | 175 | GCAUCAAGAAGAUUUAUGAGGAG | 221 |
| AD-93991 | gsasaaaaGfaAfGfAfcuacaaccauL96 | 130 | asUfsgguUfgUfAfgucuUfcUfuuuu csusu | 176 | AAGAAAAAGAAGACUACAACCAU | 222 |

TABLE 4-continued

Additional HDLBP modified sequences

| Duplex Name | Sense Sequence (5' to 3') | SEQ ID NO | Antisense Sequence (5' to 3') | SEQ ID NO | mRNA Target Sequence | SEQ ID NO |
|---|---|---|---|---|---|---|
| AD-93992 | asasaaagAfaGfAfCfuacaaccauuL96 | 131 | asAfsuggUfuGfUfagucUfuCfuuuuuscsu | 177 | AGAAAAAGAAGACUACAACCAUU | 223 |
| AD-93993 | asasaagaAfgAfCfUfacaaccauuaL96 | 132 | usAfsaugGfuUfGfuaguCfuUfcuuuususc | 178 | GAAAAAGAAGACUACAACCAUUG | 224 |
| AD-94001 | ascsuacaAfcCfAfUfugcaguggaaL96 | 133 | usUfsccaCfuGfCfaaugGfuUfguaguscsu | 179 | AGACUACAACCAUUGCAGUGGAA | 225 |
| AD-94012 | usgscaguGfgAfAfGfugaagaaauaL96 | 134 | usAfsuuuCfuUfCfacuuCfcAfcugcasasu | 180 | AUUGCAGUGGAAGUGAAGAAAUC | 226 |
| AD-94526 | gsasagagCfaAfUfUfugauccgcauL96 | 135 | asUfsgcgGfaUfCfaaauUfgCfcucuucsusc | 181 | GAGAAGAGCAAUUUGAUCCGCAU | 227 |
| AD-94608 | gsgsaucuAfaUfCfAfuugagcaaagL96 | 136 | csUfsuugCfuCfAfaugaUfuAfgauccsusu | 182 | AAGGAUCUAAUCAUUGAGCAAAG | 228 |
| AD-94613 | usasaucaUfuGfAfGfcaaagauuuaL96 | 137 | usAfsaauCfuUfUfgcucAfaUfgauuasgsa | 183 | UCUAAUCAUUGAGCAAAGAUUUC | 229 |
| AD-94621 | gsasgcaaAfgAfUfUfucaucgcacaL96 | 138 | usGfsugcGfaUfGfaaauCfuUfugcucsasa | 184 | UUGAGCAAAGAUUUCAUCGCACA | 230 |
| AD-94624 | csasaagaUfuUfCfAfucgcacaauaL96 | 139 | usAfsuugUfgCfGfaugaAfaUfcuuugscsu | 185 | AGCAAAGAUUUCAUCGCACAAUC | 231 |
| AD-94710 | asasgugaCfaUfUfGfuccagcucaaL96 | 140 | usUfsgagCfuGfGfacaaUfgUfcacuususu | 186 | AAAAGUGACAUUGUCCAGCUCAG | 232 |
| AD-94758 | csascaaaAfuAfCfAfugcagaagauL96 | 141 | asUfscuuCfuGfCfauguAfuUfuugugscsa | 187 | UGCACAAAAUACAUGCAGAAGAU | 233 |
| AD-94813 | csusguucCfgAfUfCfuucaaacaguL96 | 142 | asCfsuguUfuGfAfagauCfgGfaacagsasa | 188 | UUCUGUUCCGAUCUUCAAACAGU | 234 |
| AD-94814 | usgsuuccGfaUfCfUfucaaacaguuL96 | 143 | asAfscugUfuUfGfaagaUfcGfgaacasgsa | 189 | UCUGUUCCGAUCUUCAAACAGUU | 235 |
| AD-94822 | uscsuucaAfaCfAfGfuuucacaagaL96 | 144 | usCfsuugUfgAfAfacugUfuUfgaagasusc | 190 | GAUCUUCAAACAGUUUCACAAGA | 236 |
| AD-94823 | csusucaaAfcAfGfUfuucacaagaaL96 | 145 | usUfscuuGfuGfAfaacuGfuUfugaagsasu | 191 | AUCUUCAAACAGUUUCACAAGAA | 237 |
| AD-94824 | ususcaaaCfaGfUfUfucacaagaauL96 | 146 | asUfsucuUfgUfGfaaacUfgUfuugaasgsa | 192 | UCUUCAAACAGUUUCACAAGAAU | 238 |
| AD-94909 | cscsagcaGfaGfAfAfuagcaauucaL96 | 147 | usGfsaauUfgCfUfauucUfcUfgcuggsasa | 193 | UUCCAGCAGAGAAUAGCAAUUCA | 239 |
| AD-94915 | gsasgaauAfgCfAfAfuucagagacaL96 | 148 | usGfsucuCfuGfAfauugCfuAfuucucsusg | 194 | CAGAGAAUAGCAAUUCAGAGACC | 240 |
| AD-94916 | asgsaauaGfcAfAfUfucagagaccaL96 | 149 | usGfsgucUfcUfGfaauuGfcUfauucuscsu | 195 | AGAGAAUAGCAAUUCAGAGACCA | 241 |
| AD-94924 | asasuucaGfaGfAfCfcauuaucauaL96 | 150 | usAfsugaUfaAfUfggucUfcUfgaauusgsc | 196 | GCAAUUCAGAGACCAUUAUCAUC | 242 |
| AD-94926 | ususcagaGfaCfCfAfuuaucaucaaL96 | 151 | usUfsgauGfaUfAfauggUfcUfcugaasusu | 197 | AAUUCAGAGACCAUUAUCAUCAC | 243 |
| AD-94927 | uscsagagAfcCfAfUfuaucaucacaL96 | 152 | usGfsugaUfgAfUfaaugGfuCfucugasasu | 198 | AUUCAGAGACCAUUAUCAUCACA | 244 |
| AD-94929 | asgsagacCfaUfUfAfucaucacagaL96 | 153 | usCfsuguGfaUfGfauaaUfgGfucucusgsa | 199 | UCAGAGACCAUUAUCAUCACAGG | 245 |
| AD-95191 | csasaaccAfaGfAfGfuuucacuguuL96 | 154 | asAfscagUfgAfAfacucUfuGfguuugscsu | 200 | AGCAAACCAAGAGUUUCACUGUU | 246 |

TABLE 4-continued

| Additional HDLBP modified sequences | | | | | | |
|---|---|---|---|---|---|---|
| Duplex Name | Sense Sequence (5' to 3') | SEQ ID NO | Antisense Sequence (5' to 3') | SEQ ID NO | mRNA Target Sequence | SEQ ID NO |
| AD-95192 | asasaccaAfgAfGfUfuucacuguuaL96 | 155 | usAfsacaGfuGfAfaacuCfuUfgguuusgsc | 201 | GCAAACCAAGAGUUUCACUGUUG | 247 |
| AD-95197 | asasgaguUfuCfAfCfuguugacauaL96 | 156 | usAfsuguCfaAfCfagugAfaAfcucuusgsg | 202 | CCAAGAGUUUCACUGUUGACAUC | 248 |
| AD-95586 | csasgaaaUfuCfCfAfucgaucuguaL96 | 157 | usAfscagAfuCfGfauggAfaUfuucugsgsg | 203 | CCCAGAAAUUCCAUCGAUCUGUC | 249 |
| AD-95637 | uscsaaauUfaAfAfUfucccagacaaL96 | 158 | usUfsgucUfgGfGfaauuUfaAfuuugasasc | 204 | GUUCAAAUUAAAUUCCCAGACAG | 250 |
| AD-96564 | cscsguaaAfuUfGfUfugacgcucuuL96 | 159 | asAfsgagCfgUfCfaacaAfuUfuacggsasg | 205 | CUCCGUAAAUUGUUGACGCUCUU | 251 |
| AD-96641 | gsgsucauGfaGfCfAfuucgugcuaaL96 | 160 | usUfsagcAfcGfAfaugcUfcAfugaccsusu | 206 | AAGGUCAUGAGCAUUCGUGCUAA | 252 |
| AD-96642 | gsuscaugAfgCfAfUfucgugcuaaaL96 | 161 | usUfsuagCfaCfGfaaugCfuCfaugacscsu | 207 | AGGUCAUGAGCAUUCGUGCUAAG | 253 |
| AD-96645 | asusgagcAfuUfCfGfugcuaagauaL96 | 162 | usAfsucuUfaGfCfacgaAfuGfcucausgsa | 208 | UCAUGAGCAUUCGUGCUAAGAUA | 254 |
| AD-96648 | asgscauuCfgUfGfCfuaagauaacaL96 | 163 | usGfsuuaUfcUfUfagcaCfgAfaugcuscsa | 209 | UGAGCAUUCGUGCUAAGAUAACA | 255 |
| AD-96653 | uscsgugcUfaAfGfAfuaacagacuaL96 | 164 | usAfsgucUfgUfUfaucuUfaGfcacgasasu | 210 | AUUCGUGCUAAGAUAACAGACUC | 256 |

TABLE 5

| HDLBP in vito 10 nM and 0.1 nM Screen | | | | |
|---|---|---|---|---|
| Duplex Name | 10 nM_Avg | 10 nM_SD | 0.1 nM_Avg | 0.1 nM_SD |
| AD-93225 | 7.42 | 0.77 | 46.76 | 13.77 |
| AD-93226 | 7.81 | 1.60 | 39.90 | 8.79 |
| AD-93233 | 7.11 | 1.71 | 38.07 | 10.35 |
| AD-93247 | 5.54 | 0.70 | 55.64 | 29.86 |
| AD-93292 | 11.87 | 0.79 | 49.56 | 4.71 |
| AD-93483 | 12.52 | 1.05 | 116.97 | 15.10 |
| AD-93665 | 6.40 | 0.77 | 46.90 | 20.56 |
| AD-93701 | 6.68 | 0.70 | 65.92 | 5.55 |
| AD-93718 | 14.58 | 2.06 | 104.82 | 12.89 |
| AD-93726 | 8.75 | 1.55 | 75.18 | 17.96 |
| AD-93974 | 7.76 | 3.66 | 55.33 | 12.23 |
| AD-93991 | 7.57 | 2.60 | 66.18 | 11.90 |
| AD-93992 | 7.80 | 0.86 | 25.08 | 10.43 |
| AD-93993 | 10.61 | 2.71 | 62.57 | 28.14 |
| AD-94001 | 12.28 | 3.15 | 60.04 | 18.55 |
| AD-94012 | 10.14 | 3.00 | 48.34 | 2.34 |
| AD-94526 | 9.41 | 0.63 | 69.18 | 9.86 |
| AD-94608 | 10.72 | 0.81 | 101.60 | 12.29 |
| AD-94613 | 11.00 | 1.43 | 58.18 | 14.80 |
| AD-94621 | 10.74 | 1.08 | 105.71 | 12.52 |
| AD-94624 | 5.39 | 1.72 | 26.26 | 9.85 |
| AD-94710 | 9.89 | 1.46 | 71.01 | 10.55 |
| AD-94758 | 8.88 | 2.93 | 81.47 | 7.22 |
| AD-94813 | 5.68 | 2.12 | 41.31 | 19.27 |
| AD-94814 | 6.64 | 1.14 | 33.57 | 7.62 |
| AD-94822 | 7.58 | 1.51 | 72.99 | 17.32 |
| AD-94823 | 11.56 | 5.11 | 68.16 | 17.23 |
| AD-94824 | 6.37 | 0.70 | 33.58 | 8.86 |

TABLE 5-continued

| HDLBP in vito 10 nM and 0.1 nM Screen | | | | |
|---|---|---|---|---|
| Duplex Name | 10 nM_Avg | 10 nM_SD | 0.1 nM_Avg | 0.1 nM_SD |
| AD-94909 | 7.18 | 1.57 | 47.93 | 8.87 |
| AD-94915 | 8.45 | 1.02 | 81.72 | 3.88 |
| AD-94916 | 13.68 | 3.04 | 81.34 | 31.66 |
| AD-94924 | 5.07 | 2.27 | 14.84 | 7.35 |
| AD-94926 | 8.42 | 2.97 | 40.74 | 12.46 |
| AD-94927 | 9.05 | 1.97 | 77.95 | 15.79 |
| AD-94929 | 12.29 | 2.45 | 97.93 | 26.77 |
| AD-95191 | 7.45 | 1.12 | 49.21 | 5.60 |
| AD-95192 | 7.09 | 0.58 | 51.36 | 9.58 |
| AD-95197 | 6.10 | 2.35 | 23.82 | 9.15 |
| AD-95586 | 10.53 | 2.41 | 86.25 | 4.60 |
| AD-95637 | 10.85 | 1.48 | 78.48 | 17.48 |
| AD-96564 | 6.49 | 0.78 | 34.44 | 14.04 |
| AD-96641 | 20.01 | 5.33 | 119.42 | 15.36 |
| AD-96642 | 14.37 | 1.37 | 87.12 | 3.76 |
| AD-96645 | 13.04 | 3.42 | 80.69 | 10.13 |
| AD-96648 | 10.01 | 0.80 | 66.04 | 3.34 |
| AD-96653 | 14.35 | 1.04 | 93.18 | 14.71 |

We claim:

1. A double stranded ribonucleic acid (dsRNA) agent for inhibiting expression of a High Density Lipoprotein Binding Protein (Hdlbp/Vigilin) gene, wherein said dsRNA agent comprises a sense strand and an antisense strand forming a double stranded region, wherein the sense strand comprises at least 15 contiguous nucleotides differing by no more than 3 nucleotides from the nucleotide sequence of any one of nucleotides 373-395; 374-396; 381-403; 395-417; 440-462; 670-692; 852-874; 888-910; 905-927; 913-935; 1223-1245; 1246-1268; 1247-1269; 1248-1270; 1256-1278; 1267-1289; 1801-1823; 1908-1930; 1916-1938; 1919-1941; 2023-2045; 2071-2093; 2127-2149; 2128-2150; 2136-2158; 2137-2159; 2138-2160; 2225-2247; 2231-2253; 2232-2254; 2240-2262; 2242-2264; 2243-2265; 2245-2267; 2543-2565; 2544-2566; 2549-2571; 3017-3039; 3088-3110; 4271-4293; 4404-4426; 4405-4427; 4408-4430; 4411-4433; or 4416-4438 of the nucleotide sequence of SEQ ID NO:5, and the antisense strand comprises at least 15 contiguous nucleotides differing by no more than 3 nucleotides from the corresponding nucleotide sequence of SEQ ID NO:11.

2. The dsRNA agent of claim 1, wherein said dsRNA agent comprises at least one nucleotide comprising a nucleotide modification.

3. The dsRNA agent of a claim 1, wherein substantially all of the nucleotides of said sense strand and substantially all of the nucleotides of said antisense strand comprise a nucleotide modification; or all of the nucleotides of said sense strand and all of the nucleotides of said antisense strand comprise a nucleotide modification.

4. A double stranded ribonucleic acid (dsRNA) agent for inhibiting expression of a High Density Lipoprotein Binding Protein (Hdlbp/Vigilin) gene, wherein said dsRNA agent comprises a sense strand and an antisense strand forming a double stranded region, wherein the sense strand comprises at least 15 contiguous nucleotides differing by no more than 3 nucleotides from the nucleotide sequence of any one of nucleotides 373-395; 374-396; 381-403; 395-417; 440-462; 670-692; 852-874; 888-910; 905-927; 913-935; 1223-1245; 1246-1268; 1247-1269; 1248-1270; 1256-1278; 1267-1289; 1801-1823; 1903-1925; 1908-1930; 1916-1938; 1919-1941; 2023-2045; 2071-2093; 2127-2149; 2128-2150; 2136-2158; 2137-2159; 2138-2160; 2225-2247; 2231-2253; 2232-2254; 2240-2262; 2242-2264; 2243-2265; 2245-2267; 2543-2565; 2544-2566; 2549-2571; 3017-3039; 3088-3110; 4271-4293; 4404-4426; 4405-4427; 4408-4430; 4411-4433; or 4416-4438 of the nucleotide sequence of SEQ ID NO:5, and the antisense strand comprises at least 15 contiguous nucleotides differing by no more than 3 nucleotides from the corresponding nucleotide sequence of SEQ ID NO:11, wherein substantially all of the nucleotides of said sense strand and substantially all of the nucleotides of said antisense strand comprise a nucleotide modification, and wherein said sense strand is conjugated to a ligand attached at the 3'-terminus.

5. The dsRNA agent of claim 4, wherein all of the nucleotides of said sense strand and all of the nucleotides of said antisense strand comprise a nucleotide modification.

6. The dsRNA agent of claim 1 or 4, wherein the sense strand and the antisense strand are each independently 17-25 nucleotides in length.

7. The dsRNA agent of claim 1 or 4, wherein the sense strand and the antisense strand are each independently no more than 30 nucleotides in length.

8. The dsRNA agent of claim 1 or 4, wherein at least one strand comprises a 3' overhang of at least 1 nucleotide; or at least one strand comprises a 3' overhang of at least 2 nucleotides.

9. The dsRNA agent of claim 1, further comprising a ligand.

10. The dsRNA agent of claim 1 or 4, wherein said agent further comprises at least one phosphorothioate or methylphosphonate internucleotide linkage.

11. A cell containing the double stranded RNAi agent of claim 1 or 4.

12. A pharmaceutical composition for inhibiting expression of an Hdlbp/Vigilin gene comprising the double stranded RNAi agent of claim 1 or 4.

13. A method of inhibiting expression of a High Density Lipoprotein Binding Protein (Hdlbp/Vigilin) gene in a cell, the method comprising:

(a) contacting the cell with the double stranded RNAi agent of claim 1 or 4; and (b) maintaining the cell produced in step (a) for a time sufficient to obtain degradation of the mRNA transcript of an Hdlbp/Vigilin gene, thereby inhibiting epression of the Hdlbp/Vigilin gene in the cell.

14. The method of claim 13, wherein said cell is within a subject.

15. A method of treating a subject having a disorder that would benefit from a reduction in expression of a High Density Lipoprotein Binding Protein (Hdlbp/Vigilin) gene, comprising administering to the subject a therapeutically effective amount of the double stranded RNAi agent of claim 1 or 4, thereby treating said subject.

16. The method of claim 14 or 15, wherein the subject is human.

17. The method of claim 15, wherein the disorder is a disorder of lipid metabolism.

18. The method of claim 17, wherein the disorder of lipid metabolism is a hyperlipidemia.

19. The method of claim 15, further comprising administering an additional therapeutic agent to the subject.

20. The method of claim 15, wherein the double stranded RNAi agent is administered to the subject at a dose of about 0.01 mg/kg to about 50 mg/kg.

21. The method of claim 15, wherein the double stranded RNAi agent is administered to the subject subcutaneously.

22. The dsRNA agent of claim 1 or 4, wherein the antisense strand comprises at least 15 contiguous nucleotides differing by no more than 3 nucleotides from the nucleotide sequence of 5'-UAUGAUAAUGGUCUCUGAAUUGC-3' (SEQ ID NO:104).

23. The dsRNA agent of claim 1 or 4 , wherein the sense strand comprises at least 15 contiguous nucleotides differing by no more than 3 nucleotides from the nucleotide sequence 5'-AAUUCAGAGACCAUUAUCAUA-3' (SEQ ID NO:58).

24. The dsRNA agent of claim 23, wherein the sense strand comprises the nucleotide sequence 5'-AAUUCAGAGACCAUUAUCAUA-3' (SEQ ID NO:58) and the antisense strand comprises the nucleotide sequence of 5'-UAUGAUAAUGGUCUCUGAAUUGC-3 ‘ (SEQ ID NO:104).

25. The dsRNA agent of claim 24, wherein the sense strand comprises the nucleotide sequence 5’-asasuucaGfaGfAfCfcauuaucaua-3' (SEQ ID NO:150) and the antisense strand comprises the nucleotide sequence of 5'-usAfsugaUfaAfUfggucUfcUfgaauusgsc-3' (SEQ ID NO:196), wherein a, g, c and u are 2'-O-methyl (2'-OMe) A, G, C, and U; Af, Gf, Cf and Uf are 2'-fluoro A, G, C and U; dT is 2'-deoxythymidine; and s is a phosphorothioate linkage.

* * * * *